US012761223B2

(12) United States Patent
Lowery, III et al.

(10) Patent No.: US 12,761,223 B2
(45) Date of Patent: Oct. 13, 2026

(54) T CELL PHENOTYPES ASSOCIATED WITH RESPONSE TO ADOPTIVE CELL THERAPY

(71) Applicant: The United States of America, as represented by the Secretary, Department of Health and Human Services, Bethesda, MD (US)

(72) Inventors: Frank J. Lowery, III, Clarksburg, MD (US); Sri Krishna, Bethesda, MD (US); Paul F. Robbins, Chevy Chase, MD (US); Steven A. Rosenberg, Potomac, MD (US); Gregoire Y. Altan-Bonnet, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 845 days.

(21) Appl. No.: 18/024,430

(22) PCT Filed: Sep. 8, 2021

(86) PCT No.: PCT/US2021/049387

§ 371 (c)(1),
(2) Date: Mar. 2, 2023

(87) PCT Pub. No.: WO2022/055946

PCT Pub. Date: Mar. 17, 2022

(65) Prior Publication Data

US 2023/0258635 A1 Aug. 17, 2023

Related U.S. Application Data

(60) Provisional application No. 63/075,536, filed on Sep. 8, 2020.

(51) Int. Cl.

| | |
|---|---|
| ***A61K 40/11*** | (2025.01) |
| ***A61K 40/32*** | (2025.01) |
| ***A61K 40/42*** | (2025.01) |
| ***C12N 5/0783*** | (2010.01) |
| ***C12Q 1/6881*** | (2018.01) |
| ***G01N 33/569*** | (2006.01) |

(52) U.S. Cl.

CPC ........ *G01N 33/56972* (2013.01); *A61K 40/11* (2025.01); *A61K 40/32* (2025.01); *A61K 40/4269* (2025.01); *A61K 40/4273* (2025.01); *C12N 5/0636* (2013.01); *C12Q 1/6881* (2013.01); *A61K 2239/38* (2023.05); *A61K 2239/57* (2023.05); *C12Q 2600/158* (2013.01); *G01N 2800/52* (2013.01)

(58) Field of Classification Search

None

See application file for complete search history.

(56) References Cited

U.S. PATENT DOCUMENTS

| | | | |
|---|---|---|---|
| 7,820,174 | B2 | 10/2010 | Wang et al. |
| 7,915,036 | B2 | 3/2011 | Morgan et al. |
| 8,034,334 | B2 | 10/2011 | Dudley et al. |
| 8,088,379 | B2 | 1/2012 | Robbins et al. |
| 8,216,565 | B2 | 7/2012 | Restifo et al. |
| 8,383,099 | B2 | 2/2013 | Dudley et al. |
| 8,431,690 | B2 | 4/2013 | Wang et al. |
| 8,465,743 | B2 | 6/2013 | Rosenberg et al. |
| 8,613,932 | B2 | 12/2013 | Restifo et al. |
| 8,785,601 | B2 | 7/2014 | Rosenberg et al. |
| 9,128,080 | B2 | 9/2015 | Robbins et al. |
| 9,266,960 | B2 | 2/2016 | Morgan et al. |
| 9,345,748 | B2 | 5/2016 | Morgan et al. |
| 9,359,447 | B2 | 6/2016 | Feldman et al. |
| 9,487,573 | B2 | 11/2016 | Parkhurst et al. |
| 9,765,342 | B2 | 9/2017 | Kochenderfer |
| 9,868,774 | B2 | 1/2018 | Orentas et al. |
| 9,879,065 | B2 | 1/2018 | Robbins et al. |
| 10,072,078 | B2 | 9/2018 | Orentas et al. |

(Continued)

FOREIGN PATENT DOCUMENTS

| | | | |
|---|---|---|---|
| WO | WO 2017/048614 | A1 | 3/2017 |
| WO | WO 2018/067991 | A1 | 4/2018 |

(Continued)

OTHER PUBLICATIONS

Aagaard et al., "A Facile Lentiviral Vector System for Expression of Doxycycline-Inducible shRNAs: Knockdown of the Pre-miRNA Processing Enzyme Drosha", *Molecular Therapy*, 15(5): 938-945 (2007).

Ahlmanner et al., "CD39+ regulatory T cells accumulate in colon adenocarcinomas and display markers of increased suppressive function", *Oncotarget*, 9(97): 36993-37007 (2018).

Bendall et al., "Single-cell mass cytometry of differential immune and drug responses across a human hematopoietic continuum", *Science*, 332: 687-696 (2011).

Blank et al., "Defining 'T cell exhaustion'", *Nature Reviews Immunology*, 19: 665-674 (2019).

(Continued)

*Primary Examiner* — Michail A Belyavskyi
(74) *Attorney, Agent, or Firm* — Leydig, Voit & Mayer

(57) ABSTRACT

Disclosed are methods of obtaining a cell population enriched for T cells with a phenotype, the method comprising: (a) obtaining a bulk population of T cells from a tumor sample of a patient; (b) specifically selecting T cells with a phenotype comprising markers $CD3^+$, $CD39^-$, and $CD69^-$ from the bulk population; and (c) separating the cells selected in (b) from cells which lack the phenotype to obtain a cell population enriched for T cells with the phenotype. Related methods of treating or preventing cancer, methods of selecting a therapy for a cancer patient, and methods for predicting the clinical response to immunotherapy in a cancer patient are also disclosed. Isolated or purified cell population obtained according to the methods and related pharmaceutical compositions are also disclosed.

16 Claims, 71 Drawing Sheets

Specification includes a Sequence Listing.

(56) References Cited

U.S. PATENT DOCUMENTS

| | | | |
|---|---|---|---|
| 10,287,350 | B2 | 5/2019 | Kochenderfer |
| 2012/0244133 | A1 | 9/2012 | Rosenberg et al. |
| 2013/0116167 | A1 | 5/2013 | Morgan et al. |
| 2014/0378389 | A1 | 12/2014 | Robbins et al. |
| 2017/0218042 | A1 | 8/2017 | Tran et al. |
| 2020/0056237 | A1 | 2/2020 | Lu et al. |
| 2020/0095548 | A1 | 3/2020 | Gros et al. |

FOREIGN PATENT DOCUMENTS

| | | | |
|---|---|---|---|
| WO | 2018/127584 | A1 | 7/2018 |
| WO | WO 2018/209324 | A2 | 11/2018 |

OTHER PUBLICATIONS

Butler et al., "Integrating single-cell transcriptomic data across different conditions, technologies, and species", *Nature Biotechnology*, 36: 411-420 (2018).
Canale et al., "CD39 Expression Defines Cell Exhaustion in Tumor-Infiltrating CD8β T Cells", *Cancer Research*, 78(1): 115-128 (2018).
Cheng et al., "Multiplexed activation of endogenous genes by CRISPR-on, an RNA-guided transcriptional activator system", *Cell Research*, 23:1163-1171 (2013).
Cohen et al., "Isolation of neoantigen-specific T cells from tumor and peripheral lymphocytes", *The Journal of Clinical Investigation*, 125(10) 3981-3991 (2015).
Creelan et al., "Tumor-infiltrating lymphocyte treatment for anti-PD-1 resistant metastatic lung cancer: a phase I trial". Nature Medicine, 27(8): 1410-1418 (2021).
D'Angelo et al., "Antitumor Activity Associated with Prolonged Persistence of Adoptively Transferred NY-ESO-1c259T Cells in Synovial Sarcoma", *Cancer Discovery*, 8: 944-957 (2018).
Dudley et al., "Adoptive cell therapy for patients with metastatic melanoma: evaluation of intensive myeloablative chemoradiation preparative regimens", *Journal of Clinical Oncology*, 26, 5233-5239 (2008).
Dudley et al., "Cancer regression and autoimmunity in patients after clonal repopulation with antitumor lymphocytes", *Science*, 298, 850-854 (2002).
Dudley et al., "CD8+ enriched "young" tumor infiltrating lymphocytes can mediate regression of metastatic melanoma", *Clinical Cancer Research*, 16: 6122-6131 (2010).
Dudley et al., "Generation of tumor-infiltrating lymphocyte cultures for use in adoptive transfer therapy for melanoma patients", *Journal of Immunotherapy*, 26(4): 332-342 (2003).
Duhen et al., "Co-expression of CD39 and CD103 identifies tumor-reactive CD8 T cells in human solid tumors", *Nature Communications*, 9: 2724 (p. 1-13) (2018).
European Patent Office, International Search Report and Written Opinion issued in the International Patent Application No. PCT/US2021/049387, mailed on Nov. 29, 2021.
Finck et al., "Normalization of Mass Cytometry Data with Bead Standards", *Cytometry A.*, 83: 483-494 (2013).
Gallerano et al., "Genetically driven CD39 expression shapes human tumor-infiltrating CD8+ T-cell functions", *International Journal of Cancer*, 147: 2597-2610 (2020).
Gattinoni et al., "A human memory T-cell subset with stem cell-like properties", *Nature Medicine*, 17: 1290-1297 (2011).
Godec et al., "Compendium of immune signatures identifies conserved and species-specific biology in response to inflammation", *Immunity*, 44: 194-206 (2016).
Goff et al., "Randomized, Prospective Evaluation Comparing Intensity of Lymphodepletion Before Adoptive Transfer of Tumor-Infiltrating Lymphocytes for Patients With Metastatic Melanoma", *Journal of Clinical Oncology*, 34: 2389-2397 (2016).
Gommans et al., "Engineering zinc finger protein transcription factors: the therapeutic relevance of switching endogenous gene expression on or off at command", *Journal of Molecular Biology*, 354(3):507-519 (2005).
Gupta et al., "CD 39 Expression Identifies Terminally Exhausted CD8+ T cells", *PLOS Pathogens*, 1-21 (2015).
Halko et al., "Finding Structure with Randomness: Probabilistic Algorithms for Constructing Approximate Matrix Decompositions", *SIAM Review*, 53: 217-288 (2011).
Hanada et al., "An effective mouse model for adoptive cancer immunotherapy targeting neoantigens", *JCI Insight*, 4(10): 1-11 (2019).
Held et al., "Not All Tumor-Infiltrating CD8+ T Cells Are Created Equal" *Cancer Cell*, 39(2): 145-147 (2021).
Jansen et al., "An intra-tumoral niche maintains and differentiates stem-like CD8 T cells", *Nature*, 576: 465-470 (2019).
Jin et al., "Simplified method of the growth of human tumor infiltrating lymphocytes in gas-permeable flasks to numbers needed for patient treatment", *Journal of Immunotherapy.*, 35: 283-292 (2012).
Kalos et al., "T cells with chimeric antigen receptors have potent antitumor effects and can establish memory in patients with advanced leukemia", *Science Translational Medicine*, 3(95) 95ra73, 1-21 (2011).
Kimura et al., "A new therapeutic target: the CD69-Myl9 system in immune responses" *Seminars in Immunopathology*, 41: 349-358 (2019).
Klebanoff et al., "Determinants of successful CD8+ T cell adoptive immunotherapy for large established tumors in mice", *Clinical Cancer Research*, 17: 5343-5352 (2011).
Klebanoff et al., "Memory T cell-driven differentiation of naive cells impairs adoptive immunotherapy", *Journal of Clinical Investigation*, 126: 318-334 (2015).
Krishna et al., "Stem-like CD8 T cells mediate response of adoptive cell immunotherapy against human cancer" *Science*, 370(6522): 1328-1334 (2020).
Krishna et al., Supplementary Materials for "Stem-like CD8 T cells mediate response of adoptive cell immunotherapy against human cancer" *Science*, 370(1328): 1-43 (2020).
Kvistborg et al., "Anti-CTLA-4 therapy broadens the melanoma-reactive CD8+ T cell response", *Science Translational Medicine*, 6: 254ra128 (2014).
Liu et al., "Whole-genome comparison of Leu3 binding in vitro and in vivo reveals the importance of nucleosome occupancy in target site selection", *Genome Research*, 16: 1517-1528 (2006).
Loza et al., "T -cell specific defect in expression of the NTPDase CD39 as a biomarker for lupus", *Cell Immunology*, 271(1): 110-117 (2011).
Lu et al., "An Efficient Single-Cell RNA-Seq Approach to Identify Neoantigen-Specific T Cell Receptors" *Molecular Therapy*, 26(2): 379-389 (2018).
Lugli et al., "Superior T memory stem cell persistence supports long-lived T cell memory", *Journal of Clinical Investigation*, 123: 594-599 (2013).
Lun et al., "Pooling across cells to normalize single-cell RNA sequencing data with many zero counts", *Genome Biology*, 17:75, 1-14 (2016).
Lynn et al., "c-Jun overexpression in CAR T cells induces exhaustion resistance", *Nature*, 576: 293-300 (2019).
Mair et al., "A Targeted Multi-omic Analysis Approach Measures Protein Expression and Low-Abundance Transcripts on the Single-Cell Level", *Cell Reproduction*, 31(1); 107499 (1-32) (2020).
Miller et al., "Subsets of exhausted CD8+ T cells differentially mediate tumor control and respond to checkpoint blockade", *Nature Immunology*, 20: 326-336 (2019).
Mita et al., "Crucial role of CD69 in anti-tumor immunity through regulating the exhaustion of tumor-infiltrating T cells" *International Immunology*, 30(12): 559-567 (2018).
Park et al., "Long-Term Follow-up of CD19 CAR Therapy in Acute Lymphoblastic Leukemia", *New England Journal of Medicine*, 378: 449-459 (2018).
Parkhurst et al., "Isolation of T-Cell Receptors Specifically Reactive with Mutated Tumor-Associated Antigens from Tumor-Infiltrating Lymphocytes Based on CD137 Expression", *Clinical Cancer Research*, 23: 2491-2505 (2017).

(56) References Cited

OTHER PUBLICATIONS

Parkhurst et al., "Unique Neoantigens Arise from Somatic Mutations in Patients with Gastrointestinal Cancers", *Cancer Discovery*, 9: 1022-1035 (2019).
Pasetto et al., "Tumor- and neoantigen-reactive T-cell receptors can be identified based on their frequency in fresh tumor", *Cancer Immunology Research*, 4(9): 734-743 (2016).
Prickett et al., "Durable Complete Response from Metastatic Melanoma after Transfer of Autologous T Cells Recognizing 10 Mutated Tumor Antigens", *Cancer Immunology Research*, 4: 669-678 (2016).
Riddell et al., "The use of anti-CD3 and anti-CD28 monoclonal antibodies to clone and expand human antigen-specific T cells", *Journal of Immunotherapy Methods*, 128: 189-201 (1990).
Riviere et al., "Variable correction of Artemis deficiency by I-Sce1-meganuclease-assisted homologous recombination in murine hematopoietic stem cells", *Gene Therapy*, 21(5): 529-532 (2014).
Robbins et al., "Cutting edge: persistence of transferred lymphocyte clonotypes correlates with cancer regression in patients receiving cell transfer therapy" *Journal of Immunology*, 173, 7125-7130 (2004).
Robbins et al., "Mining exomic sequencing data to identify mutated antigens recognized by adoptively transferred tumor-reactive T cells", *Nature Medicine*, 19: 747-752 (2013).
Rosenberg et al., "Adoptive cell transfer as personalized immunotherapy for human cancer", *Science*, 348: 62-68 (2015).
Rosenberg et al., "Durable Complete Responses in Heavily Pretreated Patients with Metastatic Melanoma Using T Cell Transfer Immunotherapy", *Clinical Cancer Research*, 17: 4550-4557 (2011).
Ryzhov et al., "Role of TGF-β Signaling in Generation of CD39+ CD73+ Myeloid Cells in Tumors", *Journal of Immunology*, 194: 3155-3164 (2014).
Sade-Feldman et al., "Defining T Cell States Associated with Response to Checkpoint Immunotherapy in Melanoma", *Cell*, 175(4): 998-1013 (2018).
Sade-Feldman et al., "Defining T Cell States Associated with Response to Checkpoint Immunotherapy in Melanoma", *Cell*, 176: 1-2 (2019) (Erratum).
Scott et al., "TOX is a critical regulator of tumour-specific T cell differentiation", *Nature*, 571: 270-274 (2019).
Şenbabaoğlu et al., "Tumor immune microenvironment characterization in clear cell renal cell carcinoma identifies prognostic and immunotherapeutically relevant messenger RNA signatures", *Genome Biology*, 17: 231, 1-25 (2016).
Simoni et al., "Bystander CD8+ T cells are abundant and phenotypically distinct in human tumour infiltrates", *Nature*, 557: 575-579 (2018).
Stokeius et al., "Large-scale simultaneous measurement of epitopes and transcriptomes in single cells", *Nature Methods*, 14(9): 865-868 (2017).
Tirosh et al., "Dissecting the multicellular ecosystem of metastatic melanoma by single-cell RNA-seq", *Science*, 352: 189-196 (2016).
Tran et al., "Cancer immunotherapy based on mutation-specific cd4+ t cells in a patient with epithelial cancer", *Science*, 344: 641-645 (2014).
Tran et al., "'Final common pathway' of human cancer immunotherapy: targeting random somatic mutations", *Nature Immunology*, 18: 255-262 (2017).
Tran et al., "Minimally cultured tumor-infiltrating lymphocytes display optimal characteristics for adoptive cell therapy", *Journal of Immunotherapy*, 31: 742-751 (2008).
Tran et al., "T-Cell Transfer Therapy Targeting Mutant KRAS in Cancer", *The New England Journal of Medicine*, 375: 2255-2262 (2016).
Van Der Leun et al., "CD8+ T cell states in human cancer: insights from single-cell analysis", *Nature Reviews Cancer*, 20: 218-232 (2020).
Van Der Maaten et al., "Visualizing Data using t-SNE", *Journal of Machine Learning Research*, 9: 2579-2605 (2008).
Van Der Maaten et al., Visualizing non-metric similarities in multiple maps, *Machine Learning*, 87: 33-55 (2012).
Zacharakis et al., "Immune recognition of somatic mutations leading to complete durable regression in metastatic breast cancer", *Nature Medicine*, 24: 724-730 (2018).
Zhang et al., "Efficient construction of sequence-specific TAL effectors for modulating mammalian transcription", *Nature Biotechnology*, 29:149-153 (2011).
Zhou et al., "Differentiation and persistence of memory CD8+ T cells depend on T cell factor 1", *Immunity*, 33: 229-240 (2010).
Pereira Pinho et al., "Frequency determination of breast tumor-reactive CD4 and CD8 T cells in humans: unveiling the antitumor immune response", Oncoimmunology, 8(8): e1607674, pp. 1-11 (2019).

T CELL PHENOTYPES ASSOCIATED WITH RESPONSE TO ADOPTIVE CELL THERAPY

CROSS REFERENCE TO RELATED APPLICATIONS

This patent application is the U.S. national stage of International Patent Application No. PCT/US2021/049387, filed Sep. 8, 2021, which claims the benefit of U.S. Provisional Patent Application No. 63/075,536, filed Sep. 8, 2020, each of which is incorporated by reference in its entirety herein.

STATEMENT REGARDING FEDERALLY SPONSORED RESEARCH OR DEVELOPMENT

This invention was made with Government support under project numbers ZIA BC 010984 and ZIA BC 011726 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 134,116 ASCII (Text) named "766597 ST25.txt," dated Feb. 21, 2023.

BACKGROUND OF THE INVENTION

Adoptive cell therapy (ACT) using T cells can produce positive clinical responses in some patients. Nevertheless, several obstacles to the successful use of ACT for the treatment of cancer and other conditions remain. For example, the impact of T cell phenotype on clinical success of ACT in humans has not been elucidated. Accordingly, there is a need for improved methods of preparing cell populations for ACT.

BRIEF SUMMARY OF THE INVENTION

An embodiment of the invention provides a method of obtaining a cell population enriched for T cells with a phenotype, the method comprising: (a) obtaining a bulk population of T cells from a tumor sample of a patient; (b) specifically selecting T cells with a phenotype comprising markers CD3$^+$, CD39$^-$, and CD69$^-$ from the bulk population; and (c) separating the cells selected in (b) from cells which lack the phenotype to obtain a cell population enriched for T cells with the phenotype.

Another embodiment of the invention provides a method of obtaining a cell population enriched for T cells with a phenotype, the method comprising: (a) obtaining a bulk population of T cells from a tumor sample of a patient; (b) isolating tumor-reactive T cells from the tumor sample; (c) specifically selecting T cells with a phenotype comprising markers CD3$^+$, CD39$^-$, and CD69$^-$ from the isolated tumor-reactive T cells; and (d) separating the cells selected in (c) from cells which lack the phenotype to obtain a cell population enriched for T cells with the phenotype.

Still another embodiment of the invention provides a method of obtaining a cell population enriched for T cells with a phenotype, the method comprising: (a) obtaining a bulk population of T cells from a tumor sample of a patient; (b) isolating tumor-reactive T cells from the tumor sample; and (c) modifying the isolated tumor-reactive T cells to provide a phenotype comprising markers CD39$^-$ and CD69$^-$ to obtain a cell population enriched for T cells with the phenotype.

Another embodiment of the invention provides a method of preparing a population of cells enriched for T cells with a CD3$^+$CD39$^-$CD69$^-$ phenotype, the method comprising: (a) isolating tumor-reactive T cells from a tumor sample of a patient; and (b) modifying the isolated, tumor-reactive T cells to (i) induce expression of one or more of the following markers: AHNAK$^+$, AL592183.1$^+$, ANXA1$^+$, ANXA4$^+$, AQP3$^+$, ATM$^+$, BIN1$^+$, C10orf54$^+$, C11orf21$^+$, C16orf54$^+$, CCDC109B$^+$, CD27$^+$, CD52$^+$, CD55$^+$, CD8B$^+$, CDC25B$^+$, CDC42SE1$^+$, CLEC2B$^+$, CLIC3$^+$, CLUAP1$^+$, CRBN$^+$, CTD-3184A7.4$^+$, DDI2$^+$, DND1$^+$, EMP3$^+$, EPB41$^+$, ERN1$^+$, FAIM3$^+$, FAM65B$^+$, FBXL8$^+$, FGFBP2$^+$, GADD45B$^+$, GIMAP4$^+$, GIMAP7$^+$, GPR155$^+$, GZMM$^+$, HSD17B11$^+$, IL10RA$^+$, IL7R$^+$, ISG20$^+$, KANSL1-AS1$^+$, KLF2$^+$, KLHL24$^+$, LDLRAP1$^+$, LEF1$^+$, LGALS3$^+$, LINC00861$^+$, LITAF$^+$, LYAR$^+$, MAPKAPK5-AS1$^+$, MED15$^+$, MIAT$^+$, MIR142$^+$, MXI1, MYC$^+$, NEAT1$^+$, NOSIP$^+$, ODF2L$^+$, P2RY8$^+$, PDE6G, PIK3IP1$^+$, PLEC$^+$, PLP2$^+$, PPP2R5C$^+$, PXN$^+$, R3HDM4$^+$, RAMP1$^+$, RASA3$^+$, RASGRP2$^+$, RCBTB2$^+$, RNASET2$^+$, RP11-395B7.4$^+$, RP11-539L10.2$^+$, RP11-640M9.1$^+$, S100A10$^+$, S100A4$^+$, S100A6$^+$, S1PR1$^+$, S1PR4$^+$, SAMD3$^+$, SELL$^+$, SH3BP5$^+$, SIGIRR$^+$, SLAMF6$^+$, SLCO3A1$^+$, SORL1$^+$, STK38$^+$, SYNJ2$^+$, TCF7$^+$, TIMP1$^+$, TRADD$^+$, TSC22D3$^+$, TSPAN32$^+$, TXNIP$^+$, UBXN11$^+$, VCL$^+$, VNN2$^+$, YPEL3$^+$, ZFP36L2$^+$, ZNF276$^+$, and ZNF683$^+$; and/or (ii) inhibit expression of one or more of the following markers: ACOT7$^+$, ADAM19$^+$, AGPAT9$^+$, AGTRAP$^+$, AIF1$^+$, ASPM$^+$, ATAD2$^+$, AURKA$^+$, AURKB$^+$, BIRC3$^+$, BIRC5$^+$, BRCA1$^+$, C15orf48$^+$, CASC5$^+$, CCL3$^+$, CCNA2$^+$, CCNB1$^+$, CCNB2$^+$, CCND2$^+$, CD38$^+$, CD40LG$^+$, CD69$^+$, CD8B$^+$, CDC20$^+$, CDCA3$^+$, CDCA8$^+$, CDK1, CDKN3$^+$, CDT1$^+$, CENPA$^+$, CENPE$^+$, CENPF$^+$, CENPM$^+$, CENPW$^+$, CEP55$^+$, CISH$^+$, CKS1B$^+$, CKS2$^+$, CLSPN$^+$, CRTAM$^+$, CSF2$^+$, DLGAP5$^+$, DUSP5$^+$, DUSP6$^+$, DUT$^+$, EGR1$^+$, ENTPD1$^+$, FEN1$^+$, GINS2$^+$, GTSE1$^+$, H2AFX$^+$, HIST1H4C$^+$, HLA$^+$DQA2$^+$, HMMR$^+$, IFI27$^+$, IFNG$^+$, IL2RA$^+$, IL5$^+$, KIAA0101$^+$, KIF11$^+$, KIF23$^+$, KPNA2$^+$, KRT7$^+$, MAD2L1$^+$, MCM7V, MKI67$^+$, MX1$^+$, MYBL2$^+$, NCAPG, NDC80$^+$, NDFIP2$^+$, NUDT1$^+$, NUSAP1$^+$, ORC6$^+$, PBK$^+$, PCNA$^+$, PLKI1, RPL39L$^+$, RRM2$^+$, SGOL2$^+$, SHCBP1$^+$, SMC2$^+$, SPC25$^+$, STMN1$^+$, TESC$^+$, TK1$^+$, TNF$^+$, TNFRSF18$^+$, TNFSF1O$^+$, TOP2A$^+$, TPM4$^+$, TPX2$^+$, TUBA1B$^+$, TUBA1C$^+$, TUBB$^+$, TYMS$^+$, UBE2C$^+$, UBE2S$^+$, UBE2T$^+$, XCL1$^+$, and ZWINT$^+$, wherein inducing expression of one or more of the markers of (i) and/or inhibiting expression of one or more of the markers of (ii) induces the T cells to have the CD3$^+$CD39$^-$CD69$^-$ phenotype.

Further embodiments of the invention provide an isolated or purified cell population obtained according to any of the inventive methods and related pharmaceutical compositions comprising the same.

Another embodiment of the invention provides a method of treating or preventing a condition in a mammal, the method comprising obtaining a cell population enriched for T cells with the phenotype according to any of the inventive methods and administering the cell population or a pharmaceutical composition comprising the cell population to the mammal in an amount effective to treat or prevent the condition in the mammal, wherein the condition is cancer.

Still another embodiment of the invention provides a method of selecting a therapy for a cancer patient, the method comprising: (a) obtaining a bulk population of T cells from a tumor sample of a patient; (b) measuring the proportion of T cells in the bulk population which (i) have or (ii) lack a phenotype, wherein the phenotype comprises markers $CD3^+$, $CD39^-$, and $CD69^-$; and (c) comparing the proportion of T cells which (i) have or (ii) lack the phenotype to a control; and (d) selecting the patient for a therapy which is not immunotherapy when (i) the proportion of T cells which have the phenotype is lower than the control or (ii) the proportion of T cells which lack the phenotype is equal to or higher than the control; or (e) selecting the patient for an immunotherapy when (i) the proportion of T cells which have the phenotype is equal to or higher than the control or (ii) the proportion of T cells which lack the phenotype is lower than the control.

Another embodiment of the invention provides a method of treating cancer in a patient, the method comprising: receiving an identification of a therapy selected for a cancer patient, wherein the therapy has been selected by any of the inventive methods; and (I) treating the patient by administering a therapy which is not immunotherapy to the patient in an amount effective to treat cancer in the patient when (i) the proportion of T cells which have the phenotype is lower than the control or (ii) the proportion of T cells which lack the phenotype is equal to or higher than the control; or (II) treating the patient by administering an immunotherapy to the patient in an amount effective to treat cancer in the patient when (i) the proportion of T cells which have the phenotype is equal to or higher than the control or (ii) the proportion of T cells which lack the phenotype is lower than the control.

Still another embodiment of the invention provides a method for predicting the clinical response to immunotherapy in a cancer patient, the method comprising: (a) obtaining a bulk population of T cells from a tumor sample from the cancer patient; (b) measuring the proportion of T cells in the bulk population which (i) have or (ii) lack a phenotype, wherein the phenotype comprises markers $CD3^+$, $CD39^-$, and $CD69^-$; and (c) comparing the proportion of T cells which (i) have or (ii) lack the phenotype to a control; and (d) identifying the patient as likely to have a negative clinical response to the immunotherapy when (i) the proportion of T cells which have the phenotype is lower than the control or (ii) the proportion of T cells which lack the phenotype is equal to or higher than the control; or (e) identifying the patient as likely to have a positive clinical response to the immunotherapy when (i) the proportion of T cells which have the phenotype is equal to or higher than the control or (ii) the proportion of T cells which lack the phenotype is lower than the control.

BRIEF DESCRIPTION OF THE SEVERAL VIEWS OF THE DRAWING(S)

Figure 1A:
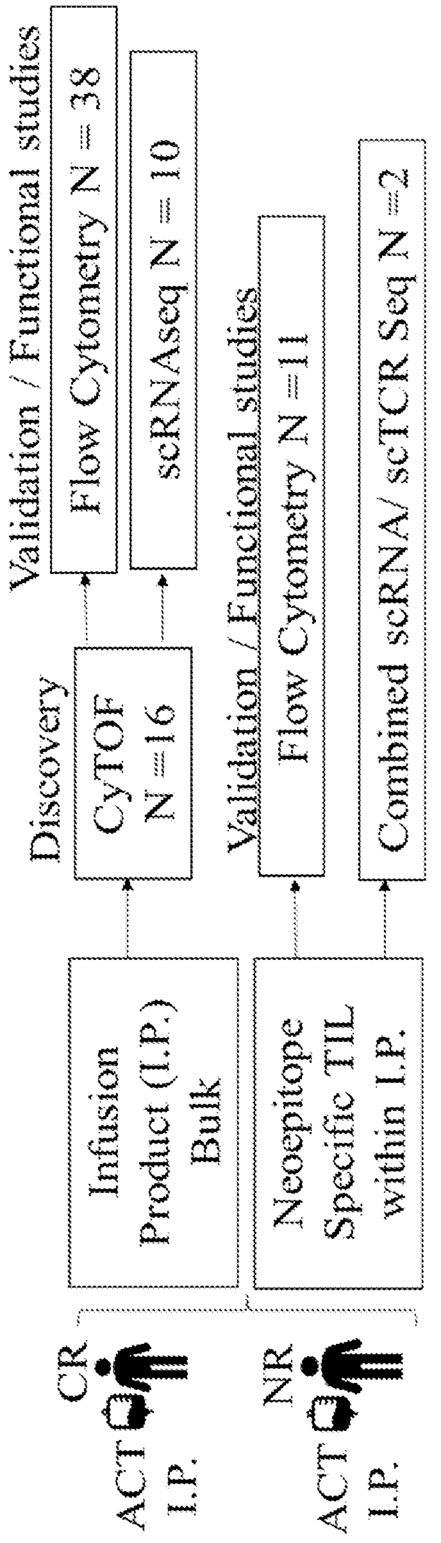
FIG. 1A is a schematic illustrating a melanoma cohort patient ACT infusion products (I.P.) and schema used for the study described in the Examples.
Figure 1B:
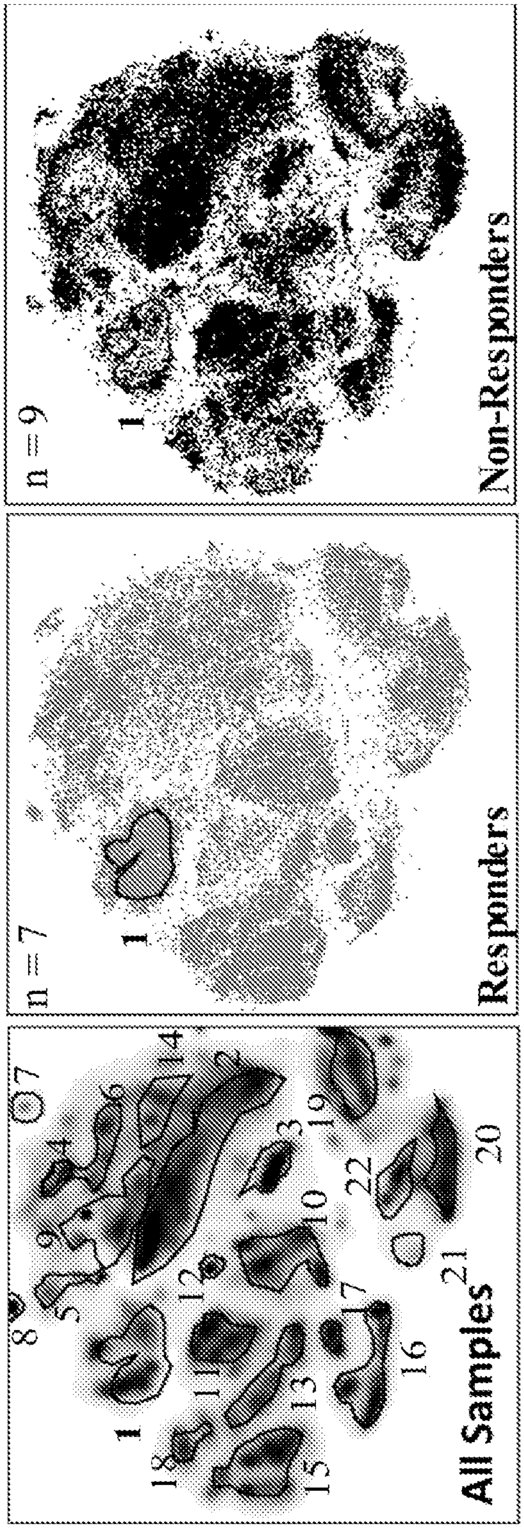
FIG. 1B shows t-SNE (t-distributed stochastic neighbor embedding) plots of live $CD45^+CD3^+$ cell clusters of I.P. from all patient I.P. (left), clusters from CR I.P. only (middle), and clusters from NR I.P. only (right). Cluster 1 represents $CD39^-CD69^-$ DN population.
Figure 1C:
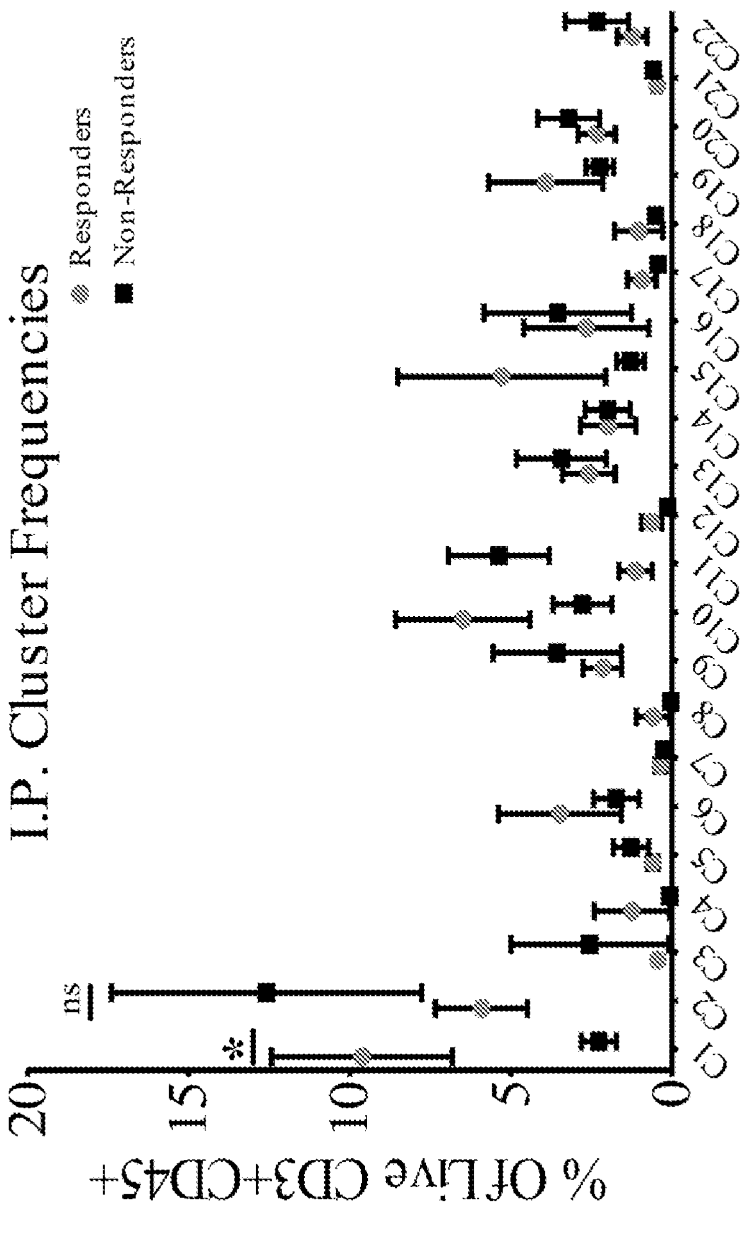
FIG. 1C is a plot showing the percentage of CR and NR I.P. cells in each cluster *P=0.0264 from two-sided Wilcoxon rank-sum test adjusted by Bonferroni correction for all clusters.
Figure 1D:
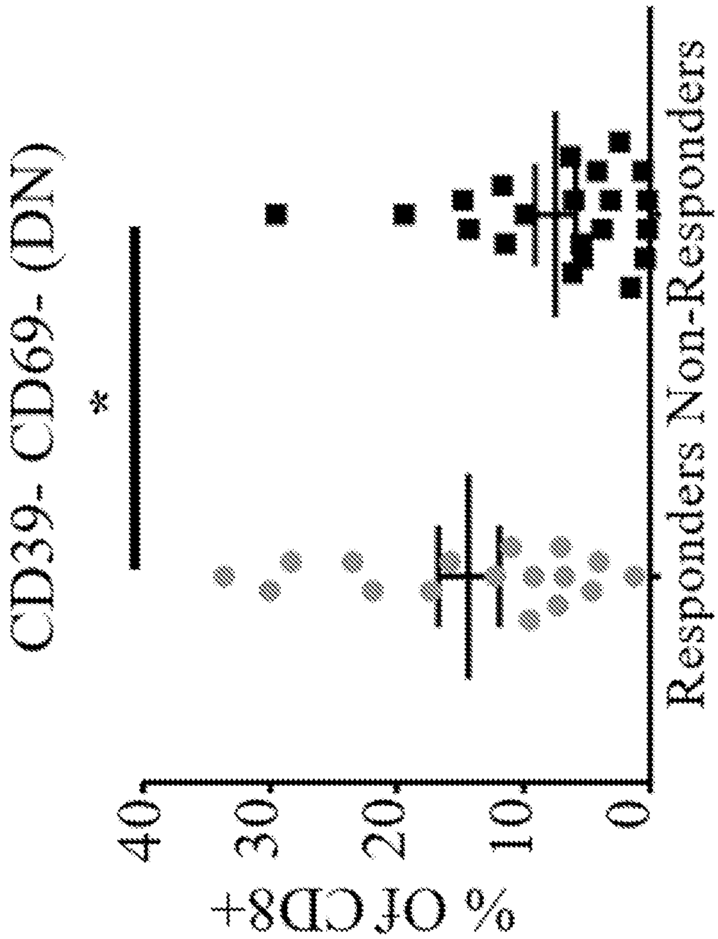
FIGS. 1D-1E are scatter plots showing the results of flow-based independent validation of CR I.P. and NR I.P. samples (N=38) showing the percentages of $CD39^-CD69^-$ (DN) cells of total $CD8^+$ (1E) and total $CD3^+$ (1F).
Figure 1E:
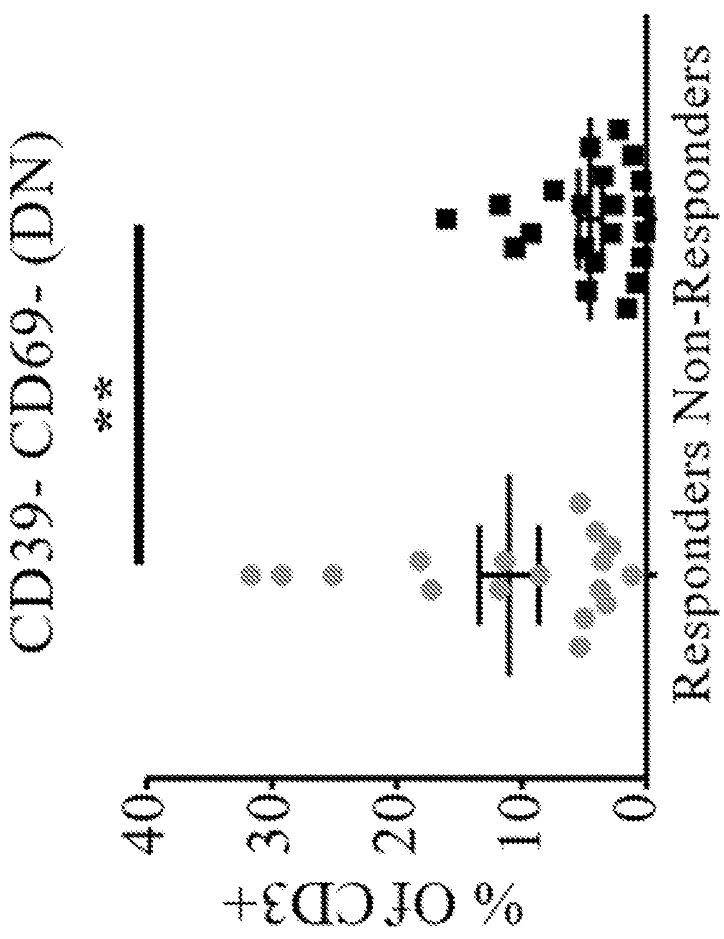
Figure 1F:
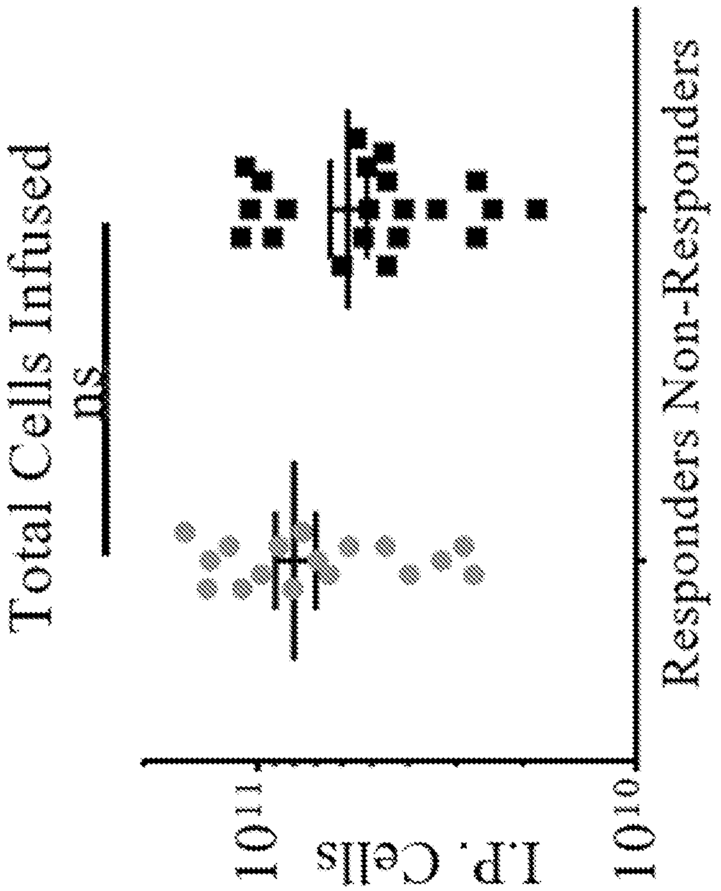
FIG. 1F is a scatter plot showing the total number of infused cells within CR I.P. and NR I.P. (N=38).
Figure 1G:
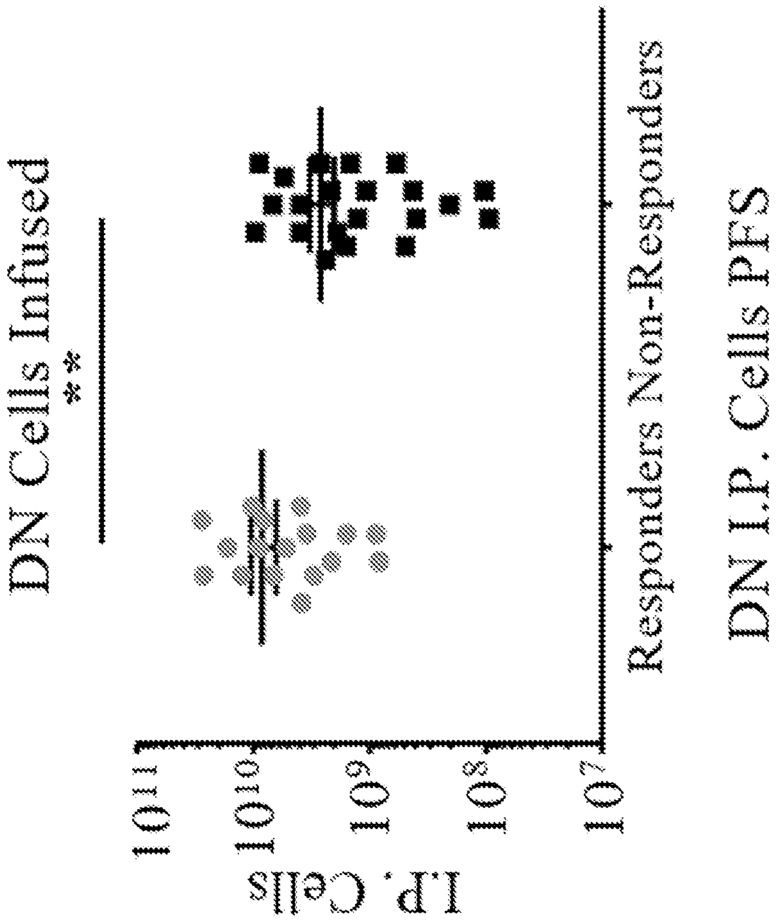
FIG. 1G is a scatter plot showing the total number of $CD8^+CD39^-CD69^-$ (DN) cells in CR I.P. and NR I.P. (N=38). *P<0.05 **P<0.01 by two-sided Wilcoxon rank-sum test.
Figure 1H:
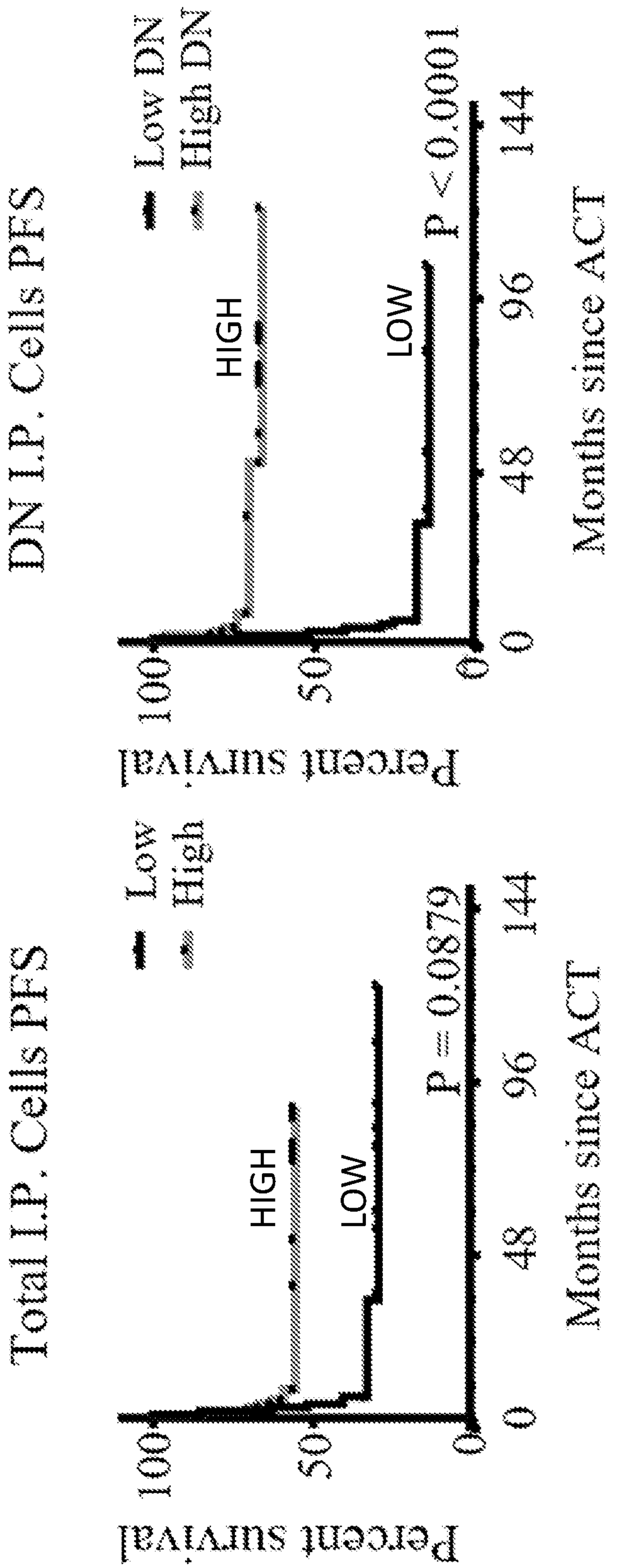
FIG. 1H shows progression-free survival (PFS) of all I.P. samples (N=54) separated by median total cell numbers infused (left) and median $CD8^+CD39^-CD69^-$ (DN) cell numbers infused (right).
Figure 1I:
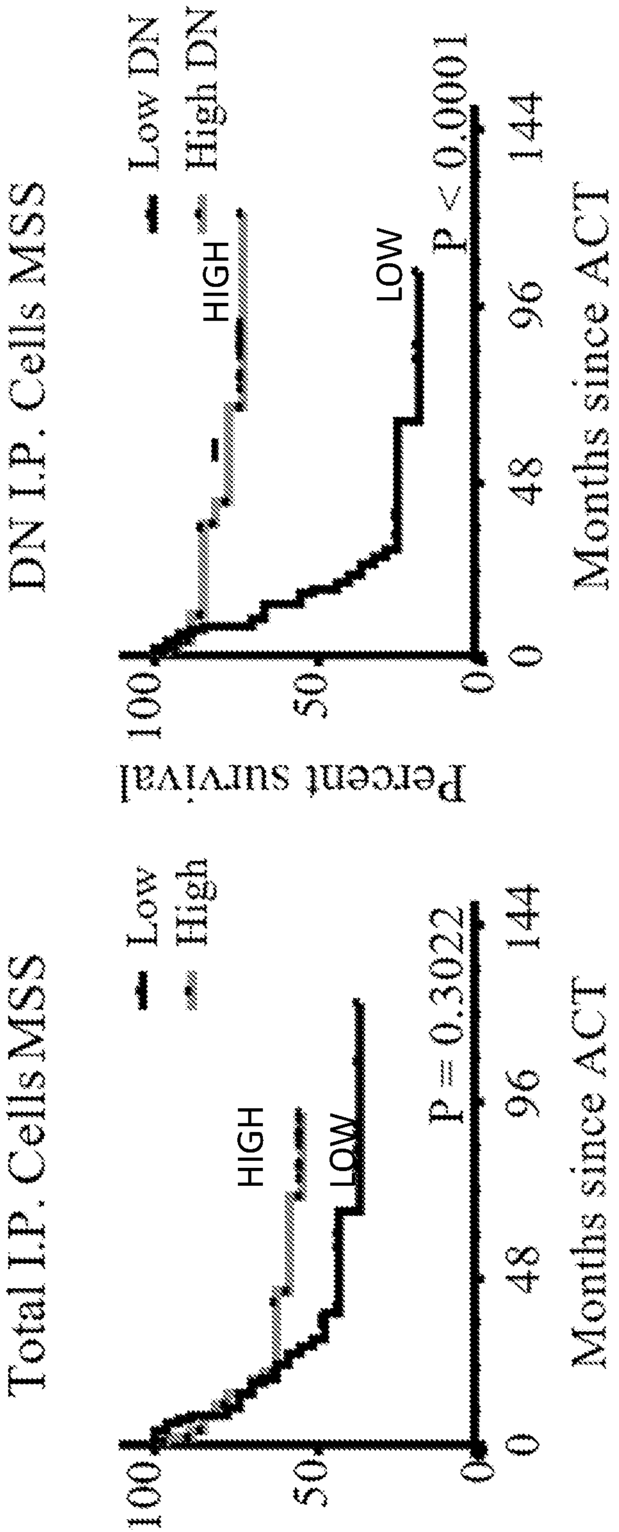

FIG. 1I shows melanoma-specific survival (MSS) of all I.P. samples (N=54) separated by median cell number infused (left) and median $CD39^-CD69^-$ cell number infused (right). "Low" indicates patients with I.P. cells less than median of the sub-group analyzed and "High" indicates patients with I.P in FIGS. 1H-1I. Cells greater than median of the sub-group were analyzed. P-values by the Log-rank Mantel-Cox test is shown in FIGS. 1H-1I.

Figure 2A:
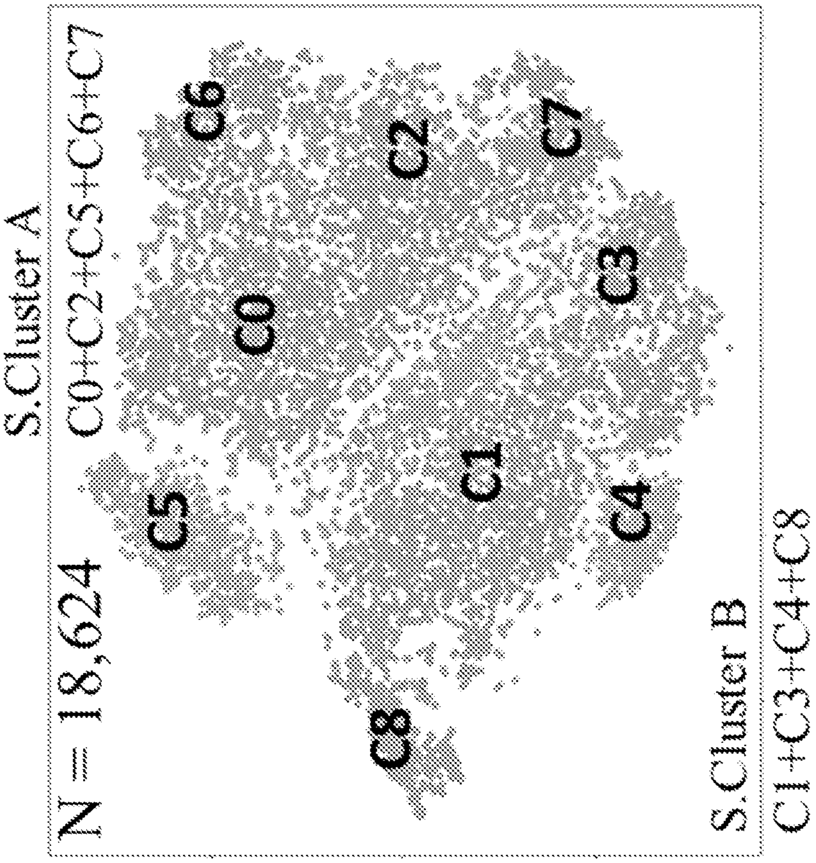

FIG. 2A is a t-SNE plot of all $CD8^+$ TILs from CR and NR I.P. (5 CRs, 5 NRs).

Figure 2B:
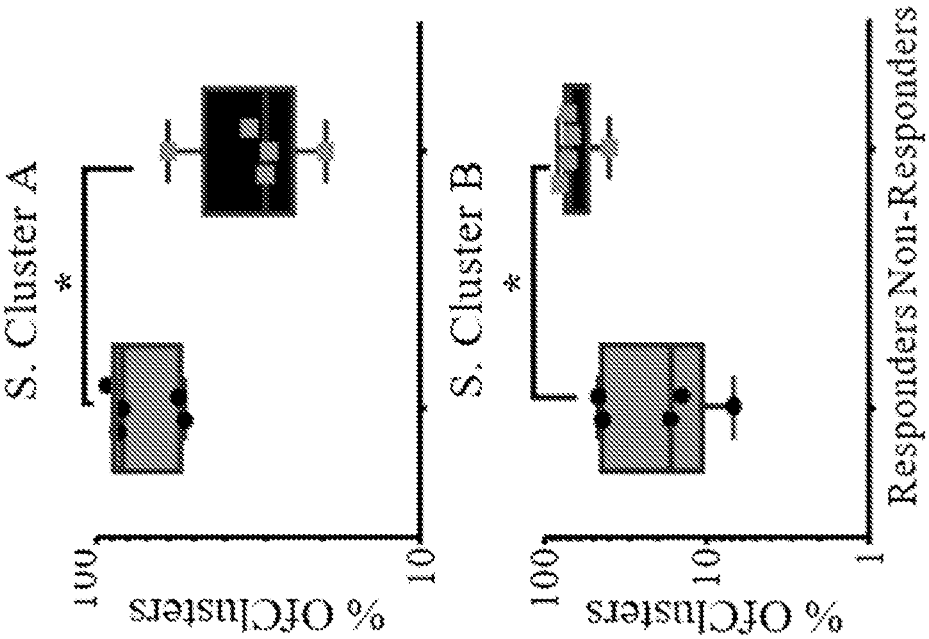

FIG. 2B is a box plot representing the percentage of S.Cluster.A (top) and S.Cluster.B (bottom) within CR and NR I.P. S.Cluster.A encompasses clusters C0, C2, C5, C6, and C7; S.Cluster.B comprises clusters C1, C3, C4, and C8. *P<0.05 by two-sided Wilcoxon rank-sum test are shown.

Figure 2C:
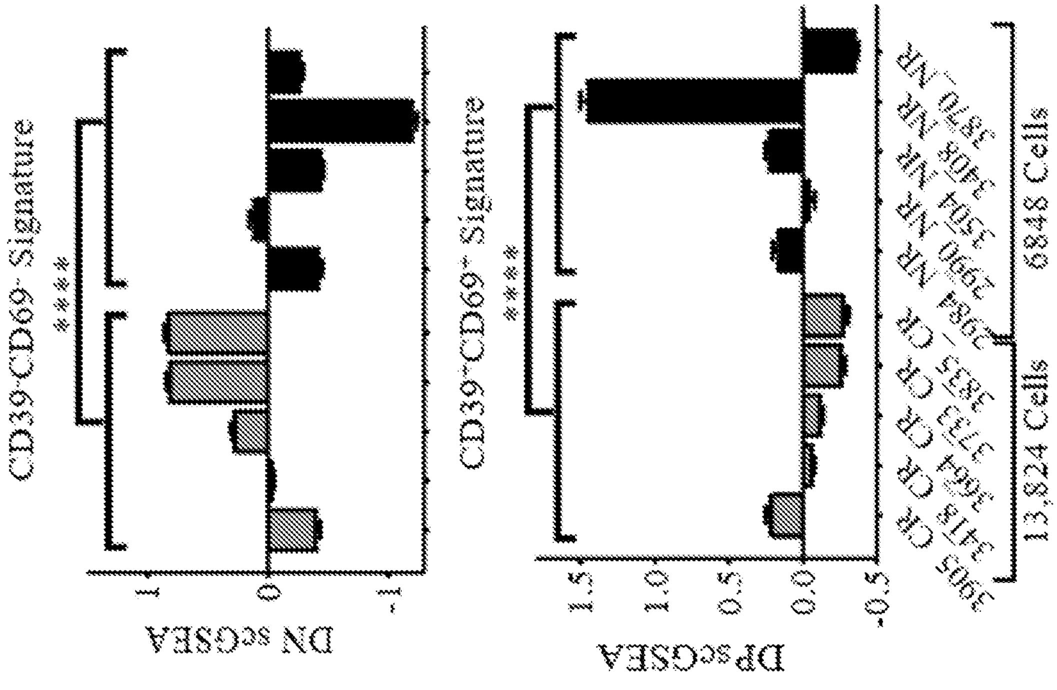

FIG. 2C is a bar graph showing the results of an analysis in which each patient I.P. was scored by DN and DP gene signature scores and their mean scGSEA scores are plotted on the y-axis. ****P<0.0001 by two-sided Wilcoxon rank-sum test comparing the mean DN and DP signature scores between CRs and NRs.

Figure 2D:
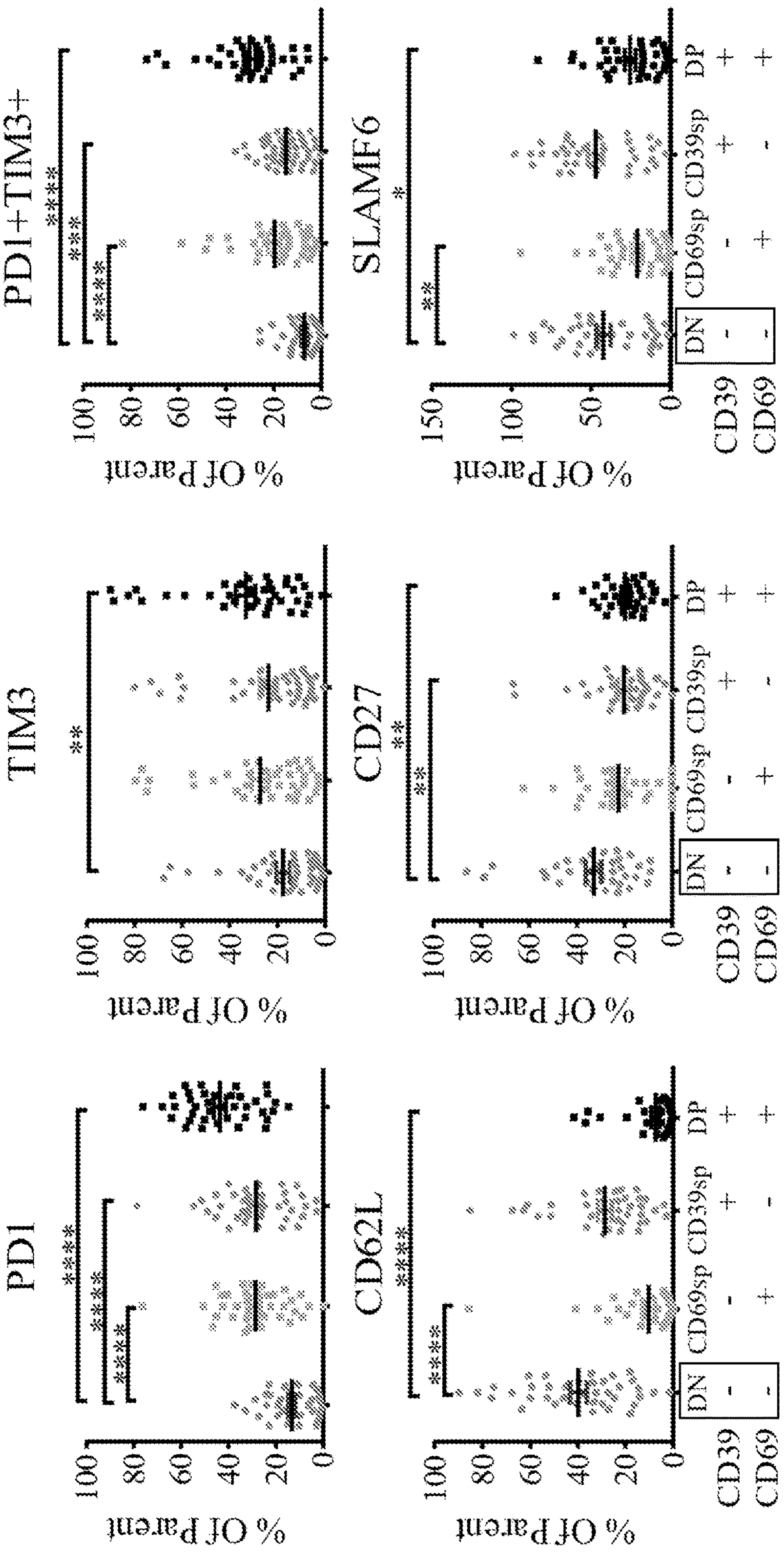

FIG. 2D shows scatter plots showing the results of a flow cytometric analysis of inhibitory and memory markers within each subset (DN [$CD39^-CD69^-$], SP [$CD39^-$ $CD69^+$, $CD39^+CD69^-$] and DP [$CD39^+CD69^+$] of patient I.P. in the validation set (n=38) expressed as % of each subset (parent gate). *P<0.05 P<0.01 *P<0.001 ****P<0.0001 comparing DN and other subsets by two-sided Wilcoxon rank-sum test corrected by Bonferroni multiple comparisons. Flow cytometric analysis shows low expression of T-cell exhaustion markers in $CD39^-CD9^-$ subsets.

Figure 2E:
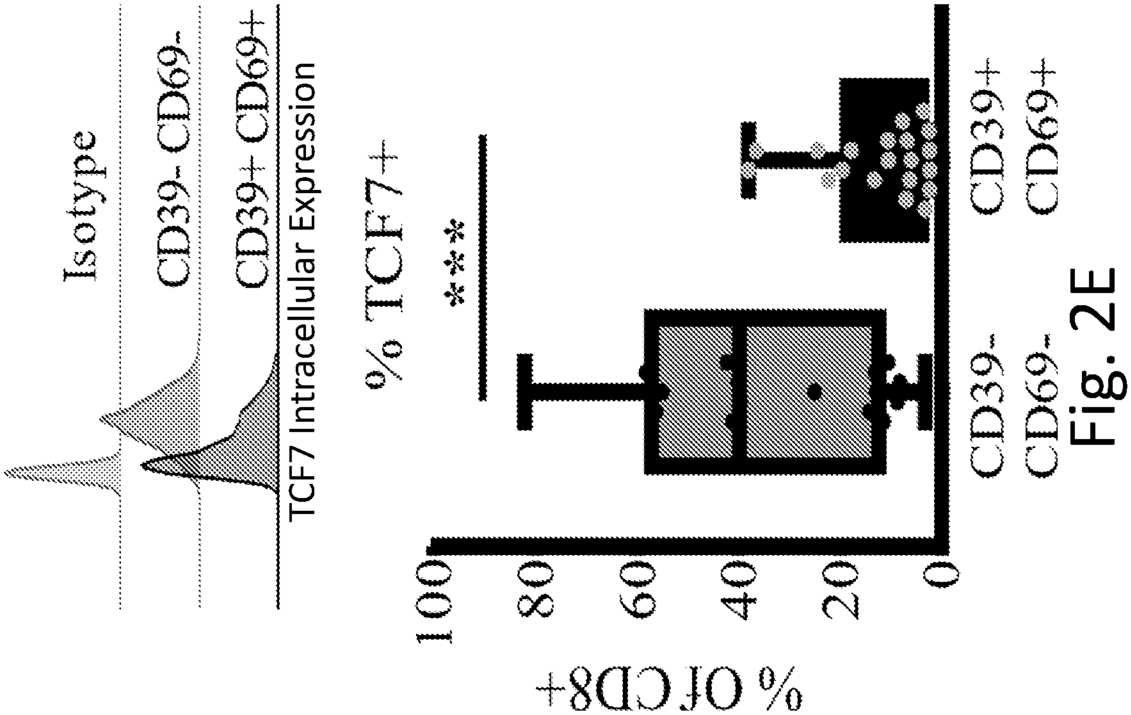

FIG. 2E is a graph showing the results of a flow cytometry analysis of intracellular TCF7 expression for DN and DP subsets. Histogram shows representative patient I.P. sample (top) and box plot shows the quantitation for 18 I.P. (bottom). ***P<0.001 by two-sided Wilcoxon rank-sum test. Flow cytometric analysis shows higher expression of T-cell stemness factor TCF7 in $CD39^-CD69^-$ subset.

Figure 2F:
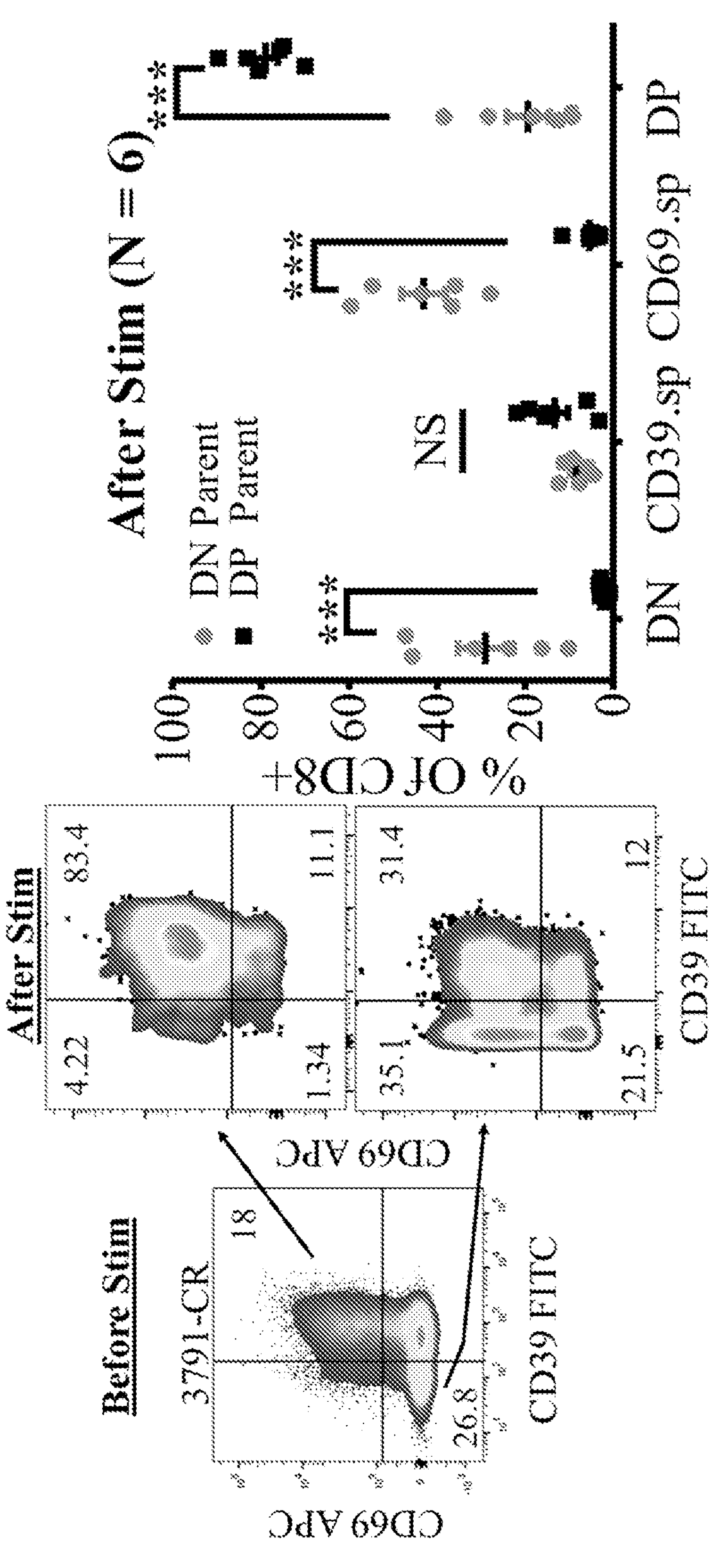

FIG. 2F shows flow cytometry plots showing the phenotypes of DN, SP, and DP states before and after anti-CD3/anti-CD28 stimulation for 48 hours of a representative patient sample (left), and dot plots quantifying phenotypes of daughter cells after stimulation of FACS-sorted DN parent (circles) or FACS-sorted DP parent (squares) ***P<0.001 by two-sided Wilcoxon rank-sum test, N=6 I.P.

Figure 2G:
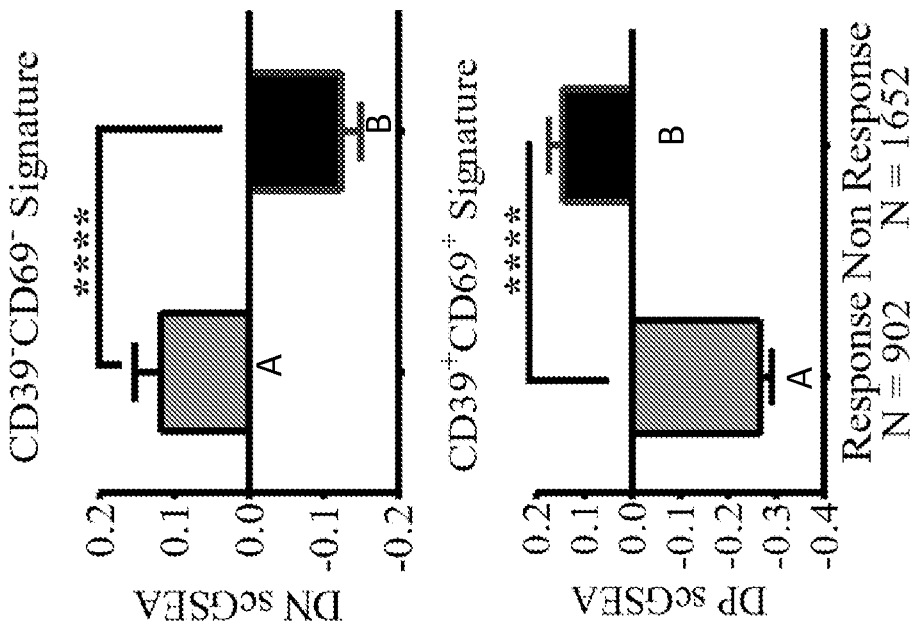

FIG. 2G shows graphs. TILs from pre ICB therapy were scored by the top DN and DP gene signature scores and mean scGSEA scores are plotted on y-axis. TILs from responding lesions are represented by A, and cells from progressing lesions are represented by B. Cell numbers and ****P<0.0001 by two-sided Wilcoxon rank-sum test are shown.

Figure 3A:
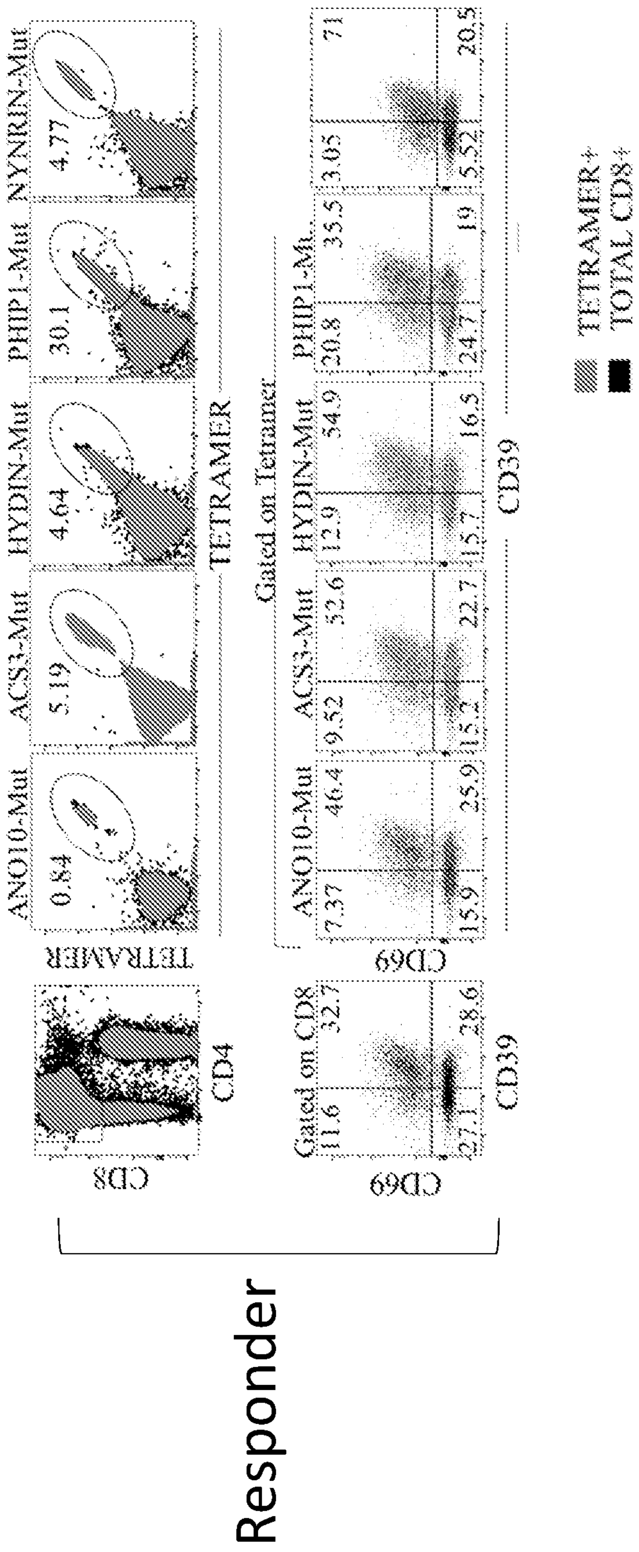

FIG. 3A shows representative CR I.P. showing detection of neoantigen-specific tetramers (top) and CD39/CD69 phenotypes of bulk CD8+ TILs and CD8+ TILs (bottom). Numbers within quadrants, listed under tetramer category represent percent of the sub-population within each $CD8^+$ $tetramer^+$ gate.

Figure 3B:
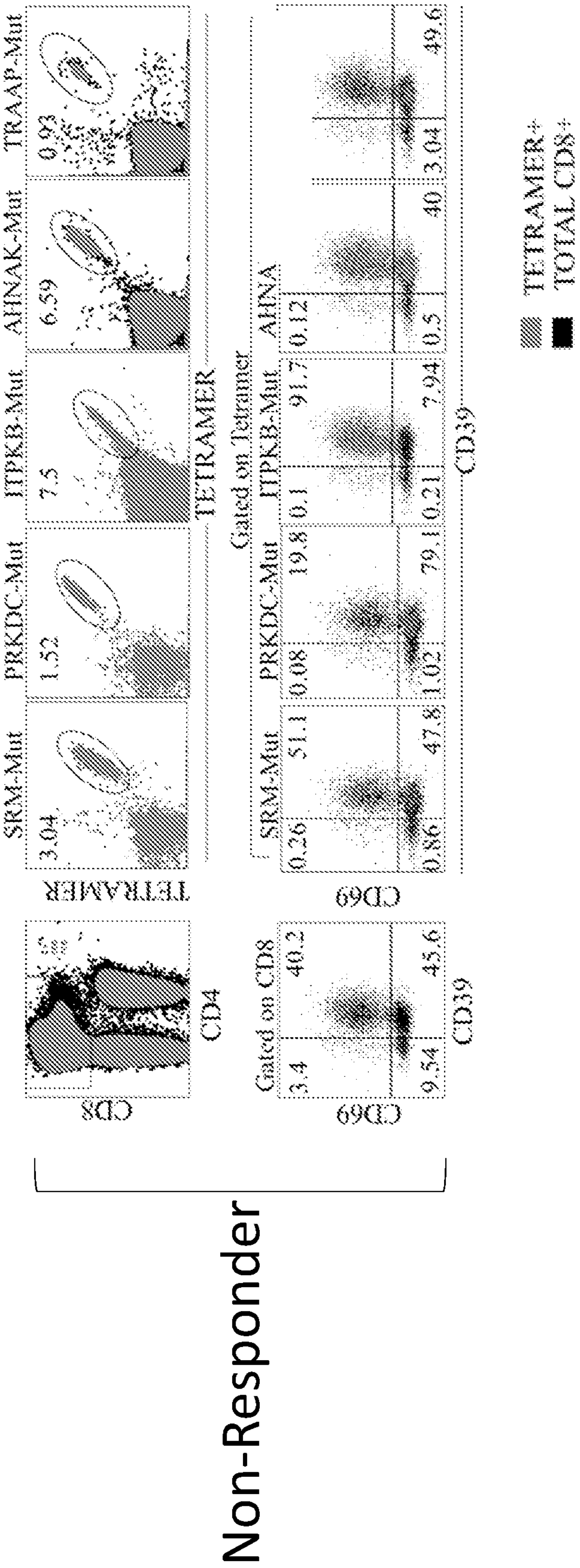

FIG. 3B shows NR I.P. with comparable number of neoantigens (top) and CD39/CD69 phenotypes of bulk $CD8^+$ TILs and $CD8^+$ $tetramer^+$ TILs (bottom). Numbers within quadrants, listed under tetramer category represent percent of the sub-population within each $CD8^+$ $tetramer^+$ gate.

Figure 3C:
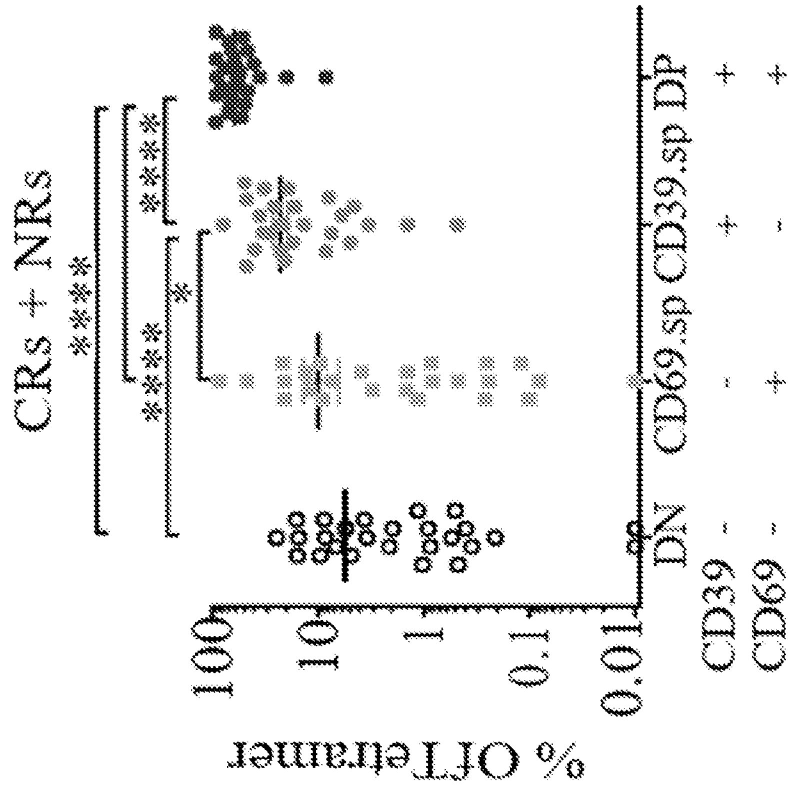

FIG. 3C shows DN, SP, and DP phenotypes within all 26 neoantigen-specific T cell populations expressed as a percent of $tetramer^+$ cells of each individual tetramer from 11 patients. CRs and NRs are combined for this data analysis (CRs+NRs). *P<0.05, ****P<0.0001 by two-sided Wilcoxon rank-sum test followed by Bonferroni correction for multiple comparisons.

Figure 3D:
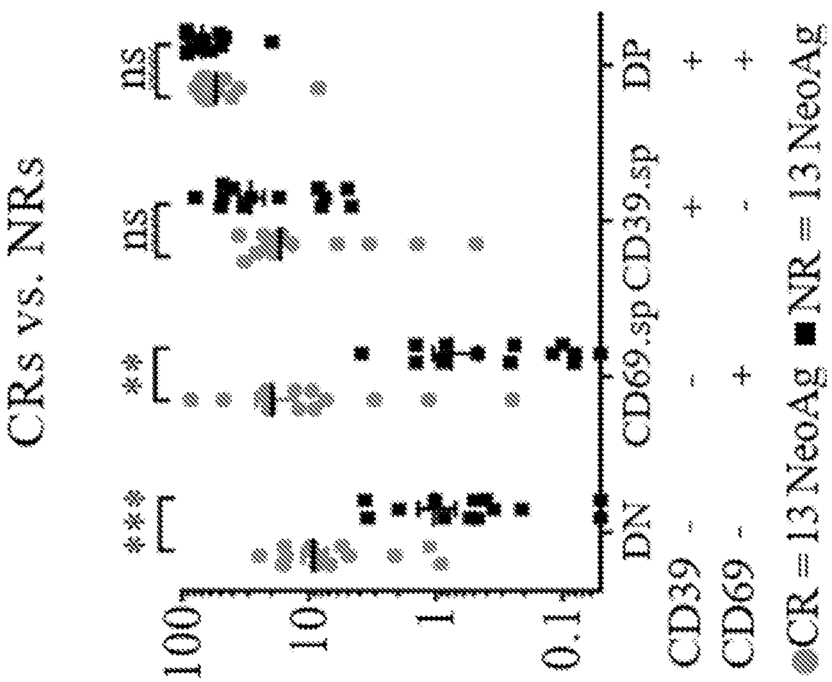

FIG. 3D is a graph showing DN, SP, and DP phenotypes of 26 neoantigen-specific TILs sub-divided by response status (CRs versus NRs). P<0.01, *P<0.001 by two-sided Wilcoxon rank-sum test between CRs and NR $tetramer^+$ cells for each subset.

Figure 3E:
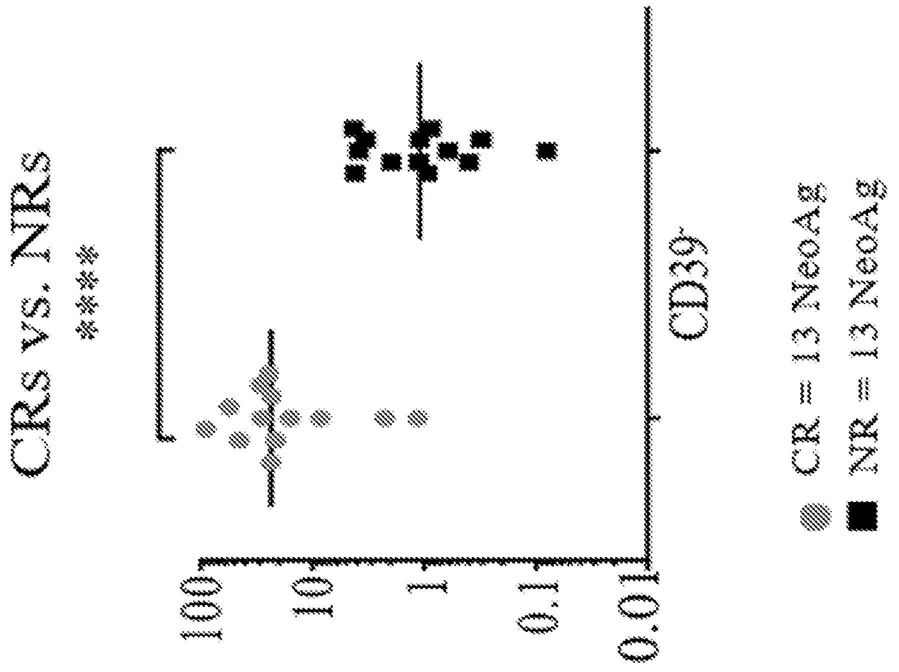

FIG. 3E is a graph showing $CD39^-$ negative neoantigen-specific $tetramer^+$ TILs ($CD39^-$ as a single marker) sub-divided by response status (CRs versus NRs). ****P<0.0001 by two-sided Wilcoxon rank-sum test.

Figure 3F:
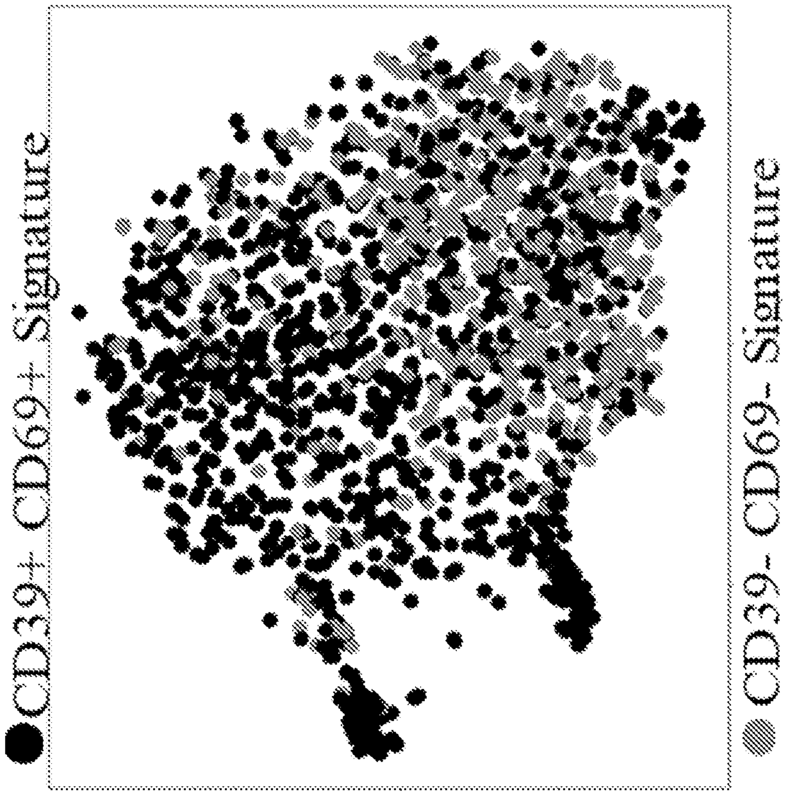

FIG. 3F is a t-SNE plot of $CD8^+$ TILs from 3713-CR I.P. showing projection of stem-like DN and differentiated DP gene signatures. Dotted lines indicate the stem-like and differentiated clusters analyzed.

Figure 3G:
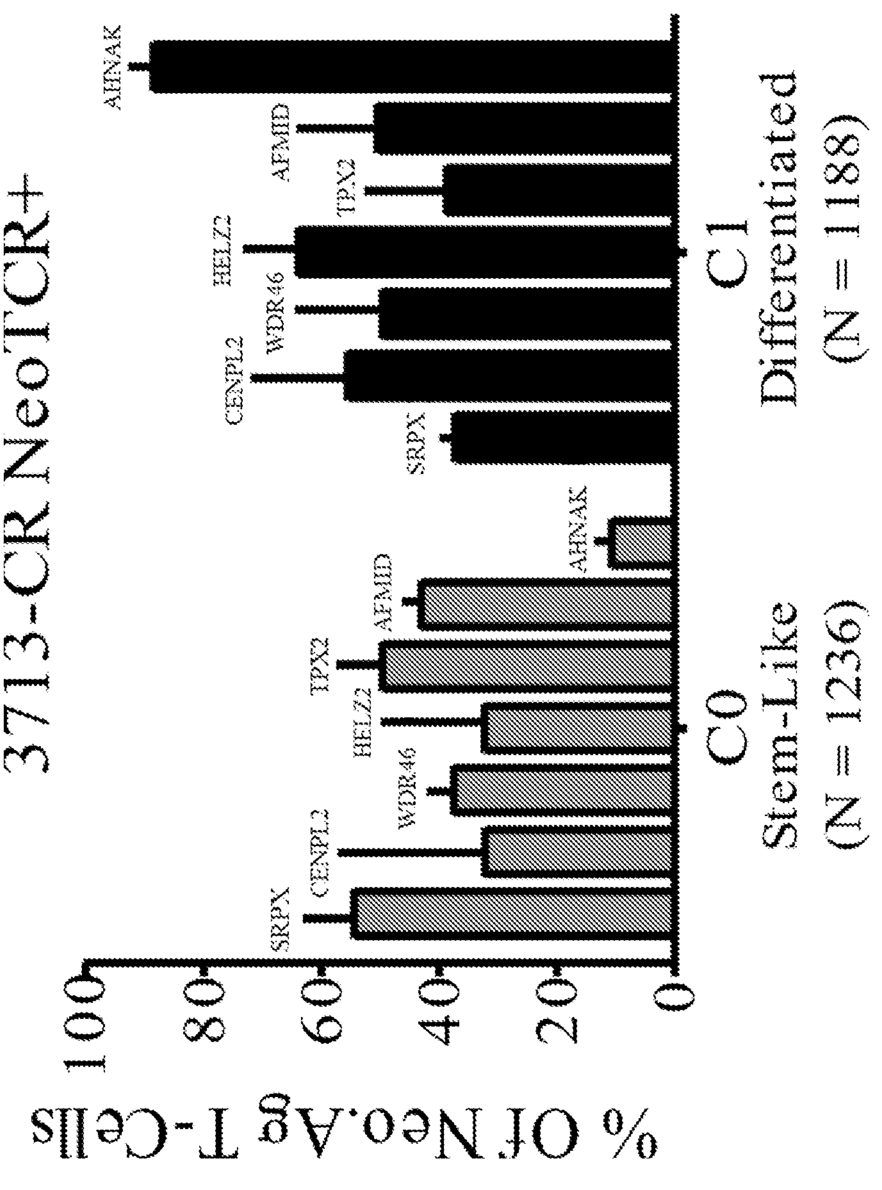

FIG. 3G is a graph showing Pt. 3713 $NeoTCR^+$ cells from stem-like C0 cluster and differentiated C1 cluster displayed as a percent of total $NeoTCR^+$ cells for each neoantigen specificity.

Figure 3H:
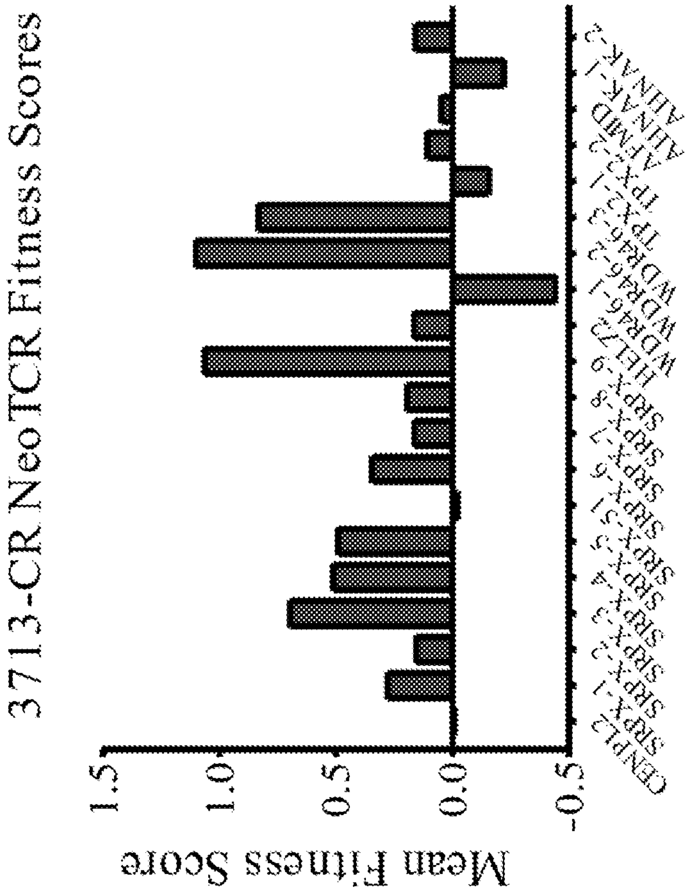

FIG. 3H is a graph showing each $NeoTCR^+$ clonotype scored by their mean fitness score (value of DN minus DP scGSEA scores). Positive values indicate clonotype enrichment in stem-like phenotypes and negative scores indicate clonotype enrichment in differentiated state.

Figure 3I:
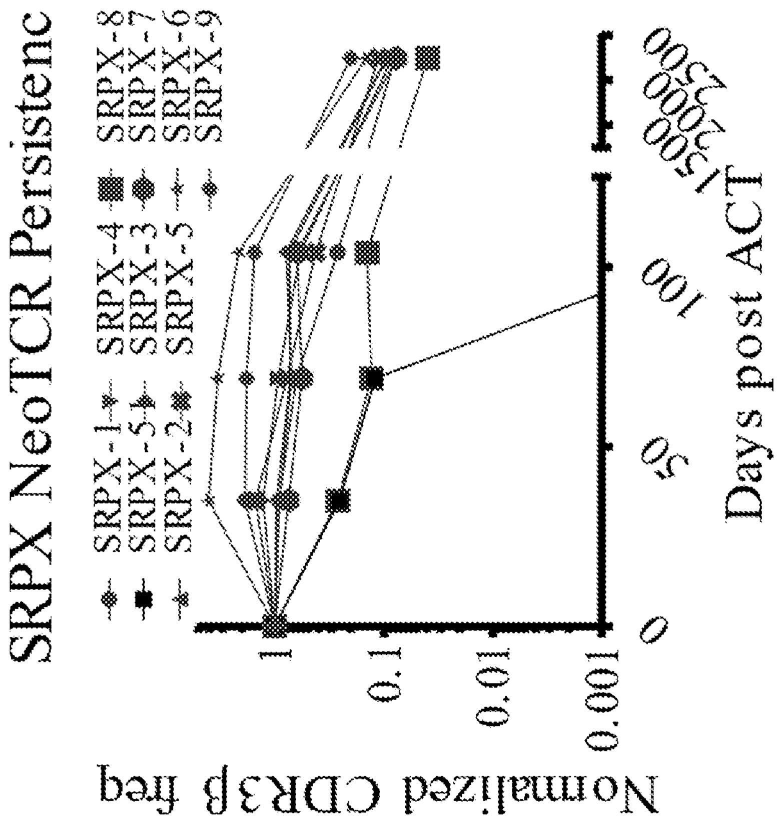

FIG. 3I is a graph showing post-ACT persistence of the immunodominant $SRPX_{mut}$ NeoTCR clonotypes from Pt. 3713-CR I.P. in peripheral blood normalized to their initial frequency in the infusion product (day 0).

Figure 3J:
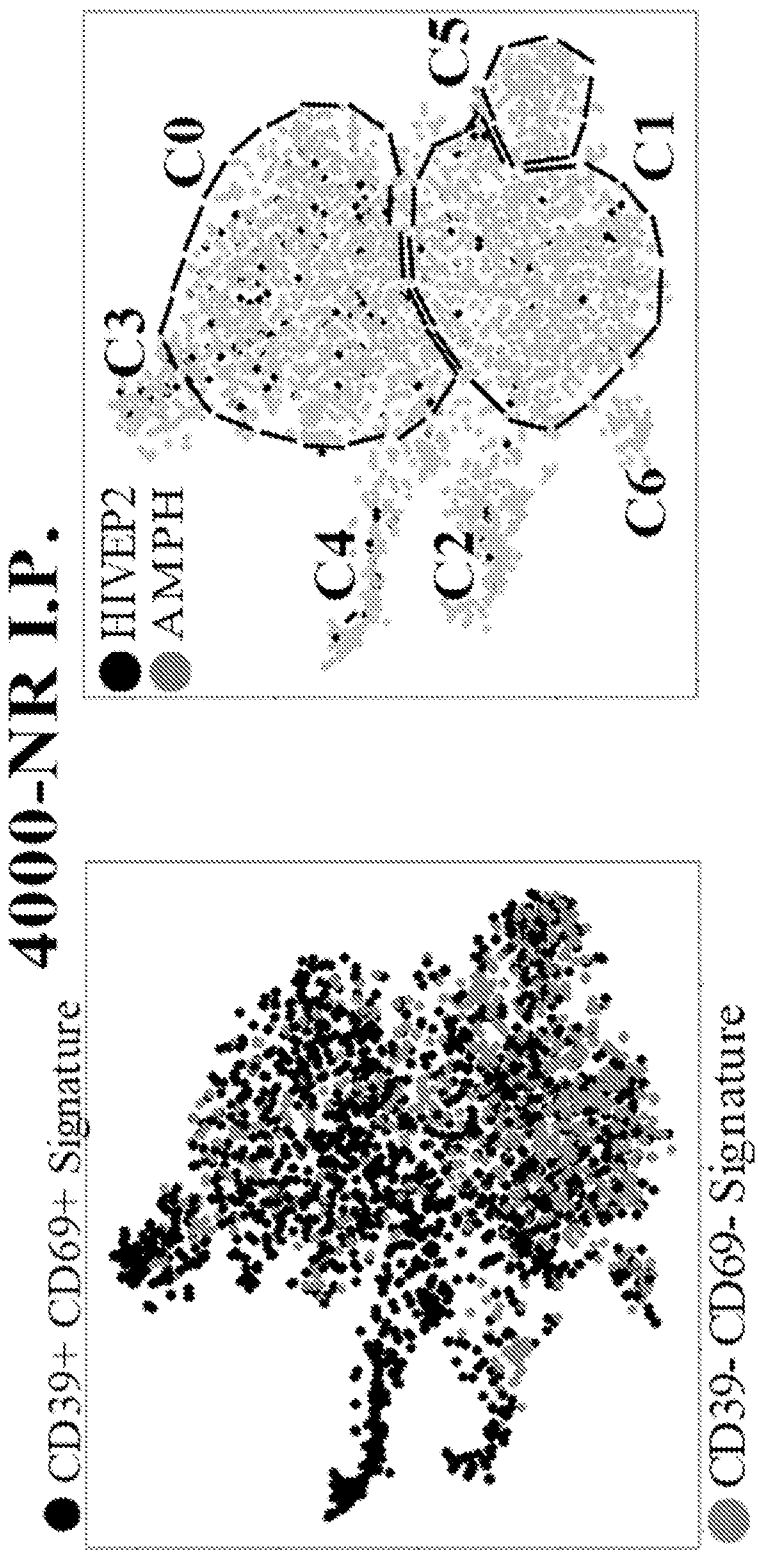

FIG. 3J is a t-SNE plot of $CD8^+$ TILs from Pt. 4000-NR I.P. showing projection of stem-like DN and differentiated DP gene signatures (left), projection of neoantigen-specific TCRs shaded by antigen specificity (right). Dotted lines indicate the stem-like and differentiated clusters analyzed.

Figure 3K:
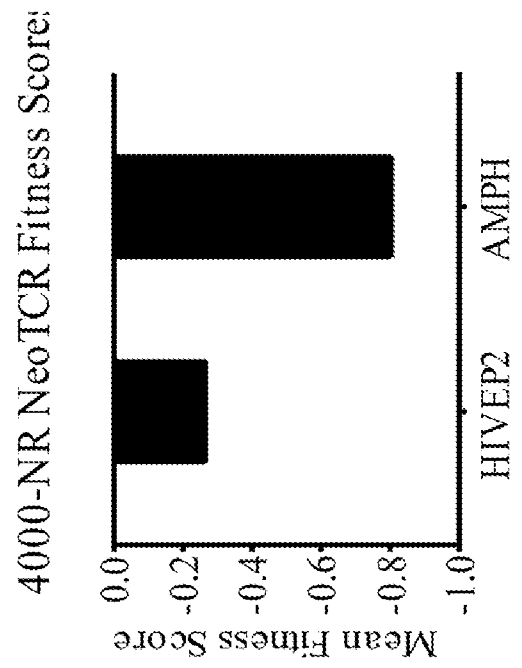

FIG. 3K is a graph showing each $NeoTCR^+$ clonotype ($HIVEP2_{mut}$, $AMPH_{mut}$) scored by their mean fitness scores as described for FIG. 3H.

Figure 3L:
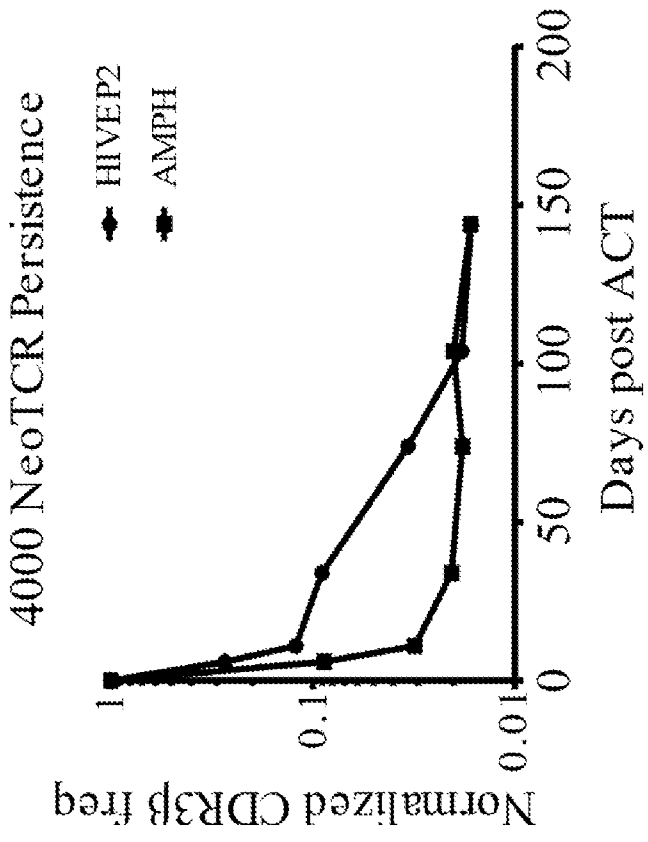

FIG. 3L is a graph showing post-ACT persistence of the $HIVEP2_{mut}$ and $AMPH_{mut}$ NeoTCR clonotypes from Pt. 4000-NR in peripheral blood normalized to their frequency in the infusion product. Patient follow-up was stopped at 150 days due to disease progression.

Figure 4A:
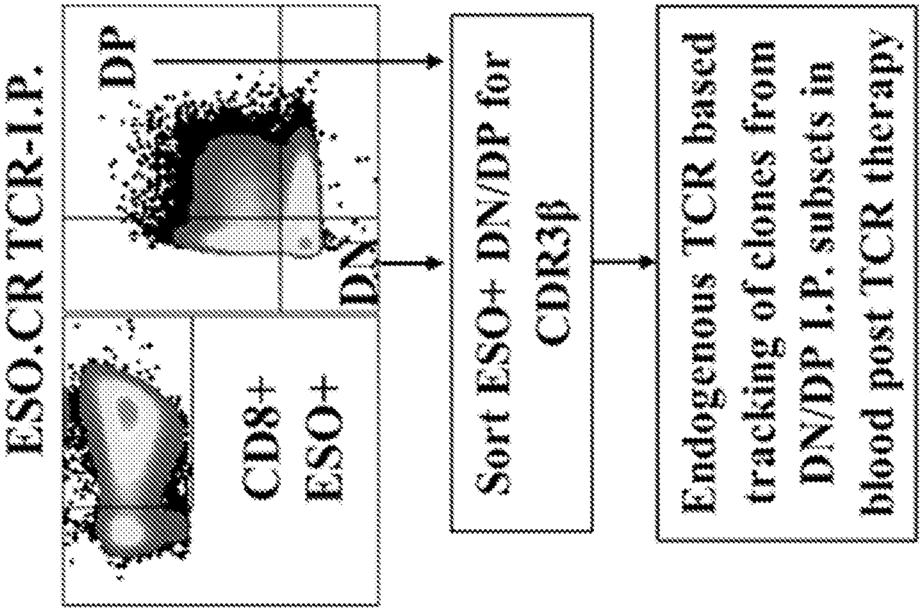

FIG. 4A is a schema for using endogenous human TCR to track NY-ESO-1 TCR-transduced ($ESO.TCR^+$) I.P. clones in post-treatment peripheral blood of a complete responder to NY-ESO-1 TCR therapy (ESO.CR).

Figure 4B:
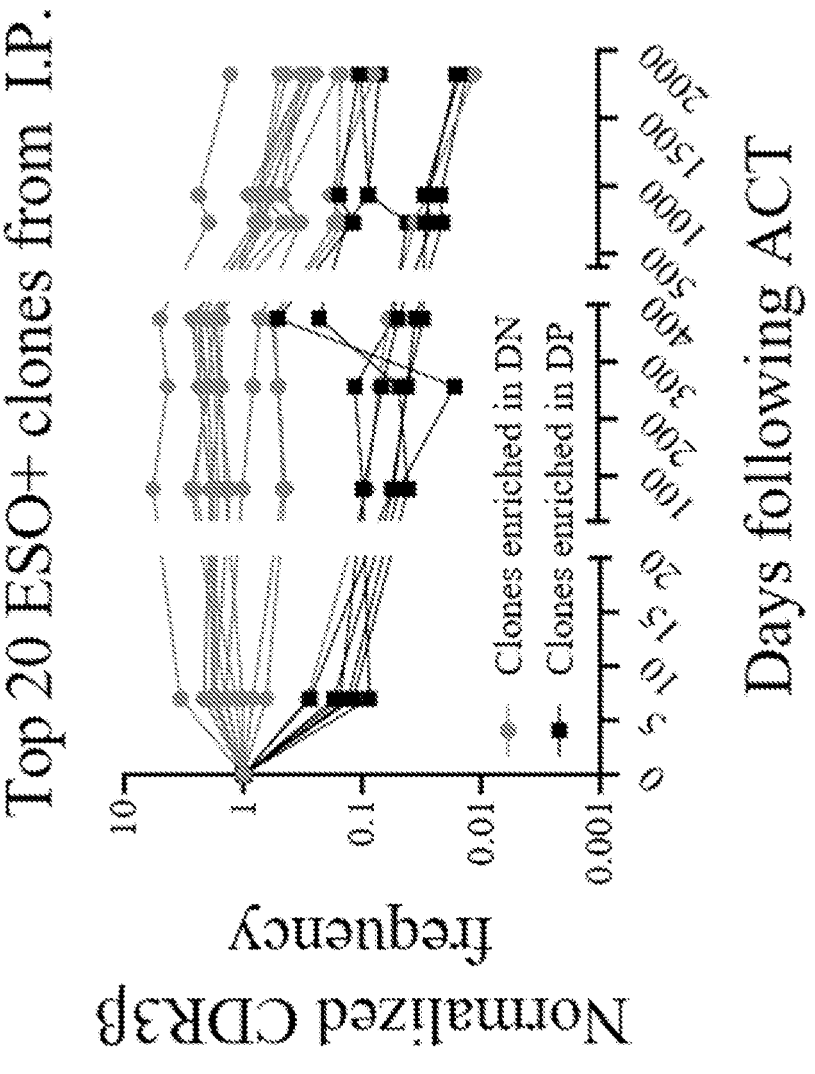

FIG. 4B is a graph showing post-treatment peripheral blood persistence of top 20 ESO.TCR+I.P. clones using endogenous human TCR according to enrichment in DN (circles) and DP (squares) phenotypes in TCR infusion product. Clones with (Frequency in DN/Frequency in DP)>1 are defined as enriched in DN state; clones with (Frequency in DN/Frequency in DP)<1 are defined as enriched in DP state.

Figure 4C:
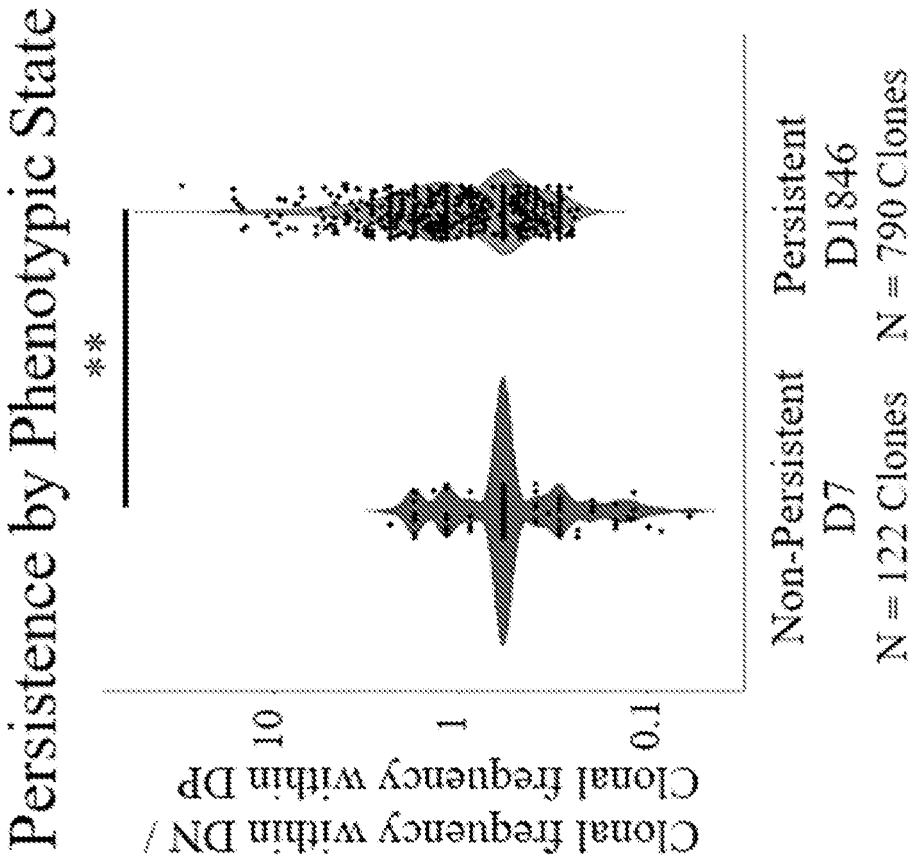

FIG. 4C is a violin plot comparing clones undetectable at day 7 post-ACT (Non-Persistent) with long-term persistent clones at day 1846 post-ACT by the ratio of their clonotypic frequency in the $CD39^-$ $CD69^-$ stem-like state to their clonotypic frequency within the $CD39^+CD69^+$ differentiated state in the I.P. A ratio>1 represents enrichment in the DN state while a ratio<1 represents enrichment in the DP state. **P<0.01 by two-sided Wilcoxon rank-sum test.

Figure 4D:
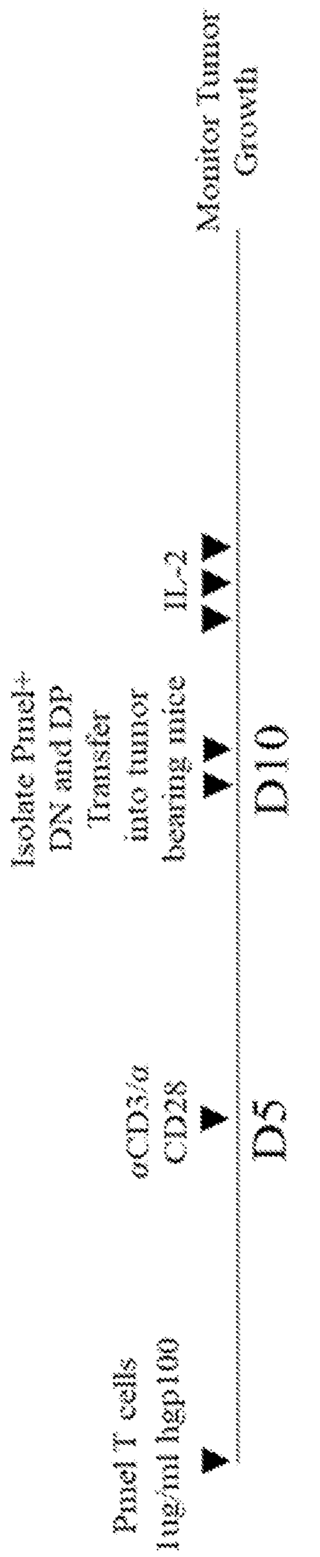

FIG. 4D is a schema of adoptive transfer of sorted DN and DP pmel-transgenic T cells into mice bearing established B16 melanoma tumors.

Figure 4E:
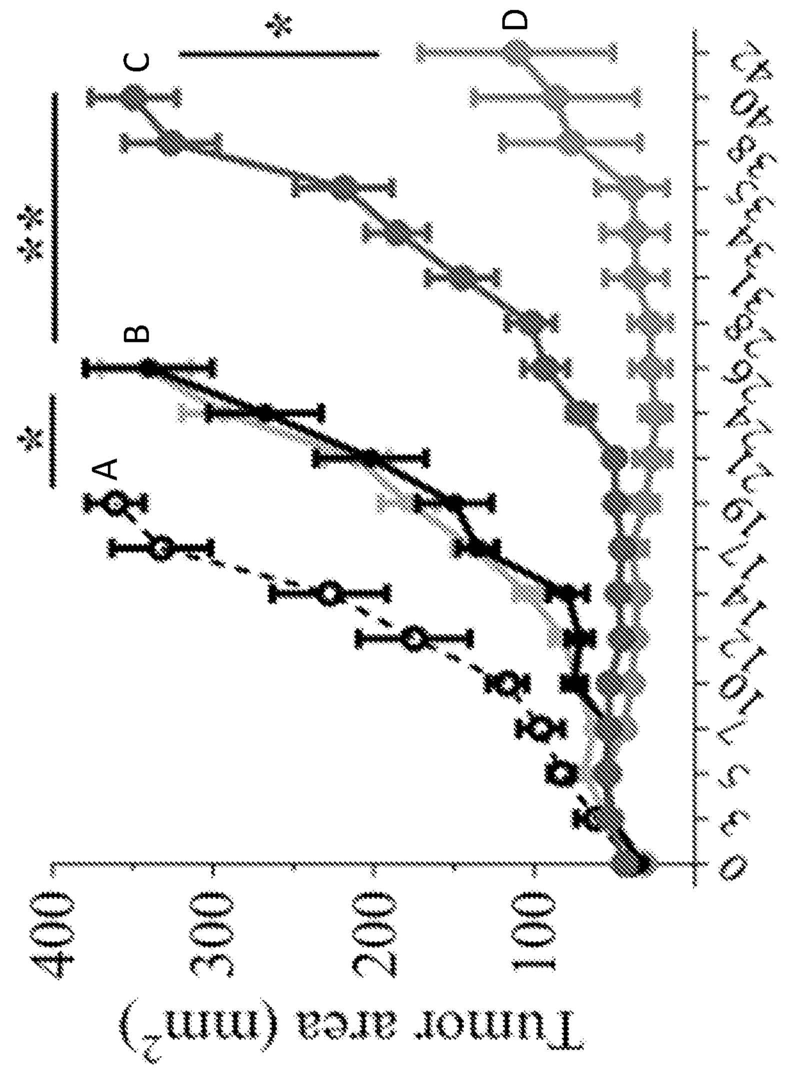

FIG. 4E is a graph showing tumor growth curves of mice bearing B16 tumors treated with pmel DN or DP T cells in two doses. N=6 mice per group. *P<0.05 **P<0.01 for tumor growth kinetics calculated by Wilcoxon rank-sum test. A represents untreated. B represents treatment with $CD39^+CD69^+$ (3e5, 5e5 dose). C represents treatment with $CD39^-CD69^-$ (3e5 dose). D represents treatment with $CD39^-CD69^-$ (5e5 dose).

Figure 4F:
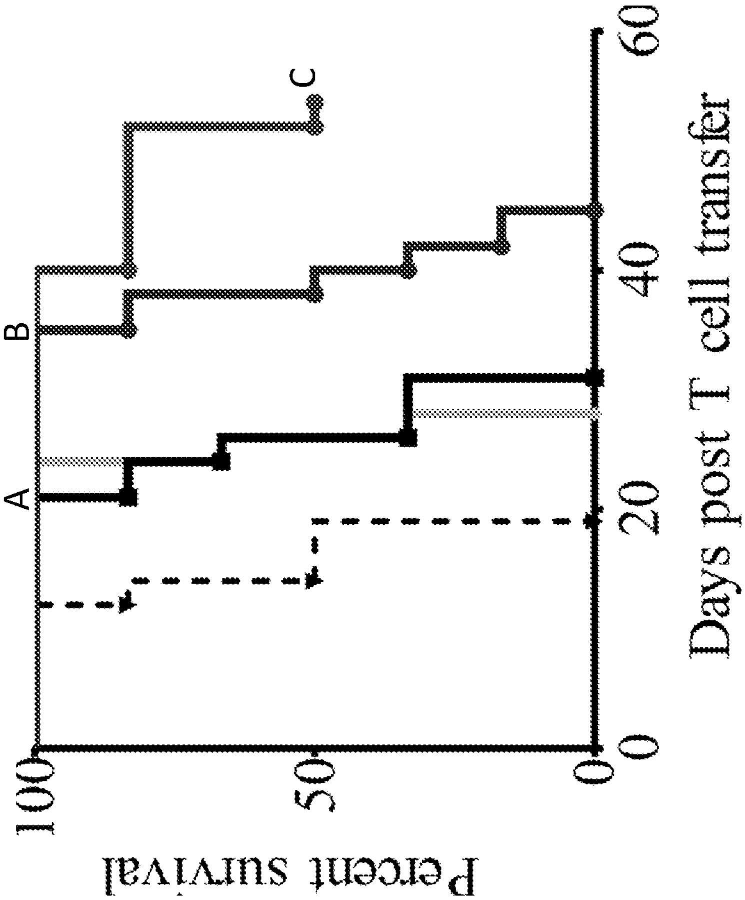

FIG. 4F is a graph showing survival curves of mice bearing B16 tumors treated with pmel DN or DP T cells in two doses. N=6 mice per group. *P<0.05 **P<0.01 for tumor growth kinetics calculated by Wilcoxon rank-sum test. The dotted line represents untreated. A (squares) represents treatment with $CD39^+CD69^+$ (3e5, 5e5 dose). B represents treatment with $CD39^-CD69^-$ (3e5 dose). C represents treatment with $CD39^-CD69^-$ (5e5 dose).

Figure 4G:
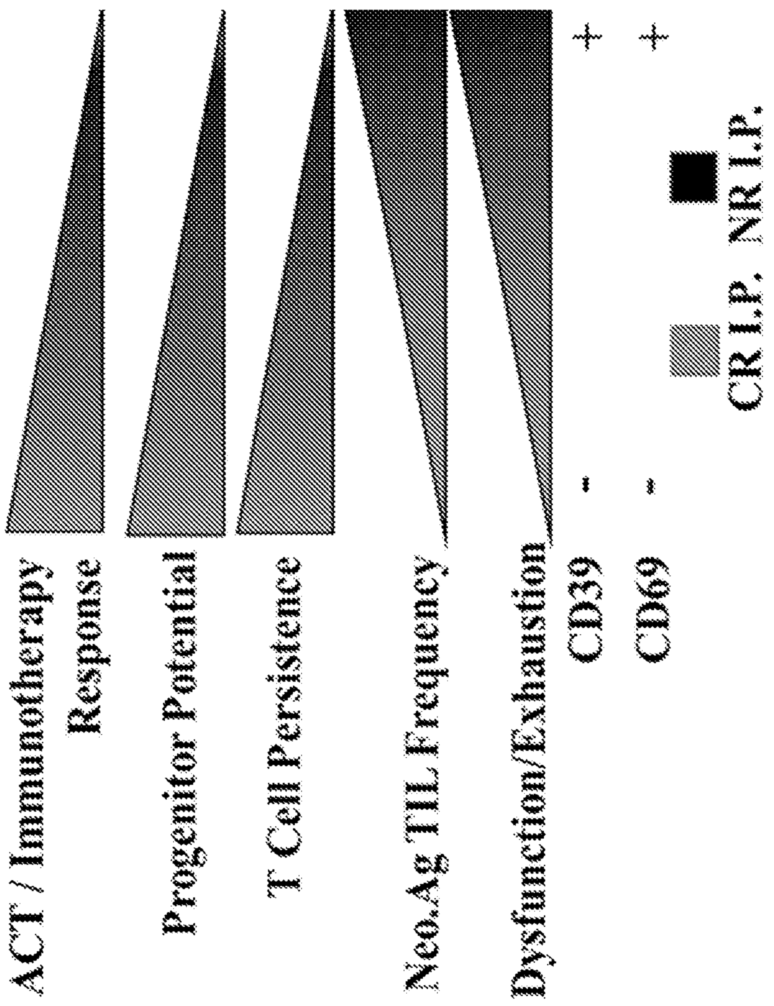

FIG. 4G is an illustration of the role of stem-like T cells in immunotherapy and ACT success and paradoxical nature of tumor mutation-reactive T cells in stem-like and terminally differentiated states.

Figure 5A:
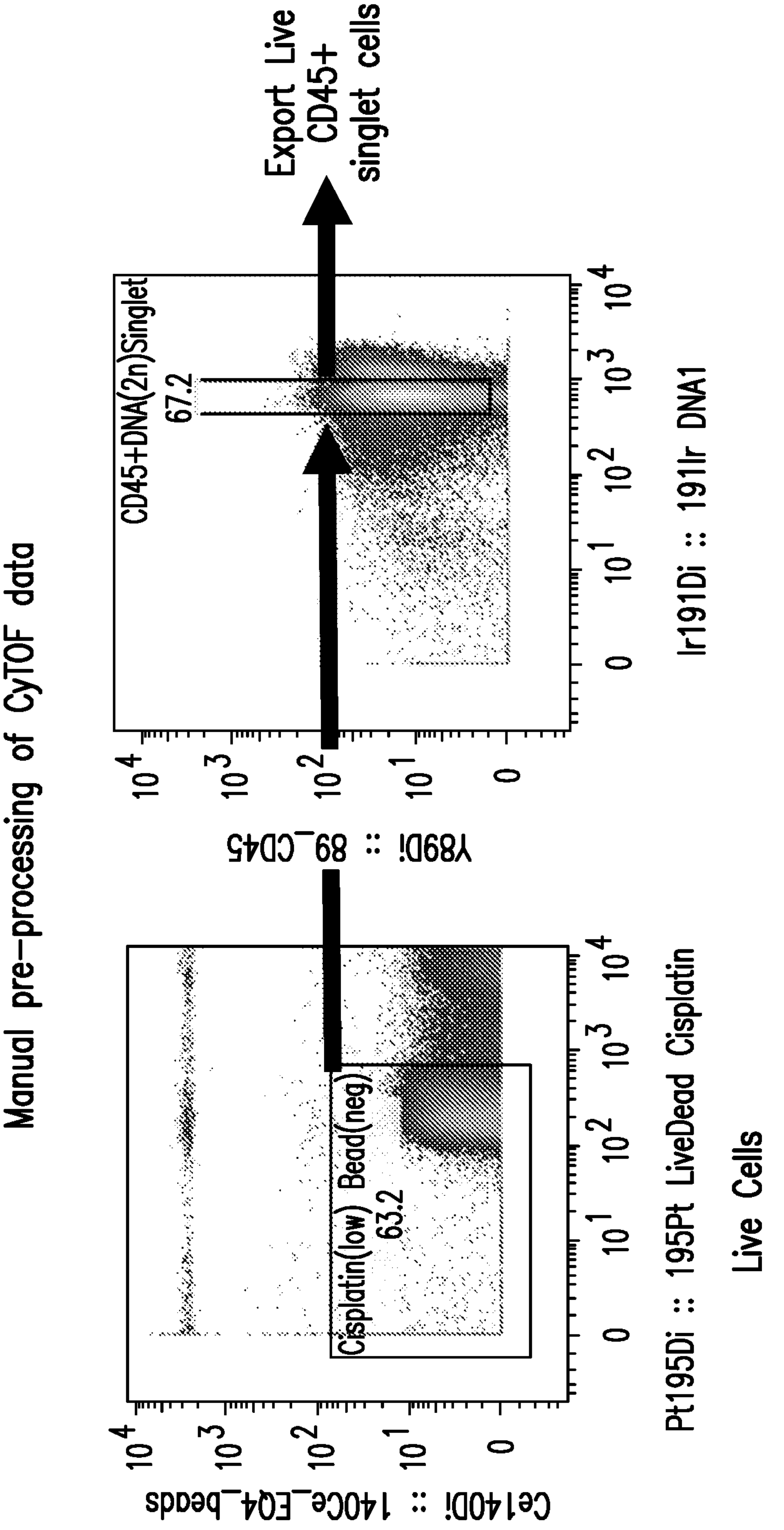

FIG. 5A shows manual gating of CyTOF data for t-SNE projection of CyTOF data (left: live-cell gate; right: $CD45^+$ DNA(2n) Singlet gate).

Figure 5B:
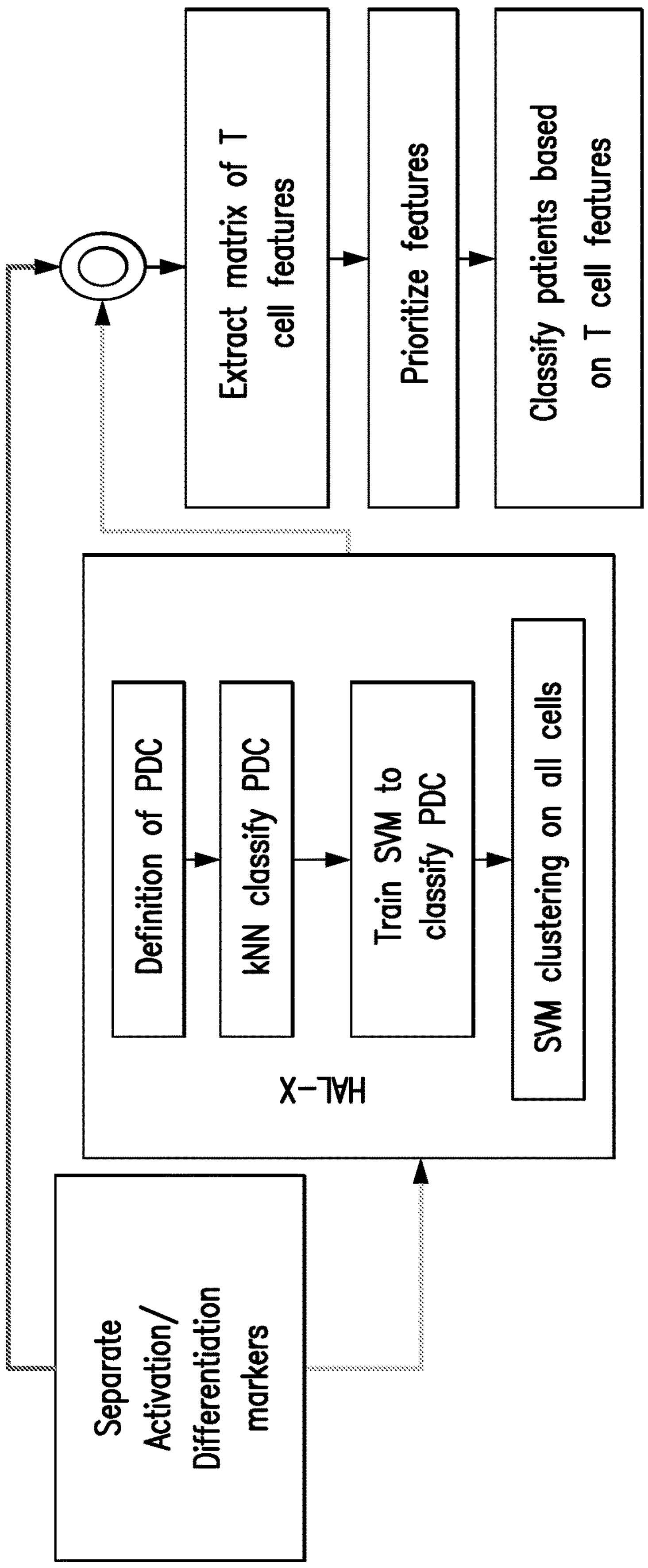

FIG. 5B is a schematic illustrating a data processing pipeline for CyTOF data: activation/exhaustion markers (CTLA-4, PD-1, CD28, LAG3, OX40, CD25, FAS, 4-1BB, HLA-DR, CD39, CD69, ICOS) were distinguished from differentiation markers (e.g. CD2, CD3, CD4, CD8 etc.) to process the data. A hierarchical agglomerative learning algorithm (HAL-X) built upon a k-nearest neighbor (kNN) classification trained on expression of differentiation markers only "pure differentiation cluster" (PDC) was used to classify cells into 22 clusters. The expression levels of activation/exhaustion markers were then measured on these 22 clusters to generate a matrix of features. Features with high discriminatory power are chosen to build a classifier of patients based on their clinical response (CR: complete response; NR: progressive disease).

Figure 5C:
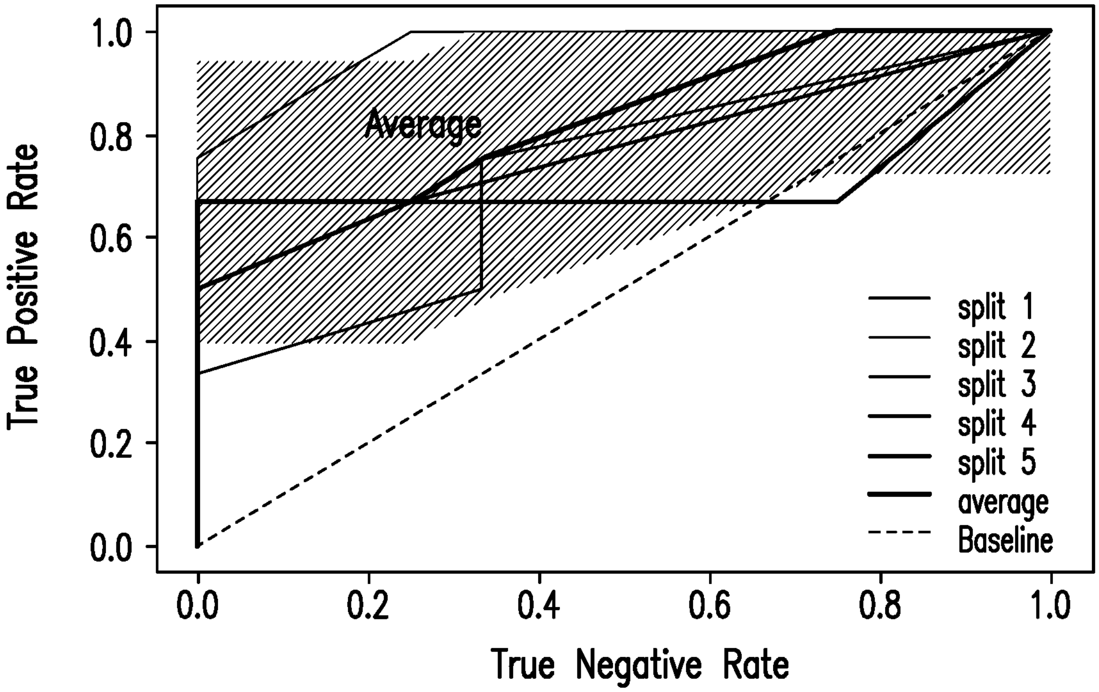

FIG. 5C shows a Receiver Operating characteristic (ROC) for the classification of patients based on activation/exhaustion markers: Area Under the Curve (AUC) is larger than 89% for the 17 patients under analysis. Five iterations ("split") are presented here corresponding to the 80%/20% split of patients' samples into random train and test subsets; "average" represents the average ROC across the five splits; "baseline" represents the ROC for a random classification.

Figure 6A:
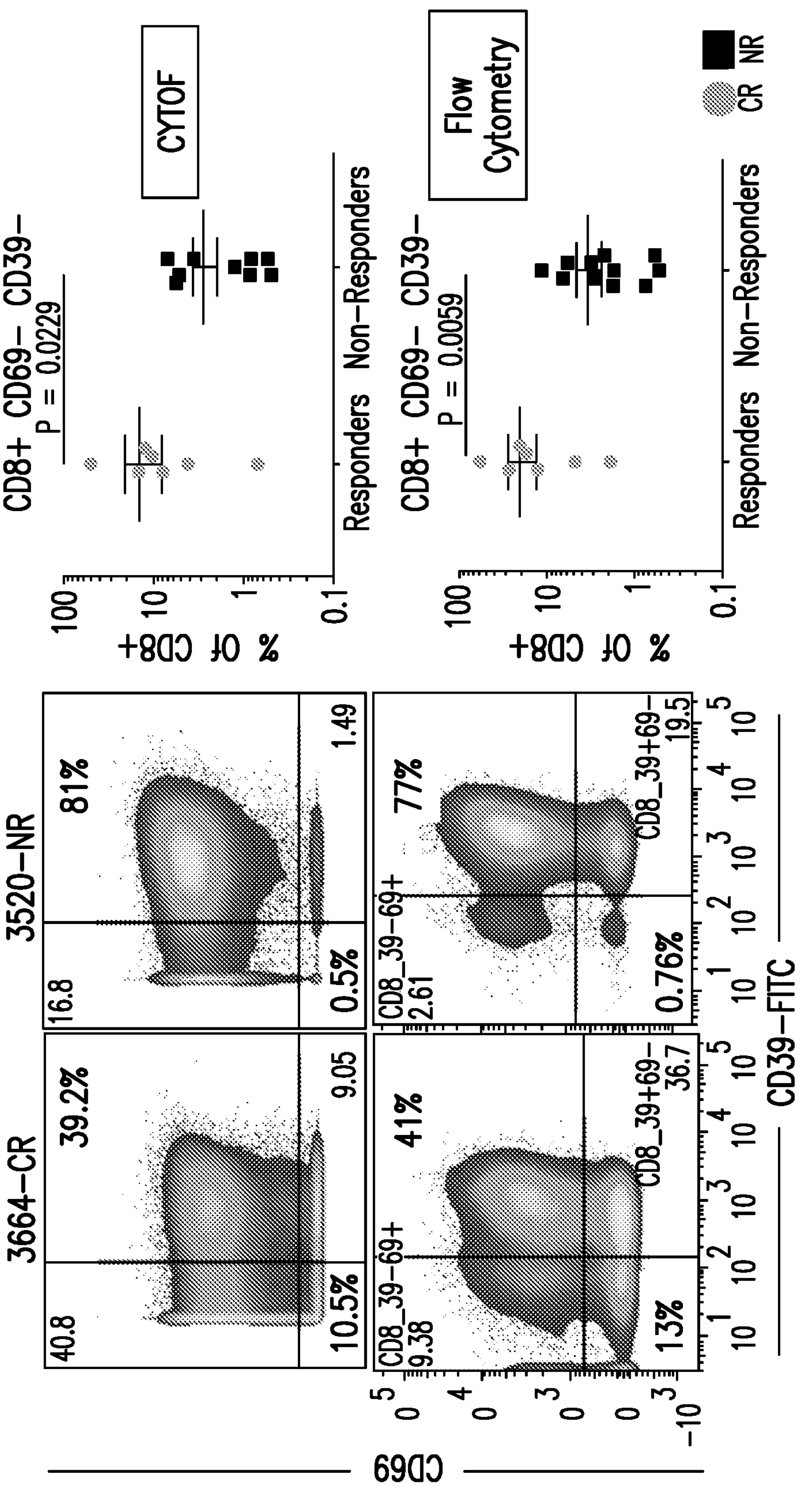

FIG. 6A shows CD39 and CD69 expression dot plots gated on CD8+ T cells from one representative CR and NR I.P. (left panel) and quantification of 16 I.P. (right panel) in the discovery set. Top row represents CyTOF data of the two patients and bottom row represents flow cytometry analysis of the same patients. Numbers indicate p-values by two-sided Wilcoxon rank-sum test.

Figure 6B:
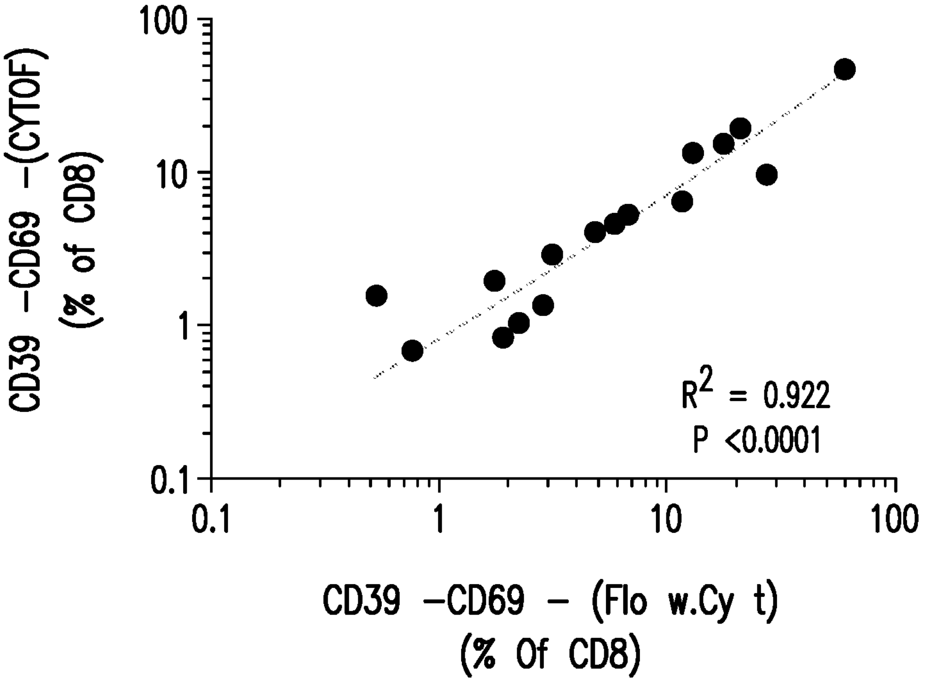

FIG. 6B shows linear regression between flow cytometry and CyTOF analysis of 16 I.P. samples analyzed for $CD39^{-}CD69^{-}$ subset.

Figure 6C:
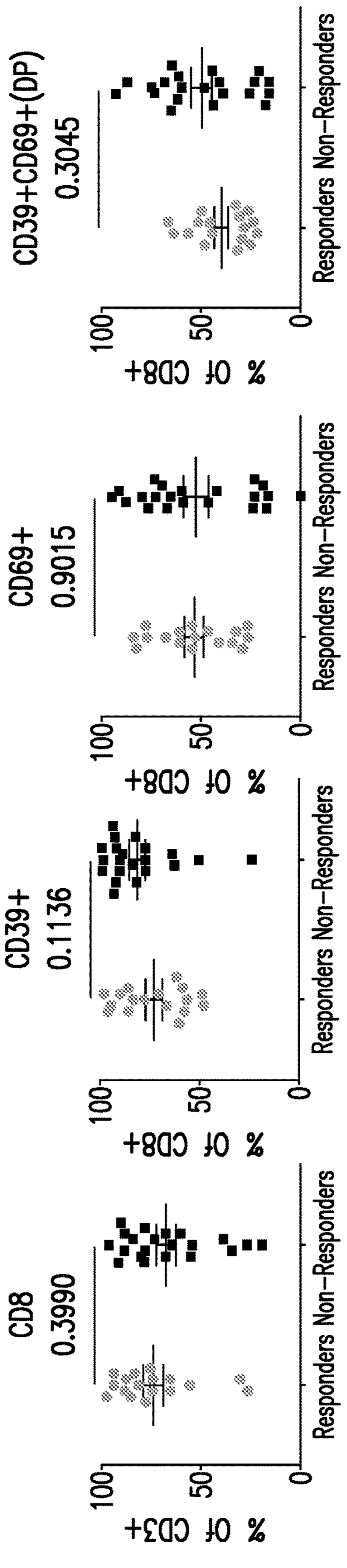
Figure 6C:
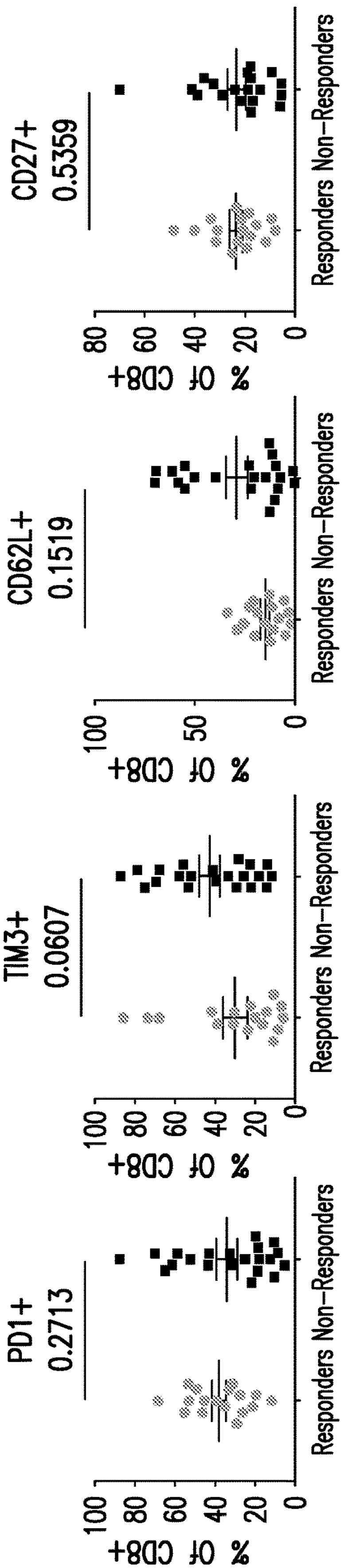
Figure 6C:
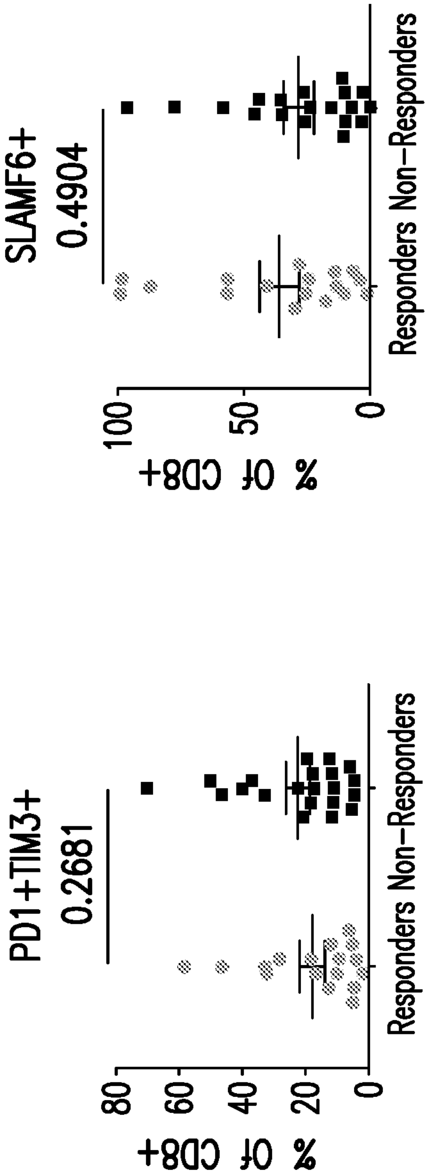

FIG. 6C shows expression profiles of various subsets in 38 validation I.P. compared between responders and non-responders. Numbers indicate p-values by two-sided Wilcoxon rank-sum test analyzed individually without multiple corrections.

Figure 7A:
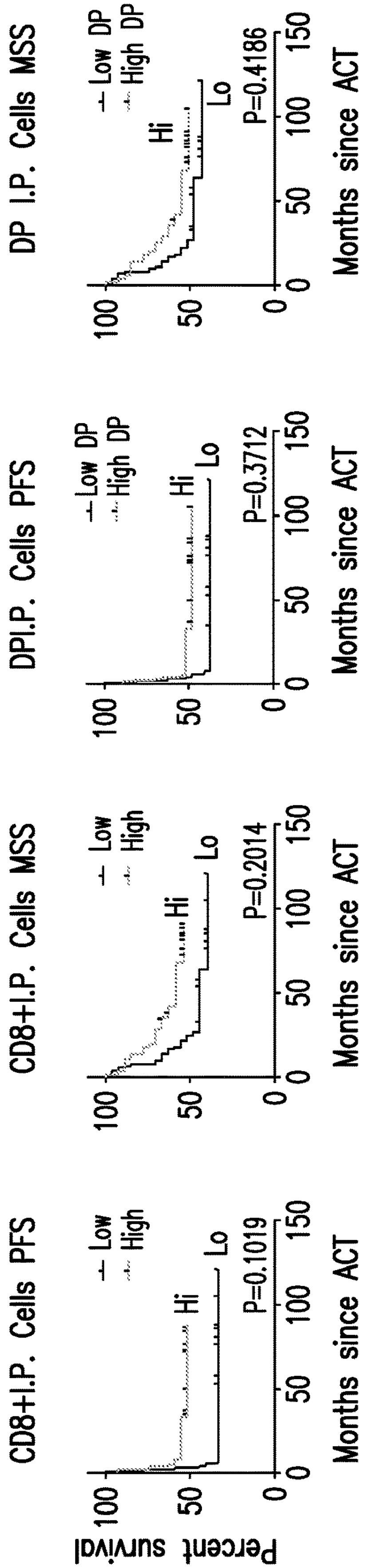
Figure 7B:
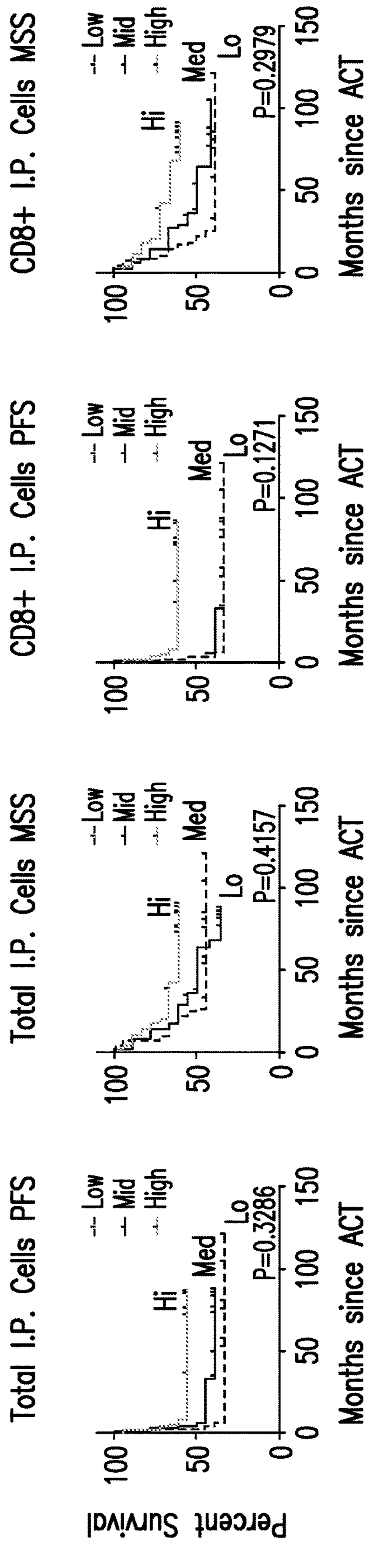
Figure 7C:
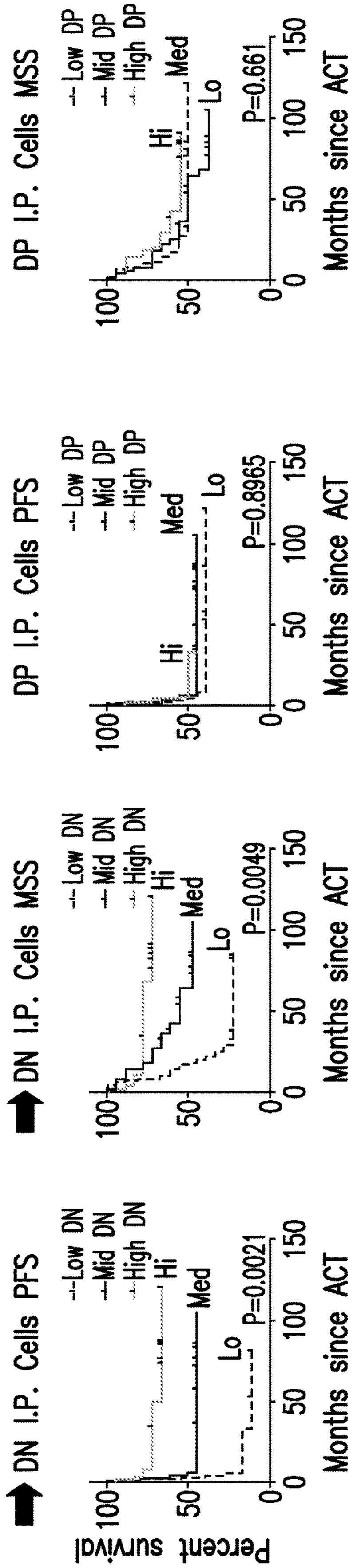

FIG. 7A-7C shows graphs showing progression-free survival and melanoma-specific survival according to cell numbers of TIL subpopulations received in infusion products. 7A: PFS and MSS of I.P. cells infused divided at median by $CD8^{+}$ cell numbers and $CD39^{+}CD69^{+}$ (DP) cell numbers received into high and low. 7B: lack of dose dependence of patient response on total cell numbers and $CD8^{+}$ cell numbers in I.P. shown by tertiles indicating Low (dashed), Middle and High tertiles of cells. 7C: dose dependence of patient response on $CD39^{-}CD69^{-}$ (DN) cell numbers and lack of dose dependence on $CD39^{+}CD69^{+}$ (DP) cell numbers in I.P. shown by tertiles indicating Low (dashed), Middle and High tertiles of cells. Arrows indicate the statistically significant tertile analyses from DN cell infused. Numbers in all plots indicate p-values by Mantel-Cox log-rank test.

Figure 8A:
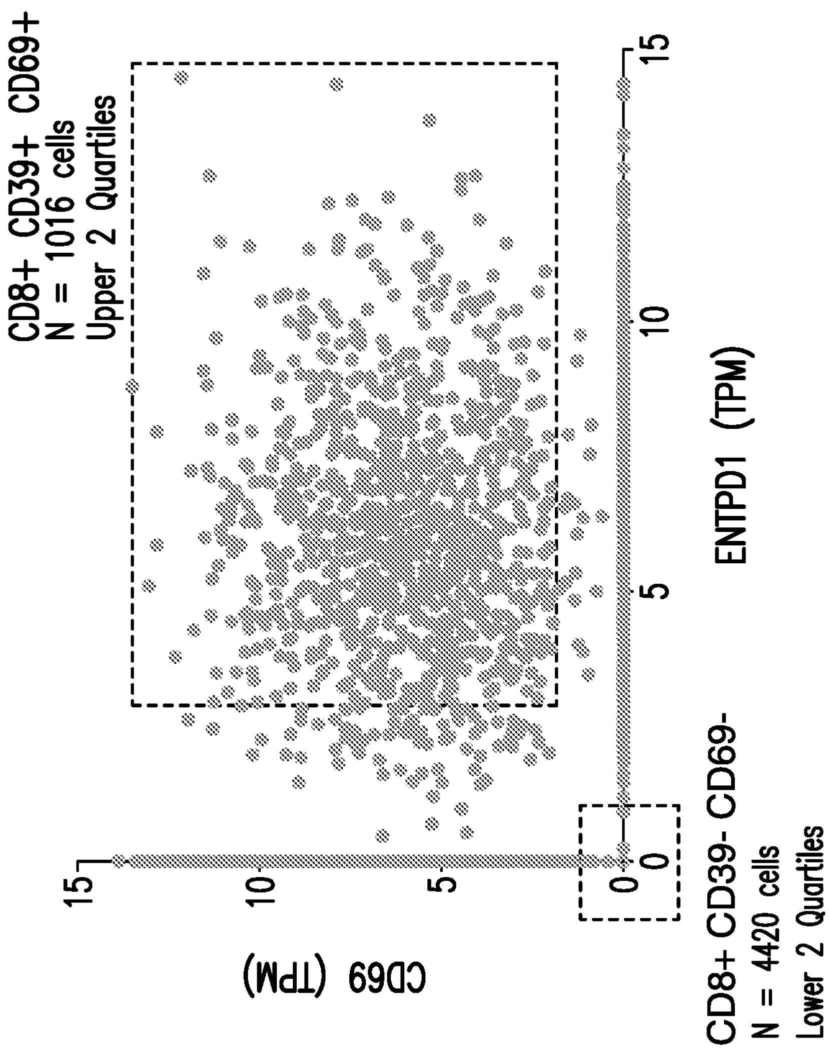

FIG. 8A shows the CD39/CD69 transcriptome analysis on 9335 single cells (circles) from 4 I.P. (2 CRs, 2 NRs) defined 4420 $CD39^{-}CD69^{-}$ cells (cells with bottom two quartiles of CD39 and CD69 co-expression) and $CD39^{+}CD69^{+}$ cells (cells co-expressing top two quartiles of CD39 and CD69).

Figure 8B:
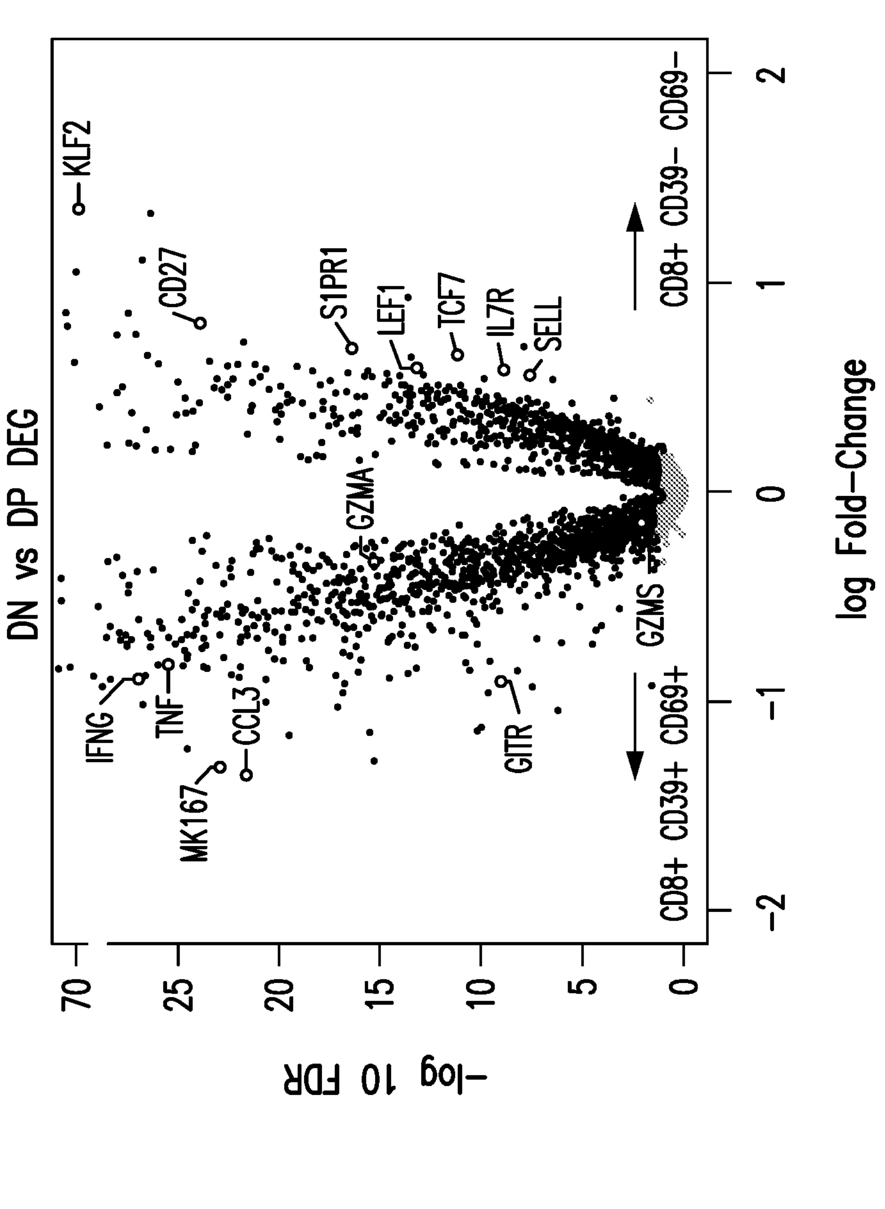

FIG. 8B shows a volcano plot of differentially expressed genes between DN and DP subsets from FIG. 8A showing statistically significant genes of interest. Full list of genes are listed in Table 3.

Figure 8C:
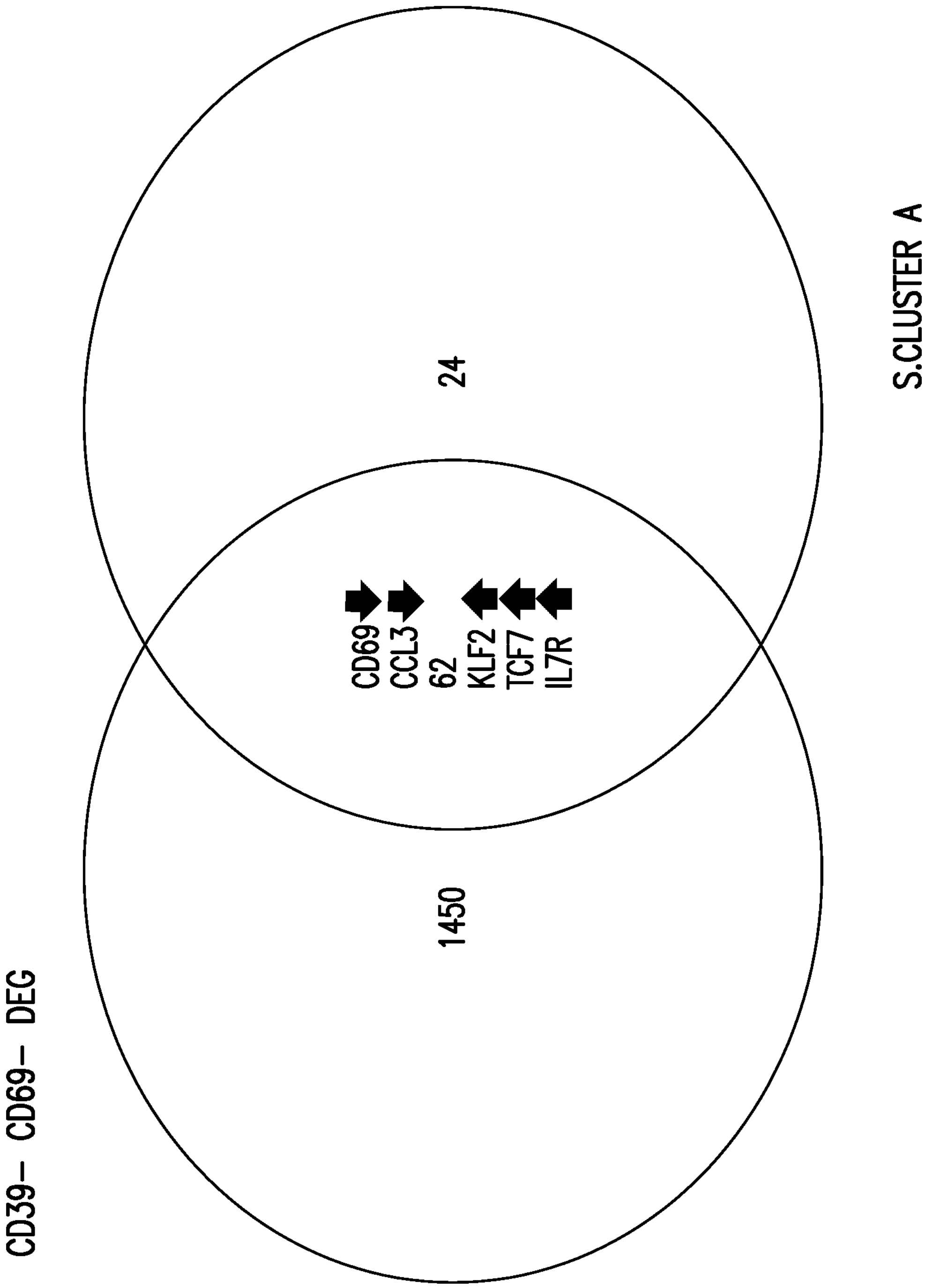

FIG. 8C shows an overlap of the number of genes found between DN vs DP DEG shown in FIG. 8B and S.Cluster.A-specific genes defined by unsupervised clustering of responder clusters shown in FIG. 2B.

Figure 9A:
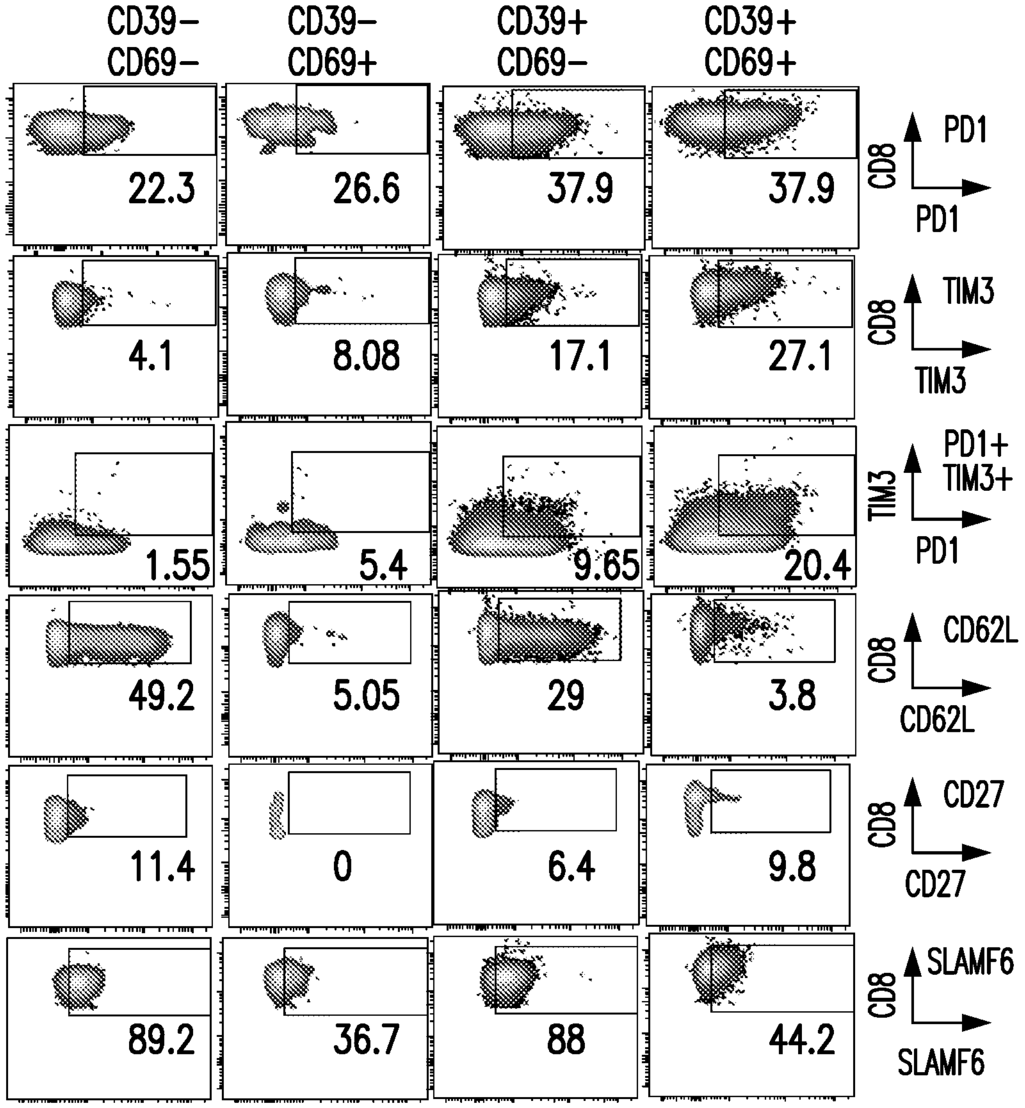

FIG. 9A shows a representative flow cytometry plot for inhibitory and memory markers from $CD39^{-}CD69^{-}$ (DN), $CD39^{+}CD69^{+}$ (DP), and $CD39^{-}CD69^{+}$, $CD39^{+}CD69^{-}$ (SP) states from $CD8^{+}$ TILs from a patient I.P. (3733-CR). Numbers indicate % of parent gate (DN, SP, and DP states).

Figure 9B:
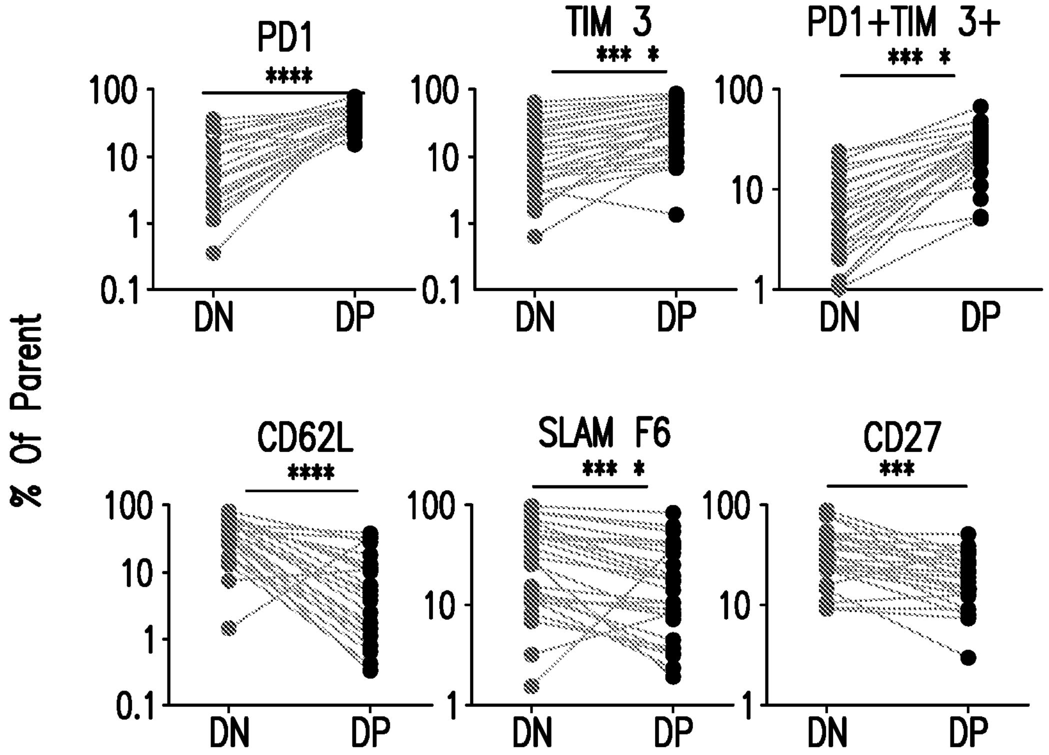

FIG. 9B shows a summary of paired analysis of the indicated cell surface markers (n=38 I.P.). *P<0.001 **P<0.0001 by paired t-tests.

Figure 10:
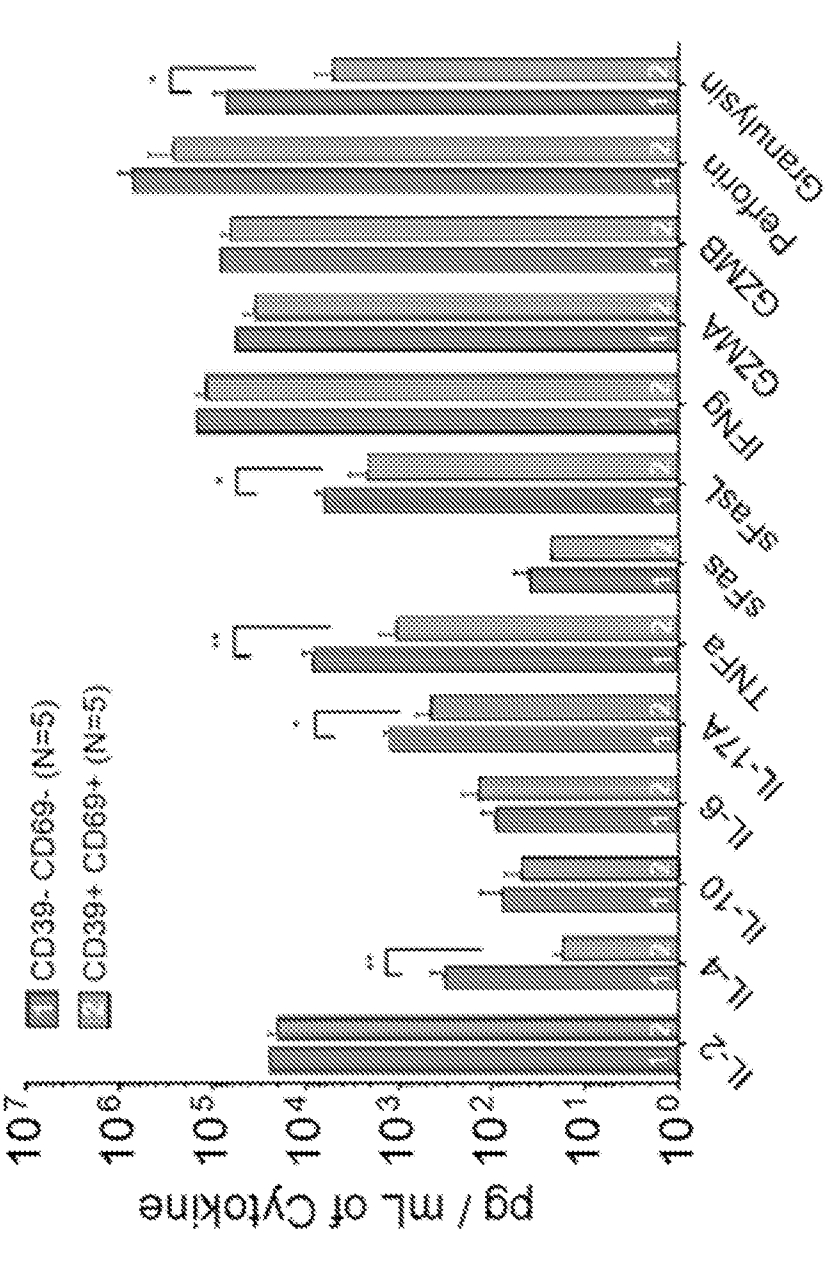

FIG. 10 is a graph showing secreted cytokines from DN and DP subsets after CD3/CD28 stimulation. DN and DP subsets were isolated from patient I.P. (N=5) and stimulated with anti-CD3/CD28 beads for 48 h followed by multi-cytokine analysis of cytokines secreted in the supernatant of daughter cells. P<0.05 P<0.01 by paired Wilcoxon test.

Figure 11A:
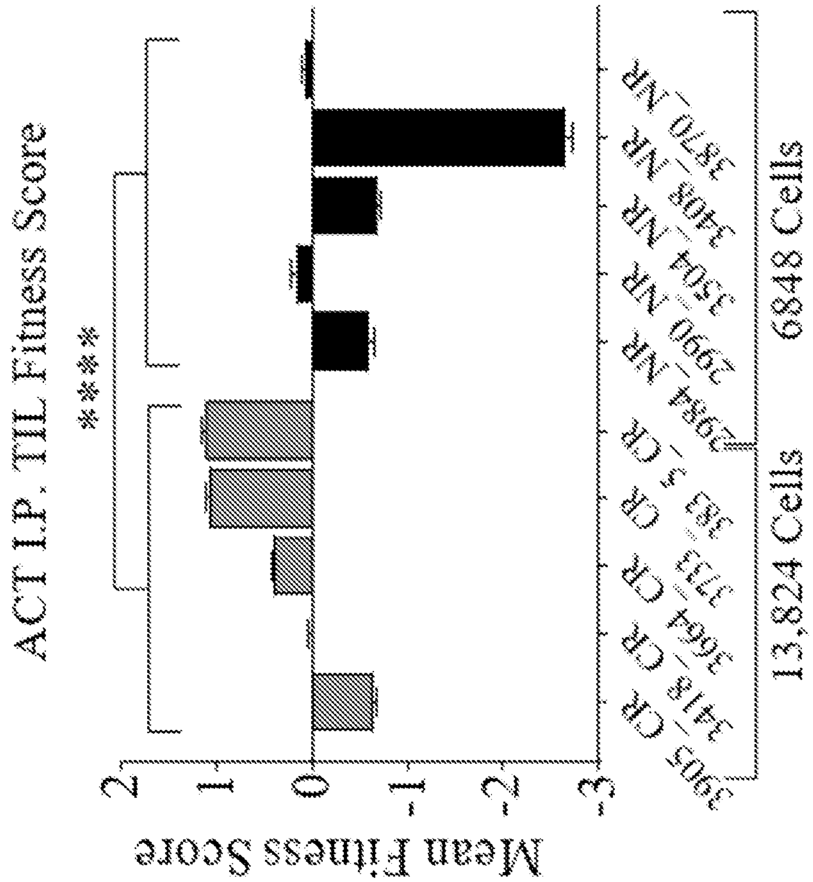
Figure 11B:
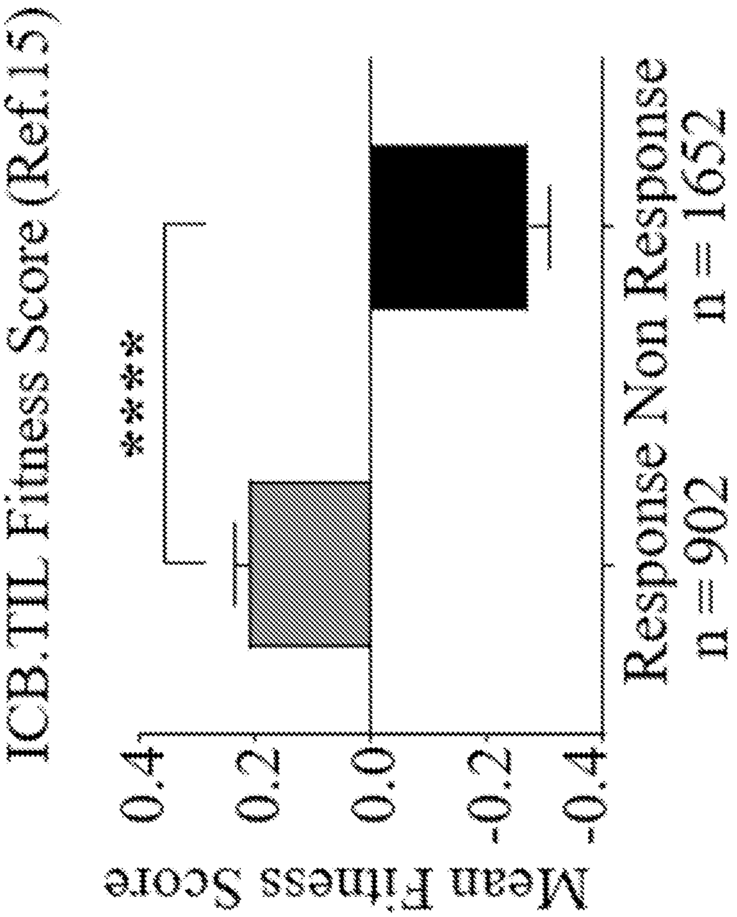

FIG. 11A-11B are graphs showing mean phenotypic fitness score of TILs from ACT I.P. (N=10) and pre-ICB–treatment $CD8^{+}$ TILs from Sade-Feldman sample cohort. Mean fitness score is defined as the difference between the normalized DN and DP scGSEA scores (DN minus DP) from each cell from patient TIL. FIG. 11A shows ACT I.P. from CRs, NRs shown in FIG. 2C. FIG. 11B shows pre-treatment TILs from Sade-Feldman cohort shown in FIG. 2G. ****P<0.0001 by two-sided Wilcoxon test.

Figure 12A:
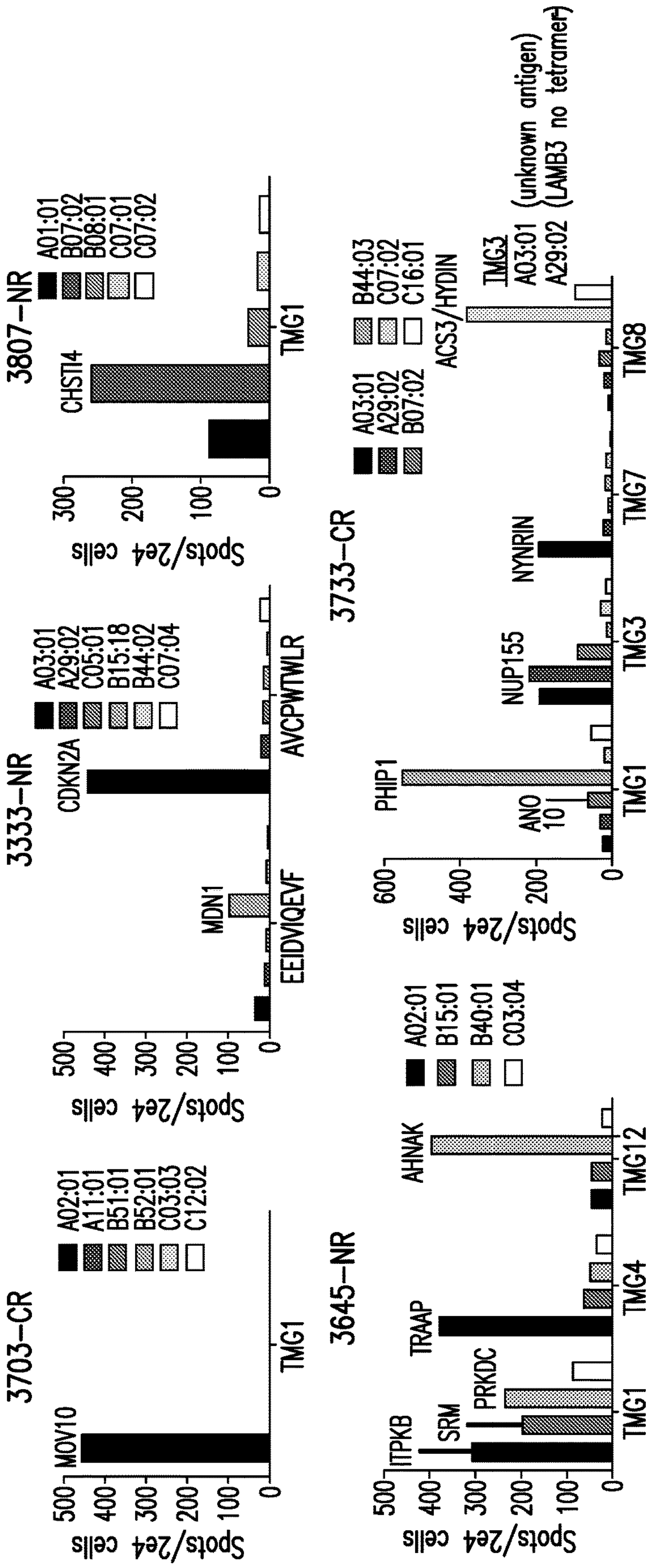

FIG. 12A shows the HLA-restriction definition for neoantigens screened in this study.

Figure 12B:
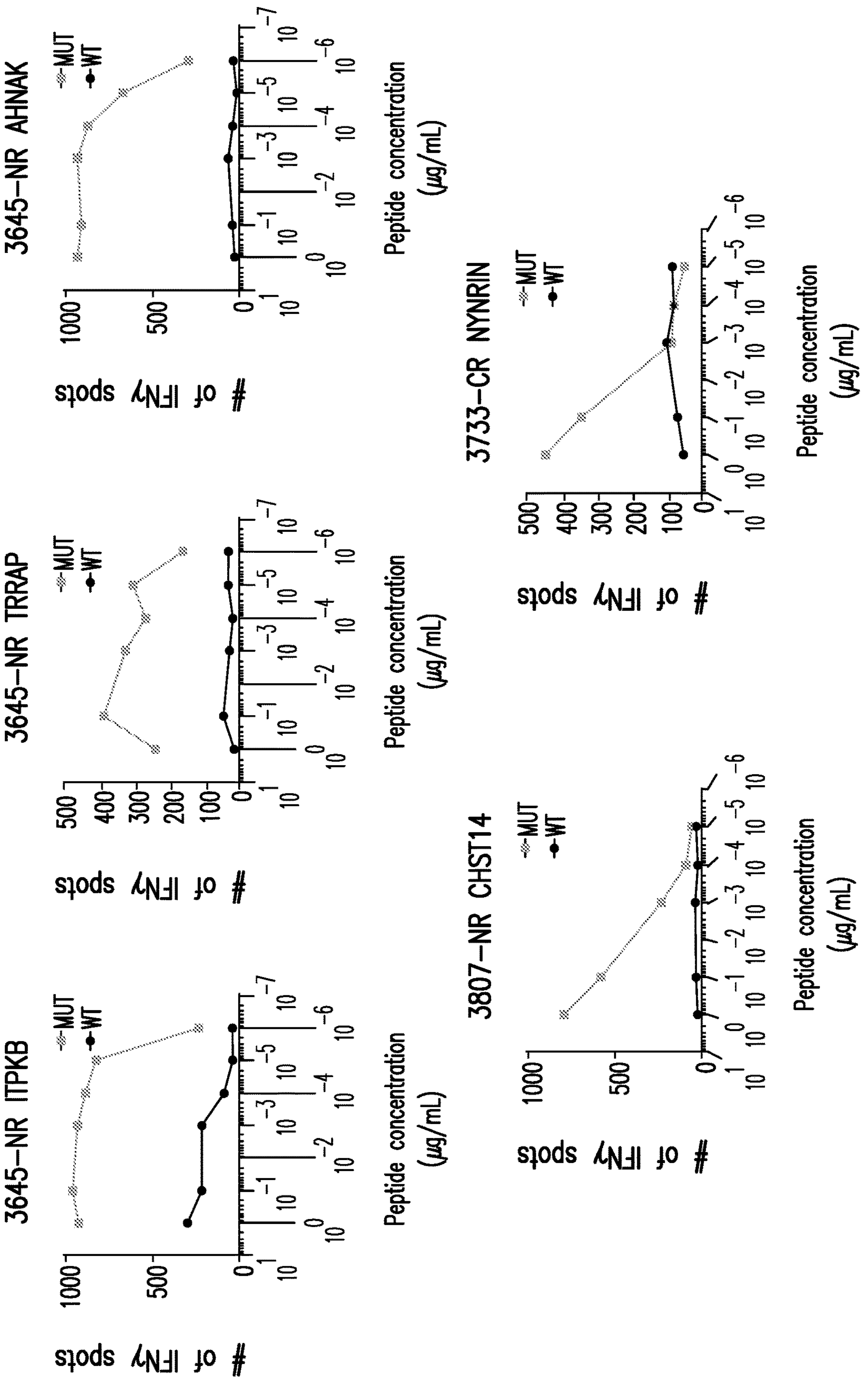
Figure 12B:
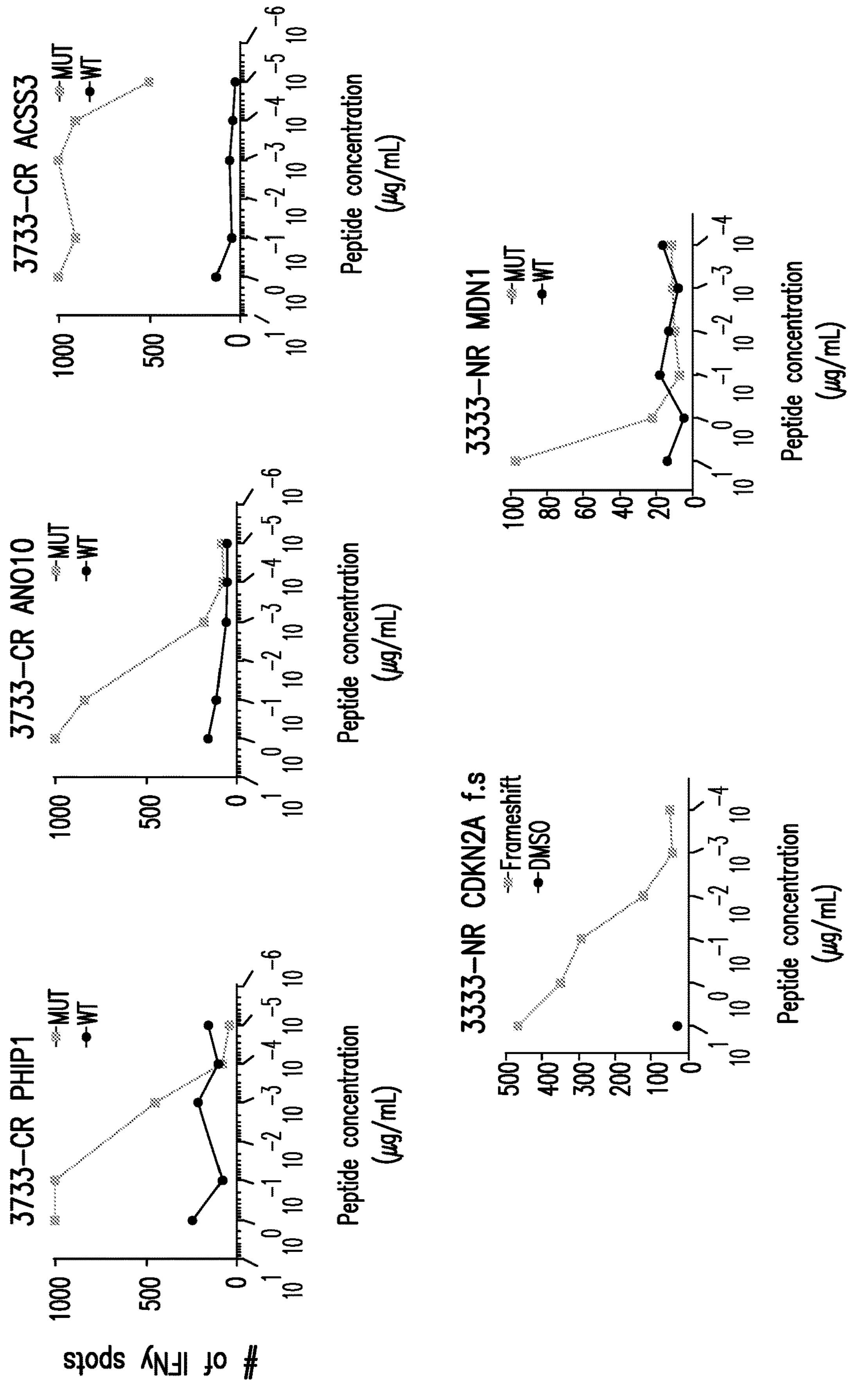
Figure 12B:
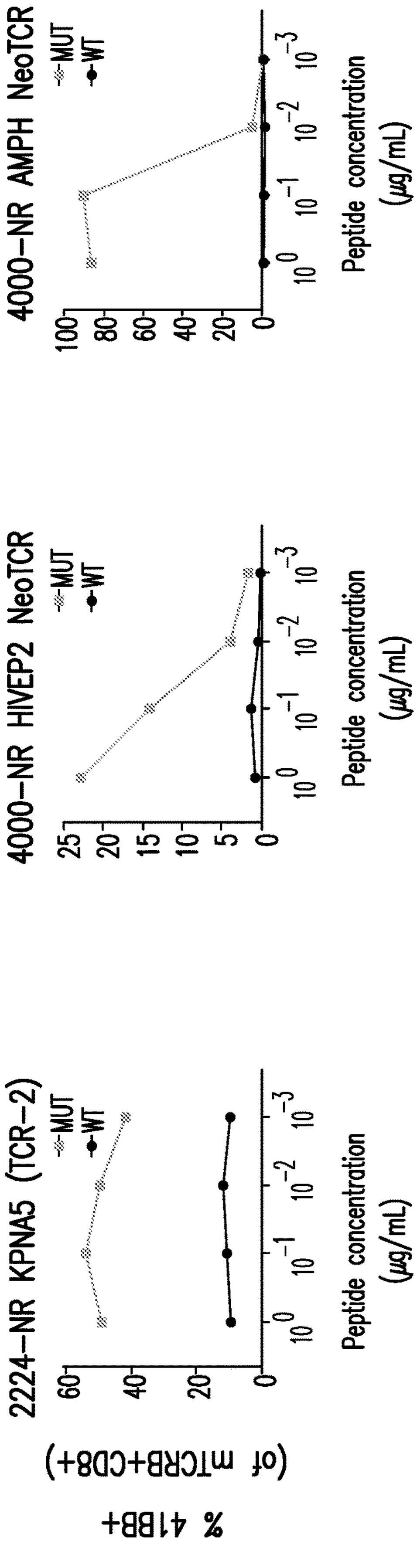

FIG. 12B shows the neoantigen specificity defined by titration of TILs or TCRs from I.P. against mutant (squares) and wild-type (circles) peptides by IFNγ ELISpots for patients screened in this study. Additional neoantigens were obtained from previously published studies. There is no wild-type for CDKN2A fs. The last two panels represent HIVEP2 and AMPH NeoTCR from Patient 4000-NR, transduced into healthy PBL and titrated against mutant and wild-type peptides using 4-1BB upregulation of $CD8^{+}$ $mTCR\beta^{+}$ subset to demonstrate NeoTCR specificity (used in FIG. 3J-3L).

Figure 13A:
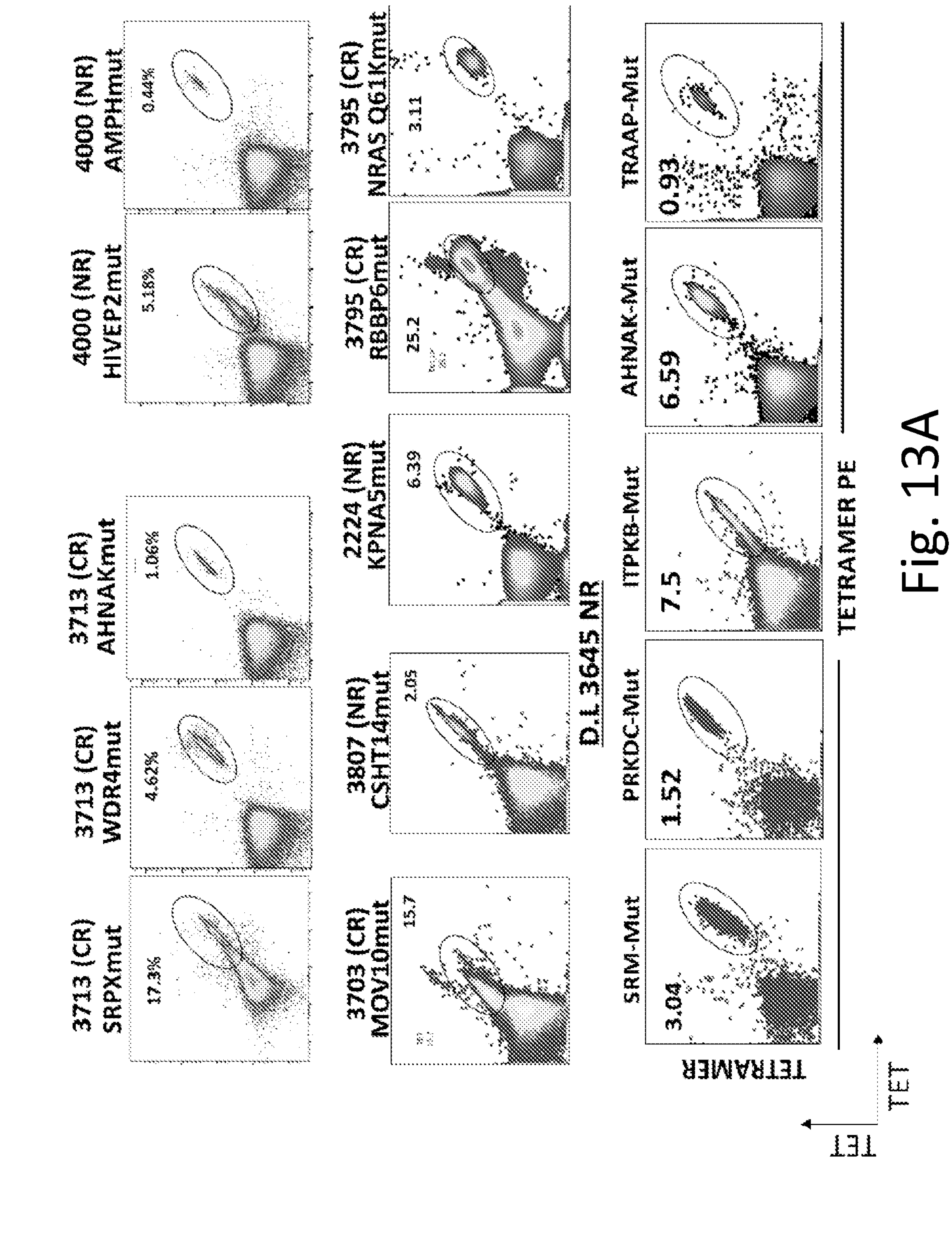
Figure 13B:
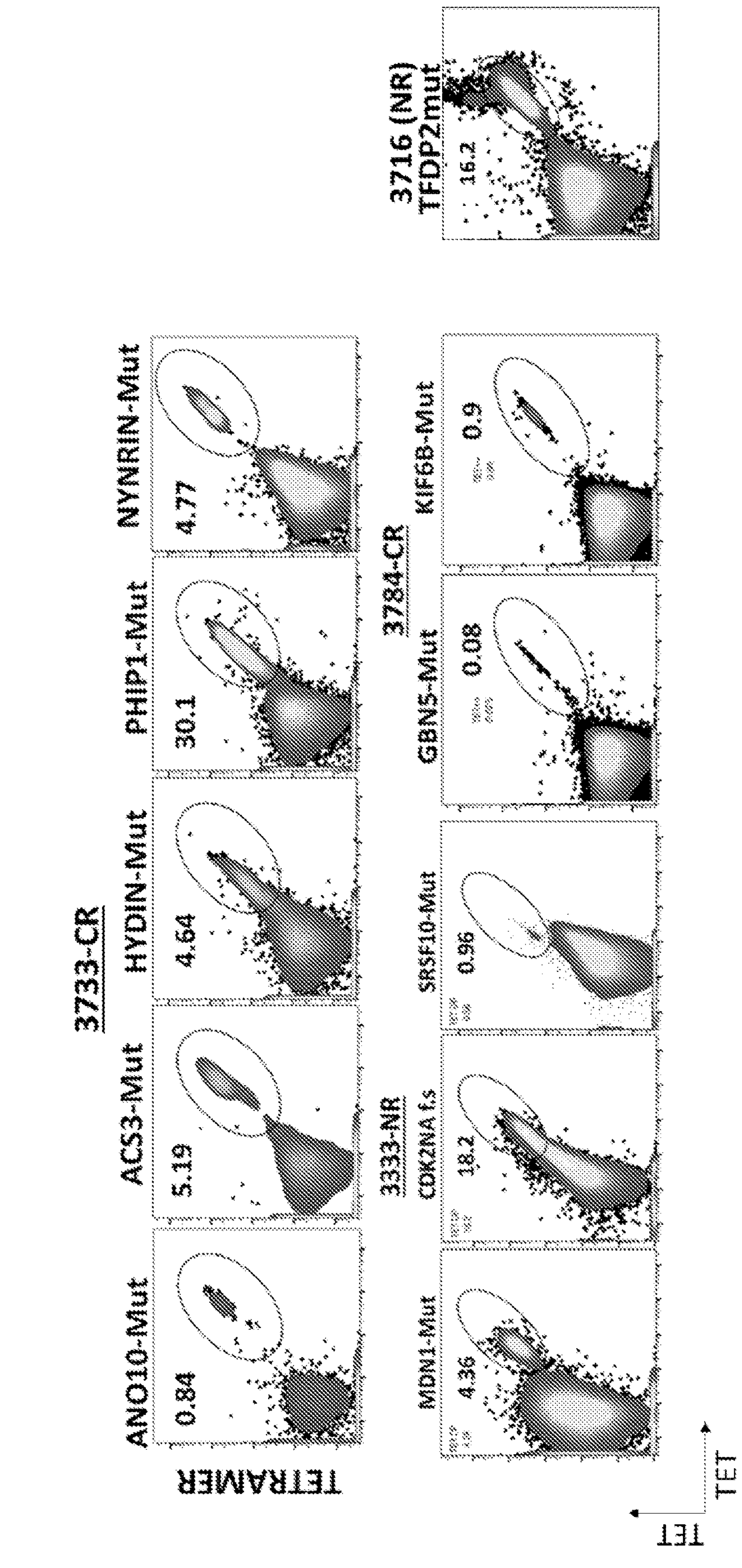

FIG. 13 shows the neoantigen T cell identification by tetramers from patient I.P. All 26 neoantigens from 11 patient I.P. shown in FIG. 3A-C detected by dual colored tetramers (materials and methods). Numbers indicate neoantigen-specific TIL as a % of CD8+ T cells within each patient I.P. Note that Pt. 3713 had other neoantigens that were non tetramerizable but with verified NeoTCRs.

Figure 14A:
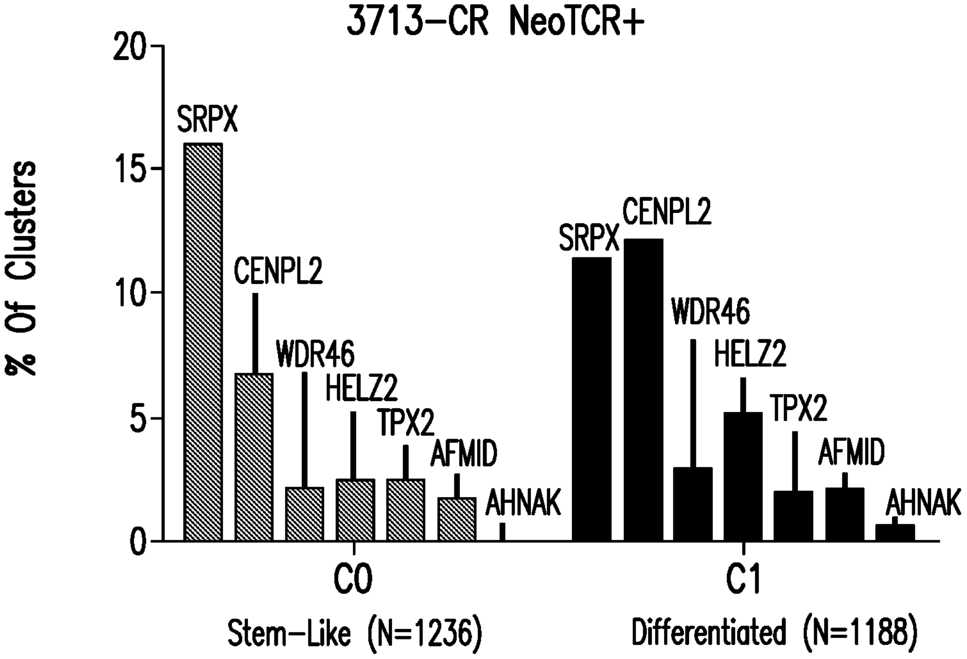

FIG. 14A shows 3713 $NeoTCR^{+}$ cells displayed as % of stem-like C0 cluster and differentiated C1 cluster shown for each NeoAg.

Figure 14B:
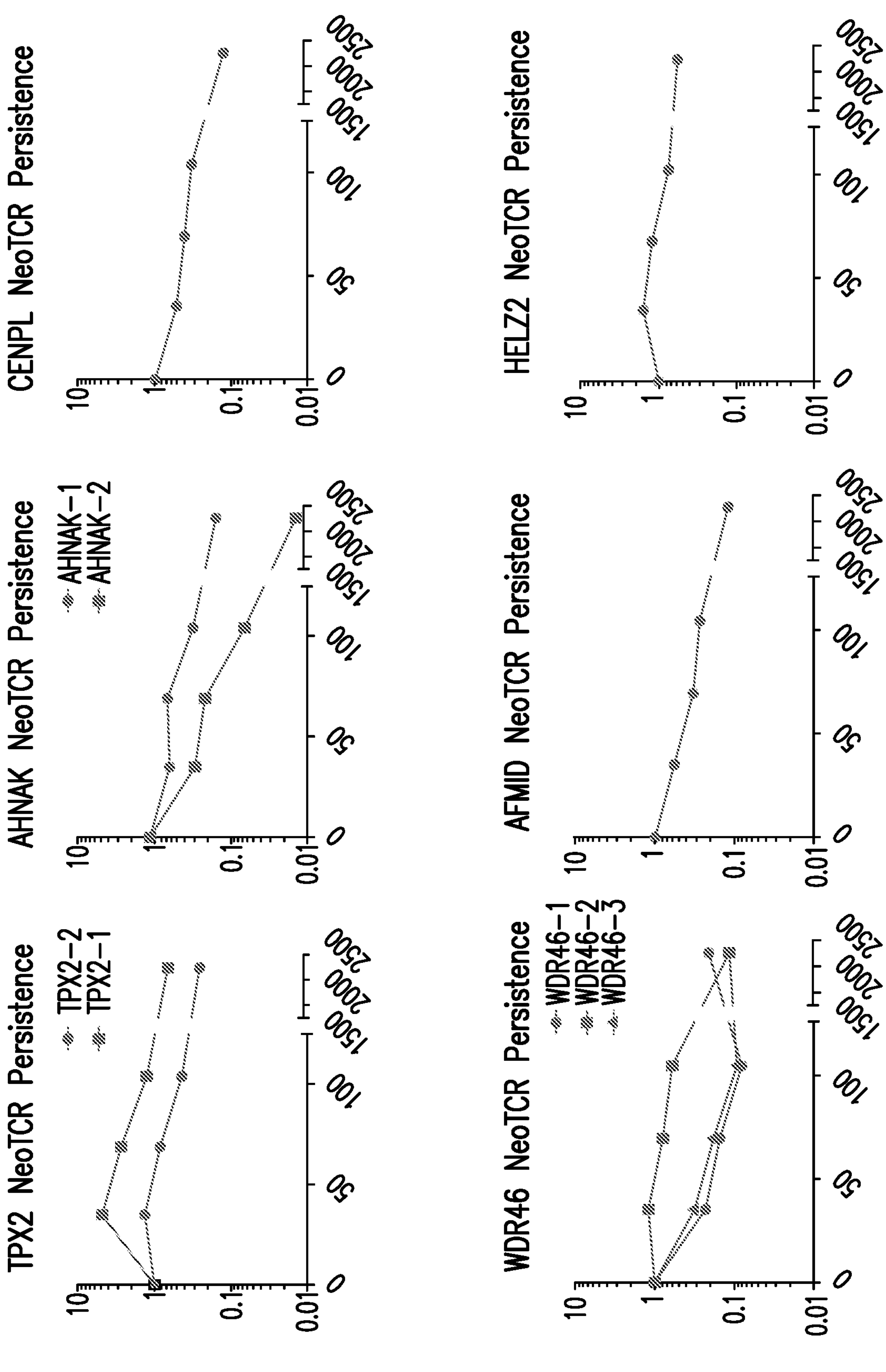

FIG. 14B shows post-ACT persistence of other sub-dominant NeoTCR clonotypes from Pt. 3713-CR in peripheral blood normalized to their frequency in the I.P., related to SRPX-NeoTCR data shown in FIG. 3I.

Figure 15A:
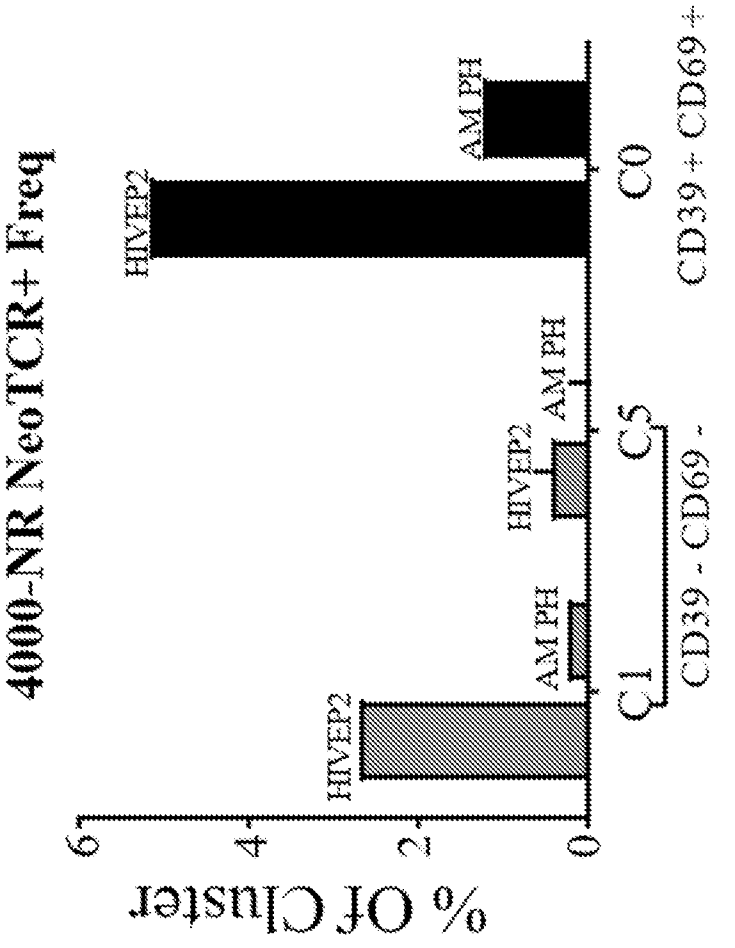

FIG. 15A shows 4000 NeoTCR+ cells displayed as a % of stem-like C1/C5 clusters and differentiated C0 cluster shown for each NeoTCR specificity.

Figure 15B:
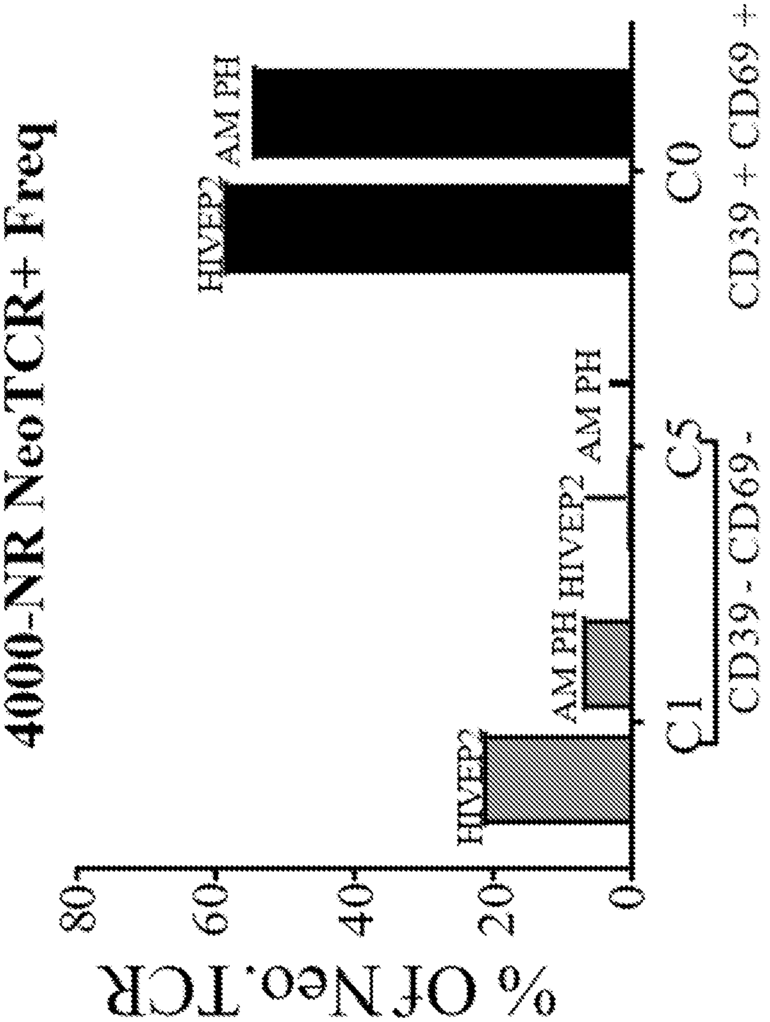

FIG. 15B shows Pt. 4000-NR NeoTCR+ cells from stem-like C1/C5 cluster and differentiated C0 cluster displayed as a % of total NeoTCR+ cells for each neoantigen specificity.

Figure 16A:
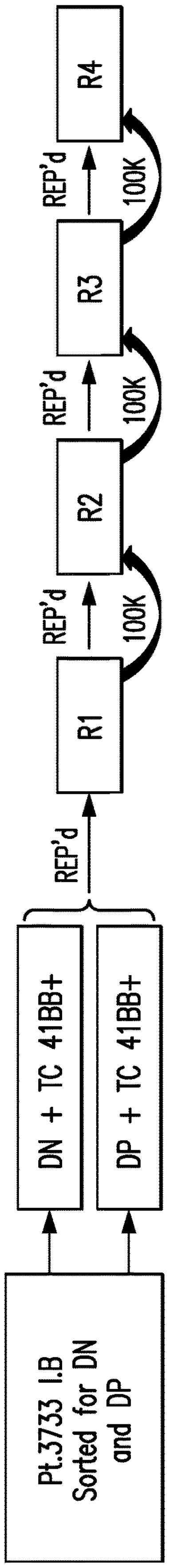

FIG. 16A is a schema for in vitro proliferation experiment. $CD39^{-}CD69^{-}$ and $CD39^{+}CD69^{+}CD8$ T cells were FACS-isolated from 3733-CR I.P. and co-cultured overnight with autologous 3733-mel tumor cell line. Tumor-reactive $CD8^{+}4\text{-}1BB^{+}$ cells from DN and DP subsets (DN $4\text{-}1BB^{+}$, DP $4\text{-}1BB^{+}$) were FACS-isolated and subjected to rapid expansion (REP, materials and methods) repeatedly using $10^{5}$ input T cells with irradiated feeders to mimic ACT TIL infusion products. Tumor reactivity and cell numbers was assessed at completion of REP culture experiment.

Figure 16B:
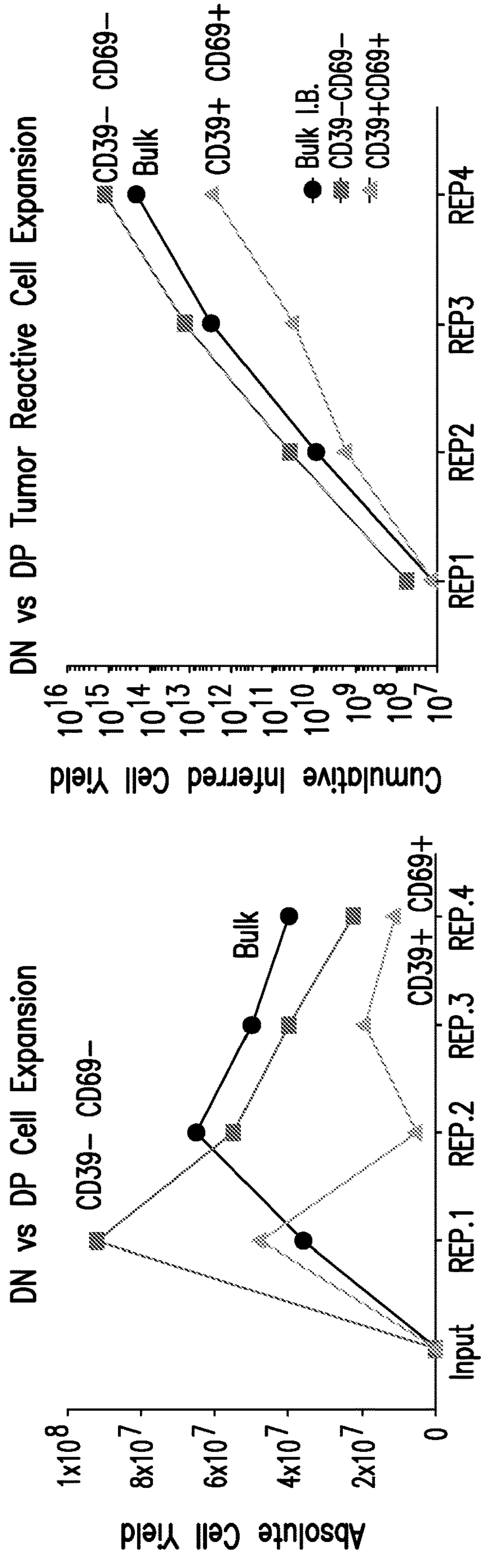

FIG. 16B shows absolute cell numbers obtained at end of each REP (left) and total tumor-reactive theoretical cell yield assuming all cells as subsequent inputs (right).

Figure 16C:
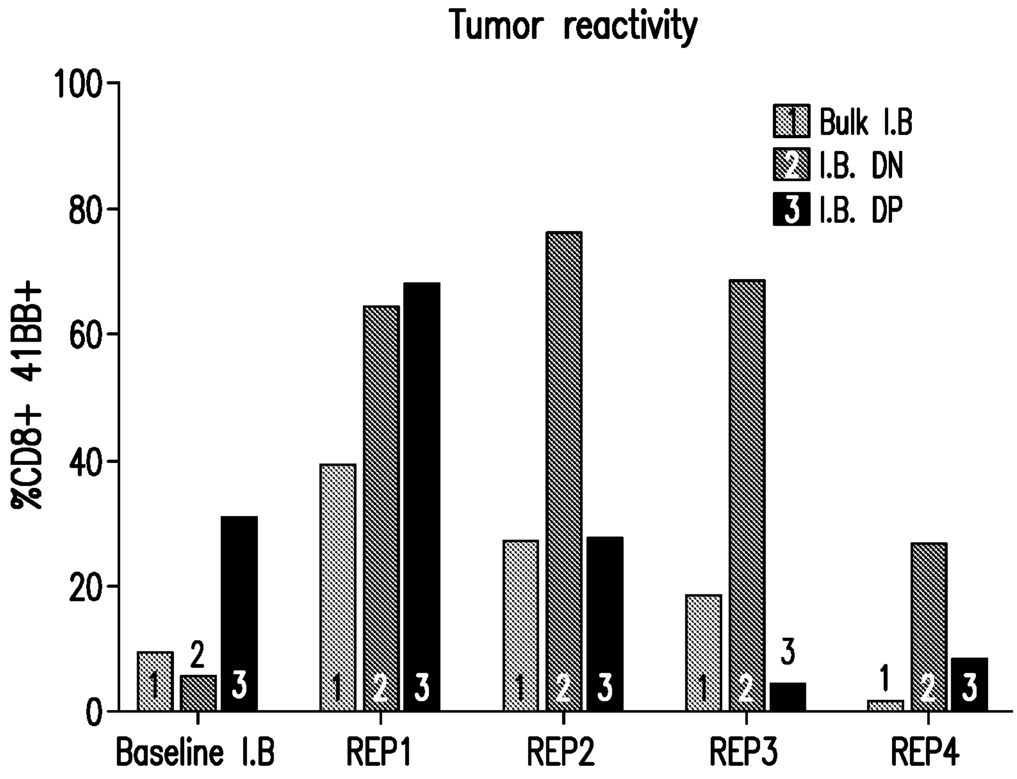

FIG. 16C shows tumor reactivity of each REP'd subset was assessed by $CD8^{+}4\text{-}1BB$ upregulation after co-culture with autologous 3733-mel tumor line from each population.

Figure 16D:
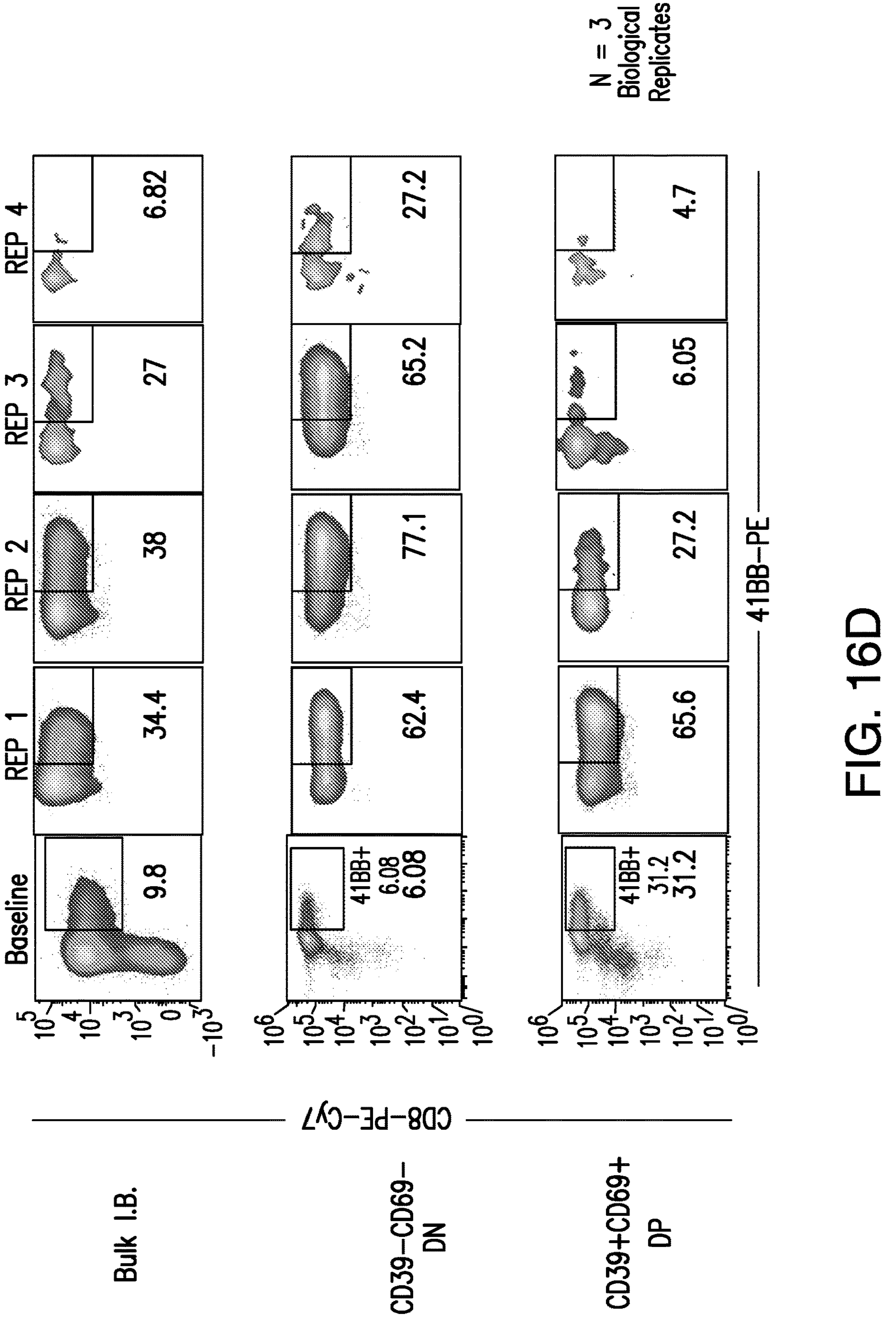

FIG. 16D shows a flow cytometry plot from one biological replicate shown in Figure S14C.

Figure 17:
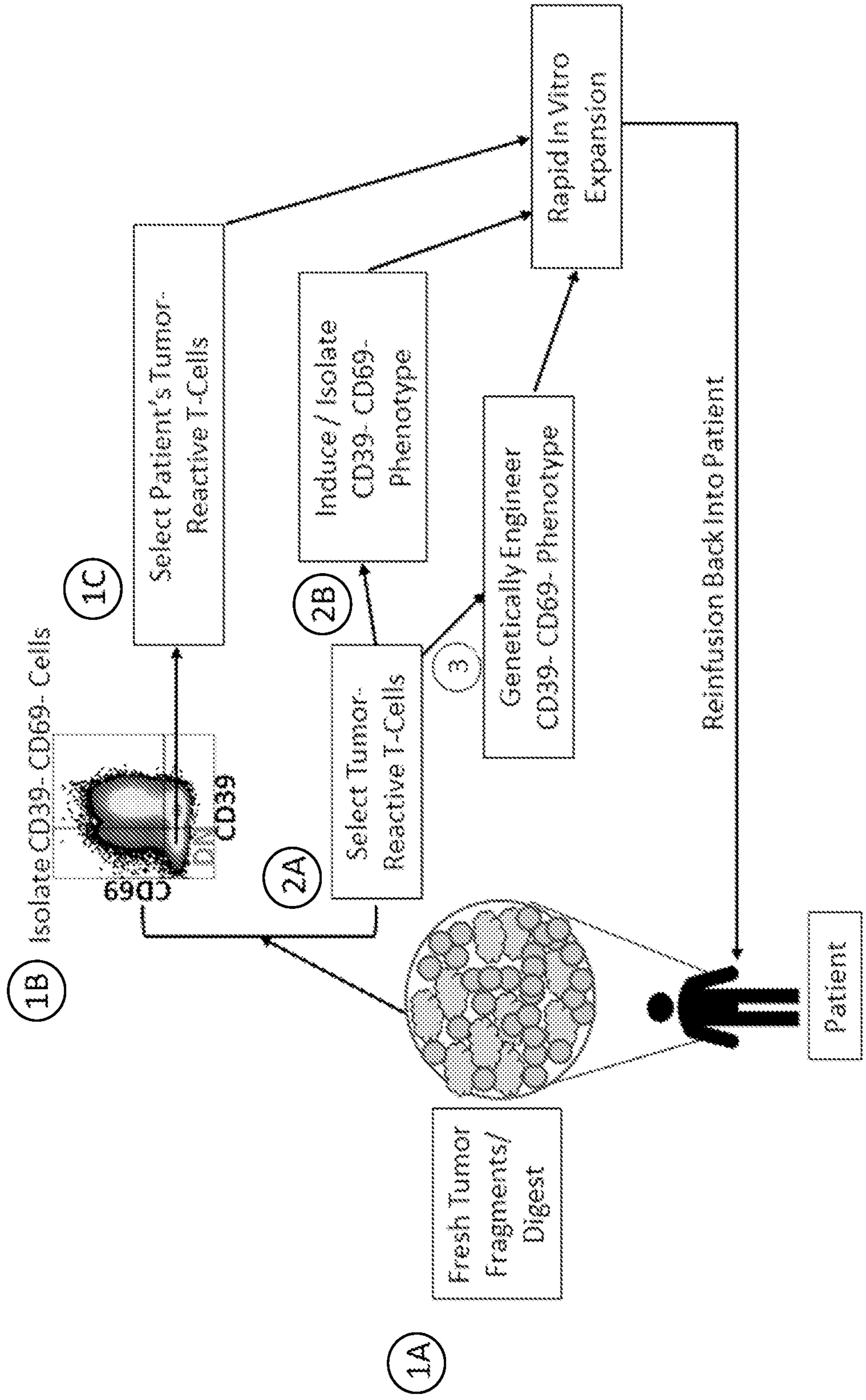

FIG. 17 is a schematic illustrating various embodiments of the inventive methods.

Figure 18A:
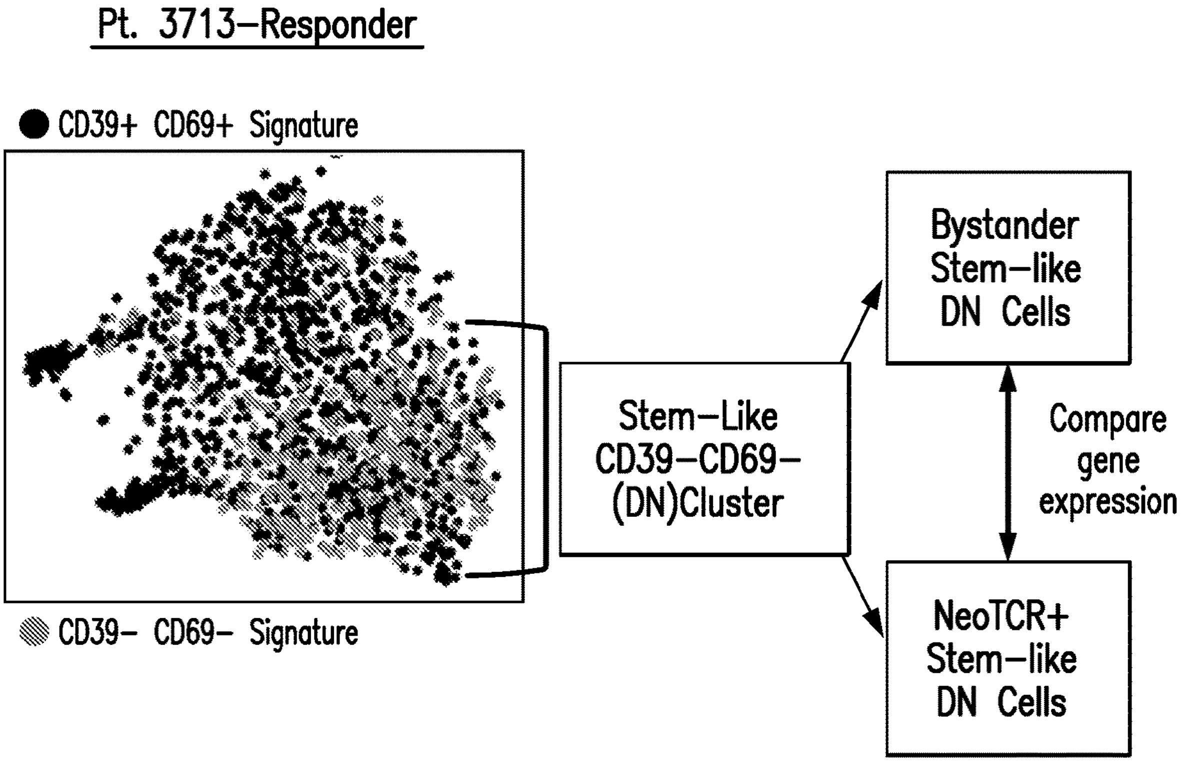

FIG. 18A is a schematic illustrating a strategy for identifying accurate markers of neoantigen specific tumor reactive stem-like T-cells that differentiate bystander stem-like T-cells in the stem-like $CD39^{-}CD69^{-}$ (DN) cluster of FIG. 3F.

Figure 18B:
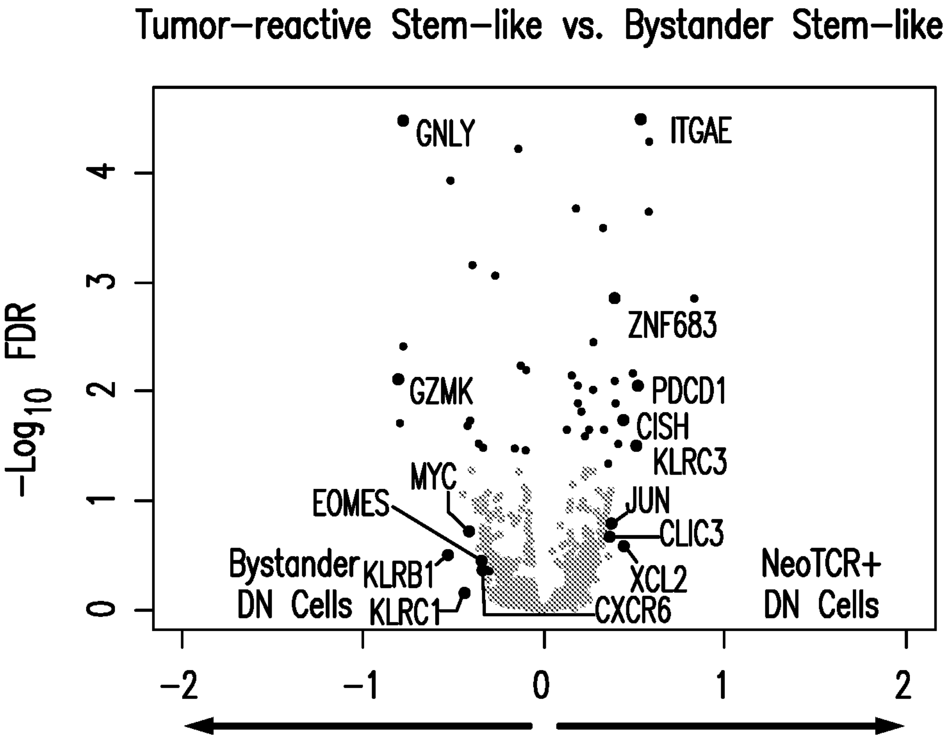

FIG. 18B shows a volcano plot of differentially expressed genes between bystander DN T cells and neoantigen-specific T cell subsets from FIG. 3F showing statistically significant genes of interest. Full list of genes are listed in Table 4.

DETAILED DESCRIPTION OF THE INVENTION

It has been discovered that a $CD39^{-}CD69^{-}$ T cell population administered to cancer patients may be associated with complete cancer regression and/or T cell persistence and that a $CD39^{+}CD69^{+}$ T cell population administered to patients may be associated with poor persistence. Although T cells administered to both responders and non-responders to ACT may include anti-tumor neoantigen-reactive $CD39^{+}CD69^{+}$ T cells, ACT responders were found to have been administered a pool of $CD39^-CD69^-$ neoantigen-specific T cells that was largely lacking in the T cells administered to ACT non-responders. Tumor-reactive $CD39^-CD69^-$ T cells may provide one or more of increased self-renewal, expansion, persistence, and anti-tumor response in the body of a patient as compared to $CD39^+CD69^+$ T cells.

An embodiment of the invention provides a method of obtaining a cell population enriched for T cells with a phenotype. The cell population may be administered to a patient, for example, for the treatment or prevention of cancer.

The method may comprise obtaining a bulk population of T cells from a tumor sample of a patient. The tumor sample may be, for example, tissue from primary tumors or tissue from the site of metastatic tumors. As such, the tumor sample may be obtained by any suitable means, including, without limitation, aspiration, biopsy, or resection.

The method may further comprise specifically selecting T cells with a phenotype comprising markers $CD3^+$, $CD39^-$, and $CD69^-$ from the bulk population. Selecting the T cells which have the phenotype may comprise sorting the T cells into separate single T cell samples and separately detecting the expression and/or non-expression of one or more markers of the phenotype by one or more single T cells. In an embodiment of the invention, specifically selecting T cells with the phenotype comprises carrying out single cell transcriptome analysis.

Detecting the expression and/or non-expression of one or more markers by the one or more single T cells may be carried out using, for example, the CHROMIUM Single Cell Gene Expression Solution system (10× Genomics, Pleasanton, CA) ("CHROMIUM system"). The CHROMIUM system performs deep profiling of complex cell populations with high-throughput digital gene expression on a cell-by-cell basis. The CHROMIUM system barcodes the cDNA of individual cells for 5' transcriptional or T cell receptor (TCR) analysis. For example, samples may start with an input of 10,000 cells and yield data for about 3000 cells/sample, with an average of about 500 genes/cell.

In an embodiment of the invention, specifically selecting T cells with the phenotype comprises carrying out Cellular Indexing of Transcriptomes and Epitopes by Sequencing (CITE-Seq) analysis. CITE-Seq is described at, for example, Stoeckius et al., *Nat. Methods,* 14(9): 865-868 (2017). Briefly, CITE-seq combines antibody-based detection of protein markers together with transcriptome profiling for many single cells in parallel. Oligonucleotide-labeled antibodies are used to integrate cellular protein and transcriptome measurements into an efficient, single-cell readout.

Because of the high dimensionality of the data yielded by the single cell transcriptome analysis (e.g., about 3000 cells/sample and about 500 genes/cell), dimensionality reduction may be carried out for analysis of the marker expression data. Accordingly, in an embodiment of the invention, specifically selecting T cells with a phenotype comprises carrying out t-Distributed Stochastic Neighbor Embedding (t-SNE) analysis. t-SNE visualizes high-dimensional data by giving each data point a location in a two or three-dimensional map. t-SNE is described at, for example, Van der Maaten and Hinton, J. *Machine Learning Res.,* 9: 2579-2605 (2008). Briefly, t-SNE is carried out in two steps. In step 1, a probability distribution is created in the high-dimensional space that dictates the relationships between various neighboring points. In step 2, a low dimensional space is recreated that follows that probability distribution as best as possible. The "t" in t-SNE comes from the t-distribution, which is the distribution used in Step 2. The "S" and "N" ("stochastic" and "neighbor") come from the use of a probability distribution across neighboring points.

The phenotype may include (i) positive expression of one or more markers, (ii) negative expression of one or more markers, or (iii) positive expression of one or more markers in combination with negative expression of one or more markers. As used herein, the term "positive" (which may be abbreviated as "+"), with reference to expression of the indicated marker, means that the T cell upregulates expression of the indicated marker as compared to other T cells in the tumor sample of the cancer patient. Upregulated expression may encompass, for example, a quantitative increase in expression of the indicated marker by an average logarithmic fold change (to the base 2) of about 0.2, about 0.5, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, or a range of any two of the foregoing values, or more. The term "negative" (which may be abbreviated as "−"), as used herein with reference to expression of the indicated marker, means that the T cell downregulates expression of the indicated marker as compared to other T cells in the tumor sample of the cancer patient. Downregulated expression may encompass, for example, a quantitative decrease in expression of the indicated marker by an average logarithmic fold change (to the base 2) of about −0.2, about −0.5, about −1, about −2, about −3, about −4, about −5, about −6, about −7, about −8, about −9, about −10, about −11, about −12, about −13, about −14, about −15, about −16, about −17, about −18, about −19, about −20, about −21, about −22, about −23, about −24, about −25, about −26, about −27, about −28, about −29, about −30, about −31, about −32, about −33, about −34, about −35, or a range of any two of the foregoing values, or more. Although downregulated expression may encompass an absence of expression of the indicated marker, downregulation also encompasses the presence of the expression of the indicated marker, albeit at a lower level as compared to other T cells in the tumor sample of the cancer patient.

Specifically selecting T cells with the phenotype may comprise detecting the presence or absence of, or measuring the quantity of, the product(s) of expression of the markers in the phenotypes described herein. In this regard, specifically selecting T cells which have the phenotype may comprise detecting the presence of protein(s) encoded by positively expressed marker(s) of the phenotype. Alternatively or additionally, specifically selecting T cells which have the phenotype may comprise detecting the absence of protein(s) encoded by marker(s) that are negative for expression in the phenotype. Alternatively or additionally, specifically selecting T cells which have the phenotype may comprise measuring the quantity of protein(s) encoded by marker(s) that are negative for expression in the phenotype. Alternatively or additionally, specifically selecting T cells which have the phenotype may comprise measuring the quantity of protein(s) encoded by marker(s) that are positive for expression in the phenotype. Alternatively or additionally, specifically selecting T cells which have the phenotype may comprise detecting the presence of RNA encoded by positively expressed marker(s) of the phenotype. Alternatively or additionally, specifically selecting T cells which have the phenotype may comprise detecting the absence of RNA encoded by marker(s) that are negative for expression in the phenotype. Alternatively or additionally, specifically selecting T cells which have the phenotype may comprise measuring the quantity of RNA encoded by positively expressed marker(s) of the phenotype. Alternatively or additionally, specifically selecting T cells which have the phenotype may comprise measuring the quantity of RNA encoded by negatively expressed marker(s) of the phenotype. In an embodiment of the invention, specifically selecting T cells which have the phenotype comprises detecting the presence and/or absence of cell surface expression of the one or more markers in the phenotype. In an embodiment of the invention, specifically selecting T cells which have the phenotype comprises measuring the quantity of cell surface expression of the one or more markers in the phenotype.

In an embodiment of the invention, the phenotype further comprises one or more of marker(s): AHNAK$^+$, AL592183.1$^+$, ANXA1$^+$, ANXA4$^+$, AQP3$^+$, ATM$^+$, BIN1$^+$, C10orf54$^+$, C11orf21$^+$, C16orf54$^+$, CCDC109B$^+$, CD27$^+$, CD52$^+$, CD55$^+$, CD8B$^+$, CDC25B$^+$, CDC42SE1$^+$, CLEC2B$^+$, CLIC3$^+$, CLUAP1$^+$, CRBN$^+$, CTD-3184A7.4$^+$, DDI2$^+$, DND1$^+$, EMP3$^+$, EPB41$^+$, ERN1$^+$, FAIM3$^+$, FAM65B$^+$, FBXL8$^+$, FGFBP2$^+$, GADD45B$^+$, GIMAP4$^+$, GIMAP7$^+$, GPR155$^+$, GZMM$^+$, HSD17B11$^+$, IL10RA$^+$, IL7R$^+$, ISG20$^+$, KANSL1-AS1$^+$, KLF2$^+$, KLHL24$^+$, LDLRAP1$^+$, LEF1$^+$, LGALS3$^+$, LINC00861$^+$, LITAF$^+$, LYAR$^+$, MAPKAPK5-AS1$^+$, MED15$^+$, MIAT$^+$, MIR142$^+$, MXI1l, MYC$^+$, NEAT1$^+$, NOSIP$^+$, ODF2L$^+$, P2RY8$^+$, PDE6G, PIK3IP1$^+$, PLEC$^+$, PLP2$^+$, PPP2R5C$^+$, PXN$^+$, R3HDM4$^+$, RAMP1$^+$, RASA3$^+$, RASGRP2$^+$, RCBTB2$^+$, RNASET2$^+$, RP11-395B7.4$^+$, RP11-539L10.2$^+$, RP11-640M9.1$^+$, S100A10$^+$, S100A4$^+$, S100A6$^+$, S1PR1$^+$, S1PR4$^+$, SAMD3$^+$, SELL$^+$, SH3BP5$^+$, SIGIRR$^+$, SLAMF6$^+$, SLCO3A1$^+$, SORL1$^+$, STK38$^+$, SYNJ2$^+$, TCF7$^+$, TIMP1$^+$, TRADD$^+$, TSC22D3$^+$, TSPAN32$^+$, TXNIP$^+$, UBXN11$^+$, VCL$^+$, VNN2$^+$, YPEL3$^+$, ZFP36L2$^+$, ZNF276$^+$, and ZNF683$^+$. In an embodiment of the invention, the phenotype further comprises any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more of the markers listed in this paragraph. In an embodiment of the invention, the phenotype further comprises all of the markers listed in this paragraph.

In an embodiment of the invention, the phenotype lacks one or more of marker(s): ACOT7$^+$, ADAM19$^+$, AGPAT9$^+$, AGTRAP$^+$, AIF1$^+$, ASPM$^+$, ATAD2$^+$, AURKA$^+$, AURKB$^+$, BIRC3$^+$, BIRC5$^+$, BRCA1$^+$, C15orf48$^+$, CASC5$^+$, CCL3$^+$, CCNA2$^+$, CCNB1$^+$, CCNB2$^+$, CCND2$^+$, CD38$^+$, CD40LG$^+$, CD69$^+$, CD8B$^+$, CDC20$^+$, CDCA3$^+$, CDCA8$^+$, CDK1$^+$, CDKN3$^+$, CDT1$^+$, CENPA$^+$, CENPE$^+$, CENPF$^+$, CENPM$^+$, CENPW$^+$, CEP55$^+$, CISH$^+$, CKS1B$^+$, CKS2$^+$, CLSPN$^+$, CRTAM$^+$, CSF2$^+$, DLGAP5$^+$, DUSP5$^+$, DUSP6$^+$, DUT$^+$, EGR1$^+$, ENTPD1$^+$, FEN1$^+$, GINS2$^+$, GTSE1$^+$, H2AFX$^+$, HIST1H4C$^+$, HLA$^+$DQA2$^+$, HMMR$^+$, IFI27$^+$, IFNG$^+$, IL2RA$^+$, IL5$^+$, KIAA0101$^+$, KIF11$^+$, KIF23$^+$, KPNA2$^+$, KRT7$^+$, MAD2L1$^+$, MCM7$^+$, MKI67$^+$, MX1$^+$, MYBL2$^+$, NCAPG$^+$, NDC80$^+$, NDFIP2$^+$, NUDT1$^+$, NUSAP1$^+$, ORC6$^+$, PBK$^+$, PCNA$^+$, PLKI1, RPL39L$^+$, RRM2$^+$, SGOL2$^+$, SHCBP1$^+$, SMC2$^+$, SPC25$^+$, STMN1$^+$, TESC$^+$, TK1$^+$, TNF$^+$, TNFRSF18$^+$, TNFSF10$^+$, TOP2A$^+$, TPM4$^+$, TPX2$^+$, TUBA1B$^+$, TUBA1C$^+$, TUBB$^+$, TYMS$^+$, UBE2C$^+$, UBE2S$^+$, UBE2T$^+$, XCL1$^+$, and ZWINT$^+$. In an embodiment of the invention, the phenotype lacks any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more of the markers listed in this paragraph. In an embodiment of the invention, the phenotype lacks all of the markers listed in this paragraph.

In an embodiment of the invention, the phenotype further comprises one or more of marker(s): AHI1$^+$, ALOX5AP$^+$, ANXA5$^+$, CD68$^+$, CD74$^+$, CD99$^+$, CDC27$^+$, CDCA7V, CISH$^+$, COTL1$^+$, CTSH$^+$, CTSW$^+$, DDX60$^+$, GTSF1$^+$, HIST1H2AG, HLA-DPA1$^+$, HLA-DRB1$^+$, HLA-DRB5$^+$, HMGN3$^+$, IGFBP3$^+$, IL32$^+$, INTS4$^+$, ITGAE$^+$, ITGB1$^+$, KLRC3$^+$, LGALS1$^+$, LIME1$^+$, PDCD1$^+$, PPM1M$^+$, PRSS57$^+$, RAB34$^+$, RBPMS$^+$, S100A11$^+$, S100A4$^+$, SNAP47$^+$, TNFRSF10A$^+$, VSIR$^+$, ZBP1$^+$, and ZNF683$^+$. In an embodiment of the invention, the phenotype further comprises any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or more of the markers listed in this paragraph. In an embodiment of the invention, the phenotype further comprises all of the markers listed in this paragraph. The phenotype described in this paragraph may be characteristic of neoantigen-specific T cells and distinguish the neoantigen-specific T cells from bystander T cells. The phrase "bystander T cells," as used herein, means T cells which have antigenic specificity for irrelevant antigens (not neoantigens).

In an embodiment of the invention, the phenotype lacks one or more of marker(s): AQP3$^+$, ASXL2$^+$, CD6$^+$, CLDND1$^+$, EEF1A1$^+$, EPB41$^+$, ERN1$^+$, FCMR, GIMAP4$^+$, GIMAP7$^+$, GNLY$^+$, GZMK$^+$, IL27RA$^+$, LINC01943$^+$, MRPL57$^+$, MT-CO1$^+$, MT-CO2$^+$, RGS10$^+$, RPL13A$^+$, RPL18$^+$, RPL18A$^+$, RPL37$^+$, RPL41$^+$, RPLP0$^+$, SFMBT2$^+$, TPT1$^+$, and TRGV10$^+$. In an embodiment of the invention, the phenotype lacks any 2, 3, 4, 5, 6, 7, 8, 9, 10, 11, 12, 13, 14, 15, 16, 17, 18, 19, 20, 21, 22, 23, 24, 25, 26, or more of the markers listed in this paragraph. In an embodiment of the invention, the phenotype lacks all of the markers listed in this paragraph. The presence of one or more of the markers in this paragraph may be characteristic of bystander T cells, and the presence of one or more of the markers in this paragraph may distinguish the bystander T cells from neoantigen-specific T cells. Conversely, a phenotype which lacks one or more of the markers described in this paragraph may be characteristic of neoantigen-specific T cells and distinguish the neoantigen-specific T cells from bystander T cells.

The phenotype may further comprise one or both of marker(s) CD8$^+$ and CD4$^+$. Alternatively, the phenotype further comprises one or both of marker(s) CD8$^-$ and CD4$^-$.

The method may further comprise separating the selected cells which have the phenotype from cells which lack the phenotype to obtain a cell population enriched for T cells with the phenotype. In this regard, the selected cells may be physically separated from unselected cells, i.e., the cells that do not have the phenotype. The selected cells may be separated from unselected cells by any suitable method such as, for example, sorting.

The cell populations enriched for T cells with the phenotype by the inventive methods may themselves be useful for any of a variety of applications, for example, adoptive cell therapy for the treatment of conditions, e.g., cancer. Alternatively or additionally, the cell populations enriched for T cells with the phenotype may be a source of tumor-reactive T cells. Accordingly, in an embodiment of the invention, the method may further comprise isolating tumor-reactive T cells from the separated T cells which have the phenotype.

An illustrative example of such an embodiment of the inventive methods is shown by the collection of items 1A, 1B, and 1C of FIG. 17.

The tumor-reactive T cells may be isolated from the separated T cells which have the phenotype in any of a variety of ways known in the art. Examples of techniques for isolating tumor-reactive T cells are described in, for example, Pasetto et al., *Cancer Immunol. Res.,* 4: 734-743 (2016); Parkhurst et al., *Clin. Cancer Res.,* 23: 2491-2505 (2017); Cohen et al., *J Clin. Invest.,* 125: 3981-3991 (2015); Lu et al., *Mol. Ther.,* 26(2): 1-10 (2018); US 2020/0056237; US 2017/0218042; WO 2017/048614; and US 2020/0095548.

The tumor-reactive T cells may have antigenic specificity for a neoantigen. The phrases "antigen-specific" and "antigenic specificity," as used herein, mean that the T cell can specifically bind to and immunologically recognize an antigen, or an epitope thereof, such that binding of the T cell to the antigen, or the epitope thereof, elicits an immune response. Neoantigens are a class of cancer antigens which arise from cancer-specific mutations in expressed protein. The term "neoantigen" relates to a peptide or protein expressed by a cancer cell that includes one or more amino acid modifications compared to the corresponding wild-type (non-mutated) peptide or protein that is expressed by a normal (non-cancerous) cell. A neoantigen may be patient-specific. A "cancer-specific mutation" is a somatic mutation that is present in the nucleic acid of a tumor or cancer cell but absent in the nucleic acid of a corresponding normal, i.e. non-tumorous or non-cancerous, cell.

In another embodiment of the invention, tumor-reactive T cells may first be isolated from the tumor sample, and then the T cells with the phenotype are selected from those isolated tumor-reactive T cells. An illustrative example of such an embodiment of the inventive methods is shown by the collection of items 1A, 2A, and 2B of FIG. 17.

In this regard, an embodiment of the invention provides a method of obtaining a cell population enriched for T cells with a phenotype, the method comprising obtaining a bulk population of T cells from a tumor sample of a patient. The bulk population of T cells may be obtained from the tumor sample as described herein with respect to other aspects of the invention.

The method may further comprise isolating tumor-reactive T cells from the tumor sample. This may be accomplished in any of a variety of ways known in the art. Examples of techniques for isolating tumor-reactive T cells from a tumor sample are described in, for example, Pasetto et al., *Cancer Immunol. Res.,* 4: 734-743 (2016); Parkhurst et al., *Clin. Cancer Res.,* 23: 2491-2505 (2017); Cohen et al., *J. Clin. Invest.,* 125: 3981-3991 (2015); Lu et al., *Mol. Ther.,* 26(2): 1-10 (2018); US 2020/0056237; US 2017/0218042; WO 2017/048614; and US 2020/0095548.

The method may further comprise specifically selecting T cells with a phenotype comprising markers $CD3^{+}$, $CD39^{-}$, and $CD69^{-}$ from the isolated tumor-reactive T cells and separating the selected cells from cells which lack the phenotype to obtain a cell population enriched for T cells with the phenotype. The phenotype may be as described herein with respect to other aspects of the invention. The specific selection of the T cells with the phenotype and the separation of the selected cells from cells which lack the phenotype may be carried out as described herein with respect to other aspects of the invention.

Tumor-reactive T cells with the phenotype may provide one or more of increased self-renewal, expansion, persistence, and anti-tumor response in the body of a patient as compared to T cells without the phenotype. Accordingly, it is contemplated that modifying tumor-reactive T cells to have the phenotype may also provide a T cell population which provides any one or more of these advantages in the body of the patient. An illustrative example of such an embodiment of the inventive methods is shown by the collection of items 1A, 2A, and 2B of FIG. 17.

Accordingly, an embodiment of the invention provides a method of obtaining a cell population enriched for T cells with a phenotype, the method comprising obtaining a bulk population of T cells from a tumor sample of a patient and isolating tumor-reactive T cells from the tumor sample. Obtaining the bulk population of T cells from the tumor sample of the patient and isolating tumor-reactive T cells from the tumor sample may be carried out as described herein with respect to other aspects of the invention.

The method may further comprise modifying the isolated tumor-reactive T cells to provide a phenotype comprising markers $CD39^{-}$ and $CD69^{-}$ to obtain a cell population enriched for T cells with the phenotype. Modifying the isolated tumor-reactive T cells to provide the $CD39^{-}CD69^{-}$ phenotype may be carried out in any suitable manner known in the art. For example, the isolated tumor-reactive T cells may be treated with CD39 inhibitor(s) and CD69 inhibitor(s).

In an embodiment of the invention, the CD39 inhibitor is any suitable agent that inhibits the expression of one or both of CD39 mRNA and CD39 protein. The CD39 inhibitor can be a nucleic acid at least about 10 nucleotides in length that specifically binds to and is complementary to a target nucleic acid encoding one or both of CD39 mRNA and CD39 protein, or a complement thereof. The CD39 inhibitor may be introduced into the isolated tumor-reactive T cells, wherein the cells are capable of expressing one or both of CD39 and CD39 protein, in an effective amount for a time and under conditions sufficient to interfere with expression of one or both of CD39 and CD39 protein, respectively.

In an embodiment of the invention, the CD69 inhibitor is any suitable agent that inhibits the expression of one or both of CD69 mRNA and CD69 protein. The CD69 inhibitor can be a nucleic acid at least about 10 nucleotides in length that specifically binds to and is complementary to a target nucleic acid encoding one or both of CD69 mRNA and CD69 protein, or a complement thereof. The CD69 inhibitor may be introduced into the isolated tumor-reactive T cells, wherein the cells are capable of expressing one or both of CD69 mRNA and CD69 protein, in an effective amount for a time and under conditions sufficient to interfere with expression of one or both of CD69 mRNA and CD69 protein, respectively.

In an embodiment of the invention, one or both of the CD39 inhibitor and CD69 inhibitor may be an artificially engineered nuclease that inhibits expression of CD39 or CD69, respectively. For example, one or both of CD39 and CD69 expression may be inhibited in the isolated tumor-reactive T cells using a genome editing technique. Genome editing techniques can modify gene expression in a target cell by inserting, replacing, or removing DNA in the genome using an artificially engineered nuclease. Examples of such nucleases may include zinc finger nucleases (ZFNs) (Gommans et al., *J Mol. Biol.,* 354(3): 507-519 (2005)), transcription activator-like effector nucleases (TALENs) (Zhang et al., *Nature Biotechnol.,* 29: $149^{-}$ 153 (2011)), the CRISPR/Cas system (Cheng et al., *Cell Res.,* 23: 1163-71 (2013)), and engineered meganucleases (Riviere et al., *Gene Ther.,* 21(5): $529^{-}$ 32 (2014)). The nucleases create specific double-stranded breaks (DSBs) at targeted locations in the genome, and use endogenous mechanisms in the cell to repair the induced break by homologous recombination (HR) and nonhomologous end-joining (NHEJ). Such techniques may be used to achieve inhibition of one or both of the CD39 and CD69 in the isolated tumor-reactive T cells. Accordingly, in an embodiment of the invention, one or both of the CD39 inhibitor and CD69 inhibitor is/are CRISPR-Cas agent(s), zinc finger agent(s), or TALEN agent(s). The TALEN agent(s) may comprise transcription activator-like effectors (TALEs) which bind to the CD39 or CD69 gene and a TALEN. The zinc finger agent(s) may comprise zinc-finger nucleases which bind to the CD39 or CD69 gene.

In an embodiment of the invention, the methods employ the CRISPR/Cas system. Accordingly, the inventive method may comprise introducing a nucleic acid encoding a Cas endonuclease and a nucleic acid encoding a single guide RNA (sgRNA) molecule into the isolated tumor-reactive T cells, wherein the sgRNA hybridizes to the CD39 or CD69 gene in the isolated tumor-reactive T cells, and forming a complex between the sgRNA and Cas endonuclease so that the Cas endonuclease introduces a double strand break in the CD39 or CD69 gene. Non-limiting examples of Cas endonucleases include Cas1 B, Cas2, Cas3, Cas4, Cas5, Cas6, Cas7, Cas8, Cas9 (also known as Csn1 and Csxl2), Cas1O, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, and Csxl7. Preferably, the Cas endonuclease is Cas9. Preferably, the sgRNA specifically hybridizes to the CD39 or CD69 gene such that the sgRNA hybridizes to the CD39 or CD69 gene, respectively, and does not hybridize to any other gene that is not the CD39 or CD69 gene, respectively. Accordingly, in an embodiment of the invention, one or both of the CD39 inhibitor and CD69 inhibitor may be CRISPR-Cas agent(s). The CRISPR-Cas agent(s) may comprise a nucleic acid encoding a Cas endonuclease and a nucleic acid encoding a single guide RNA (sgRNA) molecule into the isolated tumor-reactive T cells, wherein the sgRNA hybridizes to the CD39 or CD69 gene in the isolated tumor-reactive T cells.

The method may further comprise deleting all or a portion of one or both of the CD39 gene and the CD69 gene to decrease expression of one or both of the CD39 gene and the CD69 gene, respectively. The expression of one or both of the CD39 gene and the CD69 gene may be decreased by any amount, for example, by about 10%, about 20%, about 30%, about 40%, about 50%, about 60%, about 70%, about 80%, or about 90%. Preferably, expression of one or both of the CD39 gene and the CD69 gene is decreased so that there is no detectable expression of one or both of the CD39 gene and the CD69 gene, respectively.

In some embodiments, RNA interference (RNAi) is employed. In this regard, one or both of the CD39 inhibitor and CD69 inhibitor may comprise an RNAi agent. In an embodiment, the RNAi agent may comprise a small interfering RNA (siRNA), a short hairpin miRNA (shMIR), a microRNA (miRNA), or an antisense nucleic acid.

The sgRNA or RNAi agent, e.g., siRNA, shRNA, miRNA, and/or antisense nucleic acid can comprise overhangs. That is, not all nucleotides need bind to the target sequence. The sgRNA or RNAi nucleic acids employed can be at least about 19, at least about 40, at least about 60, at least about 80, at least about 100, at least about 120, at least about 140, at least about 160, at least about 180, at least about 200, at least about 220, at least about 240, from about 19 to about 250, from about 40 to about 240, from about 60 to about 220, from about 80 to about 200, from about 60 to about 180, from about 80 to about 160, and/or from about 100 to about 140 nucleotides in length.

The sgRNA or RNAi agent, e.g., siRNA or shRNA, can be encoded by a nucleotide sequence included in a cassette, e.g., a larger nucleic acid construct such as an appropriate vector. Examples of such vectors include lentiviral and adenoviral vectors, as well as other vectors described herein with respect to other aspects of the invention. An example of a suitable vector is described in Aagaard et al. *Mol. Ther.,* 15(5): 938-45 (2007). When present as part of a larger nucleic acid construct, the resulting nucleic acid can be longer than the comprised sgRNA or RNAi nucleic acid, e.g., greater than about 70 nucleotides in length. In some embodiments, the RNAi agent employed cleaves the target mRNA. In other embodiments, the RNAi agent employed does not cleave the target mRNA.

Any type of suitable sgRNA, siRNA, miRNA, and/or antisense nucleic acid can be employed. In an embodiment, the antisense nucleic acid comprises a nucleotide sequence complementary to at least about 8, at least about 15, at least about 19, or from about 19 to about 22 nucleotides of a nucleic acid encoding one or both of CD39 mRNA and CD39 protein or a complement thereof (or one or both of CD69 mRNA and CD69 protein or a complement thereof). In an embodiment, the siRNA may comprise, e.g., trans-acting siRNAs (tasiRNAs) and/or repeat-associated siRNAs (rasiRNAs). In another embodiment, the miRNA may comprise, e.g., a short hairpin miRNA (shMIR).

In an embodiment of the invention, one or both of the CD39 inhibitor and CD69 inhibitor may inhibit or down-regulate to some degree the expression of the encoded protein, e.g., at the DNA, RNA, or other level of regulation. In this regard, isolated tumor-reactive T cells comprising the CD39 inhibitor express none of one or both of CD39 mRNA and CD39 protein or lower levels of one or both of CD39 mRNA and CD39 protein as compared to a T cell that lacks a CD39 inhibitor. Similarly, isolated tumor-reactive T cells comprising the CD69 inhibitor express none of one or both of CD69 mRNA and CD69 protein or lower levels of one or both of CD69 mRNA and CD69 protein as compared to a T cell that lacks a CD69 inhibitor. In accordance with an embodiment of the invention, the CD39 inhibitor or CD69 inhibitor can target a nucleotide sequence of a CD39 gene or CD69 gene, respectively, or mRNA encoded by the same. Examples of human CD39 and CD69 sequences are set forth in Table 1. Other CD39 and CD69 sequences can be employed in accordance with the invention. Human and mouse antisense nucleic acids are commercially available (e.g., from OriGene Technologies, Inc., Rockville, MD or Sigma-Aldrich, St. Louis, MO) and can be prepared using the nucleic acid sequences encoding the CD39 and CD69 proteins disclosed herein and routine techniques.

TABLE 1

| Genbank Accession No. | Name |
|---|---|
| NM_001776.6 | ectonucleoside triphosphate diphosphohydrolase 1 (CD39) isoform 1 (SEQ ID NO: 1) |
| NP_001767.3 | ectonucleoside triphosphate diphosphohydrolase 1 isoform 1 (SEQ ID NO: 2) |
| NM_001098175.2 | ectonucleoside triphosphate diphosphohydrolase 1 isoform 2 (SEQ ID NO: 3) |
| NP_001091645.1 | ectonucleoside triphosphate diphosphohydrolase 1 isoform 2 (SEQ ID NO: 4) |
| NM_001164178.1 | ectonucleoside triphosphate diphosphohydrolase 1 isoform 3 (SEQ ID NO: 5) |

TABLE 1-continued

| Genbank Accession No. | Name |
|---|---|
| NP_001157650.1 | ectonucleoside triphosphate diphosphohydrolase 1 isoform 3 (SEQ ID NO: 6) |
| NM_001164179.2 | ectonucleoside triphosphate diphosphohydrolase 1 isoform 4 (SEQ ID NO: 7) |
| NP_001157651.1 | ectonucleoside triphosphate diphosphohydrolase 1 isoform 4 (SEQ ID NO: 8) |
| NM_001164181.1 | ectonucleoside triphosphate diphosphohydrolase 1 isoform 5 (SEQ ID NO: 9) |
| NP_001157653.1 | ectonucleoside triphosphate diphosphohydrolase 1 isoform 5 (SEQ ID NO: 10) |
| NM_001164182.2 | ectonucleoside triphosphate diphosphohydrolase 1 isoform 6 (SEQ ID NO: 11) |
| NP_001157654.1 | ectonucleoside triphosphate diphosphohydrolase 1 isoform 6 (SEQ ID NO: 12) |
| NM_001320916.1 | ectonucleoside triphosphate diphosphohydrolase 1 isoform 7 (SEQ ID NO: 13) |
| NP_001307845.1 | ectonucleoside triphosphate diphosphohydrolase 1 isoform 7 (SEQ ID NO: 14) |
| NM_001781.2 | early activation antigen CD69 (SEQ ID NO: 15) |
| NP_001772.1 | early activation antigen CD69 (SEQ ID NO: 16) |

In accordance with an embodiment of the invention, the CD39 inhibitor and CD69 inhibitor can target a nucleotide sequence selected from the group consisting of the 5' untranslated region (5' UTR), the 3' untranslated region (3' UTR), and the coding sequence of CD39 and CD69, respectively, complements thereof, and any combination thereof. Any suitable CD39 or CD69 target sequence can be employed. In an embodiment of the invention, the sequences of the CD39 inhibitor can be designed against a human CD39 with the sequence of SEQ ID NO: 1 but also recognize the sequence of SEQ ID NO: 3 (or vice-versa). In an embodiment of the invention, the sequences of the CD39 inhibitor can be designed against any one of the seven CD39 nucleotide sequences set forth in Table 1, but also recognize any one or more of the other six nucleotide sequences set forth in Table 1. The CD39 and CD69 inhibitors can be designed against any appropriate CD39 or CD69 DNA or mRNA sequence, respectively.

In still another embodiment of the invention, one or both of the CD39 inhibitor and CD69 inhibitor is/are an agent(s) which epigenetically inhibits expression of CD39 or CD69, respectively. Epigenetic modification of gene expression involves changes in gene expression that do not involve changes to the underlying DNA sequence. Epigenetic modification involves a change in phenotype without a change in genotype which, in turn, affects how cells read the gene.

Of course, the method of the invention can employ two or more CD39 inhibitors, any of which may be the same or different from one another. Likewise, the method of the invention can employ two or more CD69 inhibitors, any of which may be the same or different from one another.

Alternatively or additionally, the CD39$^{-}$CD69$^{-}$ phenotype may be induced in isolated tumor-reactive T cells by modifying the isolated, tumor-reactive T cells to induce and/or inhibit expression of one or more of a variety of markers. In this regard, an embodiment of the invention provides a method of preparing a population of cells enriched for T cells with a CD3$^{+}$CD39$^{-}$CD69$^{-}$ phenotype, the method comprising isolating tumor-reactive T cells from a tumor sample of a patient. Isolating tumor-reactive T cells from the tumor sample of the patient may be carried out as described herein with respect to other aspects of the invention.

The method may further comprise modifying the isolated, tumor-reactive T cells to (i) induce expression of one or more of the following markers: AHNAK$^{+}$, AL592183.1$^{+}$, ANXA1$^{+}$, ANXA4$^{+}$, AQP3$^{+}$, ATM$^{+}$, BIN1$^{+}$, C10orf54$^{+}$, C11orf21$^{+}$, C16orf54$^{+}$, CCDC109B$^{+}$, CD27$^{+}$, CD52$^{+}$, CD55$^{+}$, CD8B$^{+}$, CDC25B$^{+}$, CDC42SE1$^{+}$, CLEC2B$^{+}$, CLIC3$^{+}$, CLUAP1$^{+}$, CRBN$^{+}$, CTD-3184A7.4$^{+}$, DDI2$^{+}$, DND1$^{+}$, EMP3$^{+}$, EPB41$^{+}$, ERN1$^{+}$, FAIM3$^{+}$, FAM65B$^{+}$, FBXL8$^{+}$, FGFBP2$^{+}$, GADD45B$^{+}$, GIMAP4$^{+}$, GIMAP7$^{+}$, GPR155$^{+}$, GZMM$^{+}$, HSD17B11$^{+}$, IL10RA$^{+}$, IL7R$^{+}$, ISG20$^{+}$, KANSL1-AS1$^{+}$, KLF2$^{+}$, KLHL24$^{+}$, LDLRAP1$^{+}$, LEF1$^{+}$, LGALS3$^{+}$, LINC00861$^{+}$, LITAF$^{+}$, LYAR$^{+}$, MAPKAPK5-AS1$^{+}$, MED15$^{+}$, MIAT$^{+}$, MIR142$^{+}$, MXI1, MYC$^{+}$, NEAT1$^{+}$, NOSIP$^{+}$, ODF2L$^{+}$, P2RY8$^{+}$, PDE6G, PIK3IP1$^{+}$, PLEC$^{+}$, PLP2$^{+}$, PPP2R5C$^{+}$, PXN$^{+}$, R3HDM4$^{+}$, RAMP1$^{+}$, RASA3$^{+}$, RASGRP2$^{+}$, RCBTB2$^{+}$, RNASET2$^{+}$, RP11-395B7.4$^{+}$, RP11-539L10.2$^{+}$, RP11-640M9.1$^{+}$, S100A10$^{+}$, S100A4$^{+}$, S100A6$^{+}$, S1PR1$^{+}$, S1PR4$^{+}$, SAMD3$^{+}$, SELL$^{+}$, SH3BP5$^{+}$, SIGIRR$^{+}$, SLAMF6$^{+}$, SLCO3A1$^{+}$, SORL1$^{+}$, STK38$^{+}$, SYNJ2$^{+}$, TCF7$^{+}$, TIMP1$^{+}$, TRADD$^{+}$, TSC22D3$^{+}$, TSPAN32$^{+}$, TXNIP$^{+}$, UBXN11$^{+}$, VCL$^{+}$, VNN2$^{+}$, YPEL3$^{+}$, ZFP36L2$^{+}$, ZNF276$^{+}$, and ZNF683$^{+}$, and/or (ii) inhibit expression of one or more of the following markers: ACOT7$^{+}$, ADAM19$^{+}$, AGPAT9$^{+}$, AGTRAP$^{+}$, AIF1$^{+}$, ASPM$^{+}$, ATAD2$^{+}$, AURKA$^{+}$, AURKB$^{+}$, BIRC3$^{+}$, BIRC5$^{+}$, BRCA1$^{+}$, C15orf48$^{+}$, CASC5$^{+}$, CCL3$^{+}$, CCNA2$^{+}$, CCNB1$^{+}$, CCNB2$^{+}$, CCND2$^{+}$, CD38$^{+}$, CD40LG$^{+}$, CD69$^{+}$, CD8B$^{+}$, CDC20$^{+}$, CDCA3$^{+}$, CDCA8$^{+}$, CDK1$^{+}$, CDKN3$^{+}$, CDT1$^{+}$, CENPA$^{+}$, CENPE$^{+}$, CENPF$^{+}$, CENPM$^{+}$, CENPW$^{+}$, CEP55$^{+}$, CISH$^{+}$, CKS1B$^{+}$, CKS2$^{+}$, CLSPN$^{+}$, CRTAM$^{+}$, CSF2$^{+}$, DLGAP5$^{+}$, DUSP5$^{+}$, DUSP6$^{+}$, DUT$^{+}$, EGR1$^{+}$, ENTPD1$^{+}$, FEN1$^{+}$, GINS2$^{+}$, GTSE1$^{+}$, H2AFX$^{+}$, HIST1H4C$^{+}$, HLA$^{+}$DQA2$^{+}$, HMMR$^{+}$, IFI27$^{+}$, IFNG$^{+}$, IL2RA$^{+}$, IL5$^{+}$, KIAA0101$^{+}$, KIF11$^{+}$, KIF23$^{+}$, KPNA2$^{+}$, KRT7$^{+}$, MAD2L1$^{+}$, MCM7$^{+}$, MKI67$^{+}$, MX1$^{+}$, MYBL2$^{+}$, NCAPG, NDC80$^{+}$, NDFIP2$^{+}$, NUDT1$^{+}$, NUSAP1$^{+}$, ORC6$^{+}$, PBK$^{+}$, PCNA$^{+}$, PLK1$^{+}$, RPL39L$^{+}$, RRM2$^{+}$, SGOL2$^{+}$, SHCBP1$^{+}$, SMC2$^{+}$, SPC25$^{+}$, STMN1$^{+}$, TESC$^{+}$, TK1$^{+}$, TNF$^{+}$, TNFRSF18$^{+}$, TNFSF10$^{+}$, TOP2A$^{+}$, TPM4$^{+}$, TPX2$^{+}$, TUBA1B$^{+}$, TUBA1C$^{+}$, TUBB$^{+}$, TYMS$^{+}$, UBE2C$^{+}$, UBE2S$^{+}$, UBE2T$^{+}$, XCL1$^{+}$, and ZWINT$^{+}$, wherein inducing expression of one or more of the markers of (i) and/or inhibiting expression of one or more of the markers of (ii) induces the T cells to have the CD3$^{+}$CD39$^{-}$CD69$^{-}$ phenotype. In an embodiment of the invention, the method may further comprise modifying the isolated, tumor-reactive T cells to induce expression of any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of the markers of (i) listed in this paragraph. In an embodiment of the invention, the method may further comprise modifying the isolated, tumor-reactive T cells to induce expression of all of the markers listed in (i) of this paragraph. In an embodiment of the invention, the method may further comprise modifying the isolated, tumor-reactive T cells to inhibit expression of any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of the markers listed in (ii) this paragraph. In an embodiment of the invention, the method may further comprise modifying the isolated, tumor-reactive T cells to inhibit all of the markers listed in (ii) of this paragraph. Inducing and inhibiting expression of one or more of the markers may be carried out in any of a variety of ways known in the art. For example, the genome editing techniques described herein with respect to other aspects of the invention may be used to induce and/or inhibit expression of the one or more markers in the isolated tumor-reactive T cells. In another embodiment of the invention, the isolated tumor-reactive T cells may be modified (e.g., electroporated, transduced or transfected) so as to comprise a nucleic acid encoding one or more of the markers. The nucleic acid encoding the one or more markers may be carried in a recombinant expression vector.

In an embodiment of the invention, the method further comprises introducing a nucleic acid encoding an exogenous TCR into the cells in the population enriched for T cells with the phenotype under conditions to express the exogenous TCR by the cells. By "exogenous" is meant that the TCR is not native to (naturally-occurring on) the T cell. The exogenous TCR may be a recombinant TCR. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the recombinant TCR can be a chimeric or hybrid TCR comprised of amino acid sequences derived from TCRs from two different mammalian species. For example, the antigen-specific TCR can comprise a variable region derived from a murine TCR, and a constant region of a human TCR such that the TCR is "humanized." Any exogenous TCR having antigenic specificity for a cancer antigen (e.g., neoantigen) may be useful in the inventive methods. The TCR generally comprises two polypeptides (i.e., polypeptide chains), such as an α-chain of a TCR, a β-chain of a TCR, a γ-chain of a TCR, a δ-chain of a TCR, or a combination thereof. Such polypeptide chains of TCRs are known in the art. The cancer antigen-specific TCR can comprise any amino acid sequence, provided that the TCR can specifically bind to and immunologically recognize a cancer antigen or epitope thereof. Examples of exogenous TCRs that may be useful in the inventive methods include, but are not limited to, those disclosed in, for example, U.S. Pat. Nos. 7,820,174; 7,915,036; 8,088,379; 8,216,565; 8,431,690; 8,613,932; 8,785,601; 9,128,080; 9,345,748; 9,487,573; 9,879,065 and U.S. Patent Application Publication Nos. 2013/0116167; and 2014/0378389, each of which is incorporated herein by reference.

In an embodiment of the invention, the method further comprises introducing a nucleic acid encoding a chimeric antigen receptor (CAR) into the cells in the population enriched for T cells with the phenotype under conditions to express the CAR by the cells. Typically, a CAR comprises the antigen binding domain of an antibody, e.g., a single-chain variable fragment (scFv), fused to the transmembrane and intracellular domains of a TCR. Thus, the antigenic specificity of the CAR can be encoded by a scFv which specifically binds to the cancer antigen, or an epitope thereof. Any CAR having antigenic specificity for a cancer antigen may be useful in the inventive methods. Examples of CARs that may be useful in the inventive methods include, but are not limited to, those disclosed in, for example, U.S. Pat. Nos. 8,465,743; 9,266,960; 9,765,342; 9,359,447; 9,765,342; 9,868,774; 10,072,078; and 10,287,350, each of which is incorporated herein by reference.

The term "cancer antigen," as used herein, refers to any molecule (e.g., protein, polypeptide, peptide, lipid, carbohydrate, etc.) solely or predominantly expressed or over-expressed by a tumor cell or cancer cell, such that the antigen is associated with the tumor or cancer. The cancer antigen can additionally be expressed by normal, non-tumor, or non-cancerous cells. However, in such cases, the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor, or non-cancerous cells. Also, the cancer antigen can additionally be expressed by cells of a different state of development or maturation. For instance, the cancer antigen can be additionally expressed by cells of the embryonic or fetal stage, which cells are not normally found in an adult host. Alternatively, the cancer antigen can be additionally expressed by stem cells or precursor cells, which cells are not normally found in an adult host. Examples of cancer antigens include, but are not limited to, mesothelin, CD19, CD22, CD30, CD70, CD276 (B7H3), gp100, MART-1, Epidermal Growth Factor Receptor Variant III (EGFRVIII), Vascular Endothelial Growth Factor Receptor 2 (VEGFR-2), TRP-1, TRP-2, tyrosinase, human papillomavirus (HPV) 16 E6, HPV 16 E7, NY-BR-1, NY-ESO-1 (also known as CAG-3), SSX-2, SSX-3, SSX-4, SSX-5, SSX-9, SSX-10, MAGE-A1, MAGE-A2, BRCA, MAGE-A3, MAGE-A4, MAGE-A5, MAGE-A6, MAGE-A7, MAGE-A8, MAGE-A9, MAGE-A10, MAGE-A11, MAGE-A12, HER-2, etc. In an embodiment of the invention, the cancer antigen may be a mutated antigen that is expressed or overexpressed by tumor or cancer cells and which is not expressed by normal, non-tumor, or non-cancerous cells. Examples of such cancer antigens may include, but are not limited to, mutated KRAS and mutated p53. T cells having antigenic specificity for a cancer antigen may, advantageously, reduce or avoid cross-reactivity with normal tissues such as, for example, that which may occur using T cells having antigenic specificity for minor histocompatibility antigens. In an embodiment of the invention, the cancer antigen is a neoantigen.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

Cell populations enriched for T cells with the phenotype which comprise an endogenous cancer antigen-specific TCR (e.g., cancer neoantigen-specific TCR) can also be transformed, e.g., transduced or transfected, with one or more nucleic acids encoding an exogenous (e.g., recombinant) TCR or other recombinant receptor. Such exogenous receptors, e.g., TCRs, can confer specificity for additional antigens to the transformed T cell beyond the antigens for which the endogenous TCR is naturally specific. This can, but need not, result in the production of T cell having dual antigen specificities.

In an embodiment of the invention, a nucleic acid encoding the exogenous TCR or CAR is introduced into any suitable recombinant expression vector. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector. Examples of recombinant expression vectors that may be useful in the inventive methods include, but are not limited to, plasmids, viral vectors (retroviral vectors, gamma-retroviral vectors, or lentiviral vectors), and transposons. The vector may then, in turn, be introduced into the isolated population of T cells by any suitable technique such as, e.g., gene editing, transfection, transformation, or transduction as described, for example, Green and Sambrook, *Molecular Cloning: A Laboratory Manual* ($4^{th}$ Ed.), Cold Spring Harbor Laboratory Press (2012). Many transfection techniques are known in the art and include, for example, calcium phosphate DNA co-precipitation; DEAE-dextran; electroporation; cationic liposome-mediated transfection; tungsten particle-facilitated microparticle bombardment; and strontium phosphate DNA co-precipitation. Phage or viral vectors can be introduced into host cells, after growth of infectious particles in suitable packaging cells, many of which are commercially available.

In an embodiment of the invention, any of the inventive methods described herein further comprise expanding the number of cells in the population enriched for T cells with the phenotype obtained by the method. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J Immunother.,* 26:332-42 (2003); and Riddell et al., *J Immunol. Methods,* 128:189$^{-}$ 201 (1990). In an embodiment, expansion of the numbers of T cells is carried out by culturing the T cells with one or more non-specific T cell stimuli and one or more cytokines. Examples of non-specific T cell stimuli include, but are not limited to, one or more of irradiated allogeneic feeder cells, irradiated autologous feeder cells, anti-CD3 antibodies, anti-4-1BB antibodies, and anti-CD28 antibodies. In preferred embodiment, the non-specific T cell stimulus may be anti-CD3 antibodies and anti-CD28 antibodies conjugated to beads. Any one or more cytokines may be used in the inventive methods. Exemplary cytokines that may be useful for expanding the numbers of cells include interleukin (IL)-2, IL-7, IL-21, and IL-15. In an embodiment, expansion of the numbers of T cells is carried out by culturing the T cells with OKT3 antibody, IL-2, and feeder PBMC (e.g., irradiated allogeneic PBMC).

An embodiment of the invention further provides an isolated or purified cell population obtained according to any of the inventive methods. The cell population enriched for T cells with the phenotype produced by the inventive methods may provide any one or more of a variety of advantages. The cell population enriched for T cells with the CD39$^{-}$ CD69$^{-}$ phenotype produced by the inventive methods may provide one or more of increased self-renewal, expansion, persistence, and anti-tumor response in the body of a patient as compared to CD39$^{+}$CD69$^{+}$ T cells.

The term "isolated," as used herein, means having been removed from its natural environment. The term "purified," as used herein, means having been increased in purity, wherein "purity" is a relative term, and not to be necessarily construed as absolute purity. For example, the purity can be at least about 50%, can be greater than about 60%, about 70% or about 80%, about 90% or can be about 100%.

The cell population enriched for T cells with the phenotype produced by the inventive methods may can be a substantially homogeneous population, in which the population comprises mainly T cells produced by any of the inventive methods described herein. The cell population enriched for T cells with the phenotype produced by the inventive methods can also can be a clonal population of cells, in which all cells of the population are clones of a single T cell. In one embodiment of the invention, the population of cells is a clonal population comprising T cells comprising a recombinant expression vector encoding the exogenous TCR or CAR as described herein.

It is contemplated that the cell population enriched for T cells with the phenotype prepared by any of the inventive methods described herein may be included in a composition, such as a pharmaceutical composition. In this regard, an embodiment of the invention provides a method of obtaining a pharmaceutical composition comprising a cell population enriched for T cells with a phenotype, the method comprising obtaining a cell population enriched for T cells with the phenotype according to any of the inventive methods described herein; and combining the cell population enriched for T cells with the phenotype with a pharmaceutically acceptable carrier to obtain a pharmaceutical composition comprising a cell population enriched for T cells with the phenotype.

Preferably, the carrier is a pharmaceutically acceptable carrier. With respect to pharmaceutical compositions, the carrier can be any of those conventionally used for the administration of cells. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier may be determined in part by the particular method used to administer the cell population enriched for T cells with the phenotype. Accordingly, there are a variety of suitable formulations of the pharmaceutical composition of the invention. Suitable formulations may include any of those for parenteral, subcutaneous, intravenous, intramuscular, intraarterial, intrathecal, intratumoral, or interperitoneal administration. More than one route can be used to administer the cell population enriched for T cells with the phenotype, and in certain instances, a particular route can provide a more immediate and more effective response than another route.

Preferably, the cell population enriched for T cells with the phenotype is administered by injection, e.g., intravenously. A suitable pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the dose, e.g., number of T cells administered should be sufficient to effect, e.g., a therapeutic or prophylactic response, in the mammal over a reasonable time frame. For example, the number of T cells administered should be sufficient to bind to a cancer antigen or treat or prevent cancer in a period of from about 2 hours or longer, e.g., 12 to 24 or more hours, from the time of administration. In certain embodiments, the time period could be even longer. The number of T cells administered will be determined by, e.g., the efficacy of the particular population of T cells to be administered and the condition of the mammal (e.g., human), as well as the body weight of the mammal (e.g., human) to be treated.

Many assays for determining an administered number of T cells are known in the art. For purposes of the invention, an assay, which comprises comparing the extent to which target cells are lysed or one or more cytokines such as, e.g., IFN-γ and IL-2 is secreted upon administration of a given number of such T cells to a mammal among a set of mammals of which is each given a different number of the T cells, could be used to determine a starting number to be administered to a mammal. The extent to which target cells are lysed or cytokines such as, e.g., IFN-γ and IL-2 are secreted upon administration of a certain number can be assayed by methods known in the art. Secretion of cytokines such as, e.g., IL-2, may also provide an indication of the quality (e.g., phenotype and/or effectiveness) of a T cell preparation.

The number of T cells administered also will be determined by the existence, nature and extent of any adverse side effects that might accompany the administration of a particular population of T cells. Typically, the attending physician will decide the number of T cells with which to treat each individual patient, taking into consideration a variety of factors, such as age, body weight, general health, diet, sex, route of administration, and the severity of the condition being treated. By way of example and not intending to limit the invention, the number of T cells to be administered can be about $10\times10^6$ to about $10\times10^{11}$ cells per infusion, about $10\times10^9$ cells to about $10\times10^{11}$ cells per infusion, or $10\times10^7$ to about $10\times10^9$ cells per infusion.

It is contemplated that the cell populations enriched for T cells with the phenotype produced according to the inventive methods can be used in methods of treating or preventing cancer in a mammal. In this regard, the invention provides a method of treating or preventing cancer in a mammal, comprising administering to the mammal any of the pharmaceutical compositions or populations of T cells described herein in an amount effective to treat or prevent cancer in the mammal.

An embodiment of the invention further comprises lymphodepleting the mammal prior to administering the T cells. Examples of lymphodepletion include, but may not be limited to, nonmyeloablative lymphodepleting chemotherapy, myeloablative lymphodepleting chemotherapy, total body irradiation, etc.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset or recurrence of the disease, or a symptom or condition thereof.

For purposes of the inventive methods, wherein populations of T cells are administered, the T cells can be cells that are allogeneic or autologous to the mammal. Preferably, the cells are autologous to the mammal.

With respect to the inventive methods, the cancer can be any cancer, including any of leukemia (e.g., B cell leukemia), sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head-neck cancer, acute lymphocytic cancer, acute myeloid leukemia, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer (e.g., colon carcinoma), esophageal cancer, cervical cancer, gastrointestinal carcinoid tumor, hypopharynx cancer, larynx cancer, liver cancer, lung cancer, malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, renal cancer, small intestine cancer, soft tissue cancer, stomach cancer, testicular cancer, thyroid cancer, ureter cancer, and urinary bladder cancer.

The $CD39^{-}CD69^{-}$ T cell phenotype described herein may be useful for selecting therapies for cancer patients. Accordingly, an embodiment of the invention provides a method of selecting a therapy for a cancer patient. This method may comprise obtaining a bulk population of T cells from a tumor sample of a patient. The bulk population of T cells may be obtained from the tumor sample as described herein with respect to other aspects of the invention.

The method may further comprise measuring the proportion of T cells in the bulk population which have a phenotype, wherein the phenotype comprises markers $CD3^{+}$, $CD39^{-}$, and $CD69^{-}$; and comparing the proportion of T cells which have the phenotype to a control. Alternatively or additionally, the method may further comprise measuring the proportion of T cells in the bulk population which lack a phenotype, wherein the phenotype comprises markers $CD3^{+}$, $CD39^{-}$, and $CD69^{-}$; and comparing the proportion of T cells which (lack the phenotype to a control. The control may be, for example, the results of a study already carried out to determine the proportion of T cells which have (or lack) the phenotype in the infusion product administered to responders and non-responders to ACT in a particular cohort, e.g., a particular cancer type. For example, as shown in FIG. 1E, a median greater than 10% (of T cells with the phenotype in the total population) can be defined as being prognostic of potential response to ACT (found in complete responders) for melanoma. As shown in FIGS. 5A-5C, patient infusion products can be classified with a >80% accuracy. The proportion of T cells in the bulk population which have the phenotype may be measured using any suitable method known in the art, for example, flow cytometry.

The method may further comprise selecting the patient for a therapy which is not immunotherapy when (i) the proportion of T cells which have the phenotype is lower than the control or (ii) the proportion of T cells which lack the phenotype is equal to or higher than the control; or (e) selecting the patient for an immunotherapy when (i) the proportion of T cells which have the phenotype is equal to or higher than the control or (ii) the proportion of T cells which lack the phenotype is lower than the control.

Another embodiment of the invention provides a method of treating cancer in a patient. The method may comprise receiving an identification of a therapy selected for a cancer patient, wherein the therapy has been selected by the any of the methods described herein with respect to other aspects of the invention. The method may further comprise (I) treating the patient by administering a therapy which is not immunotherapy to the patient in an amount effective to treat cancer in the patient when (i) the proportion of T cells which have the phenotype is lower than the control or (ii) the proportion of T cells which lack the phenotype is equal to or higher than the control; or (II) treating the patient by administering an immunotherapy to the patient in an amount effective to treat cancer in the patient when (i) the proportion of T cells which have the phenotype is equal to or higher than the control or (ii) the proportion of T cells which lack the phenotype is lower than the control. The control may be as described herein with respect to other aspects of the invention.

Immunotherapy encompasses the treatment of cancer by activating or suppressing the immune system. Examples of immunotherapies include, but are not limited to, NK cell therapy, T cell therapy, B cell therapy, immune checkpoint blockade therapy, chimeric antigen receptor (CAR) therapy, antibody therapy, immune system modulator therapy, anti-cancer vaccine therapy, or any combination thereof. In an embodiment of the invention, the immunotherapy is ACT, immune checkpoint blockade therapy, immune system modulator therapy, T cell therapy, and/or CAR therapy.

Examples of therapies which are not immunotherapy include, but are not limited to, surgical resection, chemotherapy, radiotherapy, stem cell therapy, hormone therapy, targeted drug inhibitor therapy, or any combination thereof.

Another embodiment of the invention provides a method for predicting the clinical response to immunotherapy in a cancer patient. The method may comprise obtaining a bulk population of T cells from a tumor sample from the cancer patient. The bulk population of T cells may be obtained from the tumor sample as described herein with respect to other aspects of the invention. The method may further comprise measuring the proportion of T cells in the bulk population which (i) have or (ii) lack a phenotype, wherein the phenotype comprises markers $CD3^+$, $CD39^-$, and $CD69^-$, which may be carried out as described herein with respect to other aspects of the invention.

The method may further comprise comparing the proportion of T cells which (i) have or (ii) lack the phenotype to a control. The method may further comprise identifying the patient as likely to have a negative clinical response to the immunotherapy when (i) the proportion of T cells which have the phenotype is lower than the control or (ii) the proportion of T cells which lack the phenotype is equal to or higher than the control. Conversely, the method may comprise identifying the patient as likely to have a positive clinical response to the immunotherapy when (i) the proportion of T cells which have the phenotype is equal to or higher than the control or (ii) the proportion of T cells which lack the phenotype is lower than the control. The control may be as described herein with respect to other aspects of the invention.

The method for predicting the clinical response to immunotherapy in a cancer patient may be carried out before immunotherapy is administered to the patient, after immunotherapy is administered to the patient, or both before immunotherapy is administered to the patient and again after immunotherapy is administered to the patient.

The following examples further illustrate the invention but, of course, should not be construed as in any way limiting its scope.

EXAMPLES

The following Materials and Methods were employed in the experiments described in Examples 1-5.

Generation of TILs

Metastatic melanoma tumor deposits were surgically resected and processed for generation of tumor infiltrating lymphocytes (TILs) either by single-cell suspensions generated by enzymatic digest or plate culture of 2-3 $mm^3$ tumor fragments as previously described (Tran et al., *J. Immunother.,* 31: 742-751 (2008); Dudley et al., *J. Immunother.,* 26: 332-342 (2003)). Clinical infusion products were generated by rapid expansion of lymphocytes in culture with irradiated PBMC, anti-CD3 antibody, and IL-2 as previously described (Jin et al., *J. Immunother.,* 35: 283-292 (2012)).

Clinical Protocols

All patients were enrolled in one of the following experimental TIL with IL-2 ACT protocols (NCT00001832, NCT00513604, NCT01319565, NCT01468818, NCT01585415, orNCT01993719) approved by the institution research board of the National Cancer Institute, NIH (Goff et al., *J Clin. Oncol.,* 34: 2389⁻ 2397 (2016); Dudley et al., *Clin. Cancer Res.,* 16: 6122-6131 (2010)). Informed consent was obtained and documented in accordance with the principles set forth in the Declaration of Helsinki. Patients were required to be 18 years of age or older, to have measurable metastatic melanoma, to be of good performance status, to be free of systemic infections, to have received no prior anti-PD-1-targeting therapy, and to be eligible to receive high-dose IL-2 therapy. In addition, for NCT01319565, patients were required to be eligible to receive total body irradiation (TBI). Protocol treatment consisted of a non-myeloablative chemotherapy regimen of cyclophosphamide and fludarabine followed by a single infusion of autologous TILs and high-dose IL-2 to tolerance. A subset of patients received TBI during chemotherapy before cell infusion. Baseline cross-sectional imaging was performed, and extent of disease was evaluated at periodic intervals using Response Evaluation Criteria in Solid Tumors (RECIST) 1.0. Outcomes were classified as complete responses (CR), partial responses (PR) or progressive disease (NR).

Study Cohort Description

Patient samples were drawn from the clinical protocols according to clinical response and specimen availability. To exclude the influence of prior immunotherapies affecting CD8 TIL differentiation states, patients who had received prior anti-PD-1 immunotherapy or genetically engineered T cell or TCR therapies were excluded. Patients with prior anti-CTLA-4 therapy were not excluded. For this study, complete responders (CRs) were defined as any patients who experienced a complete response per RECIST 1.0 criteria. Among the patients whose disease progressed (NRs, non-responders) following ACT, in order to focus on those patients whose TIL showed a complete lack of antitumor efficacy, and to exclude tumor-intrinsic treatment failures (such as acquired resistance due to treatment), non-responders were stringently identified as the subset of patients with progressive disease whose target lesions experienced no greater than 10% reductions at any time following ACT. These criteria thus excluded patients with stable disease and partial responders from this study resulting in 54 patients with viable TIL infusion product samples available for analysis. The clinical endpoint used in the analyses was progression-free survival (PFS) survival, or melanoma-specific survival (MSS) defined as the length of time from treatment start to time of event (melanoma, death attributed to melanoma, or censor).

Mass Cytometry Staining

Frozen patient ACT infusion product samples were thawed in warm media, rested overnight without any cytokines in TIL media (RPMI with 10% human serum, L-Glutamine, and Anti-Anti) with DNAse. All reagents were from Fluidigm except where noted. Cells were first incubated with a 5 μM solution of cisplatin in PBS to mark dead cells. Cells were then washed and resuspended in MAXPAR Cell Staining Buffer (MCSB) (Fluidigm, South San Francisco, CA). Human Fc-receptor blocking solution (BioLegend, San Diego, CA) was added to each sample and incubated for 10 minutes at room temperature. All metal-labeled antibodies were purchased from Fluidigm. Biotin anti-human CD39 (BioLegend) was detected with QDOT-streptavidin conjugate (Thermo Fisher Scientific, Waltham, MA). Antibodies were diluted in MCSB at concentrations validated for minimal channel spill-over, added to each sample, and incubated for 30 minutes at room temperature, with primary staining consisting of anti-CD39 and secondary staining consisting of all other metal-coupled antibodies+Streptavidin (QDOT-streptavidin conjugate). After each staining, cells were washed with MCSB two times. Cells were then fixed for 15 minutes in a 1.6% solution of paraformaldehyde (MilliporeSigma, Burlington, MA) in PBS. Cell intercalation solution was prepared by adding CELL-ID Intercalator-Ir into MAXPAR Fix and Perm Buffer (Fluidigm) to a final concentration of 125 nM. Cells were incubated with cell intercalation solution overnight at 4° C. Cells were then washed once with MCSB and with MAXPAR Water (Fluidigm) twice. Cells were finally resuspended in a water solution containing EQ Four Element Calibration Beads (Fluidigm) at a cell concentration of $10^6$ cells/mL and filtered into cell strainer cap tubes, immediately prior to CyTOF data acquisition. Data were acquired on a HELIOS Mass Cytometer (Fluidigm) as previously described (Bendall et al., *Science.* 332: 687-696 (2011)).

Computational Methods and Statistical Analysis of Mass Cytometry Data

Raw mass cytometry data were normalized with the Normalizer algorithm as recommended by the software developers (Finck et al., *Cytometry A.,* 83: 483-494 (2013)). Data was analyzed using a custom Python script pipeline (available at github.com/Immunodynamics/CyTOF-Processing). Data were first gated as live singlet cells, using [EQ4$^-$Cisplatin$^-$] and [CD45$^+$ DNA(2n)] manual gates (FIG. 5A). Automatic identification of clusters of differentiation based on surface marker expression was performed using Hierarchical Agglomerative Learning (HAL-x). A custom-programmed algorithm (FIG. 5B) relies on cross-validated identification of high-density regions, followed by rapid random forest classification in the 35-dimensional space of surface markers identifying 22 leukocyte populations with distinctive patterns of surface marker expression. HAL-x then labeled all the cells in all samples and computed the inverse hyperbolic sine and normalized frequencies for each leukocyte population. A support-vector machine (SVM) algorithm used the TIL features to determine if samples were taken from patients undergoing complete response (CR) or progressive disease (NR) (FIG. 5C and Table 2). Table 2 shows a confusion matrix for classification of patients for their clinical outcome, based on the phenotype of the T cell infusion products (n=1700 runs). True positive (TP), true negative (TN), false positive (FP) false negative (FN). Subsequent analysis prioritized 10 activation features that best SVM-classify patients according to their clinical outcome.

TABLE 2

| | | Actual Clinical Outcome | |
|---|---|---|---|
| | | CR | NR |
| Predicted Clinical Outcome | CR | TP = 48% | FP = 11% |
| | NR | FN = 10% | TN = 31% |

Mass Cytometry Cluster Visualization

To visualize CyTOF data from the 4.8 million cells acquired from patient infusion products, FLOWJO v10.5.3 software (Ashland, OR) was used. The data was gated on live DNA$^+$, cisplatin$^-$, CD45$^+$ cells, and subsequently gated on CD3$^+$ cells to obtain 2.5 million concatenated T cells. Concatenated T cells from all the patient samples were downsampled to 100,000 cells on FLOWJO software, and gates and sample IDs were retransferred to the downsampled population. Dimensional reduction and clustering was performed using the barnes-hut approximation plugin on the program with the following parameters: Perplexity: 90, Learning rate (ETA): 200, Iterations:1000, Theta: 0.5 and were visualized on the t-SNE space (van der Maaten et al., *Machine Learning,* 87: pp. 33-55 (2012)). Clusters were defined using the autogating function on FLOWJO software. Cluster frequencies and protein expression per marker were exported, z-scaled, and analyzed using R v3.5.2 statistical environment (R. C. Team, R: A language and environment for statistical computing. Vienna, Austria: R Foundation for Statistical Computing (2014)).

Flow Cytometry Phenotyping

Frozen patient ACT I.P. samples were thawed and rested overnight without any cytokines in TIL media (RPM1 with 10% human serum) and DNAse. I.P. cells were washed once in staining buffer (1×PBS, 0.5% BSA, 2 mM EDTA) and stained with the following antibodies: anti-CD3-APC-Cy7, (SK7; 1:25, BD Biosciences, Franklin Lakes, NJ), anti-CD8-PE-Cy7 (RPA-T8, 1:300, BD Biosciences), anti-CD4-BV785 (OKT4; 1:66, BioLegend, San Diego, CA), anti-CD39$^-$ FITC (A1; 1:200, BioLegend), anti-CD69$^-$ APC (FN50; 1:25, BD Biosciences, Franklin Lakes, NJ), anti-PD-1-AF700 (EH12.2H7; 1:66, BioLegend), anti-TIM3-BV650 (7D3; 1:100, BD Biosciences), anti-CD62L-BV421 (DREG-56; 1:50, BioLegend), anti-SLAMF6-PE (hSF6.4.20, 1:50, BD Biosciences), anti-CD27-BV421 (0323, 1:50, BioLegend). Samples incubated for 30 min on ice then washed twice and resuspended in staining buffer with propidium iodide to exclude dead cells. For intracellular staining of TCF7, I.P. TILs were washed twice and fixed using TRUE-NUCLEAR Transcription Factor Buffer Set (BioLegend) according to manufacturer's instructions. Fixed and permeabilized cells were washed once and then anti-TCF7-PE antibody (1:50) was added for 20 minutes washed twice, followed by staining with CD3, CD8, CD39 and CD69 antibodies as described above. For neoantigen tetramer phenotyping samples were stained with tetramer first before adding the antibodies above. Samples were acquired on the BD LSRFORTESSA cell analyzer (BD Biosciences) and analyzed on FLOWJO v10.5.3 software. Frequencies of DN, DP, SP, and individual markers were acquired for each patient in two independent biological replicates and the median % was used to compare CRs and NRs.

Statistical Analysis

For CyTOF visual cluster comparisons, responder and non-responder clusters were first assessed using Shapiro-Wilk test for normality, and their frequencies were then compared by the Wilcoxon rank-sum test. P-values were corrected with Bonferroni multiple corrections and considered for statistical significance with an alpha of 0.05. All flow cytometric comparisons between CR and NR I.P. were similarly analyzed using the two-sided Wilcoxon rank-sum test with standard statistical significance levels *P<0.05 P<0.01 *P<0.001 **P<0.0001. Survival analyses (PFS and MSS) were performed using the Kaplan-Meier estimator. Briefly, median T cell numbers infused in the I.P. were first calculated by adjusting total reported cells infused with % of $CD3^+$ cells, and by then calculating CD8, DN, and DP % of CD3 to estimate the total CD8 cells infused, total DN cells infused and DP cells infused per each patient. Median was used to stratify high vs. low cell numbers (FIG. 1A-1I) and tertiles of cell numbers (FIG. 6A-6C**) were used to stratify low, medium, and high cell numbers infused for each of the populations. Mantel-Cox log-rank test was used to determine statistical significance of the survival distributions between patients with calculated hazard ratios (HR). DN versus DP marker expression and progenitor-daughter population was compared using paired t-tests and multi-cytokine comparison was done using paired Wilcoxon tests. For tetramer analyses, all neoantigen-specific TILs were expressed as a % of $tetramer^+$ and CR vs. NR sub-group analysis was done using the Wilcoxon rank-sum test adjusting for Bonferroni correction for multiple group comparisons. For differential gene expression analyses, a false discovery rate (FDR) of 0.1 was used to determine DEG genes. Since scRNA data is non-parametric, all CR vs. NR comparisons were performed using the Wilcoxon rank-sum test corrected by the total cell numbers being compared.

Comparison of the TCR CDR3s in patients was performed with the Wilcoxon-rank sum test. All statistical analysis was either performed on Graphpad v7.05 or in R Statistical Computing environment v3.5.2 (rproject.org) (R. C. Team, R, supra).

Neoantigen Identification

Tumor whole-exome sequencing (WES): genomic DNA (gDNA) was purified from fresh tumor (FrTu) and matched normal from autologous apheresis samples using the Qiagen ALLPREP DNA/RNA kit (Qiagen, Venlo, Netherlands), as per the manufacturer's suggestions. Whole exome library preparations and sequencing were performed by Novogene (Novogene Corporation Inc., Sacramento, CA) using the Agilent SureSelectXT2 Human All Exon V6 Kit for exome capture and Illumina platforms for paired-end, 2×150 bp sequencing at ~200× on-target coverage. Additional WES for previously published patient tumors was performed by Personal Genome Diagnostics, the Broad Institute, and in the Surgery Branch, NCI on tumor tissue and normal peripheral blood cells as previously described (Parkhurst et al., *Cancer Discov.,* 9: 1022-1035 (2019)).

Exome variant calling: alignments were performed using novoalign MPI from Novocraft to human genome build hg19. Duplicates were marked with Picard's MarkDuplicates tool. Indel realignment and base recalibration were carried out according to the GATK best practices workflow. Variants were called using Varscan2, SomaticSniper, Strelka, and Mutect. Following variant calling VCF files were merged using GATK CombineVariants tools and annotated with Annovar. The parameters to retain a called variant are as follows: a tumor and normal coverage of greater than 10, a variant allele frequency of 7% or above, variant read counts of 4 or above, and two of the four callers identifying mutations.

RNA-seg alignment, processing and variant calling: alignments were performed using the STAR two pass method to human genome build hg19. Duplicates were marked and sorted using Picard's MarkDuplicates tool. Reads were then split and trimmed using the GATK SplitNTrim tool, after which indel realignment and base recalibration were performed as done with whole exome data. A pileup file was created using the final recalibrated bam file and variants were called using Varscan2 only.

Tandem minigene screening: minigenes designed as 25mers, centered around mutated amino acids, and encompassing tumor mutations were concatenated into TMGs (10-12 TMGs per patient, 15-20 mingenes per TMG) and synthesized in pcRNA6SL plasmid (Genscript, NJ) for in vitro RNA transcription (mMESSAGE IVT Kit, Thermo Fisher Scientific) to be used for neoantigen identification as described before (Robbins et al., *Nat. Med.,* 19: 747-752 (2013); Parkhurst et al., *Cancer Discov.,* 9: 1022-1035 (2019); Tran et al., *Science,* 344: 641-645 (2014); Zacharakis et al., *Nat. Med.,* 24: 724-730 (2018)). Briefly, autologous patient-derived immature dendritic cells (DC) or CD40L-activated B-cells were generated as previously described (Parkhurst et al., *Cancer Discov.,* 9: 1022-1035 (2019); Zacharakis et al., *Nat. Med.,* 24: 724-730 (2018)), and electroporated with individual TMG RNAs (BTX or Lonza 4D), to be processed and presented by any of the patient's class I HLA molecules. Patient I.P. or pre-infusion TIL was thawed, rested overnight in TIL media with IL-2, and then cocultured the next day with RNA-electroporated autologous APCs and evaluated for recognition via interferon gamma cytokine release by ELISpot and TIL activation by 4-1BB expression as described before (Parkhurst et al., *Cancer Discov.,* 9: 1022-1035 (2019)). Once positive "hits" of TMGs were obtained in the preliminary screen, predicted candidate HLA class I minimal peptides from each potential TMG hit were synthesized using fmoc chemistry in-house. Autologous APCs were peptide pulsed in an independent deconvolution experiment (10 ug/mL) to evaluate IFNγ ELISpot and 4-1BB TIL activation to identify candidate minimal neoepitopes. Potential minimal peptides were then resynthesized at HPLC purity (Genscript, NJ) to be further used for HLA-restriction mapping (described below) and mutation specificity. Mutation specificity tests were done by peptide pulsing HPLC-grade wild-type and mutant peptides at different concentrations on autologous APCs followed by co-culturing with TIL or TCR-transduced cells to determine titration of mutant and wild-type peptides (FIG. 11A-11B).

HLA restriction mapping: rapid transfection of COS7 cells was performed using patient-specific HLA class I alleles. Gene plasmids for each individual HLA allele (100 ng/well) and the tandem minigene (TMG) containing the mutated neoantigen (50 ng/well) were combined with LIPOFECTAMINE 2000 transfection reagent (Thermo Fisher Scientific) in a flat-bottom 96-well plate. COS7 cells were added to the plate at $3\times10^4$ cells/well in culture media containing DMEM, 10% fetal bovine serum, L-glutamine, penicillin/streptomycin, and amphotericin B. Cells were incubated overnight at 37° C. The following day, the cells were washed with PBS, trypsinized, and transferred to an IFNγ capture antibody-coated ELISpot plate for co-culture with T cells ($2\times10^4$ cells/well) in RPMI 1640, 10% human serum, HEPES, L-glutamine, and penicillin/streptomycin. Following overnight co-culture at 37° C., T cell response was measured using IFNγ secretion and expression of CD137/4-1BB by flow cytometry.

Neoantigen TIL Phenotyping

Once mutation specificity was demonstrated by mutant versus wildtype peptide titration of T cell populations, neoantigen-specific T cells in the I.P. were detected and phenotyped using UV exchangeable HLA-monomers for the corresponding HLA as described before (Kvistborg et al., *Sci. Transl. Med.,* 6: 254ra128 (2014)). Briefly, neopeptides with confirmed mutant specificity were produced in-house, and 45 μg of neopeptide was co-incubated with 10 μg UV-exchangeable biotinylated HLA monomer in a 50 μL volume for 90 minutes under 366 nm UV light on ice in dark. Following neopeptide exchange, HLA tetramers were made adding 10 μL of Streptavidin-PE (Thermo Fisher Scientific) and 10 μL of Streptavidin-APC or Streptavidin-BV421 (BioLegend) in 2 μL increments every 15 minutes for 2 hours. Neoepitope tetramers were then centrifuged for 5 minutes 2000 rpm before use. For tetramer staining, cells were first resuspended in 100 μL AIM-V media (Gibco) and 1 mM Dasatinib (Thermo Fisher Scientific) for 30 minutes, followed by 0.5-2 μL tetramer in PE and APC per 100 μL staining buffer for 30 minutes on ice. Tetramer-stained cells were washed once and then phenotyping antibodies were stained and acquired as described above. Dual colored tetramers were used to acquire tetramer$^+$ events and setting of neoantigen gates. Tetramer-PE was used along with other antibodies for phenotyping. Note that Pt. 3713 had other neoantigens that were non tetramerizable but with verified NeoTCRs are shown in S11. Neoantigen TIL phenotypes were expressed as a % of Tetramer+ events to normalize CR and NR neoantigen TILs for phenoyptic comparison.

Neoantigen-Specific TCR (NeoTCR) Identification

Neoantigen-specific tetramer$^+$ TILs from I.P. were sorted using the SH800S Cell Sorter, or the MA900 Multi-Application Cell Sorter (Sony Biotechnologies, San Jose, CA) into 96-well plates with lysis buffer. One of the following two methods were used to identify NeoTCRs.

scRT-PCR: tetramer$^+$ or TMG-reactive TILs were directly sorted into RT-PCR buffer containing gene-specific primers targeting constant regions of human TCRα and TCRβ as well as forward primers pools of TCRα and TCRβ family as described before (Pasetto et al., *Cancer Immunol. Res.,* 4: 734-743 (2016)). Briefly, RT-PCR master mixes were developed using CELLSDIRECT one-step qRT-PCR kit (Thermo Fisher Scientific) using: 50° C. for 15 min, 95° C. for 2 min, 20 cycles of 95° C. 15 sec, 60° C. for 30 sec. A second PCR was individually done for TCRA and TCRB using nested TCRA and TCRB family primers with a touchdown PCR program. 3 μl of the first RT-PCR product was added as template in total 25 μl PCR mix using PLATINUM II Hot-Start PCR Master Mix (Thermo Fisher Scientific). The touchdown cycling conditions were 95° C. 5 min; higher annealing temperature step (94° C. 30 s, 60° C. 15 s, 72° C. 30 min×5 cycles); high annealing temperature step (94° C. 30 s, 55° C. 15 s, 72° C. 30 min×5 cycles), low annealing temperature step (94° C. 30 s, 50° C. 15 s, 72° C. 30 min×40 cycles), 72° C. 10 min; 4° C. The PCR products were purified and sequenced by Sanger method with an internally nested Cα and Cβ regions primers by Beckman Coulter (Schaumburg, IL).

scTCR profiling kit: tetramer$^+$ or TMG-reactive TILs were sorted into plates using either SMARTER Human scTCR a/b Profiling Kit (Takara Bio, Shiga, Japan, Cat #634432) or the Takara SMARTER Human scTCR a/b Profiling Kit—96 (Takara Bio, USA) according to manufacturer instructions. Briefly, single cells from populations of interest were sorted into wells of a 96-well plate and subjected to cDNA synthesis and amplification using SMART technology to incorporate cellular barcoding. cDNA corresponding to TCRα and TCRβ transcripts was further amplified and prepared for sequencing on an Illumina MiSeq instrument. Sequencing was performed by paired-end, 2×300 bp reads using the MiSeq Reagent Kit v3 (600 cycle) (Illumina, San Diego, CA, MS-102-3003). Read extraction and clonality counts were determined by MiXCR package (milaboratory.com/software/mixcr/). Both methods yielded TCRs that were reconstructed in the pMSGV1 vector with a murine constant TCR that was transduced into a healthy donor PBL for in vitro testing of wild-type and mutant neoepitopes as described above (Pasetto et al., *Cancer Immunol. Res.,* 4: 734-743 (2016); Parkhurst et al., *Clin. Cancer Res.* 23: 2491-2505 (2017)).

Single-Cell Transcriptome Analysis

Single-cell capture and library preparation: TILs were washed in PBS with 0.04% BSA twice by pelleting cells at 300 g for 5 min at 4° C. in a swinging-bucket centrifuge. Cells were counted for cell viability on LUNAFL automated fluorescent cell counter (Logos Biosystems, South Korea) using AO-PI. Cells were partitioned and lysed, followed by reverse transcription of mRNA with single-cell barcoding performed using the Chromium controller with either 3' gene expression chemistry v3.0 or with 5' immune cell profiling chemistry v1.0 and v1.1 (10× Genomics, Pleasanton, CA). Single-cell cDNA amplification, TCR enrichment, and library preparation was performed according to respective user guides. Following patient I.P. was sequenced using 3' GEX v3.0 for transcriptome: 2984-NR, 2990-NR, 3504-NR 3408-NR, 3870-NR, 3905-CR, 3418-CR, 3664-CR, 3733-CR, 3835-CR. The following patient I.P. were sequenced using 5' GEX+TCR v1.0 for combined RNA transcriptome and TCR identification: 3713-CR and 4000-NR.

Single-cell sequencing: single-cell gene expression libraries were sequenced on a NEXTSEQ 550 sequencer with an insert read length of 98 base pairs. For samples containing a TCR-enriched library, the VDJ region was sequenced by paired-end 150 base pair sequencing on either a MiSeq or a NEXTSEQ 550 sequencer.

scRNA data processing: sequencing output was processed using the Cell Ranger 3.0 pipeline (10× Genomics). In short, sequencing output was demultiplexed and converted to fastq file sets. The fastqs associated with gene expression libraries were aligned to the GRCh38 reference provided by 10× Genomics (refdata-cellranger-GRCh38-3.0.0) and for TCR libraries, refdata-cellranger-vdj-GRCh38-alts-ensembl-3.1.0. Unique molecular identifier- (UMI-) collapsed read counts were attributed to individual cell barcodes to generate single-cell gene expression matrices, and in the case of TCR libraries, a single-cell TCR clonotype list that included alpha and beta sequences was generated. Sequencing and single-cell assay performance were evaluated to ensure reliable gene expression and TCR clonotype results, with a target read depth of over 30,000 mean reads per single cell for gene expression and over 5,000 mean reads per single cell for VDJ datasets. Gene expression matrices representing the UMI-collapsed reads count per annotated gene for each cell barcode were generated. Cells with less than 200 genes and genes with less than 5 read counts across all cells were filtered out of the expression matrix. TCR clonotypes were defined based on TCR variable CDR3β nucleotide sequences, and single cells with two different TCR variable CDR3β nucleotide sequences (likely doublets) were excluded. The expression matrix was converted to TPM and cell barcodes were used to uniquely match to associated TCR clonotypes. CD4 cells defined by transcriptome were excluded from scRNA analysis. Cells were first normalized with convolution methods (Lun et al., *Genome Biol.,* 17: 75 (2016)). The normalized data was then decomposed using randomized principal component analysis (Halko et al., *SIAM Review,* 53: 217-288 (2011)).

scRNA analysis: all scRNA and scTCR analysis were done using R package Seurat v2.4 (Butler et al., *Nat. Biotechnol.,* 36: 411-420 (2018)). For scRNA transcriptome analysis of responders and non-responders, a single batch-corrected gene expression matrix was used as the input. Briefly, gene expression matrix was subject to standard pre-processing by regressing out highly variable genes and mitochondrial genes followed by normalization and scaling. Principal components (PCs) were generated and elbow and Jackstraw plots were used to define significant PCs for clustering. t-SNE plots were generated by the clustered PCs; clusters and super-clusters were defined for comparing CRs and NRs. Cluster markers were obtained for S.Cluster A and B by comparing individual clusters using default parameters. For combined scRNA/scTCR I.P. analysis (3713-CR and 4000-NR), an individual gene expression matrix was generated for each patient. All TRAV/TRBV genes were excluded to remove endogenous TCR expression as a source of clustering bias prior to processing by Seurat. For two cluster solution, lower resolution clustering of first and second principal components was carried out followed by analysis of frequency distribution of all CR and NR cells to denote Super Cluster A and Super Cluster B. Individual cluster markers were obtained for each cluster by default parameters on Seurat.

Combined scRNA and scTCR analysis: neoepitope-reactive TCR clonotypes (NeoTCRs) associated with individual cell barcodes using TCRB and TCRA CDR3 sequences were generated into an independent metadata file. Cells that had good quality reads for TCRA or TCRB were included in subsequent analysis. NeoTCR$^+$ cell barcode metadata was back-projected ont-SNE transcriptome clusters identified within patient clusters and were scored for DN/DP gene signatures as described below. As noted above, endogenous cellular TCRs were removed to reduce TRAV/TRBV gene expression as a source of clustering bias. Cells which failed pre-processing for transcriptome were excluded from analyses even if they had intact TCRB/TCRA reads.

Differential expression of genes (DEG) analysis: ENTPD1 (CD39) and CD69 transcript expression from single cells in patient I.P. (3664-CR, 3733-CR, 3408-NR, 3504-NR) were used to define CD39$^-$CD69$^-$ cells (bottom two quartiles of CD39, CD69 TPM) and CD39$^+$CD69$^+$ cells (top two quartiles of CD39, CD69 TPM) (FIG. 6A). DEG comparisons between DN and DP single cells were generated with the edgeR package with FDR<0.1 and fold change of 0.5. For public gene signature analysis, a gene signature matrix was generated, derived from ImmunesigDB selected by human gene sets restricted to CD8 T cells and other gene sets for a total of 568 gene sets (Godec et al., *Immunity,* 44: 194-206 (2016)). GSEA was run using default parameters on R as described before in (gsea-msigdb.org/gsea/index.jsp). Top 100 statistically significant genes that were enriched in CD39$^-$CD69$^-$ and CD39$^+$CD69$^+$ were considered as DN and DP gene signatures respectively.

Single-cell gene signature analysis: single-cell gene set enrichment analysis (scGSEA), adapted from single-sample gene set enrichment analysis (ssGSEA), is a rank-based gene signature metric that computes the expression score of a gene list relative to all other genes in RNA expression (bioconductor.org/packages/release/bioc/html/GSVA.html) on a per-sample basis (Şenbabaoğlu et al., *Genome Biol.,* 17: 231 (2016)). In brief, normalized scRNA TIL I.P. data with barcodes was used as input with gene set lists. scGSEA scores for all gene signatures were z-scaled for cross-signature comparisons across cells and samples. Clustered correlation matrix between various gene signatures from single T cells was generated using the R package Corrplot. Top two quartiles of DN and DP scGSEA scores were projected on t-SNE plots to identify clusters enriched in the respective gene signatures. Mean DN, and DP scGSEA scores were used to assess responders and non-responders using the Wilcoxon rank-sum test. Phenotypic fitness scores were calculated as the difference between each cell's DN and DP scGSEA score (DN minus DP) indicating enrichment of relatively stem-like phenotypes at the single cell level. Mean fitness scores were calculated for each patient I.P. and compared between responders and non-responders of ACT and ICB. For cross-study comparison of DN and DP subsets with gene signatures, a correlation matrix was constructed between various gene signatures from single T cells using the package Corrplot and displayed after hierarchical clustering. For TCR clonotype comparison, the mean scGSEA scores of all cells expressing a particular NeoTCR were calculated, projected on t-SNE plots, and compared between clonotypes.

Short-Term TIL Stimulation

Patient I.P. were thawed, rested overnight without cytokines, and DN (CD39$^-$CD69$^-$) and DP (CD39$^+$CD69$^+$) subsets were flow-sorted and rested for one hour. $10^5$ cells per each TIL population were then stimulated with plate-bound anti-CD3/CD28 (Invitrogen, Waltham, MA) for 48 hours in a round-bottom 96-well plate.

Multicytokine Analysis of Stimulated TIL

Following 48 hours of CD3/CD28 stimulation, 96-well plates containing the stimulated TIL were centrifuged for 5 min at 300 g and 25 μL cleared supernatant was subjected to the CD8/NK panel LEGENDPLEX (Cat. #740267, BioLegend) assay using V-bottom plates in technical replicates per manufacturer's instructions. Captured cytokines were analyzed by flow cytometry on the BD LSRFORTESSA cell analyzer (BD Biosciences). Standard curves for each cytokine were generated and concentration of secreted cytokines from stimulated TIL populations were generated using the manufacturer software (VigeneTech v8 from BioLegend).

In Vitro Anti-Tumor TIL Expansion Experiment

3733-CR I.P. was thawed and rested overnight without cytokines. The following day, CD39$^-$CD69$^-$ (DN) and CD39$^+$CD69$^+$ (DP) CD8 T cells were isolated by flow sorting; DN, DP, and bulk I.P. T cells were co-cultured overnight with the autologous 3733-mel tumor cell line at a ratio of 1:1. Tumor-reactive cells were flow-sorted from CD8$^+$4-1BB$^+$ from DN, DP, and bulk populations (DN 4-1BB$^+$, DP 4-1BB$^+$, and bulk 4-1BB$^+$) and $10^5$ cells were subjected to rapid expansion (REP) as described before (Dudley et al., *J. Immunother.,* 26: 332-342 (2003)). At the end of each REP, cells were counted and $10^5$ of the resulting cells were subjected to an additional REP while the remainder were cryopreserved. At the completion of the third REP, cryopreserved samples were thawed and recovered, and tumor reactivity was assessed by co-culture with autologous 3733-mel tumor cell line at a ratio of 1:1 in biological triplicate, with 4-1BB$^+$ as the readout of tumor reactivity. Viable cell numbers were assessed at the end of each REP. For theoretical cell expansion yield calculations (FIG. 16B), the % of 4-1BB$^+$ tumor-reactive fraction was expressed as a % of total $CD8^+$ live cells and the total cell yield from 1e5 cells was used to infer theoretical tumor-specific cell yield.

CDR3β Survey Sequencing and Tracking

Cryopreserved infusion product or PBL samples were thawed, tested for viability, and counted. The cells were either first flow-sorted for markers including CD39 and CD69 as indicated or directly pelleted, snap frozen, and sent to Adaptive Biotechnologies (Seattle, WA) for genomic DNA extraction and IMMUNOSEQ TCRB survey sequencing (v4) (Pasetto et al., *Cancer Immunol. Res.,* 4: 734-743 (2016)). Frequencies of known neoantigen-reactive CDR3β were then compared across different samples from a given patient.

NY-ESO-1-Reactive TCR Phenotyping

For experiments involving the sequencing of T cells from a patient (ESO.CR) treated with NY-ESO-1-specific TCR-transduced cells, thawed I.P. were stained for CD8, NY-ESO-1 TCR (HLA-A*02:01-SLLMWITQC (SEQ ID NO: 17) peptide tetramer, ProImmune, UK) conjugated to APC, CD39-PE, and CD69-FITC, and three populations were isolated for CDR3β survey sequencing: $CD8^+$NY-ESO-1 $TCR^+$ (bulk), $CD8^+$NY-ESO-1 $TCR^+CD39^-CD69^-$ (DN), and $CD8^+$NY-ESO-1 $TCR^+CD39^+CD69^+$ (DP). The true endogenous CDR3β frequencies within the TCR-transduced cells were estimated by normalizing endogenous CDR3β sequences to the frequency of the CDR3β of the NY-ESO-1-specific TCR construct (CASSYVGNTGELFF) (SEQ ID NO: 18). In FIG. 4B, using the normalized NY-ESO-1 TCR-expressing I.P. CDR3β data, the top 20 clones in the infusion bag were divided into DN enriched and DP enriched based on the ratio of the frequency of a given clone in the sorted DN cells to its frequency in the sorted DP cells, any clone with a DN/DP ratio>1 is considered DN enriched and any clone with a DN/DP ratio<1 is considered DP enriched. For FIG. 4C, 1311 top common clones were defined as those present in each of the bulk, DN, and DP populations. They were analyzed for their short-term (7 days) and long-term (51 months) persistence according to the ratios of their frequency within the DN and DP populations of cells sorted from the I.P.

Murine T Cell Culture

Pmel splenocytes were isolated and pulsed with human gp100(25-33) peptide and expanded for 5 days in the presence of 601U IL2 and complete mouse T cell media as previously described (24). (Klebanoff et al., *Clin. Cancer Res.,* 17: 5343-5352 (2011)). Day 5 cells were collected and restimulated with plate bound anti-CD3 (2 μg/ml) and soluble CD28 (1 μg/ml) in the presence of IL2 and expanded until day 10. After 10 days in culture the cells were fractionated into DN ($CD39^-CD69^-$) and DP ($CD39^+CD69^+$) for tumor treatment experiments.

Murine Tumor Treatment

Adult 6-8-week-old female B6 NCR (B6; $Ly5.2^+$) mice were purchased from Charles River Laboratories at NCI Frederick. B6. SJL-Ptprca Pepcb/BoyJ ($Ly5.1^+$) mice obtained from The Jackson Laboratory (Bar Harbor, ME) were maintained under specific pathogen-free conditions. For tumor treatment experiments, female B6 mice aged 6-8 weeks were injected with $3.5\times10^5$ of B16 melanoma cell line that overexpresses the chimeric human/mouse gp100 antigen KVPRNQDWL (SEQ ID NO: 19) (aa25-33) (Hanada et al., *JCI Insight,* 4 (2019), doi:10.1172/jci.insight.124405). The tumor cells were allowed to establish for ten days, and tumor-bearing mice received 6 Gy total body irradiation before the injection of the T cells. One day later, the animals were treated with FACS sorted DN ($CD39^-$ $CD69^-$) and DP ($CD39^+CD69^+$) in two doses (3e5, 5e5 per mouse). Pmel T cells that were in vitro activated and expanded for ten days at the indicated doses. Control mice receiving 1×PBS were included as controls. All treated animals received daily injections of 12 μg IL-2 i.p. for three days. All tumor measurements were performed double-blinded by an independent investigator.

ATAC Sequencing Analysis

ATAC-seq fastq files were aligned to genome build 38 using bowtie2 with—very-sensitive flag. Aligned bam files had duplicates removed using Picard's mark duplicates tool. Mitochondrial reads were removed and peaks were called using Homer v4.11.1 under the peak finding style DNase setting. Bedtools was used to merge overlapping peaks and record counts of 5' end of reads within each peak for each sample. This count matrix was used as input to EdgeR to identify differential regions using estimateGLMTagwiseDisp function. A likelihood ratio test was then performed using glmFit and glmLRT. Peaks were identified as significant if their FDR q-value as <=0.01.

Transcription Factor Motif analysis: All human Transcription factor Motifs were downloaded from CIS-BP database on 07-07-2020. GOMER (Sade-Feldman et al., *Cell,* 176: 404 (2019); Liu et al., *Genome Res.,* 16: 1517-1528 (2006)) was used to generate a binding score for all differential peaks for each motif Python's scipy.stats hypergeom module was used to calculate a minimum hypergeometric mean test over background peak rate (non-significant peaks used to generate background rate for each motif) for each motif for both double positive and double negative peaks using the top N up to 3000 scoring peaks. The p-values were then corrected by Bejamini-Hochberg FDR using python's statsmodels-.sandbox.stats.multicomp multipletests module counting each test as independent.

Example 1

This example demonstrates that a $CD39^-CD69^-$ T cell phenotype in administered T cells is associated with a positive response to ACT.

The phenotypic differences that could distinguish ACT infusion products (I.P.) administered to patients who had complete response to therapy (complete responders, CRs, N=24) from those whose disease progressed following ACT (non-responders, NRs, N=30) (FIG. 1A) was compared. These ACT I.P. were from a cohort of stage IV metastatic melanoma patients who had been treated with autologous in vitro-expanded TILs and had not experienced prior immunotherapies in the form of genetically engineered T cell therapy or anti-PD-1 blockade (Goff et al., *J Clin. Oncol.,* 34: 2389⁻ 2397 (2016); Dudley et al., *Clin. Cancer Res.,* 16: 6122-6131 (2010)).

Initial single-cell analysis of a discovery set of 4.8 million I.P. TILs from 7 CRs and 9 NRs by mass cytometry (CyTOF) revealed heterogeneous expression of 34 cell surface markers. Supervised analysis of TIL CyTOF profiles identified clusters that appeared prevalent in either CRs or NRs (FIG. 1B). Cluster 1, which was four-fold more abundant in CR I.P. relative to NR I.P. (corrected P=0.0264, FIG. 1C), corresponded to $CD8^+$ T cells with abundant CD44, CD27, and CD28, and low expression of TIM3, characterized in prior studies as memory-like (Sade-Feldman et al., *Cell,* 176: 404 (2019)) and stem-like (Jansen et al., *Nature,* 576: 465-470 (2019)) T cells. Notably, cluster 1 also had low expression of inhibitory marker CD39 and T cell activation marker CD69. Machine learning-based unsupervised clustering of T cell activation/exhaustion states to classify patients according to their clinical outcome further confirmed CD69 and CD39 expression as two significant features of most clinical relevance (FIG. 5A-5C). Of note, frequency of cluster 2, with high expression of CD39 and CD69 but lower levels of CD44, CD27, and CD28, trended higher in NR I.P. than in CR I.P., although this difference was not statistically significant (FIG. 1C).

Flow cytometric analysis of the 16 discovery samples defining CD8$^+$CD39$^-$CD69$^-$ cells as members of cluster 1 recapitulated mass cytometry data with high confidence (FIG. 6A-6B). An evaluation of an independent set of 38 I.P. (CRs n=17, NRs n=21) by multi-parameter flow cytometry revealed that the frequency of the CD8$^+$CD39$^-$CD69$^-$ TIL population was 2.5-fold higher in CR I.P. relative to NR I.P. (P=0.0096, % of CD3) supporting the association between this subset and ACT response (FIG. 1D-E). While the total number of infused T cells did not differ significantly between CR and NR I.P. in this set of 38 patient samples, the total number of infused CD8$^+$CD39$^-$CD69$^-$ cells was four-fold higher in CR I.P. than NR I.P. (P=0.0031, FIG. 1F-G). Querying individual markers, there was a modest trend towards an association between CD8$^+$ TIM3$^+$ TILs and non-response to ACT (FIG. 6C). Analyzing patient survival from all 54 patients, it was found that whereas the absolute number of infused CD39$^+$CD69$^+$ T cells, which comprised most of the CD8$^+$ TILs in patient infusion products (FIG. 6C), did not significantly affect melanoma-specific survival (MSS) or progression-free survival (PFS) in this cohort (FIGS. 7A-7C), higher numbers of CD8$^+$CD39–CD69– cells in the I.P. were significantly associated with improved progression-free survival (PFS, P<0.0001, HR=0.255, 95% confidence interval (CI) 0.1257 to 0.5186, FIG. 1H) and melanoma-specific survival (MSS, P<0.0001, HR=0.217, 95% CI 0.101 to 0.463, FIG. 1I) in a dose-dependent manner (FIG. 7A-7C tertile analysis). Furthermore, the ratio of CD8$^+$CD39$^-$CD69$^-$ to CD8$^+$CD39$^+$CD69$^+$ cells in the infusion products significantly affected MSS and PFS, suggesting that the ACT responses in this cohort were associated with the infusion of higher numbers of CD8$^+$CD39$^-$CD69$^-$ cells and not fewer CD8$^+$CD39$^+$CD69$^+$ TILs.

Example 2

This example demonstrates that positive response-associated CD39$^-$CD69$^-$ TILs are in a progenitor memory stem-like state while CD39$^+$CD69$^+$ TILs are in a terminally differentiated state.

To further explore the potential significance of CD8$^+$CD39$^-$CD69$^-$ TIL (cluster 1, double-negative: DN) and the I.P. predominant CD8$^+$CD39$^+$CD69$^+$ TIL (cluster 2, double-positive: DP), the transcriptome profile of these two subsets was evaluated (FIG. 8A). DN TILs had increased expression of quiescent T-stem-cell markers KLF2, TCF7, SIPR1, LEF1$^+$, IL7R$^+$, CD27, and SELL (CD62L) while DP TILs expressed CD38, MK167, GITR, GZMA, TNF, and IFNG found in differentiated, activated T cells (FIG. 8B, Table 3). Unsupervised clustering of 20,672 CD+ TILs by single-cell transcriptome analysis (scRNA) from 10 patient I.P. (5 CRs, 5 NRs) defined 8 clusters (FIG. 2A). Analysis of the distribution of TILs from CR and NR I.P. indicated that they segregated into a two-cluster solution (Sade-Feldman et al., *Cell,* 176: 404 (2019)) defined by S.Cluster.A (Super Cluster A, comprising clusters C0, C2, C5, C6, C7) and S.Cluster.B (Super Cluster B, comprising clusters C1, C3, C4, C8). Responder TILs were distributed more in S.Cluster.A (P=0.0317), while S.Cluster.B largely comprised non-responder TILs (P=0.03, FIG. 2B). TILs in S.Cluster.A were enriched for DN gene signature (81% overlap, FIG. 8C)

while TILs in S.Cluster.B were enriched for DP gene signature. Consistent with these analyses, CR TILs and NR TILs scored by single cell gene set enrichment analysis (scGSEA) of DN and DP gene signatures indicated that CR TILs had higher DN scores on average while NR TILs had higher DP scores ($P<4.5\times10^{-12}$ for both, FIG. 2C).

TABLE 3

| CD39$^-$ CD69$^-$ Signature | CD39$^+$ CD69$^+$ Signature |
|---|---|
| KLF2$^+$ | ENTPD1$^+$ |
| AQP3$^+$ | CD69$^+$ |
| CLIC3$^+$ | RRM2$^+$ |
| LINC00861$^+$ | TYMS$^+$ |
| CD8B$^+$ | CD8B$^+$ |
| FAM65B$^+$ | KIAA0101$^+$ |
| FGFBP2$^+$ | CCL3$^+$ |
| RASA3$^+$ | TUBA1B$^+$ |
| C10orf54$^+$ | MKI67$^+$ |
| SAMD3$^+$ | UBE2C$^+$ |
| CD27$^+$ | HLA-DQA2$^+$ |
| FAIM3$^+$ | CDK1$^+$ |
| S100A110$^+$ | STMN1$^+$ |
| LYAR$^+$ | IL5$^+$ |
| BIN1$^+$ | NDFIP2$^+$ |
| CTD-3184A7.4$^+$ | DUSP6$^+$ |
| KANSL1-AS1$^+$ | CSF2$^+$ |
| UBXN11$^+$ | XCL1$^+$ |
| ZFP36L2$^+$ | UBE2S$^+$ |
| PPP2R5C$^+$ | TOP2A$^+$ |
| LITAF$^+$ | HIST1H4C$^+$ |
| ZNF683$^+$ | AIF1$^+$ |
| S1PR1$^+$ | TUBB$^+$ |
| TCF7$^+$ | CLSPN$^+$ |
| GIMAP4$^+$ | IFI27$^+$ |
| MYC$^+$ | HMMR$^+$ |
| S1PR4$^+$ | EGR1$^+$ |
| CD52$^+$ | KPNA2$^+$ |
| STK38$^+$ | TPX2$^+$ |
| NEAT1$^+$ | ZWINT$^+$ |
| LGALS3$^+$ | TK1$^+$ |
| GZMM$^+$ | CD38$^+$ |
| SORL1$^+$ | UBE2T$^+$ |
| AL592183.1$^+$ | NUSAP1$^+$ |
| R3HDM4$^+$ | PCNA$^+$ |
| MIAT$^+$ | CENPF$^+$ |
| ANXA4$^+$ | H2AFX$^+$ |
| LEF1$^+$ | CRTAM$^+$ |
| TSC22D3$^+$ | ASPM$^+$ |
| IL7R$^+$ | GTSE1$^+$ |
| P2RY8$^+$ | TNFRSF18$^+$ |
| PLEC$^+$ | MYBL2$^+$ |
| ERN1$^+$ | CKS1B$^+$ |
| TSPAN32$^+$ | SPC25$^+$ |
| S100A4$^+$ | CDKN3$^+$ |
| SELL$^+$ | IFNG$^+$ |
| RASGRP2$^+$ | AURKA$^+$ |
| GADD45B$^+$ | FEN1$^+$ |
| C11orf21$^+$ | GINS2$^+$ |
| PIK3IP1$^+$ | CD40LG$^+$ |
| RNASET2$^+$ | AURKB$^+$ |
| S100A6$^+$ | NCAPG$^+$ |
| CCDC109B$^+$ | TNFSF10$^+$ |
| RAMP1$^+$ | PLK1$^+$ |
| RP11-640M9.1$^+$ | IL2RA$^+$ |
| GPR155$^+$ | AGPAT9$^+$ |
| TXNIP$^+$ | CCND2$^+$ |
| CDC25B$^+$ | CENPE$^+$ |
| ISG20$^+$ | CDC20$^+$ |
| TRADD$^+$ | CCNB1$^+$ |
| CRBN$^+$ | SMC2$^+$ |
| GIMAP7$^+$ | BIRC5$^+$ |
| C16orf54$^+$ | TUBA1C$^+$ |
| FBXL8$^+$ | CCNA2$^+$ |
| ODF2L$^+$ | CKS2$^+$ |
| LDLRAP1$^+$ | BIRC3$^+$ |
| MXI1$^+$ | KRT7$^+$ |
| RCBTB2$^+$ | CENPW$^+$ |
| HSD17B11$^+$ | MCM7$^+$ |

TABLE 3-continued

| CD39⁻ CD69⁻ Signature | CD39⁺ CD69⁺ Signature |
|---|---|
| CLEC2B⁺ | ADAM19⁺ |
| EMP3⁺ | TNF⁺ |
| SH3BP5⁺ | C15orf48⁺ |
| RP11-539L10.2⁺ | DLGAP5⁺ |
| MIR142⁺ | DUSP5⁺ |
| CLUAP1⁺ | KIF11⁺ |
| YPEL3⁺ | CCNB2⁺ |
| SLCO3A1⁺ | ACOT7⁺ |
| NOSIP⁺ | CASC5⁺ |
| IL10RA⁺ | PBK⁺ |
| CD55⁺ | CDCA3⁺ |
| RP11-395B7.4⁺ | TESC⁺ |
| MED15⁺ | DUT⁺ |
| ATM⁺ | CENPM⁺ |
| KLHL24⁺ | KIF23⁺ |
| ZNF276⁺ | ATAD2⁺ |
| ANXA1⁺ | SGOL2⁺ |
| PLP2⁺ | TPM4⁺ |
| AHNAK⁺ | AGTRAP⁺ |
| DDI2⁺ | MAD2L1⁺ |
| VNN2⁺ | NDC80⁺ |
| VCL⁺ | NUDT1⁺ |
| EPB41⁺ | CDT1⁺ |
| DND1⁺ | CENPA⁺ |
| MAPKAPK5-AS1⁺ | RPL39L⁺ |
| CDC42SE1⁺ | SHCBP1⁺ |
| PXN⁺ | CDCA8⁺ |
| SYNJ2⁺ | CEP55⁺ |
| SIGIRR⁺ | BRCA1⁺ |
| PDE6G⁺ | ORC6⁺ |
| SLAMF6⁺ | CISH⁺ |
| TIMP1⁺ | MX1⁺ |

Cell surface expression of inhibitory and memory markers was analyzed by flow cytometry within CD39/CD69 TIL subsets from the validation samples (n=38 I.P., FIG. 2D). Lower cell surface expression and coexpression of the exhaustion markers PD-1 and TIM3 in the DN subset relative to single positive (SP, $CD39^+CD69^-$ and $CD39^-CD69^+$) and DP subsets was observed (FIG. 2D, FIG. 9A-9B). Conversely, expression of memory markers CD62L and CD27 and progenitor marker SLAMF6 were increased in DN relative to DP subsets with variable expression within SP populations (FIG. 2D, FIG. 9A-9B). Protein expression of memory stem-like T cell marker TCF7 was five-fold higher in DN TILs relative to DP TILs (P=0.0002, n=18 I.P., FIG. 2E) consistent with the scRNA analysis. Although DN TILs in infusion products expressed higher levels of both SLAMF6 and TCF7 transcripts, TILs coexpressing TCF7 and SLAMF6 were not significantly enriched within DN subsets, and addition of SLAMF6 to DN as a surface marker was comparable to DN alone in delineating TILs associated with survival benefit in this patient subset. By contrast, DP TILs had significantly higher transcript and protein expression of the effector and exhaustion-associated transcription factor TOX relative to DN TILs. Notably, although the transcriptional profile of DN TILs resembled that of peripheral blood stem cell memory (SCM) T cells (Gattinoni et al., *Nat. Med.,* 17: 1290-1297 (2011); Lugli et al., *J Clin. Invest.,* 123: 594-599 (2013)), cell surface expression of the canonical SCM markers CD95 and CCR7 was not associated with the DN phenotype in patient TIL infusion products.

To assess if $CD39^-CD69^-$ I.P. TILs were stem-like T cells, the DN and DP subsets were isolated and stimulated using plate-bound anti-CD3/anti-CD28. Upon T cell receptor (TCR) stimulation, DN TILs underwent self-renewal, and gave rise to both single positive and $CD39^+CD69^+$DP daughter populations, while stimulated DP TILs largely remained in the same DP state, indicating a DN-progenitor state (n=6 I.P., FIG. 2F). Time-course kinetics of the daughter populations indicated that essentially all DN TILs underwent CD69 activation, but a subset of DN TILs (median=17%) rested back to the $CD39^-CD69^-$ stem-like state 5 days after initial stimulation. By contrast, both $CD39^+$ parent populations (CD39 SP and DP) appeared to terminally differentiate into a stable $CD39^+CD69^+$ state after TCR stimulation. In addition, while DP and DN TILs secreted similar levels of IL-2, IFNγ, GZMA, GZMB, and perform in response to polyclonal stimulation, DN TIL stimulation resulted in higher levels of secreted IL-17A, TNF-a, IL-4, sFasL and granulysin than DP TILs (FIG. 10). Taken together, these results indicate that ACT response-associated $CD39^-CD69^-$ TILs are in a progenitor memory stem-like state capable of differentiation into other subsets, whereas the infusion product-dominant $CD39^+CD69^+$ TILs are in a terminally differentiated state.

To understand the key regulators of these two TIL states in the infusion products, matched DN and DP TILs were isolated from three patient infusion products and their epigenetic profiles were analyzed using ATAC (assay for transposase accessible chromatin) sequencing. The presence of 4314 human transcription factor (TF) motifs in open chromatin regions of DN and DP TILs was queried. Open chromatin regions within stem-like DN TILs were enriched for numerous binding sites for SOX and C2H2-ZF family TFs including KLF4, TCF7, $LEF1^+$, and TCF7L1 consistent with those of less differentiated human T cells (Sade-Feldman et al., *Cell,* 176: 404 (2019); Lynn et al., *Nature,* 576: 293-300 (2019)). By contrast, chromatin regions within DP TILs were extensively enriched for multiple binding motifs of bZIP TFs FOSL1, FOS, JUNB, and JUND, indicating that epigenetic imprinting may be involved in maintaining the state of terminal differentiation resulting from chronic tumor cell activation (Lynn et al., *Nature,* 576: 293-300 (2019); Blank et al., *Nat. Rev. Immunol.,* 19: 665-674 (2019)).

To understand if TIL states in the I.P. corresponded to those within fresh tumor, the transcriptome profiles of 6001 $CD8^+$ T cells from a previous melanoma ICB response study (Sade-Feldman et al., *Cell,* 176: 404 (2019)) were re-analyzed using DN and DP gene signatures described above (FIG. 2G). It was found that prior to immune checkpoint therapy, TILs from ICB-responding lesions had higher $CD39^-CD69^-$ signature scores ($P=1.9\times10^{-10}$) than non-responding lesions, while TILs from lesions that progressed during ICB had higher $CD39^+CD69^+$ signature scores ($P<2.2\times10^{-16}$). Hierarchical clustering correlation analysis with T cell dysfunctional and progenitor gene signatures from other recent studies revealed that the signatures of $CD39^-CD69^-$ TILs were most similar to ICB response-associated memory and progenitor-exhausted TILs, while the gene signatures of $CD39^+CD69^+$ TILs were highly correlated with $TOX^+$ and terminally-exhausted TILs associated with poor ICB response (Sade-Feldman et al., *Cell,* 176: 404 (2019); Miller et al., Nat. Immunol., 20: 326-336 (2019); Scott et al., Nature, 571: 270-274 (2019); Tirosh et al., *Science,* 352: $189^-$ 196 (2016)). A phenotypic fitness score was developed, defined as the difference between DN stem-like signature and DP differentiated signature (DN minus DP), and scRNA from ACT I.P. and melanoma ICB TILs were scored. Single-cell fitness scores re-confirmed that responder TILs have on average more stem-like fitness compared to non-responder TILs (FIG. 11A-11B). These data suggest that stem-like TILs found in ACT responder infusion products resemble those found in ICB responses.

Example 3

This example demonstrates that at least in the context of melanoma ACT, not all $CD39^-$ TILs are bystander T cells, and that responders retain a proportion of tumor neoantigen-reactive TILs in a $CD39^-$ stem-like state.

Previous studies on stem-like and differentiated human TIL subsets were performed on bulk TIL populations lacking specific analyses of anti-tumor T cells (Sade-Feldman et al., *Cell,* 176: 404 (2019); Jansen et al., *Nature,* 576: 465-470 (2019)). Given recent findings suggesting that neoantigen-specific TILs are nearly exclusively $CD39^+$ whereas $CD39^-$ TILs represent bystander cells (Simoni et al., Nature, 557: 575-579 (2018); Duhen et al., *Nat. Commun,* 9: 2724 (2018)), it was sought to determine whether the $CD39^-$ $CD69^-$ stem-like state associated with ACT-response exist within the neoantigen-reactive T cell populations in I.P. Using the previously described tandem minigene neoantigen screening platform (Parkhurst et al., *Cancer Discov.,* 9: 1022-1035 (2019); Tran et al., *Science,* 344: 641-645 (2014); Zacharakis et al., *Nat. Med.,* 24: 724-730 (2018); Tran et al., *N. Engl. J Med.,* 375: 2255-2262 (2016)), 26 HLA class I restricted neoantigens from I.P. were defined for phenotypic evaluation (n=11 patients, FIGS. 12A-12B and 13). Stem-like and differentiated TIL subsets defined by their CD39/CD69expression were readily detectable within HLA-neoantigen $tetramer^+$ TILs as shown in representative CR and NR (FIG. 3A-3B). Combined analysis of all 26 neoantigen-specific T-cell populations indicated that they largely existed in the $CD39^+CD69^+$ terminally differentiated state, consistent with other studies reporting CD39 enrichment of neoantigen-specific T cells (median DP=62.7%, FIG. 3C) (Simoni et al., *Nature,* 557: 575-579 (2018)). Stratification of the data by ACT response status, however, revealed that the frequency of DN cells was significantly higher in neoantigen-specific TILs from CR I.P. (median=8.8%) than in NR I.P. (median=0.5%, $P=1.2\times10^{-4}$, FIG. 3D). CD39 as a single marker indicated that $CD39^-$ negative ($CD39^-$) neoantigen-reactive TILs were twenty-fold higher in CR TILs relative to NR TILs (median=23.6%, $P=1.86\times10^{-5}$, FIG. 3E). Adjusting for tumor-specific cells significantly enhanced these differences between CR and NR infusion products, wherein neoantigen-specific DN TILs were 23-fold higher in CRs (median=$2.3\times10^{8}$ cells), and $CD39^-$ TILs were 40.4-fold higher in CR (median=$1.06\times10^{9}$ cells). No differences were found in the total number of neoantigen reactive TILs, or neoantigen-reactive $CD39^+$ or DP TILs between CR and NR infusion products. These results indicate that at least in the context of melanoma ACT infusion products, not all $CD39^-$ TILs are bystander T cells as previously reported, and that a subset of tumor neoantigen-reactive TILs exist in a $CD39^-$ stem-like state in CRs. Furthermore, these data indicate that enrichment of tumor reactive neoantigen-specific TILs in differentiated subsets does not necessarily correspond to their frequency in stem-like states.

In order to explore the heterogeneity in stem-like and differentiated states of neoantigen-specific TILs at the single cell transcriptomic level, combined scRNA and scTCR sequencing were performed on I.P. from a CR (Pt. 3713) and an NR (Pt. 4000), with defined neoantigen-reactive TCRs (FIG. 3F-3L) (Prickett et al., *Cancer Immunol. Res.,* 4: $669^-$ 678 (2016); Pasetto et al., *Cancer Immunol Res.,* 4: 734-743 (2016); Parkhurst et al., *Clin. Cancer Res.,* 23: 2491-2505 (2017); Cohen et al., *J Clin. Invest.,* 125: 3981-3991 (2015)).

I.P. from responder Pt.3713 was dominated by two major clusters C0 and C1, where C0 represented the stem-like DN state and C1, the differentiated DP state (FIG. 3F). Projection of the 20 neoantigen-specific $TCR^+$ ($NeoTCR^+$) clonotypes showed a broad distribution among the two clusters (FIG. 3F-3G). The immunodominant SRPX mutation-specific NeoTCRs ($SRPX_{mut}$) were enriched in cluster C0 while other NeoTCRs varied in their prevalence within the two clusters (FIG. 3G). CDR3β sequencing of FACS-sorted DN and DP I.P. TILs confirmed this observation (FIG. 14A). Finer analysis of $SRPX_{mut}$ $NeoTCR^+$ single cells indicated that 9/10 of these clonotypes (and 15/20 of all NeoTCR clonotypes) were enriched for positive phenotypic fitness scores (FIG. 3H). As prior studies have suggested that T cell-intrinsic differences potentially impact post-ACT clonotypic persistence (Gattinoni et al., *Nat. Med.,* 17: 1290-1297 (2011); Rosenberg et al., *Clin. Cancer Res.,* 17: 4550-4557 (2011)), the post-ACT peripheral blood of the patient 3713 was analyzed. TCR repertoire sequencing revealed that the majority of NeoTCR clonotypes (18/20) persisted up to 75 months consistent with the idea of TIL expansion from the progenitor stem-like state $SRPX_{mut}$ (FIG. 3I, other NeoTCRs: FIG. 14B). Interestingly, among the 10 $SRPX_{mut}$-NeoTCRs targeting the same neo-epitope, one clonotype (TCR-51) with the lowest phenotypic fitness score declined in frequency and became undetectable only 3 months post treatment (FIG. 3H-31).

Combined scRNA and scTCR sequencing of the non-responder Pt. 4000 I.P. showed two major stem-like clusters (C1, C5) and one major differentiated cluster (C0) (FIG. 3J). However, $NeoTCR^+$ cells ($HIVEP2_{mut}$, $AMPH_{mut}$) were largely concentrated in the differentiated C0 cluster (~60%, FIG. 3J, 15A-15B). scGSEA scores from Pt. 4000 indicated that both NeoTCR clonotypes had negative phenotypic fitness scores (FIG. 3K). In stark contrast to the 3713-CR persistent clonotypes, Pt. 4000 NeoTCRs did not persist post-ACT expansion; rather both infused NeoTCRs clonotypes rapidly declined in peripheral blood following treatment (FIG. 3L). These results support prior observations and other published reports that have linked cell therapy response to post-treatment TCR persistence (Rosenberg et al., *Clin. Cancer Res.,* 17: 4550-4557 (2011); Zhou et al., *Immunity,* 33: $229^-$ 240 (2010); Kalos et al., *Sci. Transl. Med.,* 3: 95ra73 (2011)).

Example 4

This example demonstrates that T cells with the $CD39^-$ $CD69^-$ phenotype mediate anti-tumor activity and TCR persistence.

While the results described in Examples 1-3 indicated that T cell-intrinsic phenotypic differences are associated with persistence following ACT, additional factors such as TCR avidity against variable tumor antigens may also play a role in T cell persistence. To address this issue, an exploratory analysis of T cell persistence was performed in a metastatic synovial cell sarcoma patient who experienced a CR following the adoptive transfer of autologous PBMC transduced with a TCR targeting a single HLA-$A^+$02:01-restricted NY-ESO-1 epitope. Endogenous human TCRβ sequences were used as barcodes to track stem-like DN clones and differentiated DP clones within the TCR-transduced population in post-treatment blood (FIG. 4A) (D'Angelo et al., *Cancer Discov.,* 8: 944-957 (2018)). Fourteen out of the top 20 ESO TCRI.P. clonotypes were enriched in stem-like DN state while six were enriched in the differentiated DP state. Stem-like clones demonstrated a gradual decrease in their frequency over a period of five years following TCR transfer, whereas the differentiated clones declined rapidly to minor frequencies in post-treatment blood of the patient (FIG. 4B). Among 1311 top clones, long-term persistent clones (detectable at 51 months post-ACT, n=790) were significantly enriched in the stem-like state in the I.P. when compared to poorly persistent clones (those undetectable at 7 days post treatment, n=122) (P=0.0035, FIG. 4C). These analyses indicate that intrinsic stem-like phenotypes can modulate the behavior of T cell clonotypes following ACT, although further studies in larger patient cohorts in TCR and CAR trials targeting other antigens are needed to test these hypotheses.

The findings suggested that treatment with $CD39^{-}CD69^{-}$ tumor-reactive TIL might result in superior tumor control. This hypothesis was first tested in vitro by isolating tumor-reactive DN and DP populations from a CR I.P. (Pt. 3733) by co-culture with autologous 3733-mel tumor line to select for tumor-reactive TILs, followed by multiple rounds of rapid expansion to evaluate their proliferative potential and tumor recognition (FIG. 16A). It was found that the expansion of the tumor-reactive stem-like DN subsets was approximately one thousand-fold higher than the differentiated DP subset (FIG. 16B). The stem-like DN subset maintained tumor recognition while the differentiated DP subset lost tumor reactivity following subsequent rounds of expansion (FIG. 16C-16D).

To assess the in vivo anti-tumor effects of stem-like DN and differentiated DP subsets, $CD39^{-}CD69^{-}$ and $CD39^{+}CD69^{+}CD8^{+}$ murine T cell populations were isolated from in vitro-expanded Pmel transgenic TCR splenocytes and adoptive transfer of the isolated subsets into mice implanted with B16-F10 melanoma engineered to express the human gp100 antigen was performed (FIG. 4D) (Hanada et al., *JCI Insight,* 4 (2019), doi:10.1172/jci.insight.124405). While the adoptive transfer of either $3\times10^{5}$ or $5\times10^{5}$ differentiated DP Pmel T cells had a modest effect on tumor control and mouse survival, the transfer of the same numbers of stem-like DN T cells led to substantial tumor regression and improved survival in a dose-dependent manner (FIG. 4E-4F). The data also suggest that anti-tumor neoantigen-specific TIL subsets enriched for tumor reactivity (e.g. $CD39^{+}CD69^{+}$) might be terminally differentiated TILs with a relatively poor proliferative potential in vivo (FIG. 4G) (van der Leun et al., *Nat. Rev. Cancer.* 20: 218-232 (2020)).

Example 5

This example demonstrates the identification of a gene expression profile which distinguishes neoantigen-specific T cells from bystander T cells.

A reanalysis of single cell transcriptome data was done on stem-like cluster C0 (FIG. 14A) to identify whether there are any differences in gene expression selectively between neoantigen-specific T cells and bystander T cells within stem-like clusters, as shown in FIG. 18A.

The results are shown in FIG. 18B. As shown in FIG. 18B, differential gene expression was observed, in which selected genes were upregulated in stem-like neoantigen specific T cells (right side of FIG. 18B) relative to bystander T cells (left side of FIG. 18B).

The differentially expressed genes and the fold change values are shown in Table 4. In Table 4, positive log FC values indicate higher expression of the indicated gene in $CD39^{-}CD69^{-}$ neoantigen-specific T cells as compared to other T cells in the tumor sample of the cancer patient. Negative log FC values indicate higher expression of the indicated gene in $CD39^{-}CD69^{-}$ bystander T cells as compared to other T cells in the tumor sample of the cancer patient.

TABLE 4

| Gene | logFC | LR | PValue | FDR |
|---|---|---|---|---|
| GTSF1 | 0.904722 | 52.68409 | 3.92E−13 | 7.39E−10 |
| HIST1H2AG | 0.830456 | 19.79952 | 8.60E−06 | 0.001443 |
| IGFBP3 | 0.727607 | 28.15751 | 1.12E−07 | 3.67E−05 |
| RBPMS | 0.582377 | 27.32684 | 1.72E−07 | 5.19E−05 |
| RAB34 | 0.577936 | 23.86354 | 1.03E−06 | 0.000228 |
| ITGAE | 0.534229 | 28.70424 | 8.43E−08 | 3.18E−05 |
| PDCD1 | 0.516747 | 15.83315 | 6.92E−05 | 0.008839 |
| KLRC3 | 0.508533 | 12.8874 | 0.000331 | 0.031211 |
| PRSS57 | 0.49132 | 16.47669 | 4.93E−05 | 0.006884 |
| CISH | 0.43821 | 14.23973 | 0.000161 | 0.018131 |
| CDCA7 | 0.410032 | 12.99531 | 0.000312 | 0.030218 |
| AHI1 | 0.397383 | 14.93706 | 0.000111 | 0.012947 |
| ZNF683 | 0.390924 | 19.89687 | 8.17E−06 | 0.001402 |
| VSIR | 0.3893 | 16.0342 | 6.22E−05 | 0.008096 |
| INTS4 | 0.369107 | 10.71772 | 0.001061 | 0.082572 |
| TNFRSF10A | 0.367481 | 10.78281 | 0.001024 | 0.081329 |
| CDC27 | 0.361885 | 10.37136 | 0.00128 | 0.092353 |
| DDX60 | 0.358084 | 10.19647 | 0.001407 | 0.096581 |
| ZBP1 | 0.35556 | 10.58324 | 0.001141 | 0.085283 |
| CTSH | 0.35461 | 12.03861 | 0.000521 | 0.045735 |
| SNAP47 | 0.332793 | 13.68651 | 0.000216 | 0.022362 |
| CD68 | 0.329098 | 10.32952 | 0.001309 | 0.092353 |
| ITGB1 | 0.327208 | 23.12084 | 1.52E−06 | 0.000319 |
| PPM1M | 0.29741 | 10.76497 | 0.001034 | 0.081329 |
| HLA-DPA1 | 0.272018 | 17.92958 | 2.29E−05 | 0.003605 |
| HMGN3 | 0.271023 | 15.58643 | 7.88E−05 | 0.009753 |
| LIME1 | 0.267168 | 11.64913 | 0.000642 | 0.054063 |
| HLA-DRB1 | 0.24803 | 13.68182 | 0.000217 | 0.022362 |
| CTSW | 0.229738 | 11.72008 | 0.000618 | 0.053293 |
| LGALS1 | 0.229152 | 13.34317 | 0.000259 | 0.025759 |
| HLA-DRB5 | 0.219798 | 11.424 | 0.000725 | 0.060136 |
| ANXA5 | 0.207529 | 14.60361 | 0.000133 | 0.015172 |
| ALOX5AP | 0.187616 | 15.80371 | 7.03E−05 | 0.008839 |
| CD74 | 0.187555 | 14.93143 | 0.000111 | 0.012947 |
| S100A11 | 0.178481 | 24.04901 | 9.39E−07 | 0.000215 |
| IL32 | 0.157492 | 16.35793 | 5.24E−05 | 0.007182 |
| COTL1 | 0.156357 | 11.07356 | 0.000876 | 0.071071 |
| S100A4 | 0.154139 | 16.32749 | 5.33E−05 | 0.007182 |
| CD99 | 0.129953 | 13.65856 | 0.000219 | 0.022362 |
| TPT1 | −0.08952 | 10.34621 | 0.001297 | 0.092353 |
| RPL18 | −0.09533 | 10.21895 | 0.00139 | 0.096581 |
| RPL37 | −0.09537 | 10.60361 | 0.001129 | 0.085192 |
| RPL41 | −0.09863 | 16.66852 | 4.45E−05 | 0.006339 |
| MT-CO2 | −0.10308 | 12.62993 | 0.00038 | 0.034522 |
| RPL18A | −0.10578 | 10.93483 | 0.000944 | 0.075779 |
| MT-CO1 | −0.12835 | 16.85439 | 4.04E−05 | 0.005858 |
| RPL13A | −0.13976 | 11.64248 | 0.000645 | 0.054063 |
| EEF1A1 | −0.14122 | 26.91187 | 2.13E−07 | 6.09E−05 |
| RPLP0 | −0.16158 | 12.70984 | 0.000364 | 0.033482 |
| MRPL57 | −0.25044 | 10.34765 | 0.001296 | 0.092353 |
| CLDND1 | −0.26097 | 10.17924 | 0.00142 | 0.096581 |
| RGS10 | −0.26899 | 20.90167 | 4.83E−06 | 0.000869 |
| IL27RA | −0.31123 | 10.60669 | 0.001127 | 0.085192 |
| GIMAP4 | −0.34021 | 12.80429 | 0.000346 | 0.032226 |
| SFMBT2 | −0.34713 | 10.19583 | 0.001408 | 0.096581 |
| EPB41 | −0.35904 | 12.96128 | 0.000318 | 0.030383 |
| GIMAP7 | −0.39558 | 21.41986 | 3.69E−06 | 0.000696 |
| ASXL2 | −0.39846 | 11.71096 | 0.000621 | 0.053293 |
| FCMR | −0.41059 | 14.16248 | 0.000168 | 0.018613 |
| ERN1 | −0.42202 | 13.88012 | 0.000195 | 0.020714 |
| LINC01943 | −0.45099 | 10.5145 | 0.001184 | 0.087647 |
| CD6 | −0.51714 | 25.32291 | 4.85E−07 | 0.000118 |
| AQP3 | −0.77688 | 17.73469 | 2.54E−05 | 0.003912 |
| GNLY | −0.7781 | 28.56785 | 9.05E−08 | 3.25E−05 |
| TRGV10 | −0.79636 | 13.9903 | 0.000184 | 0.019814 |
| GZMK | −0.80595 | 16.16195 | 5.82E−05 | 0.0077 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of obtaining a cell population enriched for T cells with a phenotype, the method comprising:

(a) obtaining a bulk population of T cells from a tumor sample from a patient;

(b) specifically selecting T cells with a phenotype comprising markers CD3$^+$, CD39$^-$, and CD69$^-$ from the bulk population; and (c) separating the cells selected in (b) from cells which lack the phenotype to obtain a cell population enriched for T cells with the phenotype.

2. The method according to claim 1, further comprising isolating tumor-reactive T cells from the separated T cells which have the phenotype.

3. A method of obtaining a cell population enriched for T cells with a phenotype, the method comprising:

(a) obtaining a bulk population of T cells from a tumor sample from a patient;

(b) isolating tumor-reactive T cells from the tumor sample;

(c) specifically selecting T cells with a phenotype comprising markers CD3$^{30}$ , CD39$^-$, and CD69$^-$ from the isolated tumor-reactive T cells; and (d) separating the cells selected in (c) from cells which lack the phenotype to obtain a cell population enriched for T cells with the phenotype.

4. The method of claim 1, wherein selecting the isolated T cells which have the phenotype comprises carrying out t-Distributed Stochastic Neighbor Embedding (t-SNE) analysis.

5. The method of claim 1, wherein selecting the isolated T cells which have the phenotype comprises carrying out Cellular Indexing of Transcriptomes and Epitopes by Sequencing (CITE-Seq) analysis.

6. A method of obtaining a cell population enriched for T cells with a phenotype, the method comprising:

(a) obtaining a bulk population of T cells from a tumor sample from a patient;

(b) isolating tumor-reactive T cells from the tumor sample; and (c) modifying the isolated tumor-reactive T cells to provide a phenotype comprising markers CD39$^-$ and CD69$^-$ to obtain a cell population enriched for T cells with the phenotype.

7. A method of preparing a population of cells enriched for T cells with a CD3$^+$CD39$^-$CD69$^-$ phenotype, the method comprising:

(a) isolating tumor-reactive T cells from a tumor sample from a patient; and (b) modifying the isolated, tumor-reactive T cells to (i) induce expression of one or more of the following markers: AHNAK$^+$, AL592183.1$^+$, ANXA1$^+$, ANXA4$^+$, AQP3$^+$, ATM$^+$, BIN1$^+$, C10orf54$^+$, C11orf21$^+$, C16orf54$^+$, CCDC109B$^+$, CD27$^+$, CD52$^+$, CD55$^+$, CD8B$^+$, CDC25B$^+$, CDC42SE1$^+$, CLEC2B$^+$, CLIC3$^+$, CLUAP1$^+$, CRBN$^+$, CTD-3184A7.4$^+$, DDI2$^+$, DND1$^+$, EMP3$^+$, EPB41$^+$, ERN1$^+$, FAIM3$^+$, FAM65B$^+$, FBXL8$^+$, FGFBP2$^+$, GADD45B$^+$, GIMAP4$^+$, GIMAP7$^+$, GPR155$^+$, GZMM$^+$, HSD17B11$^+$, IL10RA$^+$, IL7R$^+$, ISG20$^+$, KANSL1-AS1$^+$, KLF2$^+$, KLHL24$^+$, LDLRAP1$^+$, LEF1$^+$, LGALS3$^+$, LINC00861$^+$, LITAF$^+$, LYAR$^+$, MAPKAPK5-AS1$^+$, MED15$^+$, MIAT$^+$, MIR142$^+$, MXI1$^+$, MYC$^+$, NEAT1$^+$, NOSIP$^+$, ODF2L$^+$, P2RY8$^+$, PDE6G$^+$, PIK3IP1$^+$, PLEC$^+$, PLP2$^+$, PPP2R5C$^+$, PXN$^+$, R3HDM4$^+$, RAMP1$^+$, RASA3$^+$, RASGRP2$^+$, RCBTB2$^+$, RNASET2$^+$, RP11-395B7.4$^+$, RP11-539L10.2$^+$, RP11-640M9.1$^+$, S100A10$^+$, S100A4$^+$, S100A6$^+$, S1PR1$^+$, S1PR4$^+$, SAMD3$^+$, SELL$^+$, SH3BP5$^+$, SIGIRR$^+$, SLAMF6$^+$, SLCO3A1$^+$, SORL1$^+$, STK38$^+$, SYNJ2$^+$, TCF7$^+$, TIMP1$^+$, TRADD$^+$, TSC22D3$^+$, TSPAN32$^+$, TXNIP$^+$, UBXN11$^+$, VCL$^+$, VNN2$^+$, YPEL3$^+$, ZFP36L2$^+$, ZNF276$^+$, and ZNF683$^+$, and/or (ii) inhibit expression of one or more of the following markers: ACOT7$^+$, ADAM19$^+$, AGPAT9$^+$, AGTRAP$^+$, AIF1$^+$, ASPM$^+$, ATAD2$^+$, AURKA$^+$, AURKB$^+$, BIRC3$^+$, BIRC5$^+$, BRCA1$^+$, C15orf48$^+$, CASC5$^+$, CCL3$^+$, CCNA2$^+$, CCNB1$^+$, CCNB2$^+$, CCND2$^+$, CD38$^+$, CD40LG$^+$, CD69$^+$, CD8B$^+$, CDC20$^+$, CDCA3$^+$, CDCA8$^+$, CDK1$^+$, CDKN3$^+$, CDT1$^+$, CENPA$^+$, CENPE$^+$, CENPF$^+$, CENPM$^+$, CENPW$^+$, CEP55$^+$, CISH$^+$, CKS1B$^+$, CKS2$^+$, CLSPN$^+$, CRTAM$^+$, CSF2$^+$, DLGAP5$^+$, DUSP5$^+$, DUSP6$^+$, DUT$^+$, EGR1$^+$, ENTPD1$^+$, FEN1$^+$, GINS2$^+$, GTSE1$^+$, H2AFX$^+$, HIST1H4C$^+$, HLA$^+$DQA2$^+$, HMMR$^+$, IFI27$^+$, IFNG$^+$, IL2RA$^+$, IL5$^+$, KIAA0101$^+$, KIF11$^+$, KIF23$^+$, KPNA2$^+$, KRT7$^+$, MAD2L1$^+$, MCM7$^+$, MKI67$^+$, MX1$^+$, MYBL2$^+$, NCAPG$^+$, NDC80$^+$, NDFIP2$^+$, NUDT1$^+$, NUSAP1$^+$, ORC6$^+$, PBK$^+$, PCNA$^+$, PLK1$^+$, RPL39L$^+$, RRM2$^+$, SGOL2$^+$, SHCBP1$^+$, SMC2$^+$, SPC25$^+$, STMN1$^+$, TESC$^+$, TK1$^+$, TNF$^+$, TNFRSF18$^+$, TNFSF10$^+$, TOP2A$^+$, TPM4$^+$, TPX2$^+$, TUBA1B$^+$, TUBA1C$^+$, TUBB$^+$, TYMS$^+$, UBE2C$^+$, UBE2S$^+$, UBE2T$^+$, XCL1$^+$, and ZWINT$^+$, wherein inducing expression of one or more of the markers of (i) and/or inhibiting expression of one or more of the markers of (ii) induces the T cells to have the CD3$^+$CD39$^-$CD69$^-$ phenotype.

8. A method of obtaining a pharmaceutical composition comprising a cell population enriched for T cells with a phenotype, the method comprising:

obtaining a cell population enriched for T cells with the phenotype according to the method of claim 1; and combining the cell population enriched for T cells with the phenotype with a pharmaceutically acceptable carrier to obtain a pharmaceutical composition comprising a cell population enriched for T cells with the phenotype.

9. The method according to claim 1, further comprising introducing a nucleic acid encoding an exogenous TCR into the cells in the population enriched for T cells with the phenotype under conditions to express the exogenous TCR by the cells.

10. The method of claim 1, further comprising introducing a nucleic acid encoding a chimeric antigen receptor (CAR) into the cells in the population enriched for T cells with the phenotype under conditions to express the CAR by the cells.

11. An isolated or purified cell population obtained according to the method of claim 1.

12. A pharmaceutical composition comprising the isolated or purified cell population of claim 11 and a pharmaceutically acceptable carrier.

13. The method of claim 1, wherein the phenotype further comprises one or more of marker(s): AHNAK$^{+}$, AL592183.1$^{+}$, ANXA1$^{+}$, ANXA4$^{+}$, AQP3$^{+}$, ATM$^{+}$, BIN1$^{+}$, C10orf54$^{+}$, C11orf21$^{+}$, C16orf54$^{+}$, CCDC109B$^{+}$, CD27$^{+}$, CD52$^{+}$, CD55$^{+}$, CD8B$^{+}$, CDC25B$^{+}$, CDC42SE1$^{+}$, CLEC2B$^{+}$, CLIC3$^{+}$, CLUAP1$^{+}$, CRBN$^{+}$, CTD-3184A7.4$^{+}$, DDI2$^{+}$, DND1$^{+}$, EMP3$^{+}$, EPB41$^{+}$, ERN1$^{+}$, FAIM3$^{+}$, FAM65B$^{+}$, FBXL8$^{+}$, FGFBP2$^{+}$, GADD45B$^{+}$, GIMAP4$^{+}$, GIMAP7$^{+}$, GPR155$^{+}$, GZMM$^{+}$, HSD17B11$^{+}$, IL10RA$^{+}$, IL7R$^{+}$, ISG20$^{+}$, KANSL1-AS1$^{+}$, KLF2$^{+}$, KLHL24$^{+}$, LDLRAP1$^{+}$, LEF1$^{+}$, LGALS3$^{+}$, LINC00861$^{+}$, LITAF$^{+}$, LYAR$^{+}$, MAPKAPK5-AS1$^{+}$, MED15$^{+}$, MIAT$^{+}$, MIR142$^{+}$, MXI1$^{+}$, MYC$^{+}$, NEAT1$^{+}$, NOSIP$^{+}$, ODF2L$^{+}$, P2RY8$^{+}$, PDE6G$^{+}$, PIK3IP1$^{+}$, PLEC$^{+}$, PLP2$^{+}$, PPP2R5C$^{+}$, PXN$^{+}$, R3HDM4$^{+}$, RAMP1$^{+}$, RASA3$^{+}$, RASGRP2$^{+}$, RCBTB2$^{+}$, RNASET2$^{+}$, RP11-395B7.4$^{+}$, RP11-539L10.2$^{+}$, RP11-640M9.1$^{+}$, S100A10$^{+}$, S100A4$^{+}$, S100A6$^{+}$, S1PR1$^{+}$, S1PR4$^{+}$, SAMD3$^{+}$, SELL$^{+}$, SH3BP5$^{+}$, SIGIRR$^{+}$, SLAMF6$^{+}$, SLCO3A1$^{+}$, SORL1$^{+}$, STK38$^{+}$, SYNJ2$^{+}$, TCF7$^{+}$, TIMP1$^{+}$, TRADD$^{+}$, TSC22D3$^{+}$, TSPAN32$^{+}$, TXNIP$^{+}$, UBXN11$^{+}$, VCL$^{+}$, VNN2$^{+}$, YPEL3$^{+}$, ZFP36L2$^{+}$, ZNF276$^{+}$, and ZNF683$^{+}$.

14. The method of claim 1, wherein the phenotype further comprises one or more of marker(s): ACOT7$^{-}$, ADAM19$^{-}$, AGPAT9$^{-}$, AGTRAP$^{-}$, AIF1$^{-}$, ASPM$^{-}$, ATAD2$^{-}$, AURKA$^{-}$, AURKB$^{-}$, BIRC3$^{-}$, BIRC5$^{-}$, BRCA1$^{-}$, C15orf48$^{-}$, CASC5$^{-}$, CCL3$^{-}$, CCNA2$^{-}$, CCNB1$^{-}$, CCNB2$^{-}$, CCND2$^{-}$, CD38$^{-}$, CD40LG$^{-}$, CD69$^{-}$, CD8B$^{-}$, CDC20$^{-}$, CDCA3$^{-}$, CDCA8$^{-}$, CDK1$^{-}$, CDKN3$^{-}$, CDT1$^{-}$, CENPA$^{-}$, CENPE$^{-}$, CENPF$^{-}$, CENPM$^{-}$, CENPW$^{-}$, CEP55$^{-}$, CISH$^{-}$, CKS1B$^{-}$, CKS2$^{-}$, CLSPN$^{-}$, CRTAM$^{-}$, CSF2$^{-}$, DLGAP5$^{-}$, DUSP5$^{-}$, DUSP6$^{-}$, DUT$^{-}$, EGR1$^{-}$, ENTPD1, FEN1$^{-}$, GINS2$^{-}$, GTSE1$^{-}$, H2AFX$^{-}$, HIST1H4C$^{-}$, HLA$^{-}$DQA2$^{-}$, HMMR$^{-}$, IFI27$^{-}$, IFNG$^{-}$, IL2RA$^{-}$, IL5$^{-}$, KIAA0101$^{-}$, KIF11$^{-}$, KIF23$^{-}$, KPNA2$^{-}$, KRT7$^{-}$, MAD2L1$^{-}$, MCM7$^{-}$, MKI67$^{-}$, MX1$^{-}$, MYBL2$^{-}$, NCAPG$^{-}$, NDC80$^{-}$, NDFIP2$^{-}$, NUDT1$^{-}$, NUSAP1$^{-}$, ORC6$^{-}$, PBK$^{-}$, PCNA$^{-}$, PLK1$^{-}$, RPL39L$^{-}$, RRM2$^{-}$, SGOL2$^{-}$, SHCBP1$^{-}$, SMC2$^{-}$, SPC25$^{-}$, STMN1$^{-}$, TESC$^{-}$, TK1$^{-}$, TNF$^{-}$, TNFRSF18$^{-}$, TNFSF10$^{-}$, TOP2A$^{-}$; TPM4$^{-}$, TPX2$^{-}$, TUBA1B$^{-}$, TUBA1C$^{-}$, TUBB$^{-}$, TYMS$^{-}$, UBE2C$^{-}$, UBE2S$^{-}$, UBE2T, XCL1$^{-}$, and ZWINT$^{-}$.

15. The method of claim 1, wherein the phenotype further comprises one or more of marker(s): AHI1$^{+}$, ALOX5AP$^{+}$, ANXA5$^{+}$, CD68$^{+}$, CD74$^{+}$, CD99$^{+}$, CDC27$^{+}$, CDCA7$^{+}$, CISH$^{+}$, COTL1$^{+}$, CTSH$^{+}$, CTSW$^{+}$, DDX60$^{+}$, GTSF1$^{+}$, HIST1H2AG$^{+}$, HLA-DPA1$^{+}$, HLA-DRB1$^{+}$, HLA-DRB5$^{+}$, HMGN3$^{+}$, IGFBP3$^{+}$, IL32$^{+}$, INTS4$^{+}$, ITGAE$^{+}$, ITGB1$^{+}$, KLRC3$^{+}$, LGALS1$^{+}$, LIME1$^{+}$, PDCD1$^{+}$, PPM1M$^{+}$, PRSS57$^{+}$, RAB34$^{+}$, RBPMS$^{+}$, S100A11$^{+}$, S100A4$^{+}$, SNAP47$^{+}$, TNFRSF10A$^{+}$, VSIR$^{+}$, ZBP1$^{+}$, and ZNF683$^{+}$.

16. The method of claim 1, wherein the phenotype further comprises one or more of marker(s): AQP3$^{-}$, ASXL2$^{-}$, CD6$^{-}$, CLDND1$^{-}$, EEF1A1$^{-}$, EPB41$^{-}$, ERN1$^{-}$, FCMR$^{-}$, GIMAP4$^{-}$, GIMAP7$^{-}$, GNLY$^{-}$, GZMK$^{-}$, IL27RA$^{-}$, LINC01943$^{-}$, MRPL57$^{-}$, MT$^{-}$CO1$^{-}$, MT$^{-}$CO2$^{-}$, RGS10$^{-}$, RPL13A$^{-}$, RPL18$^{-}$, RPL18A$^{-}$, RPL37$^{-}$, RPL41$^{-}$, RPLP0$^{-}$, SFMBT2$^{-}$, TPT1$^{-}$, and TRGV10$^{-}$.

* * * * *

SEQUENCE LISTING

```
<160> NUMBER OF SEQ ID NOS: 19

<210> SEQ ID NO 1
<211> LENGTH: 12493
<212> TYPE: DNA
<213> ORGANISM: Homo sapiens

<400> SEQUENCE: 1

acggagacgg accacagcaa gcagaggctg ggggggggaa agacgaggaa agaggaggaa     60

aacaaaagct gctacttatg gaagatacaa aggagtctaa cgtgaagaca ttttgctcca    120

agaatatcct agccatcctt ggcttctcct ctatcatagc tgtgatagct ttgcttgctg    180

tggggttgac ccagaacaaa gcattgccag aaaacgttaa gtatgggatt gtgctggatg    240

cgggttcttc tcacacaagt ttatacatct ataagtggcc agcagaaaag gagaatgaca    300

caggcgtggt gcatcaagta gaagaatgca gggttaaagg tcctggaatc tcaaaatttg    360

ttcagaaagt aaatgaaata ggcatttacc tgactgattg catggaaaga gctagggaag    420

tgattccaag gtcccagcac caagagacac ccgtttacct gggagccacg gcaggcatgc    480

ggttgctcag gatggaaagt gaagagttgg cagacagggt tctggatgtg gtggagagga    540

gcctcagcaa ctaccccttt gacttccagg gtgccaggat cattactggc caagaggaag    600

gtgcctatgg ctggattact atcaactatc tgctgggcaa attcagtcag aaaacaaggt    660

ggttcagcat agtcccatat gaaaccaata atcaggaaac ctttggagct ttggaccttg    720

ggggagcctc tacacaagtc acttttgtac cccaaaacca gactatcgag tccccagata    780

atgctctgca atttcgcctc tatggcaagg actacaatgt ctacacacat agcttcttgt    840

gctatgggaa ggatcaggca ctctggcaga aactggccaa ggacattcag gttgcaagta    900

atgaaattct cagggaccca tgctttcatc ctggatataa gaaggtagtg aacgtaagtg    960

acctttacaa gaccccctgc accaagagat ttgagatgac tcttccattc cagcagtttg   1020

aaatccaggg tattggaaac tatcaacaat gccatcaaag catcctggag ctcttcaaca   1080

ccagttactg ccccttactcc cagtgtgcct tcaatgggat tttcttgcca ccactccagg   1140

gggattttgg ggcattttca gctttttact ttgtgatgaa gtttttaaac ttgacatcag   1200
```

-continued

```
agaaagtctc tcaggaaaag gtgactgaga tgatgaaaaa gttctgtgct cagccttggg   1260
aggagataaa aacatcttac gctggagtaa aggagaagta cctgagtgaa tactgctttt   1320
ctggtaccta cattctctcc ctccttctgc aaggctatca tttcacagct gattcctggg   1380
agcacatcca tttcattggc aagatccagg gcagcgacgc cggctggact ttgggctaca   1440
tgctgaacct gaccaacatg atcccagctg agcaaccatt gtccacacct ctctcccact   1500
ccacctatgt cttcctcatg gttctattct ccctggtcct tttcacagtg gccatcatag   1560
gcttgcttat ctttcacaag ccttcatatt tctggaaaga tatggtatag caaaagcagc   1620
tgaaatatgc tggctggagt gaggaaaaaa atcgtccagg gagcattttc ctccatcgca   1680
gtgttcaagg ccatccttcc ctgtctgcca gggccagtct tgacgagtgt gaagcttcct   1740
tggcttttac tgaagccttt cttttggagg tattcaatat cctttgcctc aaggacttcg   1800
gcagatactg tctctttcat gagtttttcc cagctacacc tttctccttt gtactttgtg   1860
cttgtatagg ttttaaagac ctgacacctt tcataatctt tgctttataa aagaacaata   1920
ttgactttgt ctagaagaac tgagagtctt gagtcctgtg ataggaggct gagctggctg   1980
aaagaagaat ctcaggaact ggttcagttg tactctttaa gaacccccttt ctctctcctg   2040
tttgccatcc attaagaaag ccatatgatg cctttggaga aggcagacac acattccatt   2100
cccagcctgc tctgtgggta ggagaatttt ctacagtagg caaatatgtg ctaaagccaa   2160
agagttttat aaggaaatat atgtgctcat gcagtcaata cagttctcaa tcccacccaa   2220
agcaggtatg tcaataaatc acatattcct aggtgatacc caaatgctac agagtggaac   2280
actcagacct gagatttgca aaaagcagat gtaaatatat gcattcaaac atcagggctt   2340
actatgaggt aggtggtata tacatgtcac aaataaaaat acagttacaa ctcagggtca   2400
caaaaaaatgc atcttccaat gcatattttt attatggtaa aatatacata aatataattc   2460
accattttaa catttaattc atattaaata cgtacaaatc agtgacattt agtacattca   2520
cagtgttgtg ccaccatcac cactatttag ttccagaaca tttgcatcat caatacattg   2580
tctagagaca agactatcct gggtaggcag aaaccataga tcttttgtgt ttacagctat   2640
ggaaaccaac tgtaccataa agatagttca ctgagtttta aagccaagcc acatcttatt   2700
tttccaaggt ttaatttagt gagagggcag cattagtgtg gagtggcatg cttttgccct   2760
atcgtggaat ttacacatca gaatgtgcag gatccaagtc tgaaagtgtt gccacccgtc   2820
acacaacatg ggctttgttt gcttattcca tgaagcagca gctatagacc ttaccatgga   2880
aacatgaaga gaccctgcac ccctttcctt aaggattgct gcaagagtta cctgttgagc   2940
aggattgact ggtgatgttt cattctgacc ttgtcccaag ctctccatct ctagatctgg   3000
ggactgactg ttgagctgat ggggaaagaa aagctctcac acaaaccgga agccaaatgt   3060
cccctatctc ttgaatgatc aagtcacttt tgacaacatc caggtgaata taaaaactta   3120
ataaagctgt ggaaaggaac tcttaatctt cttttctgct acttaggtta aattcactag   3180
atcttgatta ggaatcaaaa ttcgaattgg gacatgttca aattctttct tgtggtagtt   3240
gcctatactg tcatcgctgc tgttggttga gcatttgtgg tgtaccacgc tgtgtgctca   3300
agggtattac attcatcttc tcatttaatc ctcacaacaa tctgaagaag gtaggtatta   3360
caattcccac ttcatagaaa cagaaactga ggttcagaga ggttaagtca tttgcccaaa   3420
tggctgagcc aaagcctacc atgtacctaa cctttatttt ctttcccgaa cataccaggc   3480
tgtctcctca taacttccaa gcatgcactt aaaactccac atgaatacaa ggttcatggg   3540
acttggtatt catagaaagg gaggcagaaa gctggtctgt tcctgatagg cttgtaattt   3600
```

```
aatatcattc tgttcatgtg ctttggatgg aagcacatct ggcatatgat gctaatcagt   3660
ggttcccata cccctggctt cctaatttta atgtttgctc acagcatagt agattgacat   3720
caaatagtgg ccgatgatga tgaaaataaa ggtcaaataa gttgagccaa taacagccgc   3780
tttttccttt ctgtctgcgt atacaaagca ctgtcatgca cacaatctat tctgaccctc   3840
acaacaaccc ataagggtgt aaatagtatt tccattttac aaatgaggat cacacaaact   3900
actacatggc agagcagata ctccaactca tgtcttctgg ttgaagccta ttgcttttc   3960
ttttctaaac actttccctc agcaagttgg aattagactt cacaagtctc cttcagagaa   4020
cacaaatctt ttcttattcc attcctgttt ggttgcctac gtccaatctc cccctcccca   4080
gagatgccaa aaaaaaaatc ctttaaggta tttgggagcc aaactcaact tgttaaaatc   4140
tcaaattatg gagacaatca gcagacacaa cctaacccca attattttgg caggaaggtt   4200
ggtttagagg cagatccagc aatctgcttt gggccactct gggtggggta ggtgaaataa   4260
gattggtcac tgttaactaa ttttaatatt ggattggcca ttggttatca ctgattacca   4320
ttctcccctg gattttcacc caggactcaa aacttggttc tgctaaccct gttcctttat   4380
gaggaacctt ttaaagattc ctttataagg tgggagtttt ttttctatga acctataggg   4440
gagaaaaaag atcagcagaa gtcattactt tttttttttt tttttttttt ttttgagaga   4500
gagtctcact ccattgccca ggctggagtg cagtggtgct atctcggctc actgcaacct   4560
ccgcctcctg ggttcaagca attctcctgc ctcagcctcc cgagtagctg ggattgcagg   4620
tgcccaccac cacacccggc taatttttgt atttttagta aagacagggt ttcaccatgt   4680
tggccaggct ggtctccaac tcccaatctc aggtgatcct attgcctcgg gctcccaaag   4740
tgctgggatt acaggagtga gccaccatgc ctggccagaa gtggttactt ctgtagacaa   4800
aagaataatg ctacttaatc aggctttctg tgtgacaaga aagagaaaga aaataaagaa   4860
gtttcaattc atccaattct taataagaaa tatgtaaata aaattttta aaattacact   4920
tcattttaat gttgtatcag tcaaggtccc tgcaagagat ggatggtatg gtacactcaa   4980
actgggtaac acaggagagt tttcagaaag caactaaatc caaaatacta tcaaggaatc   5040
aatataaaaa ttgttaatat ttttctcata ctaaattttc aaaatatttt gtgtctatta   5100
catttacagc acatcttaat taggactagc tgtgtgttca cctcacatgt ggcttgtagc   5160
taccatactg gacagcacat gtccaaaaaa atacacgtaa agttaaagtt taaaagacac   5220
aggaactaag ccctcattgt ctttcccttg ggaggtagtt taaagagcta tagatgctgt   5280
aacattcttg ctattattta ttatatatga cattattcct aaaaaagctt ttgagatcct   5340
aggttgtatt cctcaggttt tgttgccttc ccatgaagat gtgaaggcag ggatgcctgt   5400
tattcagtcc aagatgcatg acaagagacc ttgggaaagt ttcatctgga tttaaagatt   5460
aattcttgat gcttacattc catactcaaa atgtaaattt gaatattaaa ataaagatga   5520
tttttttttt ggagctagtc ttgctctgtt gcccaggctg gaatgcagtg gcatgatcat   5580
ggctcactgc agcctcgacc tcccaagctc aagcaaggct acaggtgtgc acctaagtag   5640
ctaggactac aggtgtgcac caccatgtct agctattttt ttttctgtag agacagggtt   5700
ttcctatgtt gtccaggctg gtctcgaact cctgccctca agcaatcctc ctgccttggc   5760
ctcccaaagt gttgagatta caggcgtaag ccactgcacc tggccaagat gaatatttta   5820
atagctcaca gaacaaagtt tgccacataa tgataaaatt actatgaaaa tatattccct   5880
ttattgtcag tttaaaagat gaactgagtt tcacccaaac tggtctggcc cctctctgat   5940
```

-continued

```
tcaaatacca atagttgctc tgattcaaat tccaactgtt agaacatgac agctgctcat   6000
aactagcttt gcttactaac catgtttctt tccatttgta ttaggtcctt tactttttat   6060
aacagcctca aagtttcatg aattgctgca gtaaacattg attttcatgt ttgtgagtct   6120
gcaagccagc tgggcagctc tacttcaggt ggtaagggtg gatcagacct attccatata   6180
cctcttgttc tccttgtcca gtggtttcta gggatatgtt ctcatgatga accccgcaga   6240
ggctcgtgaa agtgagagga aactaggatg cctcttaagg tcttggtcag gatggggtct   6300
cctgtcactt ctgtcacagg ctattgtaag tcatatgagc aagctcaata aaatataaac   6360
aagtcagata aacagtggga ggaatggcaa agtcatatgg ccaaggccat gagtgattaa   6420
ttttaacaca ggaaaaaagt aaagcattaa atgcgattat ttaatataca atgtcttatt   6480
aactgaaata taaaatgtgt ttactgtaaa atataatctg tttatctcac caaagaaata   6540
ttatctttaa aaaatgtcat tacttctaag acatcatcag tctgcaactt ctttccatag   6600
ccttaatcag gatgctgtgg cagctcccac attagcctcg cattctaaac tggtagatgt   6660
cctaggaaac catacatcta tgtatttttc ttattttata cgtttaggac aatgtatagc   6720
taattaccca actttttatt tgcatacaaa tctaatacaa ctgaacacaa tcagttttat   6780
cacaggtata atggattttt caatagtgag gaggtgcctc catgagcctt ctctttagaa   6840
aagtggcatt caagactctt catttgaagt gaagattgct atgtcttttg cattgctcta   6900
ttttacataa attaagttat aaattgacac tataatcaac tgacaccatg atcagtgatg   6960
atgatcaccc tcatcagcac tagagttgac ttgtttttat aacccctttg catgtatgtt   7020
gaatagcaaa gttcatcaga gaacatgtat tagtcaatgg taagtaagat actctcatct   7080
aagaaataac atcacctctt ctaatgaagt tctaagaaga gagggaagaa aaagtcttgg   7140
gagctagtca gggaatagtg tgtatttgca attacctaaa ctgaactcta ccattactcc   7200
taacccagtt cctcctcctg tgttttacat gattaatgcc acccctgcct caatgaacca   7260
agatcagctc catcactggg acctccccat tctgcctgtg caatattttt ctttttttatt   7320
tctccttcta atattactgt tattgctcca gtaaagagct gtaatatatt ttacctggac   7380
tgataccagg aatggtggtg ttgcttccaa tctgttgctg ctagattaat ctttgcaaag   7440
cacaggctta atttcattgc tgctcaacta aaaccactgg tggctttcca ttgcctacaa   7500
aataaagtca acctccccat cagacattca aggctttcaa tgatccatgg ccgccagctc   7560
tctccaggct catatcccac tccactcctc tgatgtttcc tacactacac tacactatac   7620
tacactacag ccaggtagaa tgactgttca cccaacacca ctcaggttgt cttctcaact   7680
tggaatactc ttgcaccttc aaagctcatt tcaaatgccc cttcatttgt gaagccttct   7740
ccaaatttcc aagtcagaat gtctcttcct tgtgctacca caaccottta actgagcctc   7800
cattagtgca ctgagaccat tctgttcagt gtctgggtga agcttcctgg tgaaaaatat   7860
gttacctatt tctttctgaa aagttggatt cagggatatt atcacggacc taaggtaata   7920
gttctagcca acctccctgt ccactgccag gccgactaca aaccccttctg ttgctggcga   7980
gctggtccgc accactagtt ctgcttcact ctatttatct cttgatgtaa ccatcttctt   8040
tctccaggtt ttaagaacca gcccaactcc tggttccctg atgaagcttt tattccccta   8100
gccacatgga actttttcctt tttggaacat gcctttagtt tctgtgtagt ttgccatgca   8160
gcacttcatt gtacacatta ttaaaacaga attttaagga ttagaatgaa ccttaaaaga   8220
tcatgcatct caaaatttaa tgtacataca aattacccag ggattttgtt gaaataaaaa   8280
ttatttaatt ttaattaata taaataattc agtaggtctg ggtgaggcc tgaggtttta   8340
```

```
catttccaac aagctgccag gtaaagccaa tacatctgtc caggaatcac actttgcgta   8400
tcaaaggtct agatgacatt atcattccaa agagtttctt ttacaggctc tcagatcagt   8460
gttcatccac tacctgacta ctgtcattca caggcattct gttccacagc aggccagcta   8520
acgtggtatt tacaaagctc actcctctta tacaacaatc caagtgtttc ttttgtcagt   8580
tgtctgtgcc ccaggagatc cctctctgcc ttgccttgcc ctctgccttt ggagaccagc   8640
acctcatact cagtgaaggc ctggagtgct taagagggat ttcttccagc tctcttgccc   8700
tggtcttcag tgtattagat gtattacctc catgctctca gtagaggccc ataggaaaga   8760
gtaggtaggt tatgccagct cacacgcatc ctttaaaaat ggtttagaag tttagctggt   8820
ttcttattac tcctgtctat ggatgtttcc ttctgtcact ctactaggga tgaaacagct   8880
aatcatgttc aatagttaca tttagattgg tttttaaaaa ctatgattgt attagttcgt   8940
ttccatgctg ctgataaaga catatctgag actggaaaca aaaagggttt aattggactt   9000
acagttccac atggctgggg aggcctcaaa atcaggtggg aggcaaaagg tacttcttac   9060
gtggtggcat caagagcaaa atgaggaaga agcaaaagca gaaactcttc ataaacccac   9120
cagatcttgt gggacttatt atcacgagaa tagcacagaa aagactggcc tccatgattc   9180
aattacctcc cactgcgtcc ctcccacaac atgtgggaat tctgggagat acaattcaag   9240
ttgagatttg ggtggggaca cagccaaacc atatcattcc tccctgggct cctccaaatt   9300
tcataatcct cacatttcaa aaccaatcat tccttcccaa cagttcccca aagtcttaac   9360
tcatttcagc attaacccaa aagtccacag tccaaagtct catctgagac aaggcaagtc   9420
ccttccactt acaagcctgt aaaagcaagc tagttacctc ctagatacaa tggggggtac   9480
aggtattggg taaatacagc tgttccaaat gagagaaatt ggccaaaaca aaggggttac   9540
agggtccatg caagtctgaa atccagtggg gcagtcaaat tttaaagctc cataatgatc   9600
tcctttgact ccatgtctca cattcaggtc atgctgatgc aagagatagg ttcccatggt   9660
cttgtgcagc tccgcccctg tggctttgca gagtacagcc tccctcctgg ctgctttctc   9720
aggctgatgt tgagtgtctg tagcttttcc aggcacaaga tgcaagttgg tggttgatct   9780
accattctgg ggtctaccat tctggggtct accgttctgg gactgtggcc ttcttctcac   9840
agctccacta ggcagtgccc caacagggac tctgtgtggg ggctctgccc cacatttccc   9900
ttccacactg ccctaggaga ggttccccat gagggctctg cccctgcagc aaacttttgc   9960
ctggacatcc aggtgtttcc atatatattc tgaaatctag gcagaggttc ccaaatctca  10020
attcttgaca tctctgcacc cacaggctca acatcacatg gaagctgcca atgcttgggg  10080
cctctaccct ctgaagccac agcccaagct ctatgttggc tcctttcagc catggctgga  10140
gcagctggga cacagggcac caagtcccta ggctgcacac agcacagaga ccctgggccc  10200
agcccacaaa accacttttt cctcctgggc ctctgggcct gtgatgggag gggctgccat  10260
gaaggtctct gacatgacct ggagacattt tccccatggt cttggggatt aacattaggc  10320
tccttgctgc ttatgcaaat ttctgcagcc agcttgaatt tctccttaaa aaaaatgggt  10380
ttttcttttc tactgcatca tcaggctgca gattttccac atttatgctc ttgtttccct  10440
tttaaaacag aatgttttta acagcaccca agtcaccttt tgaatgcttt gctgcttaga  10500
aatttattcc accagatacc ctaagtcatc tctctcaagc tctaagttcc acaaatctct  10560
agggcaaggg tgaaatgctg ccagtctcct tgctaaaaca taacaagggt cacctttact  10620
tcagttccca acaaggtctt catctccatc tgagaccacc tcagcctgga ccttattgtt  10680
```

-continued

```
catatcacta tcagtatttt tgtcaatgcc attcacagtc tctaggaggt tccaaacttt  10740

cctacatttt cctatcttct tctgagccct ccagattatt tcaacaccca gttccaaagt  10800

tgcttccaca ttttcgggta tcttttcagc aatgccccac tctactggta ctattagtcc  10860

attttcatgc tgctgataaa gacatacctg agactgggaa caaaaagagg tttaattgga  10920

cttatagttc cacctggctg gggaggcctc agaatcatgg caggaggtga aaggcatttc  10980

ttacacggca gcagcaagag aaaaatgaag aagcagcaaa agcagaaacc cctgataaaa  11040

ccatcagatc tcgtgagact tattcactat cacaagaata gcatgggaaa gaccagcccc  11100

cttgattcaa ttacctcccc ctgggtcctg tgggaattct ggaaggtaca attcaagttg  11160

agatttgggt ggggacacag ccaaaccata tcaatgattt tgtactttaa ccagctgaat  11220

ggaagtacaa tctcttgcta tatgacacaa taattatttg caaaatgagt aaacatatca  11280

taaggaaatt atttttacaa ggtttgaaac ctgaaatgca gtctattatc atacataact  11340

aaaaatagag cctcaataaa cagattccca gttttgaaaa tgcaacattt gtactccaca  11400

ttgtcagttt tcttaggtat atttataaat actcctataa aaatgtaaag aaacacataa  11460

tgtagattgc taattttata ataacacaag ttgattttga catccaactt attaattatg  11520

aaatgacttt tggcctagta acaatgaaaa tgggggcaaa tacagataaa tggtaattct  11580

tagaatgaac tactcagcac caattctaag tttttcttga tggtaaatca taatgttccc  11640

tttctcctcg gttctgcaat ctataggcat accataattg taatcaatag cttaaaaata  11700

tgtctctctg tcctattctg tatctgtatc tcttggattt ttacctttgc aatagtcaac  11760

tgaaccatct tcttggagta ctcatgaaga tggaagtcta catggagaat acaggatgaa  11820

tccactctgt ctcctgcagt gaagtctgtt tgaaggatgt atttggctgt cttctggaca  11880

ggccattcta ataacagaaa caaacaagtt attttaaaac ttattggaat attcaaatat  11940

taaccaaagt agaaaaatat aatacacatc catgtgccca tcacagaact tcactgatta  12000

tcatcattta gccagtcttg aagaagcaag tgctaattac aatcacaaat gaaacaagat  12060

tcagacttca tgaagagcac tgcgctataa taaaagaaga aatgagcaca tacattcttt  12120

tactgacagt caaatggtga aggtgggcag aatcattatg tgatgcaaca tggcaaaagt  12180

atacagacag tgcatccaga ggaaggcacc ttgctgaatg actagaatgg aagtaggaga  12240

cattttgcag gccccccttca tcctgcaggg agaaccagaa ccacagcagc tctatttgcc  12300

tattcctctt taaattacaa agttaaaatt tgggagtagt agaaaatcaa ttggttatct  12360

tatagagtct cctagaatat ttcattggca ttgagaaggt ggaaaatgca aattatatac  12420

tttaaaatgt aatttttgct tttcacatat gcttaaagcc taaaacctct taataaactt  12480

cttctgaaat ata                                                     12493
```

```
<210> SEQ ID NO 2
<211> LENGTH: 510
<212> TYPE: PRT
<213> ORGANISM: Homo sapiens

<400> SEQUENCE: 2

Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45
```

```
Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
            260                 265                 270

Ala Ser Asn Glu Ile Leu Arg Asp Pro Cys Phe His Pro Gly Tyr Lys
        275                 280                 285

Lys Val Val Asn Val Ser Asp Leu Tyr Lys Thr Pro Cys Thr Lys Arg
    290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
            340                 345                 350

Leu Gln Gly Asp Phe Gly Ala Phe Ser Ala Phe Tyr Phe Val Met Lys
        355                 360                 365

Phe Leu Asn Leu Thr Ser Glu Lys Val Ser Gln Glu Lys Val Thr Glu
    370                 375                 380

Met Met Lys Lys Phe Cys Ala Gln Pro Trp Glu Glu Ile Lys Thr Ser
385                 390                 395                 400

Tyr Ala Gly Val Lys Glu Lys Tyr Leu Ser Glu Tyr Cys Phe Ser Gly
                405                 410                 415

Thr Tyr Ile Leu Ser Leu Leu Leu Gln Gly Tyr His Phe Thr Ala Asp
            420                 425                 430

Ser Trp Glu His Ile His Phe Ile Gly Lys Ile Gln Gly Ser Asp Ala
        435                 440                 445

Gly Trp Thr Leu Gly Tyr Met Leu Asn Leu Thr Asn Met Ile Pro Ala
    450                 455                 460

Glu Gln Pro Leu Ser Thr Pro Leu Ser His Ser Thr Tyr Val Phe Leu
```

465 470 475 480

Met Val Leu Phe Ser Leu Val Leu Phe Thr Val Ala Ile Ile Gly Leu
485 490 495

Leu Ile Phe His Lys Pro Ser Tyr Phe Trp Lys Asp Met Val
500 505 510

<210> SEQ ID NO 3
<211> LENGTH: 12630
<212> TYPE: DNA
<213> ORGANISM: Homo sapiens

<400> SEQUENCE: 3
attctgcagt ctcctgtgta cgtgtaaaat tatgatcaaa taaatttgta tgccttttct 60
cctattaacc tgccttttt gtcagcgatt gtcagtgaaa cttcagaggg caaaggggaa 120
gttttccttg gcccctccag ttttggtgct gtgaacagga taccaaagct gctctgttct 180
tctggaagct gcaatgaagg gaaccaagga cctgacaagc cagcagaagg agtctaacgt 240
gaagacattt tgctccaaga atatcctagc catccttggc ttctcctcta tcatagctgt 300
gatagctttg cttgctgtgg ggttgaccca gaacaaagca ttgccagaaa acgttaagta 360
tgggattgtg ctggatgcgg gttcttctca cacaagttta tacatctata agtggccagc 420
agaaaaggag aatgacacag gcgtggtgca tcaagtagaa gaatgcaggg ttaaaggtcc 480
tggaatctca aaatttgttc agaaagtaaa tgaaataggc atttacctga ctgattgcat 540
ggaaagagct agggaagtga ttccaaggtc ccagcaccaa gagacacccg tttacctggg 600
agccacggca ggcatgcggt tgctcaggat ggaaagtgaa gagttggcag acagggttct 660
ggatgtggtg gagaggagcc tcagcaacta ccccttttgac ttccagggtg ccaggatcat 720
tactggccaa gaggaaggtg cctatggctg gattactatc aactatctgc tgggcaaatt 780
cagtcagaaa acaaggtggt tcagcatagt cccatatgaa accaataatc aggaaacctt 840
tggagctttg gaccttgggg gagcctctac acaagtcact tttgtacccc aaaaccagac 900
tatcgagtcc ccagataatg ctctgcaatt tcgcctctat ggcaaggact acaatgtcta 960
cacacatagc ttcttgtgct atgggaagga tcaggcactc tggcagaaac tggccaagga 1020
cattcaggtt gcaagtaatg aaattctcag ggacccatgc tttcatcctg gatataagaa 1080
ggtagtgaac gtaagtgacc tttacaagac cccctgcacc aagagatttg agatgactct 1140
tccattccag cagtttgaaa tccagggtat tggaaactat caacaatgcc atcaaagcat 1200
cctggagctc ttcaacacca gttactgccc ttactcccag tgtgccttca atgggatttt 1260
cttgccacca ctccaggggg attttggggc attttcagct tttttacttg tgatgaagtt 1320
tttaaacttg acatcagaga aagtctctca ggaaaaggtg actgagatga tgaaaaagtt 1380
ctgtgctcag ccttgggagg agataaaaac atcttacgct ggagtaaagg agaagtacct 1440
gagtgaatac tgcttttctg gtacctacat tctctccctc cttctgcaag gctatcattt 1500
cacagctgat tcctgggagc acatccattt cattggcaag atccagggca gcgacgccgg 1560
ctggactttg ggctacatgc tgaacctgac caacatgatc ccagctgagc aaccattgtc 1620
cacacctctc tcccactcca cctatgtctt cctcatggtt ctattctccc tggtcctttt 1680
cacagtggcc atcataggct tgcttatctt tcacaagcct tcatatttct ggaaagatat 1740
ggtatagcaa aagcagctga aatatgctgg ctggagtgag gaaaaaaatc gtccagggag 1800
cattttcctc catcgcagtg ttcaaggcca tccttccctg tctgccaggg ccagtcttga 1860
cgagtgtgaa gcttccttgg cttttactga agcctttctt ttggaggtat tcaatatcct 1920

```
ttgcctcaag gacttcggca gatactgtct ctttcatgag tttttcccag ctacaccttt   1980
ctcctttgta ctttgtgctt gtataggttt taaagacctg acacctttca taatctttgc   2040
tttataaaag aacaatattg actttgtcta gaagaactga gagtcttgag tcctgtgata   2100
ggaggctgag ctggctgaaa gaagaatctc aggaactggt tcagttgtac tctttaagaa   2160
ccccttttctc tctcctgttt gccatccatt aagaaagcca tatgatgcct ttggagaagg   2220
cagacacaca ttccattccc agcctgctct gtgggtagga gaattttcta cagtaggcaa   2280
atatgtgcta aagccaaaga gttttataag gaaatatatg tgctcatgca gtcaatacag   2340
ttctcaatcc cacccaaagc aggtatgtca ataaatcaca tattcctagg tgatacccaa   2400
atgctacaga gtggaacact cagacctgag atttgcaaaa agcagatgta aatatatgca   2460
ttcaaacatc agggcttact atgaggtagg tggtatatac atgtcacaaa taaaaataca   2520
gttacaactc agggtcacaa aaaatgcatc ttccaatgca tatttttatt atggtaaaat   2580
atacataaat ataattcacc attttaacat ttaattcata ttaaatacgt acaaatcagt   2640
gacatttagt acattcacag tgttgtgcca ccatcaccac tatttagttc cagaacattt   2700
gcatcatcaa tacattgtct agagacaaga ctatcctggg taggcagaaa ccatagatct   2760
tttgtgttta cagctatgga aaccaactgt accataaaga tagttcactg agttttaaag   2820
ccaagccaca tcttattttt ccaaggttta atttagtgag agggcagcat tagtgtggag   2880
tggcatgctt ttgccctatc gtggaattta cacatcagaa tgtgcaggat ccaagtctga   2940
aagtgttgcc acccgtcaca caacatgggc tttgtttgct tattccatga agcagcagct   3000
atagacctta ccatggaaac atgaagagac cctgcacccc tttccttaag gattgctgca   3060
agagttacct gttgagcagg attgactggt gatgtttcat tctgaccttg tcccaagctc   3120
tccatctcta gatctgggga ctgactgttg agctgatggg gaaagaaaag ctctcacaca   3180
aaccggaagc caaatgtccc ctatctcttg aatgatcaag tcacttttga caacatccag   3240
gtgaatataa aaacttaata aagctgtgga aaggaactct taatcttctt ttctgctact   3300
taggttaaat tcactagatc ttgattagga atcaaaattc gaattgggac atgttcaaat   3360
tctttcttgt ggtagttgcc tatactgtca tcgctgctgt tggttgagca tttgtggtgt   3420
accacgctgt gtgctcaagg gtattacatt catcttctca tttaatcctc acaacaatct   3480
gaagaaggta ggtattacaa ttcccacttc atagaaacag aaactgaggt tcagagaggt   3540
taagtcattt gcccaaatgg ctgagccaaa gcctaccatg tacctaacct ttattttctt   3600
tcccgaacat accaggctgt ctcctcataa cttccaagca tgcacttaaa actccacatg   3660
aatacaaggt tcatgggact tggtattcat agaaagggag gcagaaagct ggtctgttcc   3720
tgataggctt gtaatttaat atcattctgt tcatgtgctt tggatggaag cacatctggc   3780
atatgatgct aatcagtggt tcccataccc ctggcttcct aattttaatg tttgctcaca   3840
gcatagtaga ttgacatcaa atagtggccg atgatgatga aaataaaggt caaataagtt   3900
gagccaataa cagccgcttt tttccttctg tctgcgtata caaagcactg tcatgcacac   3960
aatctattct gaccctcaca acaacccata agggtgtaaa tagtatttcc attttacaaa   4020
tgaggatcac acaaactact acatggcaga gcagatactc caactcatgt cttctggttg   4080
aagcctattg ctttttcttt tctaaacact ttccctcagc aagttggaat tagacttcac   4140
aagtctcctt cagagaacac aaatcttttc ttattccatt cctgtttggt tgcctacgtc   4200
caatctcccc ctccccagag atgccaaaaa aaaaatcctt taaggtattt gggagccaaa   4260
```

```
ctcaacttgt taaaatctca aattatggag acaatcagca gacacaacct aaccccaatt   4320
attttggcag gaaggttggt ttagaggcag atccagcaat ctgctttggg ccactctggg   4380
tggggtaggt gaaataagat tggtcactgt taactaattt taatattgga ttggccattg   4440
gttatcactg attaccattc tcccctggat tttcacccag gactcaaaac ttggttctgc   4500
taaccctgtt cctttatgag gaacctttta aagattcctt tataaggtgg gagttttttt   4560
tctatgaacc tataggggag aaaaaagatc agcagaagtc attacttttt tttttttttt   4620
tttttttttt tgagagagag tctcactcca ttgcccaggc tggagtgcag tggtgctatc   4680
tcggctcact gcaacctccg cctcctgggt tcaagcaatt ctcctgcctc agcctcccga   4740
gtagctggga ttgcaggtgc ccaccaccac acccggctaa tttttgtatt tttagtaaag   4800
acagggtttc accatgttgg ccaggctggt ctccaactcc caatctcagg tgatcctatt   4860
gcctcgggct cccaaagtgc tgggattaca ggagtgagcc accatgcctg gccagaagtg   4920
gttacttctg tagacaaaag aataatgcta cttaatcagg ctttctgtgt gacaagaaag   4980
agaaagaaaa taaagaagtt tcaattcatc caattcttaa taagaaatat gtaaataaaa   5040
ttttttaaaa ttacacttca ttttaatgtt gtatcagtca aggtccctgc aagagatgga   5100
tggtatggta cactcaaact gggtaacaca ggagagtttt cagaaagcaa ctaaatccaa   5160
aatactatca aggaatcaat ataaaaattg ttaatatttt tctcatacta aattttcaaa   5220
atattttgtg tctattacat ttacagcaca tcttaattag gactagctgt gtgttcacct   5280
cacatgtggc ttgtagctac catactggac agcacatgtc caaaaaaata cacgtaaagt   5340
taaagtttaa aagacacagg aactaagccc tcattgtctt tcccttggga ggtagtttaa   5400
agagctatag atgctgtaac attcttgcta ttatttatta tatatgacat tattcctaaa   5460
aaagcttttg agatcctagg ttgtattcct caggttttgt tgccttccca tgaagatgtg   5520
aaggcaggga tgcctgttat tcagtccaag atgcatgaca agagaccttg ggaaagtttc   5580
atctggattt aaagattaat tcttgatgct tacattccat actcaaaatg taaatttgaa   5640
tattaaaata aagatgattt tttttttgga gctagtcttg ctctgttgcc caggctggaa   5700
tgcagtggca tgatcatggc tcactgcagc ctcgacctcc caagctcaag caaggctaca   5760
ggtgtgcacc taagtagcta ggactacagg tgtgcaccac catgtctagc tatttttttt   5820
tctgtagaga cagggtttcc ctatgttgtc caggctggtc tcgaactcct gccctcaagc   5880
aatcctcctg ccttggcctc ccaaagtgtt gagattacag gcgtaagcca ctgcacctgg   5940
ccaagatgaa tattttaata gctcacagaa caaagtttgc cacataatga taaaattact   6000
atgaaaatat attcccttta ttgtcagttt aaaagatgaa ctgagtttca cccaaactgg   6060
tctggcccct ctctgattca aataccaata gttgctctga ttcaaattcc aactgttaga   6120
acatgacagc tgctcataac tagctttgct tactaaccat gtttctttcc atttgtatta   6180
ggtcctttac tttttataac agcctcaaag tttcatgaat tgctgcagta aacattgatt   6240
ttcatgtttg tgagtctgca agccagctgg gcagctctac ttcaggtggt aagggtggat   6300
cagacctatt ccatatacct cttgttctcc ttgtccagtg gtttctaggg atatgttctc   6360
atgatgaacc ccgcagaggc tcgtgaaagt gagaggaaac taggatgcct cttaaggtct   6420
tggtcaggat ggggtctcct gtcacttctg tcacaggcta ttgtaagtca tatgagcaag   6480
ctcaataaaa tataaacaag tcagataaac agtgggagga atggcaaagt catatggcca   6540
aggccatgag tgattaattt taacacagga aaaaagtaaa gcattaaatg cgattattta   6600
atatacaatg tcttattaac tgaaatataa aatgtgttta ctgtaaaata taatctgttt   6660
```

```
atctcaccaa agaaatatta tctttaaaaa atgtcattac ttctaagaca tcatcagtct   6720
gcaacttctt tccatagcct taatcaggat gctgtggcag ctcccacatt agcctcgcat   6780
tctaaactgg tagatgtcct aggaaaccat acatctatgt atttttctta ttttatacgt   6840
ttaggacaat gtatagctaa ttacccaact ttttatttgc atacaaatct aatacaactg   6900
aacacaatca gttttatcac aggtataatg gatttttcaa tagtgaggag gtgcctccat   6960
gagccttctc tttagaaaag tggcattcaa gactcttcat ttgaagtgaa gattgctatg   7020
tcttttgcat tgctctattt tacataaatt aagttataaa ttgacactat aatcaactga   7080
caccatgatc agtgatgatg atcaccctca tcagcactag agttgacttg tttttataac   7140
ccctttgcat gtatgttgaa tagcaaagtt catcagagaa catgtattag tcaatggtaa   7200
gtaagatact ctcatctaag aaataacatc acctcttcta atgaagttct aagaagagag   7260
ggaagaaaaa gtcttgggag ctagtcaggg aatagtgtgt atttgcaatt acctaaactg   7320
aactctacca ttactcctaa cccagttcct cctcctgtgt tttacatgat taatgccacc   7380
cctgcctcaa tgaaccaaga tcagctccat cactgggacc tccccattct gcctgtgcaa   7440
tatttttctt ttttatttct ccttctaata ttactgttat tgctccagta aagagctgta   7500
atatatttta cctggactga taccaggaat ggtggtgttg cttccaatct gttgctgcta   7560
gattaatctt tgcaaagcac aggcttaatt tcattgctgc tcaactaaaa ccactggtgg   7620
ctttccattg cctacaaaat aaagtcaacc tccccatcag acattcaagg ctttcaatga   7680
tccatggccg ccagctctct ccaggctcat atcccactcc actcctctga tgtttcctac   7740
actacactac actatactac actacagcca ggtagaatga ctgttcaccc aacaccactc   7800
aggttgtctt ctcaacttgg aatactcttg caccttcaaa gctcatttca aatgcccctt   7860
catttgtgaa gccttctcca aatttccaag tcagaatgtc tcttccttgt gctaccacaa   7920
ccctttaact gagcctccat tagtgcactg agaccattct gttcagtgtc tgggtgaagc   7980
ttcctggtga aaaatatgtt acctatttct ttctgaaaag ttggattcag ggatattatc   8040
acggacctaa ggtaatagtt ctagccaacc tccctgtcca ctgccaggcc gactacaaac   8100
ccttctgttg ctggcgagct ggtccgcacc actagttctg cttcactcta tttatctctt   8160
gatgtaacca tcttctttct ccaggtttta agaaccagcc caactcctgg ttccctgatg   8220
aagcttttat tcccctagcc acatggaact tttccttttt ggaacatgcc tttagtttct   8280
gtgtagtttg ccatgcagca cttcattgta cacattatta aaacagaatt ttaaggatta   8340
gaatgaacct taaaagatca tgcatctcaa aatttaatgt acatacaaat tacccaggga   8400
ttttgttgaa ataaaaatta tttaatttta attaatataa ataattcagt aggtctgggg   8460
tgaggcctga ggttttacat ttccaacaag ctgccaggta aagccaatac atctgtccag   8520
gaatcacact ttgcgtatca aaggtctaga tgacattatc attccaaaga gtttctttta   8580
caggctctca gatcagtgtt catccactac ctgactactg tcattcacag gcattctgtt   8640
ccacagcagg ccagctaacg tggtatttac aaagctcact cctcttatac aacaatccaa   8700
gtgtttcttt tgtcagttgt ctgtgcccca ggagatccct ctctgccttg ccttgccctc   8760
tgcctttgga gaccagcacc tcatactcag tgaaggcctg gagtgcttaa gagggatttc   8820
ttccagctct cttgccctgg tcttcagtgt attagatgta ttacctccat gctctcagta   8880
gaggcccata ggaaagagta ggtaggttat gccagctcac acgcatcctt taaaaatggt   8940
ttagaagttt agctggtttc ttattactcc tgtctatgga tgtttccttc tgtcactcta   9000
```

ctagggatga aacagctaat catgttcaat agttacattt agattggttt ttaaaaacta 9060
tgattgtatt agttcgtttc catgctgctg ataaagacat atctgagact ggaaacaaaa 9120
agggtttaat tggacttaca gttccacatg gctggggagg cctcaaaatc aggtgggagg 9180
caaaaggtac ttcttacgtg gtggcatcaa gagcaaaatg aggaagaagc aaaagcagaa 9240
actcttcata aacccaccag atcttgtggg acttattatc acgagaatag cacagaaaag 9300
actggcctcc atgattcaat tacctcccac tgcgtccctc ccacaacatg tgggaattct 9360
gggagataca attcaagttg agatttgggt ggggacacag ccaaaccata tcattcctcc 9420
ctgggctcct ccaaatttca taatcctcac atttcaaaac caatcattcc ttcccaacag 9480
ttccccaaag tcttaactca tttcagcatt aacccaaaag tccacagtcc aaagtctcat 9540
ctgagacaag gcaagtccct tccacttaca agcctgtaaa agcaagctag ttacctccta 9600
gatacaatgg ggggtacagg tattgggtaa atacagctgt tccaaatgag agaaattggc 9660
caaaacaaag gggttacagg gtccatgcaa gtctgaaatc cagtggggca gtcaaatttt 9720
aaagctccat aatgatctcc tttgactcca tgtctcacat tcaggtcatg ctgatgcaag 9780
agataggttc ccatggtctt gtgcagctcc gcccctgtgg ctttgcagag tacagcctcc 9840
ctcctggctg ctttctcagg ctgatgttga gtgtctgtag cttttccagg cacaagatgc 9900
aagttggtgg ttgatctacc attctggggt ctaccattct ggggtctacc gttctgggac 9960
tgtggccttc ttctcacagc tccactaggc agtgccccaa cagggactct gtgtgggggc 10020
tctgccccac atttcccttc cacactgccc taggagaggt tccccatgag ggctctgccc 10080
ctgcagcaaa cttttgcctg gacatccagg tgtttccata tatattctga aatctaggca 10140
gaggttccca aatctcaatt cttgacatct ctgcacccac aggctcaaca tcacatggaa 10200
gctgccaatg cttggggcct ctaccctctg aagccacagc ccaagctcta tgttggctcc 10260
tttcagccat ggctggagca gctgggacac agggcaccaa gtccctaggc tgcacacagc 10320
acagagaccc tgggcccagc ccacaaaacc actttttcct cctgggcctc tgggcctgtg 10380
atgggagggg ctgccatgaa ggtctctgac atgacctgga gacattttcc ccatggtctt 10440
ggggattaac attaggctcc ttgctgctta tgcaaatttc tgcagccagc ttgaatttct 10500
ccttaaaaaa aatgggtttt tcttttctac tgcatcatca ggctgcagat tttccacatt 10560
tatgctcttg tttccctttt aaaacagaat gtttttaaca gcacccaagt caccttttga 10620
atgctttgct gcttagaaat ttattccacc agatacccta agtcatctct ctcaagctct 10680
aagttccaca aatctctagg gcaagggtga aatgctgcca gtctccttgc taaaacataa 10740
caagggtcac ctttacttca gttcccaaca aggtcttcat ctccatctga gaccacctca 10800
gcctggacct tattgttcat atcactatca gtatttttgt caatgccatt cacagtctct 10860
aggaggttcc aaactttcct acattttcct atcttcttct gagccctcca gattatttca 10920
acacccagtt ccaaagttgc ttccacattt tcgggtatct tttcagcaat gccccactct 10980
actggtacta ttagtccatt ttcatgctgc tgataaagac atacctgaga ctgggaacaa 11040
aaagaggttt aattggactt atagttccac ctggctgggg aggcctcaga atcatggcag 11100
gaggtgaaag gcatttctta cacggcagca gcaagagaaa aatgaagaag cagcaaaagc 11160
agaaacccct gataaaacca tcagatctcg tgagacttat tcactatcac aagaatagca 11220
tgggaaagac cagccccctt gattcaatta cctccccctg ggtcctgtgg gaattctgga 11280
aggtacaatt caagttgaga tttgggtggg gacacagcca aaccatatca atgattttgt 11340
actttaacca gctgaatgga agtacaatct cttgctatat gacacaataa ttatttgcaa 11400

```
aatgagtaaa catatcataa ggaaattatt tttacaaggt ttgaaacctg aaatgcagtc  11460

tattatcata cataactaaa aatagagcct caataaacag attcccagtt ttgaaaatgc  11520

aacatttgta ctccacattg tcagttttct taggtatatt tataaatact cctataaaaa  11580

tgtaaagaaa cacataatgt agattgctaa ttttataata acacaagttg attttgacat  11640

ccaacttatt aattatgaaa tgacttttgg cctagtaaca atgaaaatgg gggcaaatac  11700

agataaatgg taattcttag aatgaactac tcagcaccaa ttctaagttt ttcttgatgg  11760

taaatcataa tgttcccttt ctcctcggtt ctgcaatcta taggcatacc ataattgtaa  11820

tcaatagctt aaaaatatgt ctctctgtcc tattctgtat ctgtatctct tggattttta  11880

cctttgcaat agtcaactga accatcttct tggagtactc atgaagatgg aagtctacat  11940

ggagaataca ggatgaatcc actctgtctc ctgcagtgaa gtctgtttga aggatgtatt  12000

tggctgtctt ctggacaggc cattctaata acagaaacaa acaagttatt ttaaaactta  12060

ttggaatatt caaatattaa ccaaagtaga aaaatataat acacatccat gtgcccatca  12120

cagaacttca ctgattatca tcatttagcc agtcttgaag aagcaagtgc taattacaat  12180

cacaaatgaa acaagattca gacttcatga agagcactgc gctataataa aagaagaaat  12240

gagcacatac attcttttac tgacagtcaa atggtgaagg tgggcagaat cattatgtga  12300

tgcaacatgg caaaagtata cagacagtgc atccagagga aggcaccttg ctgaatgact  12360

agaatggaag taggagacat tttgcaggcc cccttcatcc tgcagggaga accagaacca  12420

cagcagctct atttgcctat tcctctttaa attacaaagt taaaatttgg gagtagtaga  12480

aaatcaattg gttatcttat agagtctcct agaatatttc attggcattg agaaggtgga  12540

aaatgcaaat tatatacttt aaaatgtaat ttttgctttt cacatatgct taaagcctaa  12600

aacctcttaa taaacttctt ctgaaatata                                    12630
```

<210> SEQ ID NO 4
<211> LENGTH: 517
<212> TYPE: PRT
<213> ORGANISM: Homo sapiens

<400> SEQUENCE: 4

```
Met Lys Gly Thr Lys Asp Leu Thr Ser Gln Gln Lys Glu Ser Asn Val
1               5                   10                  15

Lys Thr Phe Cys Ser Lys Asn Ile Leu Ala Ile Leu Gly Phe Ser Ser
            20                  25                  30

Ile Ile Ala Val Ile Ala Leu Leu Ala Val Gly Leu Thr Gln Asn Lys
        35                  40                  45

Ala Leu Pro Glu Asn Val Lys Tyr Gly Ile Val Leu Asp Ala Gly Ser
    50                  55                  60

Ser His Thr Ser Leu Tyr Ile Tyr Lys Trp Pro Ala Glu Lys Glu Asn
65                  70                  75                  80

Asp Thr Gly Val Val His Gln Val Glu Glu Cys Arg Val Lys Gly Pro
                85                  90                  95

Gly Ile Ser Lys Phe Val Gln Lys Val Asn Glu Ile Gly Ile Tyr Leu
            100                 105                 110

Thr Asp Cys Met Glu Arg Ala Arg Glu Val Ile Pro Arg Ser Gln His
        115                 120                 125

Gln Glu Thr Pro Val Tyr Leu Gly Ala Thr Ala Gly Met Arg Leu Leu
    130                 135                 140

Arg Met Glu Ser Glu Glu Leu Ala Asp Arg Val Leu Asp Val Val Glu
```

```
145                 150                 155                 160

Arg Ser Leu Ser Asn Tyr Pro Phe Asp Phe Gln Gly Ala Arg Ile Ile
                165                 170                 175

Thr Gly Gln Glu Glu Gly Ala Tyr Gly Trp Ile Thr Ile Asn Tyr Leu
            180                 185                 190

Leu Gly Lys Phe Ser Gln Lys Thr Arg Trp Phe Ser Ile Val Pro Tyr
        195                 200                 205

Glu Thr Asn Asn Gln Glu Thr Phe Gly Ala Leu Asp Leu Gly Gly Ala
    210                 215                 220

Ser Thr Gln Val Thr Phe Val Pro Gln Asn Gln Thr Ile Glu Ser Pro
225                 230                 235                 240

Asp Asn Ala Leu Gln Phe Arg Leu Tyr Gly Lys Asp Tyr Asn Val Tyr
                245                 250                 255

Thr His Ser Phe Leu Cys Tyr Gly Lys Asp Gln Ala Leu Trp Gln Lys
            260                 265                 270

Leu Ala Lys Asp Ile Gln Val Ala Ser Asn Glu Ile Leu Arg Asp Pro
        275                 280                 285

Cys Phe His Pro Gly Tyr Lys Lys Val Val Asn Val Ser Asp Leu Tyr
    290                 295                 300

Lys Thr Pro Cys Thr Lys Arg Phe Glu Met Thr Leu Pro Phe Gln Gln
305                 310                 315                 320

Phe Glu Ile Gln Gly Ile Gly Asn Tyr Gln Gln Cys His Gln Ser Ile
                325                 330                 335

Leu Glu Leu Phe Asn Thr Ser Tyr Cys Pro Tyr Ser Gln Cys Ala Phe
            340                 345                 350

Asn Gly Ile Phe Leu Pro Pro Leu Gln Gly Asp Phe Gly Ala Phe Ser
        355                 360                 365

Ala Phe Tyr Phe Val Met Lys Phe Leu Asn Leu Thr Ser Glu Lys Val
    370                 375                 380

Ser Gln Glu Lys Val Thr Glu Met Met Lys Lys Phe Cys Ala Gln Pro
385                 390                 395                 400

Trp Glu Glu Ile Lys Thr Ser Tyr Ala Gly Val Lys Glu Lys Tyr Leu
                405                 410                 415

Ser Glu Tyr Cys Phe Ser Gly Thr Tyr Ile Leu Ser Leu Leu Leu Gln
            420                 425                 430

Gly Tyr His Phe Thr Ala Asp Ser Trp Glu His Ile His Phe Ile Gly
        435                 440                 445

Lys Ile Gln Gly Ser Asp Ala Gly Trp Thr Leu Gly Tyr Met Leu Asn
    450                 455                 460

Leu Thr Asn Met Ile Pro Ala Glu Gln Pro Leu Ser Thr Pro Leu Ser
465                 470                 475                 480

His Ser Thr Tyr Val Phe Leu Met Val Leu Phe Ser Leu Val Leu Phe
                485                 490                 495

Thr Val Ala Ile Ile Gly Leu Leu Ile Phe His Lys Pro Ser Tyr Phe
            500                 505                 510

Trp Lys Asp Met Val
        515


<210> SEQ ID NO 5
<211> LENGTH: 12515
<212> TYPE: DNA
<213> ORGANISM: Homo sapiens

<400> SEQUENCE: 5
```

-continued

```
cctgttgctc tttgctctaa tgagccttga gaaaggattg ctggtcatgg gaccagaggc     60
tttatgggga gggaagaact gttcttgact ttcagttttt cgagcgggtt tcaagagtct    120
aacgtgaaga cattttgctc caagaatatc ctagccatcc ttggcttctc ctctatcata    180
gctgtgatag ctttgcttgc tgtggggttg acccagaaca aagcattgcc agaaaacgtt    240
aagtatggga ttgtgctgga tgcgggttct tctcacacaa gtttatacat ctataagtgg    300
ccagcagaaa aggagaatga cacaggcgtg gtgcatcaag tagaagaatg cagggttaaa    360
ggtcctggaa tctcaaaatt tgttcagaaa gtaaatgaaa taggcattta cctgactgat    420
tgcatggaaa gagctaggga agtgattcca aggtcccagc accaagagac acccgtttac    480
ctgggagcca cggcaggcat gcggttgctc aggatggaaa gtgaagagtt ggcagacagg    540
gttctggatg tggtggagag gagcctcagc aactacccct ttgacttcca gggtgccagg    600
atcattactg gccaagagga aggtgcctat ggctggatta ctatcaacta tctgctgggc    660
aaattcagtc agaaaacaag gtggttcagc atagtcccat atgaaaccaa taatcaggaa    720
acctttggag ctttggacct tgggggagcc tctacacaag tcacttttgt accccaaaac    780
cagactatcg agtccccaga taatgctctg caatttcgcc tctatggcaa ggactacaat    840
gtctacacac atagcttctt gtgctatggg aaggatcagg cactctggca gaaactggcc    900
aaggacattc aggttgcaag taatgaaatt ctcagggacc catgctttca tcctggatat    960
aagaaggtag tgaacgtaag tgacctttac aagacccccct gcaccaagag atttgagatg   1020
actcttccat tccagcagtt tgaaatccag ggtattggaa actatcaaca atgccatcaa   1080
agcatcctgg agctcttcaa caccagttac tgcccttact cccagtgtgc cttcaatggg   1140
attttcttgc caccactcca gggggatttt ggggcatttt cagcttttta ctttgtgatg   1200
aagtttttaa acttgacatc agagaaagtc tctcaggaaa aggtgactga gatgatgaaa   1260
aagttctgtg ctcagccttg ggaggagata aaaacatctt acgctggagt aaaggagaag   1320
tacctgagtg aatactgctt ttctggtacc tacattctct ccctccttct gcaaggctat   1380
catttcacag ctgattcctg ggagcacatc catttcattg gcaagatcca gggcagcgac   1440
gccggctgga ctttgggcta catgctgaac ctgaccaaca tgatcccagc tgagcaacca   1500
ttgtccacac ctctctccca ctccacctat gtcttcctca tggttctatt ctccctggtc   1560
cttttcacag tggccatcat aggcttgctt atctttcaca agccttcata tttctggaaa   1620
gatatggtat agcaaaagca gctgaaatat gctggctgga gtgaggaaaa aaatcgtcca   1680
gggagcattt tcctccatcg cagtgttcaa ggccatcctt ccctgtctgc cagggccagt   1740
cttgacgagt gtgaagcttc cttggctttt actgaagcct ttcttttgga ggtattcaat   1800
atcctttgcc tcaaggactt cggcagatac tgtctctttc atgagttttt cccagctaca   1860
cctttctcct ttgtactttg tgcttgtata ggttttaaag acctgacacc tttcataatc   1920
tttgctttat aaaagaacaa tattgacttt gtctagaaga actgagagtc ttgagtcctg   1980
tgataggagg ctgagctggc tgaaagaaga atctcaggaa ctggttcagt tgtactcttt   2040
aagaacccct ttctctctcc tgtttgccat ccattaagaa agccatatga tgcctttgga   2100
gaaggcagac acacattcca ttcccagcct gctctgtggg taggagaatt ttctacagta   2160
ggcaaatatg tgctaaagcc aaagagtttt ataaggaaat atatgtgctc atgcagtcaa   2220
tacagttctc aatcccaccc aaagcaggta tgtcaataaa tcacatattc ctaggtgata   2280
cccaaatgct acagagtgga acactcagac ctgagatttg caaaaagcag atgtaaatat   2340
atgcattcaa acatcagggc ttactatgag gtaggtggta tatacatgtc acaaataaaa   2400
```

atacagttac aactcagggt cacaaaaaat gcatcttcca atgcatattt ttattatggt 2460
aaaatataca taaatataat tcaccatttt aacatttaat tcatattaaa tacgtacaaa 2520
tcagtgacat ttagtacatt cacagtgttg tgccaccatc accactattt agttccagaa 2580
catttgcatc atcaatacat tgtctagaga caagactatc ctgggtaggc agaaaccata 2640
gatcttttgt gtttacagct atggaaacca actgtaccat aaagatagtt cactgagttt 2700
taaagccaag ccacatctta tttttccaag gtttaattta gtgagagggc agcattagtg 2760
tggagtggca tgcttttgcc ctatcgtgga atttacacat cagaatgtgc aggatccaag 2820
tctgaaagtg ttgccacccg tcacacaaca tgggctttgt ttgcttattc catgaagcag 2880
cagctataga ccttaccatg gaaacatgaa gagaccctgc accccttTcc ttaaggattg 2940
ctgcaagagt tacctgttga gcaggattga ctggtgatgt ttcattctga ccttgtccca 3000
agctctccat ctctagatct ggggactgac tgttgagctg atggggaaag aaaagctctc 3060
acacaaaccg gaagccaaat gtcccctatc tcttgaatga tcaagtcact tttgacaaca 3120
tccaggtgaa tataaaaact taataaagct gtggaaagga actcttaatc ttcttttctg 3180
ctacttaggt taaattcact agatcttgat taggaatcaa aattcgaatt gggacatgtt 3240
caaattcttt cttgtggtag ttgcctatac tgtcatcgct gctgttggtt gagcatttgt 3300
ggtgtaccac gctgtgtgct caagggtatt acattcatct tctcatttaa tcctcacaac 3360
aatctgaaga aggtaggtat tacaattccc acttcataga aacagaaact gaggttcaga 3420
gaggttaagt catttgccca aatggctgag ccaaagccta ccatgtacct aacctttatt 3480
ttctttcccg aacataccag gctgtctcct cataacttcc aagcatgcac ttaaaactcc 3540
acatgaatac aaggttcatg ggacttggta ttcatagaaa gggaggcaga aagctggtct 3600
gttcctgata ggcttgtaat ttaatatcat tctgttcatg tgctttggat ggaagcacat 3660
ctggcatatg atgctaatca gtggttccca taccccctggc ttcctaattt taatgtttgc 3720
tcacagcata gtagattgac atcaaatagt ggccgatgat gatgaaaata aaggtcaaat 3780
aagttgagcc aataacagcc gctttttttcc ttctgtctgc gtatacaaag cactgtcatg 3840
cacacaatct attctgaccc tcacaacaac ccataagggt gtaaatagta tttccatttt 3900
acaaatgagg atcacacaaa ctactacatg gcagagcaga tactccaact catgtcttct 3960
ggttgaagcc tattgctttt tcttttctaa acactttccc tcagcaagtt ggaattagac 4020
ttcacaagtc tccttcagag aacacaaatc ttttcttatt ccattcctgt ttggttgcct 4080
acgtccaatc tccccctccc cagagatgcc aaaaaaaaaa tcctttaagg tatttgggag 4140
ccaaactcaa cttgttaaaa tctcaaatta tggagacaat cagcagacac aacctaaccc 4200
caattatttt ggcaggaagg ttggtttaga ggcagatcca gcaatctgct ttgggccact 4260
ctgggtgggg taggtgaaat aagattggtc actgttaact aattttaata ttggattggc 4320
cattggttat cactgattac cattctcccc tggattttca cccaggactc aaaacttggt 4380
tctgctaacc ctgttccttt atgaggaacc ttttaaagat tcctttataa ggtgggagtt 4440
tttttctat gaacctatag gggagaaaaa agatcagcag aagtcattac tttttttttt 4500
tttttttttt ttttttgaga gagagtctca ctccattgcc caggctggag tgcagtggtg 4560
ctatctcggc tcactgcaac ctccgcctcc tgggttcaag caattctcct gcctcagcct 4620
cccgagtagc tgggattgca ggtgcccacc accacacccg gctaattttt gtatttttag 4680
taaagacagg gtttcaccat gttggccagg ctggtctcca actcccaatc tcaggtgatc 4740

-continued ctattgcctc gggctcccaa agtgctggga ttacaggagt gagccaccat gcctggccag 4800
aagtggttac ttctgtagac aaaagaataa tgctacttaa tcaggctttc tgtgtgacaa 4860
gaaagagaaa gaaaataaag aagtttcaat tcatccaatt cttaataaga aatatgtaaa 4920
taaaattttt taaaattaca cttcatttta atgttgtatc agtcaaggtc cctgcaagag 4980
atggatggta tggtacactc aaactgggta acacaggaga gttttcagaa agcaactaaa 5040
tccaaaatac tatcaaggaa tcaatataaa aattgttaat atttttctca tactaaattt 5100
tcaaaatatt ttgtgtctat tacatttaca gcacatctta attaggacta gctgtgtgtt 5160
cacctcacat gtggcttgta gctaccatac tggacagcac atgtccaaaa aaatacacgt 5220
aaagttaaag tttaaaagac acaggaacta agccctcatt gtctttccct tgggaggtag 5280
tttaaagagc tatagatgct gtaacattct tgctattatt tattatatat gacattattc 5340
ctaaaaaagc ttttgagatc ctaggttgta ttcctcaggt tttgttgcct tcccatgaag 5400
atgtgaaggc agggatgcct gttattcagt ccaagatgca tgacaagaga ccttgggaaa 5460
gtttcatctg gatttaaaga ttaattcttg atgcttacat tccatactca aaatgtaaat 5520
ttgaatatta aaataaagat gatttttttt ttggagctag tcttgctctg ttgcccaggc 5580
tggaatgcag tggcatgatc atggctcact gcagcctcga cctcccaagc tcaagcaagg 5640
ctacaggtgt gcacctaagt agctaggact acaggtgtgc accaccatgt ctagctattt 5700
tttttctgt agagacaggg ttttcctatg ttgtccaggc tggtctcgaa ctcctgccct 5760
caagcaatcc tcctgccttg gcctcccaaa gtgttgagat tacaggcgta agccactgca 5820
cctggccaag atgaatattt taatagctca cagaacaaag tttgccacat aatgataaaa 5880
ttactatgaa aatatattcc ctttattgtc agtttaaaag atgaactgag tttcacccaa 5940
actggtctgg cccctctctg attcaaatac caatagttgc tctgattcaa attccaactg 6000
ttagaacatg acagctgctc ataactagct ttgcttacta accatgtttc tttccatttg 6060
tattaggtcc tttacttttt ataacagcct caaagtttca tgaattgctg cagtaaacat 6120
tgattttcat gtttgtgagt ctgcaagcca gctgggcagc tctacttcag gtggtaaggg 6180
tggatcagac ctattccata tacctcttgt tctccttgtc cagtggtttc tagggatatg 6240
ttctcatgat gaaccccgca gaggctcgtg aaagtgagag gaaactagga tgcctcttaa 6300
ggtcttggtc aggatggggt ctcctgtcac ttctgtcaca ggctattgta agtcatatga 6360
gcaagctcaa taaaatataa acaagtcaga taaacagtgg gaggaatggc aaagtcatat 6420
ggccaaggcc atgagtgatt aattttaaca caggaaaaaa gtaaagcatt aaatgcgatt 6480
atttaatata caatgtctta ttaactgaaa tataaaatgt gtttactgta aaatataatc 6540
tgtttatctc accaaagaaa tattatcttt aaaaaatgtc attacttcta agacatcatc 6600
agtctgcaac ttctttccat agccttaatc aggatgctgt ggcagctccc acattagcct 6660
cgcattctaa actggtagat gtcctaggaa accatacatc tatgtatttt tcttatttta 6720
tacgtttagg acaatgtata gctaattacc caacttttta tttgcataca aatctaatac 6780
aactgaacac aatcagtttt atcacaggta taatggattt ttcaatagtg aggaggtgcc 6840
tccatgagcc ttctctttag aaaagtggca ttcaagactc ttcatttgaa gtgaagattg 6900
ctatgtcttt tgcattgctc tattttacat aaattaagtt ataaattgac actataatca 6960
actgacacca tgatcagtga tgatgatcac cctcatcagc actagagttg acttgttttt 7020
ataacccctt tgcatgtatg ttgaatagca aagttcatca gagaacatgt attagtcaat 7080
ggtaagtaag atactctcat ctaagaaata acatcacctc ttctaatgaa gttctaagaa 7140

```
gagagggaag aaaaagtctt gggagctagt cagggaatag tgtgtatttg caattaccta   7200
aactgaactc taccattact cctaacccag ttcctcctcc tgtgttttac atgattaatg   7260
ccacccctgc ctcaatgaac caagatcagc tccatcactg ggacctcccc attctgcctg   7320
tgcaatattt ttcttttttta tttctccttc taatattact gttattgctc cagtaaagag   7380
ctgtaatata ttttacctgg actgatacca ggaatggtgg tgttgcttcc aatctgttgc   7440
tgctagatta atctttgcaa agcacaggct taatttcatt gctgctcaac taaaaccact   7500
ggtggctttc cattgcctac aaaataaagt caacctcccc atcagacatt caaggctttc   7560
aatgatccat ggccgccagc tctctccagg ctcatatccc actccactcc tctgatgttt   7620
cctacactac actacactat actacactac agccaggtag aatgactgtt cacccaacac   7680
cactcaggtt gtcttctcaa cttggaatac tcttgcacct tcaaagctca tttcaaatgc   7740
cccttcattt gtgaagcctt ctccaaattt ccaagtcaga atgtctcttc cttgtgctac   7800
cacaaccctt taactgagcc tccattagtg cactgagacc attctgttca gtgtctgggt   7860
gaagcttcct ggtgaaaaat atgttaccta tttctttctg aaaagttgga ttcagggata   7920
ttatcacgga cctaaggtaa tagttctagc caacctccct gtccactgcc aggccgacta   7980
caaacccttc tgttgctggc gagctggtcc gcaccactag ttctgcttca ctctatttat   8040
ctcttgatgt aaccatcttc tttctccagg ttttaagaac cagcccaact cctggttccc   8100
tgatgaagct tttattcccc tagccacatg gaactttttcc tttttggaac atgcctttag   8160
tttctgtgta gtttgccatg cagcacttca ttgtacacat tattaaaaca gaattttaag   8220
gattagaatg aaccttaaaa gatcatgcat ctcaaaattt aatgtacata caaattaccc   8280
agggattttg ttgaaataaa aattatttaa ttttaattaa tataaataat tcagtaggtc   8340
tggggtgagg cctgaggttt tacatttcca acaagctgcc aggtaaagcc aatacatctg   8400
tccaggaatc acactttgcg tatcaaaggt ctagatgaca ttatcattcc aaagagtttc   8460
ttttacaggc tctcagatca gtgttcatcc actacctgac tactgtcatt cacaggcatt   8520
ctgttccaca gcaggccagc taacgtggta tttacaaagc tcactcctct tatacaacaa   8580
tccaagtgtt tcttttgtca gttgtctgtg ccccaggaga tccctctctg ccttgccttg   8640
ccctctgcct ttggagacca gcacctcata ctcagtgaag gcctggagtg cttaagaggg   8700
atttcttcca gctctcttgc cctggtcttc agtgtattag atgtattacc tccatgctct   8760
cagtagaggc ccataggaaa gagtaggtag gttatgccag ctcacacgca tcctttaaaa   8820
atggtttaga agtttagctg gtttcttatt actcctgtct atggatgttt ccttctgtca   8880
ctctactagg gatgaaacag ctaatcatgt tcaatagtta catttagatt ggtttttaaa   8940
aactatgatt gtattagttc gtttccatgc tgctgataaa gacatatctg agactggaaa   9000
caaaaagggt ttaattggac ttacagttcc acatggctgg ggaggcctca aaatcaggtg   9060
ggaggcaaaa ggtacttctt acgtggtggc atcaagagca aaatgaggaa gaagcaaaag   9120
cagaaactct tcataaaccc accagatctt gtgggactta ttatcacgag aatagcacag   9180
aaaagactgg cctccatgat tcaattacct ccccactgcgt ccctcccaca acatgtggga   9240
attctgggag atacaattca agttgagatt tgggtgggga cacagccaaa ccatatcatt   9300
cctccctggg ctcctccaaa tttcataatc ctcacatttc aaaaccaatc attccttccc   9360
aacagttccc caaagtctta actcatttca gcattaaccc aaaagtccac agtccaaagt   9420
ctcatctgag acaaggcaag tcccttccac ttacaagcct gtaaaagcaa gctagttacc   9480
```

tcctagatac aatggggggt acaggtattg ggtaaataca gctgttccaa atgagagaaa 9540
ttggccaaaa caaaggggtt acagggtcca tgcaagtctg aaatccagtg ggcagtcaa 9600
attttaaagc tccataatga tctcctttga ctccatgtct cacattcagg tcatgctgat 9660
gcaagagata ggttcccatg gtcttgtgca gctccgcccc tgtggctttg cagagtacag 9720
cctccctcct ggctgctttc tcaggctgat gttgagtgtc tgtagctttt ccaggcacaa 9780
gatgcaagtt ggtggttgat ctaccattct ggggtctacc attctggggt ctaccgttct 9840
gggactgtgg ccttcttctc acagctccac taggcagtgc cccaacaggg actctgtgtg 9900
ggggctctgc cccacatttc ccttccacac tgccctagga gaggttcccc atgagggctc 9960
tgcccctgca gcaaactttt gcctggacat ccaggtgttt ccatatatat tctgaaatct 10020
aggcagaggt tcccaaatct caattcttga catctctgca cccacaggct caacatcaca 10080
tggaagctgc caatgcttgg ggcctctacc ctctgaagcc acagcccaag ctctatgttg 10140
gctcctttca gccatggctg gagcagctgg gacacagggc accaagtccc taggctgcac 10200
acagcacaga gaccctgggc ccagcccaca aaaccacttt ttcctcctgg gcctctgggc 10260
ctgtgatggg aggggctgcc atgaaggtct ctgacatgac ctggagacat tttccccatg 10320
gtcttgggga ttaacattag gctccttgct gcttatgcaa atttctgcag ccagcttgaa 10380
tttctcctta aaaaaaatgg gtttttcttt tctactgcat catcaggctg cagattttcc 10440
acatttatgc tcttgtttcc cttttaaaac agaatgtttt taacagcacc caagtcacct 10500
tttgaatgct ttgctgctta gaaatttatt ccaccagata ccctaagtca tctctctcaa 10560
gctctaagtt ccacaaatct ctagggcaag ggtgaaatgc tgccagtctc cttgctaaaa 10620
cataacaagg gtcaccttta cttcagttcc caacaaggtc ttcatctcca tctgagacca 10680
cctcagcctg gaccttattg ttcatatcac tatcagtatt tttgtcaatg ccattcacag 10740
tctctaggag gttccaaact ttcctacatt ttcctatctt cttctgagcc ctccagatta 10800
tttcaacacc cagttccaaa gttgcttcca cattttcggg tatcttttca gcaatgcccc 10860
actctactgg tactattagt ccattttcat gctgctgata aagacatacc tgagactggg 10920
aacaaaaaga ggtttaattg gacttatagt tccacctggc tggggaggcc tcagaatcat 10980
ggcaggaggt gaaaggcatt tcttacacgg cagcagcaag agaaaaatga agaagcagca 11040
aaagcagaaa cccctgataa aaccatcaga tctcgtgaga cttattcact atcacaagaa 11100
tagcatggga aagaccagcc ccccttgattc aattacctcc ccctgggtcc tgtgggaatt 11160
ctggaaggta caattcaagt tgagatttgg gtggggacac agccaaacca tatcaatgat 11220
tttgtacttt aaccagctga atggaagtac aatctcttgc tatatgacac aataattatt 11280
tgcaaaatga gtaaacatat cataaggaaa ttatttttac aaggtttgaa acctgaaatg 11340
cagtctatta tcatacataa ctaaaaatag agcctcaata aacagattcc cagttttgaa 11400
aatgcaacat ttgtactcca cattgtcagt tttcttaggt atatttataa atactcctat 11460
aaaaatgtaa agaaacacat aatgtagatt gctaatttta taataacaca agttgatttt 11520
gacatccaac ttattaatta tgaaatgact tttggcctag taacaatgaa aatgggggca 11580
aatacagata aatggtaatt cttagaatga actactcagc accaattcta agtttttctt 11640
gatggtaaat cataatgttc cctttctcct cggttctgca atctataggc ataccataat 11700
tgtaatcaat agcttaaaaa tatgtctctc tgtcctattc tgtatctgta tctcttggat 11760
ttttaccttt gcaatagtca actgaaccat cttcttggag tactcatgaa gatggaagtc 11820
tacatggaga atacaggatg aatccactct gtctcctgca gtgaagtctg tttgaaggat 11880
gtatttggct gtcttctgga caggccattc taataacaga aacaaacaag ttattttaaa 11940
acttattgga atattcaaat attaaccaaa gtagaaaaat ataatacaca tccatgtgcc 12000
catcacagaa cttcactgat tatcatcatt tagccagtct tgaagaagca agtgctaatt 12060
acaatcacaa atgaaacaag attcagactt catgaagagc actgcgctat aataaaagaa 12120
gaaatgagca catacattct tttactgaca gtcaaatggt gaaggtgggc agaatcatta 12180
tgtgatgcaa catggcaaaa gtatacagac agtgcatcca gaggaaggca ccttgctgaa 12240
tgactagaat ggaagtagga gacattttgc aggccccctt catcctgcag ggagaaccag 12300
aaccacagca gctctatttg cctattcctc tttaaattac aaagttaaaa tttgggagta 12360
gtagaaaatc aattggttat cttatagagt ctcctagaat atttcattgg cattgagaag 12420
gtggaaaatg caaattatat actttaaaat gtaatttttg cttttcacat atgcttaaag 12480
cctaaaacct cttaataaac ttcttctgaa atata 12515

<210> SEQ ID NO 6
<211> LENGTH: 522
<212> TYPE: PRT
<213> ORGANISM: Homo sapiens

<400> SEQUENCE: 6

Met Gly Arg Glu Glu Leu Phe Leu Thr Phe Ser Phe Ser Ser Gly Phe
1 5 10 15

Gln Glu Ser Asn Val Lys Thr Phe Cys Ser Lys Asn Ile Leu Ala Ile
20 25 30

Leu Gly Phe Ser Ser Ile Ile Ala Val Ile Ala Leu Leu Ala Val Gly
35 40 45

Leu Thr Gln Asn Lys Ala Leu Pro Glu Asn Val Lys Tyr Gly Ile Val
50 55 60

Leu Asp Ala Gly Ser Ser His Thr Ser Leu Tyr Ile Tyr Lys Trp Pro
65 70 75 80

Ala Glu Lys Glu Asn Asp Thr Gly Val Val His Gln Val Glu Glu Cys
85 90 95

Arg Val Lys Gly Pro Gly Ile Ser Lys Phe Val Gln Lys Val Asn Glu
100 105 110

Ile Gly Ile Tyr Leu Thr Asp Cys Met Glu Arg Ala Arg Glu Val Ile
115 120 125

Pro Arg Ser Gln His Gln Glu Thr Pro Val Tyr Leu Gly Ala Thr Ala
130 135 140

Gly Met Arg Leu Leu Arg Met Glu Ser Glu Glu Leu Ala Asp Arg Val
145 150 155 160

Leu Asp Val Val Glu Arg Ser Leu Ser Asn Tyr Pro Phe Asp Phe Gln
165 170 175

Gly Ala Arg Ile Ile Thr Gly Gln Glu Glu Gly Ala Tyr Gly Trp Ile
180 185 190

Thr Ile Asn Tyr Leu Leu Gly Lys Phe Ser Gln Lys Thr Arg Trp Phe
195 200 205

Ser Ile Val Pro Tyr Glu Thr Asn Asn Gln Glu Thr Phe Gly Ala Leu
210 215 220

Asp Leu Gly Gly Ala Ser Thr Gln Val Thr Phe Val Pro Gln Asn Gln
225 230 235 240

Thr Ile Glu Ser Pro Asp Asn Ala Leu Gln Phe Arg Leu Tyr Gly Lys
245 250 255

```
Asp Tyr Asn Val Tyr Thr His Ser Phe Leu Cys Tyr Gly Lys Asp Gln
            260                 265                 270

Ala Leu Trp Gln Lys Leu Ala Lys Asp Ile Gln Val Ala Ser Asn Glu
        275                 280                 285

Ile Leu Arg Asp Pro Cys Phe His Pro Gly Tyr Lys Lys Val Val Asn
    290                 295                 300

Val Ser Asp Leu Tyr Lys Thr Pro Cys Thr Lys Arg Phe Glu Met Thr
305                 310                 315                 320

Leu Pro Phe Gln Gln Phe Glu Ile Gln Gly Ile Gly Asn Tyr Gln Gln
                325                 330                 335

Cys His Gln Ser Ile Leu Glu Leu Phe Asn Thr Ser Tyr Cys Pro Tyr
            340                 345                 350

Ser Gln Cys Ala Phe Asn Gly Ile Phe Leu Pro Pro Leu Gln Gly Asp
        355                 360                 365

Phe Gly Ala Phe Ser Ala Phe Tyr Phe Val Met Lys Phe Leu Asn Leu
    370                 375                 380

Thr Ser Glu Lys Val Ser Gln Glu Lys Val Thr Glu Met Met Lys Lys
385                 390                 395                 400

Phe Cys Ala Gln Pro Trp Glu Glu Ile Lys Thr Ser Tyr Ala Gly Val
                405                 410                 415

Lys Glu Lys Tyr Leu Ser Glu Tyr Cys Phe Ser Gly Thr Tyr Ile Leu
            420                 425                 430

Ser Leu Leu Leu Gln Gly Tyr His Phe Thr Ala Asp Ser Trp Glu His
        435                 440                 445

Ile His Phe Ile Gly Lys Ile Gln Gly Ser Asp Ala Gly Trp Thr Leu
    450                 455                 460

Gly Tyr Met Leu Asn Leu Thr Asn Met Ile Pro Ala Glu Gln Pro Leu
465                 470                 475                 480

Ser Thr Pro Leu Ser His Ser Thr Tyr Val Phe Leu Met Val Leu Phe
                485                 490                 495

Ser Leu Val Leu Phe Thr Val Ala Ile Ile Gly Leu Leu Ile Phe His
            500                 505                 510

Lys Pro Ser Tyr Phe Trp Lys Asp Met Val
        515                 520
```

<210> SEQ ID NO 7
<211> LENGTH: 12370
<212> TYPE: DNA
<213> ORGANISM: Homo sapiens

<400> SEQUENCE: 7

```
acggagacgg accacagcaa gcagaggctg gggggggaa agacgaggaa agaggaggaa      60

aacaaaagct gctacttatg gaagatacaa aggagtctaa cgtgaagaca ttttgctcca     120

agaatatcct agccatcctt ggcttctcct ctatcatagc tgtgatagct ttgcttgctg     180

tggggttgac ccagaacaaa gcattgccag aaaacgttaa gtatgggatt gtgctggatg     240

cgggttcttc tcacacaagt ttatacatct ataagtggcc agcagaaaag gagaatgaca     300

caggcgtggt gcatcaagta gaagaatgca gggttaaagg tcctggaatc tcaaaatttg     360

ttcagaaagt aaatgaaata ggcatttacc tgactgattg catggaaaga gctagggaag     420

tgattccaag gtcccagcac caagagacac ccgtttacct gggagccacg gcaggcatgc     480

ggttgctcag gatggaaagt gaagagttgg cagacagggt tctggatgtg gtggagagga     540

gcctcagcaa ctacccctt gacttccagg gtgccaggat cattactggc caagaggaag     600
```

-continued

```
gtgcctatgg ctggattact atcaactatc tgctgggcaa attcagtcag aaaacaaggt    660
ggttcagcat agtcccatat gaaaccaata atcaggaaac ctttggagct ttggaccttg    720
ggggagcctc tacacaagtc acttttgtac cccaaaacca gactatcgag tccccagata    780
atgctctgca atttcgcctc tatggcaagg actacaatgt ctacacacat agcttcttgt    840
gctatgggaa ggatcaggca ctctggcaga aactggccaa ggacattcag cagtttgaaa    900
tccagggtat tggaaactat caacaatgcc atcaaagcat cctggagctc ttcaacacca    960
gttactgccc ttactcccag tgtgccttca atgggatttt cttgccacca ctccaggggg   1020
attttggggc attttcagct tttactttg  tgatgaagtt tttaaacttg acatcagaga   1080
aagtctctca ggaaaaggtg actgagatga tgaaaaagtt ctgtgctcag ccttgggagg   1140
agataaaaac atcttacgct ggagtaaagg agaagtacct gagtgaatac tgcttttctg   1200
gtacctacat tctctccctc cttctgcaag gctatcattt cacagctgat tcctgggagc   1260
acatccattt cattggcaag atccagggca gcgacgccgg ctggactttg ggctacatgc   1320
tgaacctgac caacatgatc ccagctgagc aaccattgtc cacacctctc tcccactcca   1380
cctatgtctt cctcatggtt ctattctccc tggtcctttt cacagtggcc atcataggct   1440
tgcttatctt tcacaagcct tcatatttct ggaaagatat ggtatagcaa aagcagctga   1500
aatatgctgg ctggagtgag gaaaaaaatc gtccagggag cattttcctc catcgcagtg   1560
ttcaaggcca tccttccctg tctgccaggg ccagtcttga cgagtgtgaa gcttccttgg   1620
cttttactga agcctttctt ttggaggtat tcaatatcct ttgcctcaag gacttcggca   1680
gatactgtct ctttcatgag tttttcccag ctacaccttt ctcctttgta ctttgtgctt   1740
gtataggttt taaagacctg acacctttca taatctttgc tttataaaag aacaatattg   1800
actttgtcta gaagaactga gagtcttgag tcctgtgata ggaggctgag ctggctgaaa   1860
gaagaatctc aggaactggt tcagttgtac tctttaagaa ccccttttctc tctcctgttt   1920
gccatccatt aagaaagcca tatgatgcct ttggagaagg cagacacaca ttccattccc   1980
agcctgctct gtgggtagga gaattttcta cagtaggcaa atatgtgcta aagccaaaga   2040
gttttataag gaaatatatg tgctcatgca gtcaatacag ttctcaatcc cacccaaagc   2100
aggtatgtca ataaatcaca tattcctagg tgatacccaa atgctacaga gtggaacact   2160
cagacctgag atttgcaaaa agcagatgta aatatatgca ttcaaacatc agggcttact   2220
atgaggtagg tggtatatac atgtcacaaa taaaaataca gttacaactc agggtcacaa   2280
aaaatgcatc ttccaatgca tatttttatt atggtaaaat atacataaat ataattcacc   2340
attttaacat ttaattcata ttaaatacgt acaaatcagt gacatttagt acattcacag   2400
tgttgtgcca ccatcaccac tatttagttc cagaacattt gcatcatcaa tacattgtct   2460
agagacaaga ctatcctggg taggcagaaa ccatagatct tttgtgttta cagctatgga   2520
aaccaactgt accataaaga tagttcactg agttttaaag ccaagccaca tcttattttt   2580
ccaaggttta atttagtgag agggcagcat tagtgtggag tggcatgctt ttgccctatc   2640
gtggaattta cacatcagaa tgtgcaggat ccaagtctga aagtgttgcc acccgtcaca   2700
caacatgggc tttgtttgct tattccatga agcagcagct atagacctta ccatggaaac   2760
atgaagagac cctgcacccc tttccttaag gattgctgca agagttacct gttgagcagg   2820
attgactggt gatgtttcat tctgaccttg tcccaagctc tccatctcta gatctgggga   2880
ctgactgttg agctgatggg gaaagaaaag ctctcacaca aaccggaagc caaatgtccc   2940
ctatctcttg aatgatcaag tcacttttga caacatccag gtgaatataa aaacttaata   3000
```

```
aagctgtgga aaggaactct taatcttctt ttctgctact taggttaaat tcactagatc   3060
ttgattagga atcaaaattc gaattgggac atgttcaaat tctttcttgt ggtagttgcc   3120
tatactgtca tcgctgctgt tggttgagca tttgtggtgt accacgctgt gtgctcaagg   3180
gtattacatt catcttctca tttaatcctc acaacaatct gaagaaggta ggtattacaa   3240
ttcccacttc atagaaacag aaactgaggt tcagagaggt taagtcattt gcccaaatgg   3300
ctgagccaaa gcctaccatg tacctaacct ttattttctt tcccgaacat accaggctgt   3360
ctcctcataa cttccaagca tgcacttaaa actccacatg aatacaaggt tcatgggact   3420
tggtattcat agaaagggag gcagaaagct ggtctgttcc tgataggctt gtaatttaat   3480
atcattctgt tcatgtgctt tggatggaag cacatctggc atatgatgct aatcagtggt   3540
tcccataccc ctggcttcct aattttaatg tttgctcaca gcatagtaga ttgacatcaa   3600
atagtggccg atgatgatga aaataaaggt caaataagtt gagccaataa cagccgcttt   3660
tttccttctg tctgcgtata caaagcactg tcatgcacac aatctattct gaccctcaca   3720
acaacccata agggtgtaaa tagtatttcc attttacaaa tgaggatcac acaaactact   3780
acatggcaga gcagatactc caactcatgt cttctggttg aagcctattg ctttttcttt   3840
tctaaacact ttccctcagc aagttggaat tagacttcac aagtctcctt cagagaacac   3900
aaatcttttc ttattccatt cctgtttggt tgcctacgtc caatctcccc ctccccagag   3960
atgccaaaaa aaaaatcctt taaggtattt gggagccaaa ctcaacttgt taaaatctca   4020
aattatggag acaatcagca gacacaacct aaccccaatt attttggcag gaaggttggt   4080
ttagaggcag atccagcaat ctgctttggg ccactctggg tggggtaggt gaaataagat   4140
tggtcactgt taactaattt taatattgga ttggccattg gttatcactg attaccattc   4200
tcccctggat tttcacccag gactcaaaac ttggttctgc taaccctgtt cctttatgag   4260
gaacctttta aagattcctt tataaggtgg gagttttttt tctatgaacc tataggggag   4320
aaaaaagatc agcagaagtc attacttttt tttttttttt tttttttttt tgagagagag   4380
tctcactcca ttgcccaggc tggagtgcag tggtgctatc tcggctcact gcaacctccg   4440
cctcctgggt tcaagcaatt ctcctgcctc agcctcccga gtagctggga ttgcaggtgc   4500
ccaccaccac acccggctaa tttttgtatt tttagtaaag acagggtttc accatgttgg   4560
ccaggctggt ctccaactcc caatctcagg tgatcctatt gcctcgggct cccaaagtgc   4620
tgggattaca ggagtgagcc accatgcctg gccagaagtg gttacttctg tagacaaaag   4680
aataatgcta cttaatcagg ctttctgtgt gacaagaaag agaaagaaaa taaagaagtt   4740
tcaattcatc caattcttaa taagaaatat gtaaataaaa ttttttaaaa ttacacttca   4800
ttttaatgtt gtatcagtca aggtccctgc aagagatgga tggtatggta cactcaaact   4860
gggtaacaca ggagagtttt cagaaagcaa ctaaatccaa aatactatca aggaatcaat   4920
ataaaaattg ttaatatttt tctcatacta aattttcaaa atattttgtg tctattacat   4980
ttacagcaca tcttaattag gactagctgt gtgttcacct cacatgtggc ttgtagctac   5040
catactggac agcacatgtc caaaaaaata cacgtaaagt taaagtttaa aagacacagg   5100
aactaagccc tcattgtctt tcccttggga ggtagtttaa agagctatag atgctgtaac   5160
attcttgcta ttatttatta tatatgacat tattcctaaa aaagcttttg agatcctagg   5220
ttgtattcct caggttttgt tgccttccca tgaagatgtg aaggcaggga tgcctgttat   5280
tcagtccaag atgcatgaca agagaccttg ggaaagtttc atctggattt aaagattaat   5340
```

```
tcttgatgct tacattccat actcaaaatg taaatttgaa tattaaaata aagatgattt   5400
tttttttgga gctagtcttg ctctgttgcc caggctggaa tgcagtggca tgatcatggc   5460
tcactgcagc ctcgacctcc caagctcaag caaggctaca ggtgtgcacc taagtagcta   5520
ggactacagg tgtgcaccac catgtctagc tatttttttt tctgtagaga cagggttttc   5580
ctatgttgtc caggctggtc tcgaactcct gccctcaagc aatcctcctg ccttggcctc   5640
ccaaagtgtt gagattacag gcgtaagcca ctgcacctgg ccaagatgaa tattttaata   5700
gctcacagaa caaagtttgc cacataatga taaaattact atgaaaatat attcccttta   5760
ttgtcagttt aaaagatgaa ctgagtttca cccaaactgg tctggcccct ctctgattca   5820
aataccaata gttgctctga ttcaaattcc aactgttaga acatgacagc tgctcataac   5880
tagctttgct tactaaccat gtttctttcc atttgtatta ggtcctttac tttttataac   5940
agcctcaaag tttcatgaat tgctgcagta aacattgatt ttcatgtttg tgagtctgca   6000
agccagctgg gcagctctac ttcaggtggt aagggtggat cagacctatt ccatatacct   6060
cttgttctcc ttgtccagtg gtttctaggg atatgttctc atgatgaacc ccgcagaggc   6120
tcgtgaaagt gagaggaaac taggatgcct cttaaggtct tggtcaggat ggggtctcct   6180
gtcacttctg tcacaggcta ttgtaagtca tatgagcaag ctcaataaaa tataaacaag   6240
tcagataaac agtgggagga atggcaaagt catatggcca aggccatgag tgattaattt   6300
taacacagga aaaaagtaaa gcattaaatg cgattattta atatacaatg tcttattaac   6360
tgaaatataa aatgtgttta ctgtaaaata taatctgttt atctcaccaa agaaatatta   6420
tctttaaaaa atgtcattac ttctaagaca tcatcagtct gcaacttctt tccatagcct   6480
taatcaggat gctgtggcag ctcccacatt agcctcgcat tctaaactgg tagatgtcct   6540
aggaaaccat acatctatgt atttttctta ttttatacgt ttaggacaat gtatagctaa   6600
ttacccaact ttttatttgc atacaaatct aatacaactg aacacaatca gttttatcac   6660
aggtataatg gatttttcaa tagtgaggag gtgcctccat gagccttctc tttagaaaag   6720
tggcattcaa gactcttcat ttgaagtgaa gattgctatg tcttttgcat tgctctattt   6780
tacataaatt aagttataaa ttgacactat aatcaactga caccatgatc agtgatgatg   6840
atcaccctca tcagcactag agttgacttg tttttataac ccctttgcat gtatgttgaa   6900
tagcaaagtt catcagagaa catgtattag tcaatggtaa gtaagatact ctcatctaag   6960
aaataacatc acctcttcta atgaagttct aagaagagag ggaagaaaaa gtcttgggag   7020
ctagtcaggg aatagtgtgt atttgcaatt acctaaactg aactctacca ttactcctaa   7080
cccagttcct cctcctgtgt tttacatgat taatgccacc cctgcctcaa tgaaccaaga   7140
tcagctccat cactgggacc tccccattct gcctgtgcaa tatttttctt ttttatttct   7200
ccttctaata ttactgttat tgctccagta aagagctgta atatatttta cctggactga   7260
taccaggaat ggtggtgttg cttccaatct gttgctgcta gattaatctt tgcaaagcac   7320
aggcttaatt tcattgctgc tcaactaaaa ccactggtgg ctttccattg cctacaaaat   7380
aaagtcaacc tccccatcag acattcaagg ctttcaatga tccatggccg ccagctctct   7440
ccaggctcat atcccactcc actcctctga tgtttcctac actacactac actatactac   7500
actacagcca ggtagaatga ctgttcaccc aacaccactc aggttgtctt ctcaacttgg   7560
aatactcttg caccttcaaa gctcatttca aatgcccctt catttgtgaa gccttctcca   7620
aatttccaag tcagaatgtc tcttccttgt gctaccacaa ccctttaact gagcctccat   7680
tagtgcactg agaccattct gttcagtgtc tgggtgaagc ttcctggtga aaaatatgtt   7740
```

```
acctatttct ttctgaaaag ttggattcag ggatattatc acggacctaa ggtaatagtt   7800
ctagccaacc tccctgtcca ctgccaggcc gactacaaac ccttctgttg ctggcgagct   7860
ggtccgcacc actagttctg cttcactcta tttatctctt gatgtaacca tcttctttct   7920
ccaggtttta agaaccagcc caactcctgg ttccctgatg aagcttttat tcccctagcc   7980
acatggaact tttccttttt ggaacatgcc tttagtttct gtgtagtttg ccatgcagca   8040
cttcattgta cacattatta aaacagaatt ttaaggatta gaatgaacct taaaagatca   8100
tgcatctcaa aatttaatgt acatacaaat tacccaggga ttttgttgaa ataaaaatta   8160
tttaatttta attaatataa ataattcagt aggtctgggg tgaggcctga ggttttacat   8220
ttccaacaag ctgccaggta aagccaatac atctgtccag gaatcacact ttgcgtatca   8280
aaggtctaga tgacattatc attccaaaga gtttctttta caggctctca gatcagtgtt   8340
catccactac ctgactactg tcattcacag gcattctgtt ccacagcagg ccagctaacg   8400
tggtatttac aaagctcact cctcttatac aacaatccaa gtgtttcttt tgtcagttgt   8460
ctgtgcccca ggagatccct ctctgccttg ccttgccctc tgcctttgga gaccagcacc   8520
tcatactcag tgaaggcctg gagtgcttaa gagggatttc ttccagctct cttgccctgg   8580
tcttcagtgt attagatgta ttacctccat gctctcagta gaggcccata ggaaagagta   8640
ggtaggttat gccagctcac acgcatcctt taaaaatggt ttagaagttt agctggtttc   8700
ttattactcc tgtctatgga tgtttccttc tgtcactcta ctagggatga aacagctaat   8760
catgttcaat agttacattt agattggttt ttaaaaacta tgattgtatt agttcgtttc   8820
catgctgctg ataaagacat atctgagact ggaaacaaaa agggtttaat tggacttaca   8880
gttccacatg gctggggagg cctcaaaatc aggtgggagg caaaaggtac ttcttacgtg   8940
gtggcatcaa gagcaaaatg aggaagaagc aaaagcagaa actcttcata aacccaccag   9000
atcttgtggg acttattatc acgagaatag cacagaaaag actggcctcc atgattcaat   9060
tacctcccac tgcgtccctc ccacaacatg tgggaattct gggagataca attcaagttg   9120
agatttgggt ggggacacag ccaaaccata tcattcctcc ctgggctcct ccaaatttca   9180
taatcctcac atttcaaaac caatcattcc ttcccaacag ttccccaaag tcttaactca   9240
tttcagcatt aacccaaaag tccacagtcc aaagtctcat ctgagacaag gcaagtccct   9300
tccacttaca agcctgtaaa agcaagctag ttacctccta gatacaatgg ggggtacagg   9360
tattgggtaa atacagctgt tccaaatgag agaaattggc caaaacaaag gggttacagg   9420
gtccatgcaa gtctgaaatc cagtggggca gtcaaatttt aaagctccat aatgatctcc   9480
tttgactcca tgtctcacat tcaggtcatg ctgatgcaag agataggttc ccatggtctt   9540
gtgcagctcc gcccctgtgg ctttgcagag tacagcctcc ctcctggctg ctttctcagg   9600
ctgatgttga gtgtctgtag cttttccagg cacaagatgc aagttggtgg ttgatctacc   9660
attctggggt ctaccattct ggggtctacc gttctgggac tgtggccttc ttctcacagc   9720
tccactaggc agtgccccaa cagggactct gtgtgggggc tctgccccac atttcccttc   9780
cacactgccc taggagaggt tccccatgag ggctctgccc ctgcagcaaa cttttgcctg   9840
gacatccagg tgtttccata tatattctga aatctaggca gaggttccca aatctcaatt   9900
cttgacatct ctgcacccac aggctcaaca tcacatggaa gctgccaatg cttggggcct   9960
ctaccctctg aagccacagc ccaagctcta tgttggctcc tttcagccat ggctggagca  10020
gctgggacac agggcaccaa gtccctaggc tgcacacagc acagagaccc tgggcccagc  10080
```

```
ccacaaaacc actttttcct cctgggcctc tgggcctgtg atgggagggg ctgccatgaa  10140
ggtctctgac atgacctgga gacattttcc ccatggtctt ggggattaac attaggctcc  10200
ttgctgctta tgcaaatttc tgcagccagc ttgaatttct ccttaaaaaa aatgggtttt  10260
tcttttctac tgcatcatca ggctgcagat tttccacatt tatgctcttg tttccctttt  10320
aaaacagaat gtttttaaca gcacccaagt caccttttga atgctttgct gcttagaaat  10380
ttattccacc agatacccta agtcatctct ctcaagctct aagttccaca aatctctagg  10440
gcaagggtga aatgctgcca gtctccttgc taaaacataa caagggtcac ctttacttca  10500
gttcccaaca aggtcttcat ctccatctga gaccacctca gcctggacct tattgttcat  10560
atcactatca gtatttttgt caatgccatt cacagtctct aggaggttcc aaactttcct  10620
acattttcct atcttcttct gagccctcca gattatttca acacccagtt ccaaagttgc  10680
ttccacattt tcgggtatct tttcagcaat gccccactct actggtacta ttagtccatt  10740
ttcatgctgc tgataaagac atacctgaga ctgggaacaa aaagaggttt aattggactt  10800
atagttccac ctggctgggg aggcctcaga atcatggcag gaggtgaaag gcatttctta  10860
cacggcagca gcaagagaaa aatgaagaag cagcaaaagc agaaacccct gataaaacca  10920
tcagatctcg tgagacttat tcactatcac aagaatagca tgggaaagac cagccccctt  10980
gattcaatta cctccccctg ggtcctgtgg gaattctgga aggtacaatt caagttgaga  11040
tttgggtggg gacacagcca aaccatatca atgattttgt actttaacca gctgaatgga  11100
agtacaatct cttgctatat gacacaataa ttatttgcaa aatgagtaaa catatcataa  11160
ggaaattatt tttacaaggt ttgaaacctg aaatgcagtc tattatcata cataactaaa  11220
aatagagcct caataaacag attcccagtt ttgaaaatgc aacatttgta ctccacattg  11280
tcagttttct taggtatatt tataaatact cctataaaaa tgtaaagaaa cacataatgt  11340
agattgctaa ttttataata acacaagttg attttgacat ccaacttatt aattatgaaa  11400
tgacttttgg cctagtaaca atgaaaatgg gggcaaatac agataaatgg taattcttag  11460
aatgaactac tcagcaccaa ttctaagttt ttcttgatgg taaatcataa tgttcccttt  11520
ctcctcggtt ctgcaatcta taggcatacc ataattgtaa tcaatagctt aaaaatatgt  11580
ctctctgtcc tattctgtat ctgtatctct tggattttta cctttgcaat agtcaactga  11640
accatcttct tggagtactc atgaagatgg aagtctacat ggagaataca ggatgaatcc  11700
actctgtctc ctgcagtgaa gtctgtttga aggatgtatt tggctgtctt ctggacaggc  11760
cattctaata acagaaacaa acaagttatt ttaaaactta ttggaatatt caaatattaa  11820
ccaaagtaga aaaatataat acacatccat gtgcccatca cagaacttca ctgattatca  11880
tcatttagcc agtcttgaag aagcaagtgc taattacaat cacaaatgaa acaagattca  11940
gacttcatga agagcactgc gctataataa aagaagaaat gagcacatac attcttttac  12000
tgacagtcaa atggtgaagg tgggcagaat cattatgtga tgcaacatgg caaaagtata  12060
cagacagtgc atccagagga aggcaccttg ctgaatgact agaatggaag taggagacat  12120
tttgcaggcc cccttcatcc tgcagggaga accagaacca cagcagctct atttgcctat  12180
tcctctttaa attacaaagt taaaatttgg gagtagtaga aaatcaattg gttatcttat  12240
agagtctcct agaatatttc attggcattg agaaggtgga aaatgcaaat tatatacttt  12300
aaaatgtaat ttttgctttt cacatatgct taaagcctaa aacctcttaa taaacttctt  12360
ctgaaatata                                                         12370
```

<210> SEQ ID NO 8
<211> LENGTH: 469
<212> TYPE: PRT
<213> ORGANISM: Homo sapiens

<400> SEQUENCE: 8

```
Met Glu Asp Thr Lys Glu Ser Asn Val Lys Thr Phe Cys Ser Lys Asn
1               5                   10                  15

Ile Leu Ala Ile Leu Gly Phe Ser Ser Ile Ile Ala Val Ile Ala Leu
            20                  25                  30

Leu Ala Val Gly Leu Thr Gln Asn Lys Ala Leu Pro Glu Asn Val Lys
        35                  40                  45

Tyr Gly Ile Val Leu Asp Ala Gly Ser Ser His Thr Ser Leu Tyr Ile
    50                  55                  60

Tyr Lys Trp Pro Ala Glu Lys Glu Asn Asp Thr Gly Val Val His Gln
65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
            100                 105                 110

Arg Glu Val Ile Pro Arg Ser Gln His Gln Glu Thr Pro Val Tyr Leu
        115                 120                 125

Gly Ala Thr Ala Gly Met Arg Leu Leu Arg Met Glu Ser Glu Glu Leu
    130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
            180                 185                 190

Thr Arg Trp Phe Ser Ile Val Pro Tyr Glu Thr Asn Asn Gln Glu Thr
        195                 200                 205

Phe Gly Ala Leu Asp Leu Gly Gly Ala Ser Thr Gln Val Thr Phe Val
    210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Gln
            260                 265                 270

Phe Glu Ile Gln Gly Ile Gly Asn Tyr Gln Gln Cys His Gln Ser Ile
        275                 280                 285

Leu Glu Leu Phe Asn Thr Ser Tyr Cys Pro Tyr Ser Gln Cys Ala Phe
    290                 295                 300

Asn Gly Ile Phe Leu Pro Pro Leu Gln Gly Asp Phe Gly Ala Phe Ser
305                 310                 315                 320

Ala Phe Tyr Phe Val Met Lys Phe Leu Asn Leu Thr Ser Glu Lys Val
                325                 330                 335

Ser Gln Glu Lys Val Thr Glu Met Met Lys Lys Phe Cys Ala Gln Pro
            340                 345                 350

Trp Glu Glu Ile Lys Thr Ser Tyr Ala Gly Val Lys Glu Lys Tyr Leu
        355                 360                 365

Ser Glu Tyr Cys Phe Ser Gly Thr Tyr Ile Leu Ser Leu Leu Leu Gln
    370                 375                 380
```

```
Gly Tyr His Phe Thr Ala Asp Ser Trp Glu His Ile His Phe Ile Gly
385                 390                 395                 400

Lys Ile Gln Gly Ser Asp Ala Gly Trp Thr Leu Gly Tyr Met Leu Asn
                405                 410                 415

Leu Thr Asn Met Ile Pro Ala Glu Gln Pro Leu Ser Thr Pro Leu Ser
            420                 425                 430

His Ser Thr Tyr Val Phe Leu Met Val Leu Phe Ser Leu Val Leu Phe
        435                 440                 445

Thr Val Ala Ile Ile Gly Leu Leu Ile Phe His Lys Pro Ser Tyr Phe
    450                 455                 460

Trp Lys Asp Met Val
465
```

<210> SEQ ID NO 9
<211> LENGTH: 12387
<212> TYPE: DNA
<213> ORGANISM: Homo sapiens

<400> SEQUENCE: 9

```
cctgttgctc tttgctctaa tgagccttga gaaaggattg ctggtcatgg gaccagaggc     60

tttatgggga gggaagaact gttcttgact ttcagttttt cgagcgggtt tcaagtatgg    120

gattgtgctg gatgcgggtt cttctcacac aagtttatac atctataagt ggccagcaga    180

aaaggagaat gacacaggcg tggtgcatca agtagaagaa tgcagggtta aaggtcctgg    240

aatctcaaaa tttgttcaga aagtaaatga aataggcatt tacctgactg attgcatgga    300

aagagctagg gaagtgattc caaggtccca gcaccaagag acacccgttt acctgggagc    360

cacggcaggc atgcggttgc tcaggatgga aagtgaagag ttggcagaca gggttctgga    420

tgtggtggag aggagcctca gcaactaccc ctttgacttc cagggtgcca ggatcattac    480

tggccaagag gaaggtgcct atggctggat tactatcaac tatctgctgg gcaaattcag    540

tcagaaaaca aggtggttca gcatagtccc atatgaaacc aataatcagg aaacctttgg    600

agctttggac cttgggggag cctctacaca agtcactttt gtaccccaaa accagactat    660

cgagtcccca gataatgctc tgcaatttcg cctctatggc aaggactaca atgtctacac    720

acatagcttc ttgtgctatg ggaaggatca ggcactctgg cagaaactgg ccaaggacat    780

tcaggttgca agtaatgaaa ttctcaggga cccatgcttt catcctggat ataagaaggt    840

agtgaacgta agtgaccttt acaagacccc ctgcaccaag agatttgaga tgactcttcc    900

attccagcag tttgaaatcc agggtattgg aaactatcaa caatgccatc aaagcatcct    960

ggagctcttc aacaccagtt actgccctta ctcccagtgt gccttcaatg ggattttctt   1020

gccaccactc caggggggatt ttggggcatt ttcagctttt tactttgtga tgaagttttt   1080

aaacttgaca tcagagaaag tctctcagga aaaggtgact gagatgatga aaaagttctg   1140

tgctcagcct tgggaggaga taaaaacatc ttacgctgga gtaaaggaga agtacctgag   1200

tgaatactgc ttttctggta cctacattct ctccctcctt ctgcaaggct atcatttcac   1260

agctgattcc tgggagcaca tccatttcat tggcaagatc cagggcagcg acgccggctg   1320

gactttgggc tacatgctga acctgaccaa catgatccca gctgagcaac cattgtccac   1380

acctctctcc cactccacct atgtcttcct catggttcta ttctccctgg tcctttttcac   1440

agtggccatc ataggcttgc ttatctttca caagccttca tatttctgga aagatatggt   1500

atagcaaaag cagctgaaat atgctggctg gagtgaggaa aaaaatcgtc cagggagcat   1560

tttcctccat cgcagtgttc aaggccatcc ttccctgtct gccagggcca gtcttgacga   1620
```

```
gtgtgaagct tccttggctt ttactgaagc ctttcttttg gaggtattca atatcctttg   1680
cctcaaggac ttcggcagat actgtctctt tcatgagttt ttcccagcta cacctttctc   1740
ctttgtactt tgtgcttgta taggttttaa agacctgaca cctttcataa tctttgcttt   1800
ataaaagaac aatattgact ttgtctagaa gaactgagag tcttgagtcc tgtgatagga   1860
ggctgagctg gctgaaagaa gaatctcagg aactggttca gttgtactct ttaagaaccc   1920
ctttctctct cctgtttgcc atccattaag aaagccatat gatgcctttg gagaaggcag   1980
acacacattc cattcccagc ctgctctgtg ggtaggagaa ttttctacag taggcaaata   2040
tgtgctaaag ccaaagagtt ttataaggaa atatatgtgc tcatgcagtc aatacagttc   2100
tcaatcccac ccaaagcagg tatgtcaata aatcacatat tcctaggtga tacccaaatg   2160
ctacagagtg gaacactcag acctgagatt tgcaaaaagc agatgtaaat atatgcattc   2220
aaacatcagg gcttactatg aggtaggtgg tatatacatg tcacaaataa aaatacagtt   2280
acaactcagg gtcacaaaaa atgcatcttc caatgcatat ttttattatg gtaaaatata   2340
cataaatata attcaccatt ttaacattta attcatatta aatacgtaca aatcagtgac   2400
atttagtaca ttcacagtgt tgtgccacca tcaccactat ttagttccag aacatttgca   2460
tcatcaatac attgtctaga gacaagacta tcctgggtag gcagaaacca tagatctttt   2520
gtgtttacag ctatggaaac caactgtacc ataaagatag ttcactgagt tttaaagcca   2580
agccacatct tatttttcca aggtttaatt tagtgagagg gcagcattag tgtggagtgg   2640
catgcttttg ccctatcgtg gaatttacac atcagaatgt gcaggatcca agtctgaaag   2700
tgttgccacc cgtcacacaa catgggcttt gtttgcttat tccatgaagc agcagctata   2760
gaccttacca tggaaacatg aagagaccct gcaccccttt ccttaaggat tgctgcaaga   2820
gttacctgtt gagcaggatt gactggtgat gtttcattct gaccttgtcc caagctctcc   2880
atctctagat ctggggactg actgttgagc tgatggggaa agaaaagctc tcacacaaac   2940
cggaagccaa atgtccccta tctcttgaat gatcaagtca cttttgacaa catccaggtg   3000
aatataaaaa cttaataaag ctgtggaaag gaactcttaa tcttcttttc tgctacttag   3060
gttaaattca ctagatcttg attaggaatc aaaattcgaa ttgggacatg ttcaaattct   3120
ttcttgtggt agttgcctat actgtcatcg ctgctgttgg ttgagcattt gtggtgtacc   3180
acgctgtgtg ctcaagggta ttacattcat cttctcattt aatcctcaca acaatctgaa   3240
gaaggtaggt attacaattc ccacttcata gaaacagaaa ctgaggttca gagaggttaa   3300
gtcatttgcc caaatggctg agccaaagcc taccatgtac ctaaccttta ttttctttcc   3360
cgaacatacc aggctgtctc ctcataactt ccaagcatgc acttaaaact ccacatgaat   3420
acaaggttca tgggacttgg tattcataga aagggaggca gaaagctggt ctgttcctga   3480
taggcttgta atttaatatc attctgttca tgtgctttgg atggaagcac atctggcata   3540
tgatgctaat cagtggttcc catacccctg gcttcctaat tttaatgttt gctcacagca   3600
tagtagattg acatcaaata gtggccgatg atgatgaaaa taaaggtcaa ataagttgag   3660
ccaataacag ccgctttttt ccttctgtct gcgtatacaa agcactgtca tgcacacaat   3720
ctattctgac cctcacaaca acccataagg gtgtaaatag tatttccatt ttacaaatga   3780
ggatcacaca aactactaca tggcagagca gatactccaa ctcatgtctt ctggttgaag   3840
cctattgctt tttcttttct aaacactttc cctcagcaag ttggaattag acttcacaag   3900
tctccttcag agaacacaaa tcttttctta ttccattcct gtttggttgc ctacgtccaa   3960
```

-continued

```
tctcccccctc cccagagatg ccaaaaaaaa aatcctttaa ggtatttggg agccaaactc   4020
aacttgttaa aatctcaaat tatggagaca atcagcagac acaacctaac cccaattatt   4080
ttggcaggaa ggttggttta gaggcagatc cagcaatctg ctttgggcca ctctgggtgg   4140
ggtaggtgaa ataagattgg tcactgttaa ctaattttaa tattggattg gccattggtt   4200
atcactgatt accattctcc cctggatttt cacccaggac tcaaaacttg gttctgctaa   4260
ccctgttcct ttatgaggaa ccttttaaag attcctttat aaggtgggag ttttttttct   4320
atgaacctat aggggagaaa aaagatcagc agaagtcatt actttttttt tttttttttt   4380
ttttttttga gagagagtct cactccattg cccaggctgg agtgcagtgg tgctatctcg   4440
gctcactgca acctccgcct cctgggttca agcaattctc ctgcctcagc ctcccgagta   4500
gctgggattg caggtgccca ccaccacacc cggctaattt ttgtattttt agtaaagaca   4560
gggtttcacc atgttggcca ggctggtctc caactcccaa tctcaggtga tcctattgcc   4620
tcgggctccc aaagtgctgg gattacagga gtgagccacc atgcctggcc agaagtggtt   4680
acttctgtag acaaaagaat aatgctactt aatcaggctt tctgtgtgac aagaaagaga   4740
aagaaaataa agaagtttca attcatccaa ttcttaataa gaaatatgta aataaaattt   4800
tttaaaatta cacttcattt taatgttgta tcagtcaagg tccctgcaag agatggatgg   4860
tatggtacac tcaaactggg taacacagga gagttttcag aaagcaacta aatccaaaat   4920
actatcaagg aatcaatata aaaattgtta atatttttct catactaaat tttcaaaata   4980
ttttgtgtct attacattta cagcacatct taattaggac tagctgtgtg ttcacctcac   5040
atgtggcttg tagctaccat actggacagc acatgtccaa aaaaatacac gtaaagttaa   5100
agtttaaaag acacaggaac taagccctca ttgtctttcc cttgggaggt agtttaaaga   5160
gctatagatg ctgtaacatt cttgctatta tttattatat atgacattat tcctaaaaaa   5220
gcttttgaga tcctaggttg tattcctcag gttttgttgc cttcccatga agatgtgaag   5280
gcagggatgc ctgttattca gtccaagatg catgacaaga gaccttggga aagtttcatc   5340
tggatttaaa gattaattct tgatgcttac attccatact caaaatgtaa atttgaatat   5400
taaaataaag atgatttttt ttttggagct agtcttgctc tgttgcccag gctggaatgc   5460
agtggcatga tcatggctca ctgcagcctc gacctcccaa gctcaagcaa ggctacaggt   5520
gtgcacctaa gtagctagga ctacaggtgt gcaccaccat gtctagctat ttttttttct   5580
gtagagacag ggttttccta tgttgtccag gctggtctcg aactcctgcc ctcaagcaat   5640
cctcctgcct tggcctccca aagtgttgag attacaggcg taagccactg cacctggcca   5700
agatgaatat tttaatagct cacagaacaa agtttgccac ataatgataa aattactatg   5760
aaaatatatt ccctttattg tcagtttaaa agatgaactg agtttcaccc aaactggtct   5820
ggcccctctc tgattcaaat accaatagtt gctctgattc aaattccaac tgttagaaca   5880
tgacagctgc tcataactag ctttgcttac taaccatgtt tctttccatt tgtattaggt   5940
cctttacttt ttataacagc ctcaaagttt catgaattgc tgcagtaaac attgattttc   6000
atgtttgtga gtctgcaagc cagctgggca gctctacttc aggtggtaag ggtggatcag   6060
acctattcca tatacctctt gttctccttg tccagtggtt tctagggata tgttctcatg   6120
atgaaccccg cagaggctcg tgaaagtgag aggaaactag gatgcctctt aaggtcttgg   6180
tcaggatggg gtctcctgtc acttctgtca caggctattg taagtcatat gagcaagctc   6240
aataaaatat aaacaagtca gataaacagt gggaggaatg gcaaagtcat atggccaagg   6300
ccatgagtga ttaattttaa cacaggaaaa aagtaaagca ttaaatgcga ttatttaata   6360
```

```
tacaatgtct tattaactga aatataaaat gtgtttactg taaaatataa tctgtttatc   6420
tcaccaaaga aatattatct ttaaaaaatg tcattacttc taagacatca tcagtctgca   6480
acttctttcc atagccttaa tcaggatgct gtggcagctc ccacattagc ctcgcattct   6540
aaactggtag atgtcctagg aaaccataca tctatgtatt tttcttattt tatacgttta   6600
ggacaatgta tagctaatta cccaactttt tatttgcata caaatctaat acaactgaac   6660
acaatcagtt ttatcacagg tataatggat ttttcaatag tgaggaggtg cctccatgag   6720
ccttctcttt agaaaagtgg cattcaagac tcttcatttg aagtgaagat tgctatgtct   6780
tttgcattgc tctattttac ataaattaag ttataaattg acactataat caactgacac   6840
catgatcagt gatgatgatc accctcatca gcactagagt tgacttgttt ttataacccc   6900
tttgcatgta tgttgaatag caaagttcat cagagaacat gtattagtca atggtaagta   6960
agatactctc atctaagaaa taacatcacc tcttctaatg aagttctaag aagagaggga   7020
agaaaaagtc ttgggagcta gtcagggaat agtgtgtatt tgcaattacc taaactgaac   7080
tctaccatta ctcctaaccc agttcctcct cctgtgtttt acatgattaa tgccacccct   7140
gcctcaatga accaagatca gctccatcac tgggacctcc ccattctgcc tgtgcaatat   7200
ttttcttttt tatttctcct tctaatatta ctgttattgc tccagtaaag agctgtaata   7260
tattttacct ggactgatac caggaatggt ggtgttgctt ccaatctgtt gctgctagat   7320
taatctttgc aaagcacagg cttaatttca ttgctgctca actaaaacca ctggtggctt   7380
tccattgcct acaaaataaa gtcaacctcc ccatcagaca ttcaaggctt tcaatgatcc   7440
atggccgcca gctctctcca ggctcatatc ccactccact cctctgatgt ttcctacact   7500
acactacact atactacact acagccaggt agaatgactg ttcacccaac accactcagg   7560
ttgtcttctc aacttggaat actcttgcac cttcaaagct catttcaaat gccccttcat   7620
ttgtgaagcc ttctccaaat ttccaagtca gaatgtctct tccttgtgct accacaaccc   7680
tttaactgag cctccattag tgcactgaga ccattctgtt cagtgtctgg gtgaagcttc   7740
ctggtgaaaa atatgttacc tatttctttc tgaaaagttg gattcaggga tattatcacg   7800
gacctaaggt aatagttcta gccaacctcc ctgtccactg ccaggccgac tacaaaccct   7860
tctgttgctg gcgagctggt ccgcaccact agttctgctt cactctattt atctcttgat   7920
gtaaccatct tctttctcca ggttttaaga accagcccaa ctcctggttc cctgatgaag   7980
cttttattcc cctagccaca tggaactttt cctttttgga acatgccttt agtttctgtg   8040
tagtttgcca tgcagcactt cattgtacac attattaaaa cagaatttta aggattagaa   8100
tgaaccttaa aagatcatgc atctcaaaat ttaatgtaca tacaaattac ccagggattt   8160
tgttgaaata aaaattattt aattttaatt aatataaata attcagtagg tctggggtga   8220
ggcctgaggt tttacatttc caacaagctg ccaggtaaag ccaatacatc tgtccaggaa   8280
tcacactttg cgtatcaaag gtctagatga cattatcatt ccaaagagtt tcttttacag   8340
gctctcagat cagtgttcat ccactacctg actactgtca ttcacaggca ttctgttcca   8400
cagcaggcca gctaacgtgg tatttacaaa gctcactcct cttatacaac aatccaagtg   8460
tttcttttgt cagttgtctg tgccccagga gatccctctc tgccttgcct tgccctctgc   8520
ctttggagac cagcacctca tactcagtga aggcctggag tgcttaagag ggatttcttc   8580
cagctctctt gccctggtct tcagtgtatt agatgtatta cctccatgct ctcagtagag   8640
gcccatagga aagagtaggt aggttatgcc agctcacacg catcctttaa aaatggttta   8700
```

```
gaagtttagc tggtttctta ttactcctgt ctatggatgt ttccttctgt cactctacta   8760
gggatgaaac agctaatcat gttcaatagt tacatttaga ttggttttta aaaactatga   8820
ttgtattagt tcgtttccat gctgctgata aagacatatc tgagactgga aacaaaaagg   8880
gtttaattgg acttacagtt ccacatggct ggggaggcct caaaatcagg tgggaggcaa   8940
aaggtacttc ttacgtggtg gcatcaagag caaaatgagg aagaagcaaa agcagaaact   9000
cttcataaac ccaccagatc ttgtgggact tattatcacg agaatagcac agaaaagact   9060
ggcctccatg attcaattac ctcccactgc gtccctccca caacatgtgg gaattctggg   9120
agatacaatt caagttgaga tttgggtggg gacacagcca aaccatatca ttcctccctg   9180
ggctcctcca aatttcataa tcctcacatt tcaaaaccaa tcattccttc ccaacagttc   9240
cccaaagtct taactcattt cagcattaac ccaaaagtcc acagtccaaa gtctcatctg   9300
agacaaggca agtcccttcc acttacaagc ctgtaaaagc aagctagtta cctcctagat   9360
acaatggggg gtacaggtat tgggtaaata cagctgttcc aaatgagaga aattggccaa   9420
aacaaagggg ttacagggtc catgcaagtc tgaaatccag tggggcagtc aaattttaaa   9480
gctccataat gatctccttt gactccatgt ctcacattca ggtcatgctg atgcaagaga   9540
taggttccca tggtcttgtg cagctccgcc cctgtggctt tgcagagtac agcctccctc   9600
ctggctgctt tctcaggctg atgttgagtg tctgtagctt ttccaggcac aagatgcaag   9660
ttggtggttg atctaccatt ctggggtcta ccattctggg gtctaccgtt ctgggactgt   9720
ggccttcttc tcacagctcc actaggcagt gccccaacag ggactctgtg tgggggctct   9780
gccccacatt tcccttccac actgccctag gagaggttcc ccatgagggc tctgcccctg   9840
cagcaaactt ttgcctggac atccaggtgt ttccatatat attctgaaat ctaggcagag   9900
gttcccaaat ctcaattctt gacatctctg cacccacagg ctcaacatca catggaagct   9960
gccaatgctt ggggcctcta ccctctgaag ccacagccca agctctatgt tggctccttt  10020
cagccatggc tggagcagct gggacacagg gcaccaagtc cctaggctgc acacagcaca  10080
gagaccctgg gcccagccca caaaaccact ttttcctcct gggcctctgg gcctgtgatg  10140
ggaggggctg ccatgaaggt ctctgacatg acctggagac attttcccca tggtcttggg  10200
gattaacatt aggctccttg ctgcttatgc aaatttctgc agccagcttg aatttctcct  10260
taaaaaaaat gggtttttct tttctactgc atcatcaggc tgcagatttt ccacatttat  10320
gctcttgttt cccttttaaa acagaatgtt tttaacagca cccaagtcac cttttgaatg  10380
ctttgctgct tagaaattta ttccaccaga taccctaagt catctctctc aagctctaag  10440
ttccacaaat ctctagggca agggtgaaat gctgccagtc tccttgctaa aacataacaa  10500
gggtcacctt tacttcagtt cccaacaagg tcttcatctc catctgagac cacctcagcc  10560
tggaccttat tgttcatatc actatcagta tttttgtcaa tgccattcac agtctctagg  10620
aggttccaaa ctttcctaca ttttcctatc ttcttctgag ccctccagat tatttcaaca  10680
cccagttcca aagttgcttc cacattttcg ggtatctttt cagcaatgcc ccactctact  10740
ggtactatta gtccattttc atgctgctga taaagacata cctgagactg ggaacaaaaa  10800
gaggtttaat tggacttata gttccacctg gctggggagg cctcagaatc atggcaggag  10860
gtgaaaggca tttcttacac ggcagcagca agagaaaaat gaagaagcag caaaagcaga  10920
aacccctgat aaaaccatca gatctcgtga gacttattca ctatcacaag aatagcatgg  10980
gaaagaccag ccccccttgat tcaattacct ccccctgggt cctgtgggaa ttctggaagg  11040
tacaattcaa gttgagattt gggtggggac acagccaaac catatcaatg attttgtact  11100
```

ttaaccagct gaatggaagt acaatctctt gctatatgac acaataatta tttgcaaaat 11160
gagtaaacat atcataagga aattattttt acaaggtttg aaacctgaaa tgcagtctat 11220
tatcatacat aactaaaaat agagcctcaa taaacagatt cccagttttg aaaatgcaac 11280
atttgtactc cacattgtca gttttcttag gtatatttat aaatactcct ataaaaatgt 11340
aaagaaacac ataatgtaga ttgctaattt tataataaca caagttgatt ttgacatcca 11400
acttattaat tatgaaatga cttttggcct agtaacaatg aaaatggggg caaatacaga 11460
taaatggtaa ttcttagaat gaactactca gcaccaattc taagtttttc ttgatggtaa 11520
atcataatgt tccctttctc ctcggttctg caatctatag gcataccata attgtaatca 11580
atagcttaaa aatatgtctc tctgtcctat tctgtatctg tatctcttgg atttttacct 11640
ttgcaatagt caactgaacc atcttcttgg agtactcatg aagatggaag tctacatgga 11700
gaatacagga tgaatccact ctgtctcctg cagtgaagtc tgtttgaagg atgtatttgg 11760
ctgtcttctg gacaggccat tctaataaca gaaacaaaca agttatttta aaacttattg 11820
gaatattcaa atattaacca aagtagaaaa atataataca catccatgtg cccatcacag 11880
aacttcactg attatcatca tttagccagt cttgaagaag caagtgctaa ttacaatcac 11940
aaatgaaaca agattcagac ttcatgaaga gcactgcgct ataataaaag aagaaatgag 12000
cacatacatt cttttactga cagtcaaatg gtgaaggtgg gcagaatcat tatgtgatgc 12060
aacatggcaa aagtatacag acagtgcatc cagaggaagg caccttgctg aatgactaga 12120
atggaagtag gagacatttt gcaggccccc ttcatcctgc agggagaacc agaaccacag 12180
cagctctatt tgcctattcc tctttaaatt acaaagttaa aatttgggag tagtagaaaa 12240
tcaattggtt atcttataga gtctcctaga atatttcatt ggcattgaga aggtggaaaa 12300
tgcaaattat atactttaaa atgtaatttt tgcttttcac atatgcttaa agcctaaaac 12360
ctcttaataa acttcttctg aaatata 12387

<210> SEQ ID NO 10
<211> LENGTH: 402
<212> TYPE: PRT
<213> ORGANISM: Homo sapiens

<400> SEQUENCE: 10

Met Glu Arg Ala Arg Glu Val Ile Pro Arg Ser Gln His Gln Glu Thr
1 5 10 15

Pro Val Tyr Leu Gly Ala Thr Ala Gly Met Arg Leu Leu Arg Met Glu
20 25 30

Ser Glu Glu Leu Ala Asp Arg Val Leu Asp Val Val Glu Arg Ser Leu
35 40 45

Ser Asn Tyr Pro Phe Asp Phe Gln Gly Ala Arg Ile Ile Thr Gly Gln
50 55 60

Glu Glu Gly Ala Tyr Gly Trp Ile Thr Ile Asn Tyr Leu Leu Gly Lys
65 70 75 80

Phe Ser Gln Lys Thr Arg Trp Phe Ser Ile Val Pro Tyr Glu Thr Asn
85 90 95

Asn Gln Glu Thr Phe Gly Ala Leu Asp Leu Gly Gly Ala Ser Thr Gln
100 105 110

Val Thr Phe Val Pro Gln Asn Gln Thr Ile Glu Ser Pro Asp Asn Ala
115 120 125

Leu Gln Phe Arg Leu Tyr Gly Lys Asp Tyr Asn Val Tyr Thr His Ser
130 135 140

```
Phe Leu Cys Tyr Gly Lys Asp Gln Ala Leu Trp Gln Lys Leu Ala Lys
145                 150                 155                 160

Asp Ile Gln Val Ala Ser Asn Glu Ile Leu Arg Asp Pro Cys Phe His
                165                 170                 175

Pro Gly Tyr Lys Lys Val Val Asn Val Ser Asp Leu Tyr Lys Thr Pro
            180                 185                 190

Cys Thr Lys Arg Phe Glu Met Thr Leu Pro Phe Gln Gln Phe Glu Ile
        195                 200                 205

Gln Gly Ile Gly Asn Tyr Gln Gln Cys His Gln Ser Ile Leu Glu Leu
    210                 215                 220

Phe Asn Thr Ser Tyr Cys Pro Tyr Ser Gln Cys Ala Phe Asn Gly Ile
225                 230                 235                 240

Phe Leu Pro Pro Leu Gln Gly Asp Phe Gly Ala Phe Ser Ala Phe Tyr
                245                 250                 255

Phe Val Met Lys Phe Leu Asn Leu Thr Ser Glu Lys Val Ser Gln Glu
            260                 265                 270

Lys Val Thr Glu Met Met Lys Lys Phe Cys Ala Gln Pro Trp Glu Glu
        275                 280                 285

Ile Lys Thr Ser Tyr Ala Gly Val Lys Glu Lys Tyr Leu Ser Glu Tyr
    290                 295                 300

Cys Phe Ser Gly Thr Tyr Ile Leu Ser Leu Leu Leu Gln Gly Tyr His
305                 310                 315                 320

Phe Thr Ala Asp Ser Trp Glu His Ile His Phe Ile Gly Lys Ile Gln
                325                 330                 335

Gly Ser Asp Ala Gly Trp Thr Leu Gly Tyr Met Leu Asn Leu Thr Asn
            340                 345                 350

Met Ile Pro Ala Glu Gln Pro Leu Ser Thr Pro Leu Ser His Ser Thr
        355                 360                 365

Tyr Val Phe Leu Met Val Leu Phe Ser Leu Val Leu Phe Thr Val Ala
    370                 375                 380

Ile Ile Gly Leu Leu Ile Phe His Lys Pro Ser Tyr Phe Trp Lys Asp
385                 390                 395                 400

Met Val
```

<210> SEQ ID NO 11
<211> LENGTH: 12342
<212> TYPE: DNA
<213> ORGANISM: Homo sapiens

<400> SEQUENCE: 11

```
acggagacgg accacagcaa gcagaggctg ggggggggaa agacgaggaa agaggaggaa     60

aacaaaagct gctacttatg gaagatacaa aggagtctaa cgtgaagaca ttttgctcca    120

agaatatcct agccatcctt ggcttctcct ctatcatagc tgtgatagct ttgcttgctg    180

tggggttgac ccagaacaaa gcattgccag aaaacgttaa gtatgggatt gtgctggatg    240

cgggttcttc tcacacaagt ttatacatct ataagtggcc agcagaaaag gagaatgaca    300

caggcgtggt gcatcaagta gaagaatgca gggttaaagg atggaaagtg aagagttggc    360

agacagggtt ctggatgtgg tggagaggag cctcagcaac taccccttg acttccaggg    420

tgccaggatc attactggcc aagaggaagg tgcctatggc tggattacta tcaactatct    480

gctgggcaaa ttcagtcaga aaacaaggtg gttcagcata gtcccatatg aaaccaataa    540

tcaggaaacc tttggagctt tggaccttgg gggagcctct acacaagtca cttttgtacc    600
```

-continued

```
ccaaaaccag actatcgagt ccccagataa tgctctgcaa tttcgcctct atggcaagga    660
ctacaatgtc tacacacata gcttcttgtg ctatgggaag gatcaggcac tctggcagaa    720
actggccaag gacattcagg ttgcaagtaa tgaaattctc agggacccat gctttcatcc    780
tggatataag aaggtagtga acgtaagtga cctttacaag accccctgca ccaagagatt    840
tgagatgact cttccattcc agcagtttga aatccagggt attggaaact atcaacaatg    900
ccatcaaagc atcctggagc tcttcaacac cagttactgc ccttactccc agtgtgcctt    960
caatgggatt ttcttgccac cactccaggg ggattttggg gcattttcag ctttttactt   1020
tgtgatgaag tttttaaact tgacatcaga gaaagtctct caggaaaagg tgactgagat   1080
gatgaaaaag ttctgtgctc agccttggga ggagataaaa acatcttacg ctggagtaaa   1140
ggagaagtac ctgagtgaat actgcttttc tggtacctac attctctccc tccttctgca   1200
aggctatcat ttcacagctg attcctggga gcacatccat ttcattggca agatccaggg   1260
cagcgacgcc ggctggactt tgggctacat gctgaacctg accaacatga tcccagctga   1320
gcaaccattg tccacacctc tctcccactc cacctatgtc ttcctcatgg ttctattctc   1380
cctggtcctt ttcacagtgg ccatcatagg cttgcttatc tttcacaagc cttcatattt   1440
ctggaaagat atggtatagc aaaagcagct gaaatatgct ggctggagtg aggaaaaaaa   1500
tcgtccaggg agcattttcc tccatcgcag tgttcaaggc catccttccc tgtctgccag   1560
ggccagtctt gacgagtgtg aagcttcctt ggcttttact gaagcctttc ttttggaggt   1620
attcaatatc ctttgcctca aggacttcgg cagatactgt ctctttcatg agtttttccc   1680
agctacacct ttctcctttg tactttgtgc ttgtataggt tttaaagacc tgacaccttt   1740
cataatcttt gctttataaa agaacaatat tgactttgtc tagaagaact gagagtcttg   1800
agtcctgtga taggaggctg agctggctga aagaagaatc tcaggaactg gttcagttgt   1860
actctttaag aacccctttc tctctcctgt ttgccatcca ttaagaaagc catatgatgc   1920
ctttggagaa ggcagacaca cattccattc ccagcctgct ctgtgggtag gagaattttc   1980
tacagtaggc aaatatgtgc taaagccaaa gagttttata aggaaatata tgtgctcatg   2040
cagtcaatac agttctcaat cccacccaaa gcaggtatgt caataaatca catattccta   2100
ggtgataccc aaatgctaca gagtggaaca ctcagacctg agatttgcaa aaagcagatg   2160
taaatatatg cattcaaaca tcagggctta ctatgaggta ggtggtatat acatgtcaca   2220
aataaaaata cagttacaac tcagggtcac aaaaaatgca tcttccaatg catattttta   2280
ttatggtaaa atatacataa atataattca ccattttaac atttaattca tattaaatac   2340
gtacaaatca gtgacattta gtacattcac agtgttgtgc caccatcacc actatttagt   2400
tccagaacat ttgcatcatc aatacattgt ctagagacaa gactatcctg ggtaggcaga   2460
aaccatagat cttttgtgtt tacagctatg gaaaccaact gtaccataaa gatagttcac   2520
tgagttttaa agccaagcca catcttattt ttccaaggtt taatttagtg agagggcagc   2580
attagtgtgg agtggcatgc ttttgcccta tcgtggaatt tacacatcag aatgtgcagg   2640
atccaagtct gaaagtgttg ccacccgtca cacaacatgg gctttgtttg cttattccat   2700
gaagcagcag ctatagacct taccatggaa acatgaagag accctgcacc cctttcctta   2760
aggattgctg caagagttac ctgttgagca ggattgactg gtgatgtttc attctgacct   2820
tgtcccaagc tctccatctc tagatctggg gactgactgt tgagctgatg gggaaagaaa   2880
agctctcaca caaaccggaa gccaaatgtc ccctatctct tgaatgatca agtcactttt   2940
gacaacatcc aggtgaatat aaaaacttaa taaagctgtg gaaaggaact cttaatcttc   3000
```

```
ttttctgcta cttaggttaa attcactaga tcttgattag gaatcaaaat tcgaattggg   3060
acatgttcaa attctttctt gtggtagttg cctatactgt catcgctgct gttggttgag   3120
catttgtggt gtaccacgct gtgtgctcaa gggtattaca ttcatcttct catttaatcc   3180
tcacaacaat ctgaagaagg taggtattac aattcccact tcatagaaac agaaactgag   3240
gttcagagag gttaagtcat ttgcccaaat ggctgagcca aagcctacca tgtacctaac   3300
ctttattttc tttcccgaac ataccaggct gtctcctcat aacttccaag catgcactta   3360
aaactccaca tgaatacaag gttcatggga cttggtattc atagaaaggg aggcagaaag   3420
ctggtctgtt cctgataggc ttgtaattta atatcattct gttcatgtgc tttggatgga   3480
agcacatctg gcatatgatg ctaatcagtg gttcccatac ccctggcttc ctaattttaa   3540
tgtttgctca cagcatagta gattgacatc aaatagtggc cgatgatgat gaaaataaag   3600
gtcaaataag ttgagccaat aacagccgct tttttccttc tgtctgcgta tacaaagcac   3660
tgtcatgcac acaatctatt ctgaccctca caacaaccca taagggtgta aatagtattt   3720
ccattttaca aatgaggatc acacaaacta ctacatggca gagcagatac tccaactcat   3780
gtcttctggt tgaagcctat tgctttttct tttctaaaca ctttccctca gcaagttgga   3840
attagacttc acaagtctcc ttcagagaac acaaatcttt tcttattcca ttcctgtttg   3900
gttgcctacg tccaatctcc ccctccccag agatgccaaa aaaaaaatcc tttaaggtat   3960
ttgggagcca aactcaactt gttaaaatct caaattatgg agacaatcag cagacacaac   4020
ctaaccccaa ttattttggc aggaaggttg gtttagaggc agatccagca atctgctttg   4080
ggccactctg ggtggggtag gtgaaataag attggtcact gttaactaat tttaatattg   4140
gattggccat tggttatcac tgattaccat tctcccctgg attttcaccc aggactcaaa   4200
acttggttct gctaaccctg ttcctttatg aggaaccttt taaagattcc tttataaggt   4260
gggagttttt tttctatgaa cctatagggg agaaaaaaga tcagcagaag tcattacttt   4320
tttttttttt tttttttttt tttgagagag agtctcactc cattgcccag gctggagtgc   4380
agtggtgcta tctcggctca ctgcaacctc cgcctcctgg gttcaagcaa ttctcctgcc   4440
tcagcctccc gagtagctgg gattgcaggt gcccaccacc acacccggct aatttttgta   4500
tttttagtaa agacagggtt tcaccatgtt ggccaggctg gtctccaact cccaatctca   4560
ggtgatccta ttgcctcggg ctcccaaagt gctgggatta caggagtgag ccaccatgcc   4620
tggccagaag tggttacttc tgtagacaaa agaataatgc tacttaatca ggctttctgt   4680
gtgacaagaa agagaaagaa aataaagaag tttcaattca tccaattctt aataagaaat   4740
atgtaaataa aatttttaa aattacactt cattttaatg ttgtatcagt caaggtccct   4800
gcaagagatg gatggtatgg tacactcaaa ctgggtaaca caggagagtt ttcagaaagc   4860
aactaaatcc aaaatactat caaggaatca atataaaaat tgttaatatt tttctcatac   4920
taaattttca aaatatttg tgtctattac atttacagca catcttaatt aggactagct   4980
gtgtgttcac ctcacatgtg gcttgtagct accatactgg acagcacatg tccaaaaaaa   5040
tacacgtaaa gttaaagttt aaaagacaca ggaactaagc cctcattgtc tttcccttgg   5100
gaggtagttt aaagagctat agatgctgta acattcttgc tattatttat tatatatgac   5160
attattccta aaaaagcttt tgagatccta ggttgtattc ctcaggtttt gttgccttcc   5220
catgaagatg tgaaggcagg gatgcctgtt attcagtcca agatgcatga caagagacct   5280
tgggaaagtt tcatctggat ttaaagatta attcttgatg cttacattcc atactcaaaa   5340
```

-continued

```
tgtaaatttg aatattaaaa taaagatgat tttttttttg gagctagtct tgctctgttg   5400
cccaggctgg aatgcagtgg catgatcatg gctcactgca gcctcgacct cccaagctca   5460
agcaaggcta caggtgtgca cctaagtagc taggactaca ggtgtgcacc accatgtcta   5520
gctatttttt tttctgtaga gacagggttt tcctatgttg tccaggctgg tctcgaactc   5580
ctgccctcaa gcaatcctcc tgccttggcc tcccaaagtg ttgagattac aggcgtaagc   5640
cactgcacct ggccaagatg aatattttaa tagctcacag aacaaagttt gccacataat   5700
gataaaatta ctatgaaaat atattccctt tattgtcagt ttaaaagatg aactgagttt   5760
cacccaaact ggtctggccc ctctctgatt caaataccaa tagttgctct gattcaaatt   5820
ccaactgtta gaacatgaca gctgctcata actagctttg cttactaacc atgtttcttt   5880
ccatttgtat taggtccttt actttttata acagcctcaa agtttcatga attgctgcag   5940
taaacattga ttttcatgtt tgtgagtctg caagccagct gggcagctct acttcaggtg   6000
gtaagggtgg atcagaccta ttccatatac ctcttgttct ccttgtccag tggtttctag   6060
ggatatgttc tcatgatgaa ccccgcagag gctcgtgaaa gtgagaggaa actaggatgc   6120
ctcttaaggt cttggtcagg atggggtctc ctgtcacttc tgtcacaggc tattgtaagt   6180
catatgagca agctcaataa aatataaaca agtcagataa acagtgggag gaatggcaaa   6240
gtcatatggc caaggccatg agtgattaat tttaacacag gaaaaaagta aagcattaaa   6300
tgcgattatt taatatacaa tgtcttatta actgaaatat aaaatgtgtt tactgtaaaa   6360
tataatctgt ttatctcacc aaagaaatat tatctttaaa aaatgtcatt acttctaaga   6420
catcatcagt ctgcaacttc tttccatagc cttaatcagg atgctgtggc agctcccaca   6480
ttagcctcgc attctaaact ggtagatgtc ctaggaaacc atacatctat gtatttttct   6540
tattttatac gtttaggaca atgtatagct aattacccaa ctttttattt gcatacaaat   6600
ctaatacaac tgaacacaat cagttttatc acaggtataa tggatttttc aatagtgagg   6660
aggtgcctcc atgagccttc tctttagaaa agtggcattc aagactcttc atttgaagtg   6720
aagattgcta tgtcttttgc attgctctat tttacataaa ttaagttata aattgacact   6780
ataatcaact gacaccatga tcagtgatga tgatcaccct catcagcact agagttgact   6840
tgtttttata accccttttgc atgtatgttg aatagcaaag ttcatcagag aacatgtatt   6900
agtcaatggt aagtaagata ctctcatcta agaaataaca tcacctcttc taatgaagtt   6960
ctaagaagag agggaagaaa aagtcttggg agctagtcag ggaatagtgt gtatttgcaa   7020
ttacctaaac tgaactctac cattactcct aacccagttc ctcctcctgt gttttacatg   7080
attaatgcca cccctgcctc aatgaaccaa gatcagctcc atcactggga cctccccatt   7140
ctgcctgtgc aatattttc tttttattt ctccttctaa tattactgtt attgctccag   7200
taaagagctg taatatattt tacctggact gataccagga atggtggtgt tgcttccaat   7260
ctgttgctgc tagattaatc tttgcaaagc acaggcttaa tttcattgct gctcaactaa   7320
aaccactggt ggctttccat tgcctacaaa ataaagtcaa cctccccatc agacattcaa   7380
ggctttcaat gatccatggc cgccagctct ctccaggctc atatcccact ccactcctct   7440
gatgtttcct acactacact acactatact acactacagc caggtagaat gactgttcac   7500
ccaacaccac tcaggttgtc ttctcaactt ggaatactct tgcaccttca aagctcattt   7560
caaatgcccc ttcatttgtg aagccttctc caaatttcca agtcagaatg tctcttcctt   7620
gtgctaccac aaccctttaa ctgagcctcc attagtgcac tgagaccatt ctgttcagtg   7680
tctgggtgaa gcttcctggt gaaaaatatg ttacctattt ctttctgaaa agttggattc   7740
```

agggatatta tcacggacct aaggtaatag ttctagccaa cctccctgtc cactgccagg 7800
ccgactacaa acccttctgt tgctggcgag ctggtccgca ccactagttc tgcttcactc 7860
tatttatctc ttgatgtaac catcttcttt ctccaggttt taagaaccag cccaactcct 7920
ggttccctga tgaagctttt attcccctag ccacatggaa cttttccttt ttggaacatg 7980
cctttagttt ctgtgtagtt tgccatgcag cacttcattg tacacattat taaaacagaa 8040
ttttaaggat tagaatgaac cttaaaagat catgcatctc aaaatttaat gtacatacaa 8100
attacccagg gattttgttg aaataaaaat tatttaattt taattaatat aaataattca 8160
gtaggtctgg ggtgaggcct gaggttttac atttccaaca agctgccagg taaagccaat 8220
acatctgtcc aggaatcaca ctttgcgtat caaaggtcta gatgacatta tcattccaaa 8280
gagtttcttt tacaggctct cagatcagtg ttcatccact acctgactac tgtcattcac 8340
aggcattctg ttccacagca ggccagctaa cgtggtattt acaaagctca ctcctcttat 8400
acaacaatcc aagtgtttct tttgtcagtt gtctgtgccc caggagatcc ctctctgcct 8460
tgccttgccc tctgcctttg gagaccagca cctcatactc agtgaaggcc tggagtgctt 8520
aagagggatt tcttccagct ctcttgccct ggtcttcagt gtattagatg tattacctcc 8580
atgctctcag tagaggccca taggaaagag taggtaggtt atgccagctc acacgcatcc 8640
tttaaaaatg gtttagaagt ttagctggtt tcttattact cctgtctatg gatgtttcct 8700
tctgtcactc tactagggat gaaacagcta atcatgttca atagttacat ttagattggt 8760
ttttaaaaac tatgattgta ttagttcgtt tccatgctgc tgataaagac atatctgaga 8820
ctggaaacaa aaagggttta attggactta cagttccaca tggctgggga ggcctcaaaa 8880
tcaggtggga ggcaaaaggt acttcttacg tggtggcatc aagagcaaaa tgaggaagaa 8940
gcaaaagcag aaactcttca taaacccacc agatcttgtg ggacttatta tcacgagaat 9000
agcacagaaa agactggcct ccatgattca attacctccc actgcgtccc tcccacaaca 9060
tgtgggaatt ctgggagata caattcaagt tgagatttgg gtggggacac agccaaacca 9120
tatcattcct ccctgggctc ctccaaattt cataatcctc acatttcaaa accaatcatt 9180
ccttcccaac agttccccaa agtcttaact catttcagca ttaacccaaa agtccacagt 9240
ccaaagtctc atctgagaca aggcaagtcc cttccactta caagcctgta aaagcaagct 9300
agttacctcc tagatacaat ggggggtaca ggtattgggt aaatacagct gttccaaatg 9360
agagaaattg gccaaaacaa aggggttaca gggtccatgc aagtctgaaa tccagtgggg 9420
cagtcaaatt ttaaagctcc ataatgatct cctttgactc catgtctcac attcaggtca 9480
tgctgatgca agagataggt tcccatggtc ttgtgcagct ccgcccctgt ggctttgcag 9540
agtacagcct ccctcctggc tgctttctca ggctgatgtt gagtgtctgt agcttttcca 9600
ggcacaagat gcaagttggt ggttgatcta ccattctggg gtctaccatt ctggggtcta 9660
ccgttctggg actgtggcct tcttctcaca gctccactag gcagtgcccc aacagggact 9720
ctgtgtgggg gctctgcccc acatttccct tccacactgc cctaggagag gttccccatg 9780
agggctctgc ccctgcagca aacttttgcc tggacatcca ggtgtttcca tatatattct 9840
gaaatctagg cagaggttcc caaatctcaa ttcttgacat ctctgcaccc acaggctcaa 9900
catcacatgg aagctgccaa tgcttggggc ctctaccctc tgaagccaca gcccaagctc 9960
tatgttggct cctttcagcc atggctggag cagctgggac acagggcacc aagtccctag 10020
gctgcacaca gcacagagac cctgggccca gcccacaaaa ccactttttc ctcctgggcc 10080

-continued

```
tctgggcctg tgatgggagg ggctgccatg aaggtctctg acatgacctg gagacatttt  10140
ccccatggtc ttggggatta acattaggct ccttgctgct tatgcaaatt tctgcagcca  10200
gcttgaattt ctccttaaaa aaaatgggtt tttcttttct actgcatcat caggctgcag  10260
attttccaca tttatgctct tgtttccctt ttaaaacaga atgtttttaa cagcacccaa  10320
gtcacctttt gaatgctttg ctgcttagaa atttattcca ccagataccc taagtcatct  10380
ctctcaagct ctaagttcca caaatctcta gggcaagggt gaaatgctgc cagtctcctt  10440
gctaaaacat aacaagggtc acctttactt cagttcccaa caaggtcttc atctccatct  10500
gagaccacct cagcctggac cttattgttc atatcactat cagtattttt gtcaatgcca  10560
ttcacagtct ctaggaggtt ccaaactttc ctacattttc ctatcttctt ctgagccctc  10620
cagattattt caacacccag ttccaaagtt gcttccacat tttcgggtat cttttcagca  10680
atgccccact ctactggtac tattagtcca ttttcatgct gctgataaag acatacctga  10740
gactgggaac aaaaagaggt ttaattggac ttatagttcc acctggctgg ggaggcctca  10800
gaatcatggc aggaggtgaa aggcatttct tacacggcag cagcaagaga aaaatgaaga  10860
agcagcaaaa gcagaaaccc ctgataaaac catcagatct cgtgagactt attcactatc  10920
acaagaatag catgggaaag accagccccc ttgattcaat tacctccccc tgggtcctgt  10980
gggaattctg gaaggtacaa ttcaagttga gatttgggtg gggacacagc caaaccatat  11040
caatgatttt gtactttaac cagctgaatg gaagtacaat ctcttgctat atgacacaat  11100
aattatttgc aaaatgagta aacatatcat aaggaaatta tttttacaag gtttgaaacc  11160
tgaaatgcag tctattatca tacataacta aaaatagagc ctcaataaac agattcccag  11220
ttttgaaaat gcaacatttg tactccacat tgtcagtttt cttaggtata tttataaata  11280
ctcctataaa aatgtaaaga aacacataat gtagattgct aattttataa taacacaagt  11340
tgattttgac atccaactta ttaattatga aatgactttt ggcctagtaa caatgaaaat  11400
gggggcaaat acagataaat ggtaattctt agaatgaact actcagcacc aattctaagt  11460
ttttcttgat ggtaaatcat aatgttccct ttctcctcgg ttctgcaatc tataggcata  11520
ccataattgt aatcaatagc ttaaaaatat gtctctctgt cctattctgt atctgtatct  11580
cttggatttt tacctttgca atagtcaact gaaccatctt cttggagtac tcatgaagat  11640
ggaagtctac atggagaata caggatgaat ccactctgtc tcctgcagtg aagtctgttt  11700
gaaggatgta tttggctgtc ttctggacag gccattctaa taacagaaac aaacaagtta  11760
ttttaaaact tattggaata ttcaaatatt aaccaaagta gaaaaatata atacacatcc  11820
atgtgcccat cacagaactt cactgattat catcatttag ccagtcttga agaagcaagt  11880
gctaattaca atcacaaatg aaacaagatt cagacttcat gaagagcact gcgctataat  11940
aaaagaagaa atgagcacat acattctttt actgacagtc aaatggtgaa ggtgggcaga  12000
atcattatgt gatgcaacat ggcaaaagta tacagacagt gcatccagag gaaggcacct  12060
tgctgaatga ctagaatgga agtaggagac attttgcagg ccccccttcat cctgcaggga 12120
gaaccagaac cacagcagct ctatttgcct attcctcttt aaattacaaa gttaaaattt  12180
gggagtagta gaaaatcaat tggttatctt atagagtctc ctagaatatt tcattggcat  12240
tgagaaggtg gaaaatgcaa attatatact ttaaaatgta atttttgctt ttcacatatg  12300
cttaaagcct aaaacctctt aataaacttc ttctgaaata ta                      12342
```

<210> SEQ ID NO 12
<211> LENGTH: 372

<212> TYPE: PRT
<213> ORGANISM: Homo sapiens

<400> SEQUENCE: 12

```
Met Glu Ser Glu Glu Leu Ala Asp Arg Val Leu Asp Val Val Glu Arg
1               5                   10                  15

Ser Leu Ser Asn Tyr Pro Phe Asp Phe Gln Gly Ala Arg Ile Ile Thr
            20                  25                  30

Gly Gln Glu Glu Gly Ala Tyr Gly Trp Ile Thr Ile Asn Tyr Leu Leu
        35                  40                  45

Gly Lys Phe Ser Gln Lys Thr Arg Trp Phe Ser Ile Val Pro Tyr Glu
    50                  55                  60

Thr Asn Asn Gln Glu Thr Phe Gly Ala Leu Asp Leu Gly Gly Ala Ser
65                  70                  75                  80

Thr Gln Val Thr Phe Val Pro Gln Asn Gln Thr Ile Glu Ser Pro Asp
                85                  90                  95

Asn Ala Leu Gln Phe Arg Leu Tyr Gly Lys Asp Tyr Asn Val Tyr Thr
            100                 105                 110

His Ser Phe Leu Cys Tyr Gly Lys Asp Gln Ala Leu Trp Gln Lys Leu
        115                 120                 125

Ala Lys Asp Ile Gln Val Ala Ser Asn Glu Ile Leu Arg Asp Pro Cys
    130                 135                 140

Phe His Pro Gly Tyr Lys Lys Val Val Asn Val Ser Asp Leu Tyr Lys
145                 150                 155                 160

Thr Pro Cys Thr Lys Arg Phe Glu Met Thr Leu Pro Phe Gln Gln Phe
                165                 170                 175

Glu Ile Gln Gly Ile Gly Asn Tyr Gln Gln Cys His Gln Ser Ile Leu
            180                 185                 190

Glu Leu Phe Asn Thr Ser Tyr Cys Pro Tyr Ser Gln Cys Ala Phe Asn
        195                 200                 205

Gly Ile Phe Leu Pro Pro Leu Gln Gly Asp Phe Gly Ala Phe Ser Ala
    210                 215                 220

Phe Tyr Phe Val Met Lys Phe Leu Asn Leu Thr Ser Glu Lys Val Ser
225                 230                 235                 240

Gln Glu Lys Val Thr Glu Met Met Lys Lys Phe Cys Ala Gln Pro Trp
                245                 250                 255

Glu Glu Ile Lys Thr Ser Tyr Ala Gly Val Lys Glu Lys Tyr Leu Ser
            260                 265                 270

Glu Tyr Cys Phe Ser Gly Thr Tyr Ile Leu Ser Leu Leu Leu Gln Gly
        275                 280                 285

Tyr His Phe Thr Ala Asp Ser Trp Glu His Ile His Phe Ile Gly Lys
    290                 295                 300

Ile Gln Gly Ser Asp Ala Gly Trp Thr Leu Gly Tyr Met Leu Asn Leu
305                 310                 315                 320

Thr Asn Met Ile Pro Ala Glu Gln Pro Leu Ser Thr Pro Leu Ser His
                325                 330                 335

Ser Thr Tyr Val Phe Leu Met Val Leu Phe Ser Leu Val Leu Phe Thr
            340                 345                 350

Val Ala Ile Ile Gly Leu Leu Ile Phe His Lys Pro Ser Tyr Phe Trp
        355                 360                 365

Lys Asp Met Val
    370
```

<210> SEQ ID NO 13

<211> LENGTH: 2171
<212> TYPE: DNA
<213> ORGANISM: Homo sapiens

<400> SEQUENCE: 13

```
cctgttgctc tttgctctaa tgagccttga gaaaggattg ctggtcatgg gaccagaggc      60
tttatgggga gggaagaact gttcttgact ttcagttttt cgagcgggtt tcaagagtct     120
aacgtgaaga cattttgctc caagaatatc ctagccatcc ttggcttctc ctctatcata     180
gctgtgatag ctttgcttgc tgtggggttg acccagaaca aagcattgcc agaaaacgtt     240
aagtatggga ttgtgctgga tgcgggttct tctcacacaa gtttatacat ctataagtgg     300
ccagcagaaa aggagaatga cacaggcgtg gtgcatcaag tagaagaatg cagggttaaa     360
ggtcctggaa tctcaaaatt tgttcagaaa gtaaatgaaa taggcattta cctgactgat     420
tgcatggaaa gagctaggga agtgattcca aggtcccagc accaagagac acccgtttac     480
ctgggagcca cggcaggcat gcggttgctc aggatggaaa gtgaagagtt ggcagacagg     540
gttctggatg tggtggagag gagcctcagc aactacccct ttgacttcca gggtgccagg     600
atcattactg gccaagagga aggtgcctat ggctggatta ctatcaacta tctgctgggc     660
aaattcagtc agaaaacaag gtggttcagc atagtcccat atgaaaccaa taatcaggaa     720
acctttggag ctttggacct tgggggagcc tctacacaag tcacttttgt accccaaaac     780
cagactatcg agtccccaga taatgctctg caatttcgcc tctatggcaa ggactacaat     840
gtctacacac atagcttctt gtgctatggg aaggatcagg cactctggca gaaactggcc     900
aaggacattc aggttgcaag taatgaaatt ctcagggacc catgctttca tcctggatat     960
aagaaggtag tgaacgtaag tgacctttac aagaccccct gcaccaagag atttgagatg    1020
actcttccat tccagcagtt tgaaatccag ggtattggaa actatcaaca atgccatcaa    1080
agcatcctgg agctcttcaa caccagttac tgcccttact cccagtgtgc cttcaatggg    1140
attttcttgc caccactcca gggggatttt ggggcatttt cagcttttta ctttgtgatg    1200
aagtttttaa acttgacatc agagaaagtc tctcaggaaa aggtgactga gatgatgaaa    1260
aagttctgtg ctcagccttg ggaggagata aaaacatctt acgctggagt aaaggagaag    1320
tacctgagtg aatactgctt ttctggtacc tacattctct ccctccttct gcaaggctat    1380
catttcacag ctgattcctg ggagcacatc catttcattg gcaagtcaac tgaaccatct    1440
tcttggagta ctcatgaaga tggaagtcta catggagaat acaggatgaa tccactctgt    1500
ctcctgcagt gaagtctgtt tgaaggatgt atttggctgt cttctggaca ggccattcta    1560
ataacagaaa caaacaagtt attttaaaac ttattggaat attcaaatat taaccaaagt    1620
agaaaaatat aatacacatc catgtgccca tcacagaact tcactgatta tcatcattta    1680
gccagtcttg aagaagcaag tgctaattac aatcacaaat gaaacaagat tcagacttca    1740
tgaagagcac tgcgctataa taaaagaaga aatgagcaca tacattcttt tactgacagt    1800
caaatggtga aggtgggcag aatcattatg tgatgcaaca tggcaaaagt atacagacag    1860
tgcatccaga ggaaggcacc ttgctgaatg actagaatgg aagtaggaga cattttgcag    1920
gccccccttca tcctgcaggg agaaccagaa ccacagcagc tctatttgcc tattcctctt    1980
taaattacaa agttaaaatt tgggagtagt agaaaatcaa ttggttatct tatagagtct    2040
cctagaatat ttcattggca ttgagaaggt ggaaaatgca aattatatac tttaaaatgt    2100
aatttttgct tttcacatat gcttaaagcc taaaacctct taataaactt cttctgaaat    2160
ataaaaaaaa a                                                         2171
```

<210> SEQ ID NO 14
<211> LENGTH: 482
<212> TYPE: PRT
<213> ORGANISM: Homo sapiens

<400> SEQUENCE: 14

```
Met Gly Arg Glu Glu Leu Phe Leu Thr Phe Ser Phe Ser Ser Gly Phe
1               5                   10                  15

Gln Glu Ser Asn Val Lys Thr Phe Cys Ser Lys Asn Ile Leu Ala Ile
            20                  25                  30

Leu Gly Phe Ser Ser Ile Ile Ala Val Ile Ala Leu Leu Ala Val Gly
        35                  40                  45

Leu Thr Gln Asn Lys Ala Leu Pro Glu Asn Val Lys Tyr Gly Ile Val
    50                  55                  60

Leu Asp Ala Gly Ser Ser His Thr Ser Leu Tyr Ile Tyr Lys Trp Pro
65                  70                  75                  80

Ala Glu Lys Glu Asn Asp Thr Gly Val Val His Gln Val Glu Glu Cys
                85                  90                  95

Arg Val Lys Gly Pro Gly Ile Ser Lys Phe Val Gln Lys Val Asn Glu
            100                 105                 110

Ile Gly Ile Tyr Leu Thr Asp Cys Met Glu Arg Ala Arg Glu Val Ile
        115                 120                 125

Pro Arg Ser Gln His Gln Glu Thr Pro Val Tyr Leu Gly Ala Thr Ala
    130                 135                 140

Gly Met Arg Leu Leu Arg Met Glu Ser Glu Glu Leu Ala Asp Arg Val
145                 150                 155                 160

Leu Asp Val Val Glu Arg Ser Leu Ser Asn Tyr Pro Phe Asp Phe Gln
                165                 170                 175

Gly Ala Arg Ile Ile Thr Gly Gln Glu Glu Gly Ala Tyr Gly Trp Ile
            180                 185                 190

Thr Ile Asn Tyr Leu Leu Gly Lys Phe Ser Gln Lys Thr Arg Trp Phe
        195                 200                 205

Ser Ile Val Pro Tyr Glu Thr Asn Asn Gln Glu Thr Phe Gly Ala Leu
    210                 215                 220

Asp Leu Gly Gly Ala Ser Thr Gln Val Thr Phe Val Pro Gln Asn Gln
225                 230                 235                 240

Thr Ile Glu Ser Pro Asp Asn Ala Leu Gln Phe Arg Leu Tyr Gly Lys
                245                 250                 255

Asp Tyr Asn Val Tyr Thr His Ser Phe Leu Cys Tyr Gly Lys Asp Gln
            260                 265                 270

Ala Leu Trp Gln Lys Leu Ala Lys Asp Ile Gln Val Ala Ser Asn Glu
        275                 280                 285

Ile Leu Arg Asp Pro Cys Phe His Pro Gly Tyr Lys Lys Val Val Asn
    290                 295                 300

Val Ser Asp Leu Tyr Lys Thr Pro Cys Thr Lys Arg Phe Glu Met Thr
305                 310                 315                 320

Leu Pro Phe Gln Gln Phe Glu Ile Gln Gly Ile Gly Asn Tyr Gln Gln
                325                 330                 335

Cys His Gln Ser Ile Leu Glu Leu Phe Asn Thr Ser Tyr Cys Pro Tyr
            340                 345                 350

Ser Gln Cys Ala Phe Asn Gly Ile Phe Leu Pro Pro Leu Gln Gly Asp
        355                 360                 365

Phe Gly Ala Phe Ser Ala Phe Tyr Phe Val Met Lys Phe Leu Asn Leu
```

```
    370                 375                 380

Thr Ser Glu Lys Val Ser Gln Glu Lys Val Thr Glu Met Met Lys Lys
385                 390                 395                 400

Phe Cys Ala Gln Pro Trp Glu Glu Ile Lys Thr Ser Tyr Ala Gly Val
                405                 410                 415

Lys Glu Lys Tyr Leu Ser Glu Tyr Cys Phe Ser Gly Thr Tyr Ile Leu
            420                 425                 430

Ser Leu Leu Leu Gln Gly Tyr His Phe Thr Ala Asp Ser Trp Glu His
        435                 440                 445

Ile His Phe Ile Gly Lys Ser Thr Glu Pro Ser Ser Trp Ser Thr His
    450                 455                 460

Glu Asp Gly Ser Leu His Gly Glu Tyr Arg Met Asn Pro Leu Cys Leu
465                 470                 475                 480

Leu Gln


<210> SEQ ID NO 15
<211> LENGTH: 1676
<212> TYPE: DNA
<213> ORGANISM: Homo sapiens

<400> SEQUENCE: 15

agactcaaca agagctccag caaagacttt cactgtagct tgacttgacc tgagattaac     60

tagggaatct tgagaataaa gatgagctct gaaaattgtt tcgtagcaga gaacagctct    120

ttgcatccgg agagtggaca agaaaatgat gccaccagtc cccatttctc aacacgtcat    180

gaagggtcct tccaagttcc tgtcctgtgt gctgtaatga atgtggtctt catcaccatt    240

ttaatcatag ctctcattgc cttatcagtg ggccaataca attgtccagg ccaatacaca    300

ttctcaatgc catcagacag ccatgtttct tcatgctctg aggactgggt tggctaccag    360

aggaaatgct actttatttc tactgtgaag aggagctgga cttcagccca aaatgcttgt    420

tctgaacatg gtgctactct tgctgtcatt gattctgaaa aggacatgaa ctttctaaaa    480

cgatacgcag gtagagagga acactgggtt ggactgaaaa aggaacctgg tcacccatgg    540

aagtggtcaa atggcaaaga atttaacaac tggttcaacg ttacagggtc tgacaagtgt    600

gtttttctga aaaacacaga ggtcagcagc atggaatgtg agaagaattt atactggata    660

tgtaacaaac cttacaaata ataaggaaac atgttcactt attgactatt atagaatgga    720

actcaaggaa atctgtgtca gtggatgctg ctctgtggtc cgaagtcttc catagagact    780

ttgtgaaaaa aaattttata gtgtcttggg aattttcttc caaacagaac tatggaaaaa    840

aaggaagaaa ttccaggaaa atctgcactg tgggctttta ttgccatgag ctagaagcat    900

cacaggttga ccaataacca tgcccaagaa tgagaagaat gactatgcaa cctttggatg    960

cactttatat tattttgaat ccagaaataa tgaaataact aggcgtggac ttactattta   1020

ttgctgaatg actaccaaca gtgagagccc ttcatgcatt tgcactattg gaaggagtta   1080

gatgttggta ctagatactg aatgtaaaca aaggaattat ggctggtaac ataggttttt   1140

agtctaattg aatcccttaa actcagggag catttataaa tggacaaatg cttatgaaac   1200

taagatttgt aatatttctc tctttttaga gaaatttgcc aatttacttt gttatttttc   1260

cccaaaaaga atgggatgat catgtattta tttttttact tcctcagctg tagacaggtc   1320

cttttcgatg gtacatattt ctttgccttt ataatctttt atacagtgtc ttacagagaa   1380

aagacataag caaagactat gaggaatatt tgcaagacat agaatagtgt tggaaaatgt   1440

gcaatatgtg atgtggcaaa tctctattag gaaatattct gtaatcttca gacctagaat   1500
```

```
aatactagtc ttataatagg tttgtgactt tcctaaatca attctattac gtgcaatact   1560

tcaatacttc atttaaaata tttttatgtg caataaaatg tatttgtttg tattttgtgt   1620

tcagtacaat tataagctgt ttttatatat gtgaaataaa agtagaataa acacaa       1676


<210> SEQ ID NO 16
<211> LENGTH: 199
<212> TYPE: PRT
<213> ORGANISM: Homo sapiens

<400> SEQUENCE: 16

Met Ser Ser Glu Asn Cys Phe Val Ala Glu Asn Ser Ser Leu His Pro
1               5                   10                  15

Glu Ser Gly Gln Glu Asn Asp Ala Thr Ser Pro His Phe Ser Thr Arg
            20                  25                  30

His Glu Gly Ser Phe Gln Val Pro Val Leu Cys Ala Val Met Asn Val
        35                  40                  45

Val Phe Ile Thr Ile Leu Ile Ile Ala Leu Ile Ala Leu Ser Val Gly
    50                  55                  60

Gln Tyr Asn Cys Pro Gly Gln Tyr Thr Phe Ser Met Pro Ser Asp Ser
65                  70                  75                  80

His Val Ser Ser Cys Ser Glu Asp Trp Val Gly Tyr Gln Arg Lys Cys
                85                  90                  95

Tyr Phe Ile Ser Thr Val Lys Arg Ser Trp Thr Ser Ala Gln Asn Ala
            100                 105                 110

Cys Ser Glu His Gly Ala Thr Leu Ala Val Ile Asp Ser Glu Lys Asp
        115                 120                 125

Met Asn Phe Leu Lys Arg Tyr Ala Gly Arg Glu Glu His Trp Val Gly
    130                 135                 140

Leu Lys Lys Glu Pro Gly His Pro Trp Lys Trp Ser Asn Gly Lys Glu
145                 150                 155                 160

Phe Asn Asn Trp Phe Asn Val Thr Gly Ser Asp Lys Cys Val Phe Leu
                165                 170                 175

Lys Asn Thr Glu Val Ser Ser Met Glu Cys Glu Lys Asn Leu Tyr Trp
            180                 185                 190

Ile Cys Asn Lys Pro Tyr Lys
        195


<210> SEQ ID NO 17
<211> LENGTH: 9
<212> TYPE: PRT
<213> ORGANISM: Homo sapiens

<400> SEQUENCE: 17

Ser Leu Leu Met Trp Ile Thr Gln Cys
1               5


<210> SEQ ID NO 18
<211> LENGTH: 14
<212> TYPE: PRT
<213> ORGANISM: Homo sapiens

<400> SEQUENCE: 18

Cys Ala Ser Ser Tyr Val Gly Asn Thr Gly Glu Leu Phe Phe
1               5                   10


<210> SEQ ID NO 19
<211> LENGTH: 9
```

-continued

<212> TYPE: PRT
<213> ORGANISM: Artificial Sequence
<220> FEATURE:
<223> OTHER INFORMATION: Synthetic

<400> SEQUENCE: 19

Lys Val Pro Arg Asn Gln Asp Trp Leu
1 5